US 8,450,307 B2
May 28, 2013

(12) United States Patent
Sargent et al.

(10) Patent No.: US 8,450,307 B2
(45) Date of Patent: May 28, 2013

(54) THERAPEUTIC AGENTS, AND METHODS OF MAKING AND USING THE SAME

(75) Inventors: Bruce J. Sargent, Albany, NY (US); Henry Pauls, Oakville (CA); Judd M. Berman, Toronto (CA); Jailall Ramnauth, Brampton (CA); Peter Sampson, Oakville (CA); Andras Toro, Toronto (CA); Fernando J. Martin, Lancaster, PA (US); Matthew D. Surman, Albany, NY (US); Helene Y. Decornez, Clifton Park, NY (US); David D. Manning, Duanesburg, NY (US)

(73) Assignee: Affinium Pharmaceuticals, Inc., Toronto (CA)

( * ) Notice: Subject to any disclaimer, the term of this patent is extended or adjusted under 35 U.S.C. 154(b) by 970 days.

(21) Appl. No.: 11/628,569

(22) PCT Filed: Jun. 6, 2005

(86) PCT No.: PCT/US2005/019805
§ 371 (c)(1),
(2), (4) Date: Dec. 11, 2009

(87) PCT Pub. No.: WO2007/053131
PCT Pub. Date: May 10, 2007

(65) Prior Publication Data
US 2010/0093705 A1  Apr. 15, 2010

Related U.S. Application Data

(60) Provisional application No. 60/576,945, filed on Jun. 4, 2004.

(51) Int. Cl.
*C07D 401/12* (2006.01)
*C07D 405/12* (2006.01)
*C07D 409/12* (2006.01)
*C07D 498/04* (2006.01)
*A61K 31/551* (2006.01)
*A61K 31/5365* (2006.01)

(52) U.S. Cl.
USPC .......................... 514/221; 514/230.5; 540/504

(58) Field of Classification Search
USPC ........... 540/504; 544/105; 546/123; 514/221, 514/230.5, 300
See application file for complete search history.

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |
| 6,406,880 B1 | 6/2002 | Thornton |
| 6,423,341 B1 | 7/2002 | Yamaguchi |
| 6,423,741 B1 | 7/2002 | Khanuja et al. |
| 6,428,579 B1 | 8/2002 | Valentini |
| 6,432,444 B1 | 8/2002 | Fischetti et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |

(Continued)

FOREIGN PATENT DOCUMENTS

| | | |
|---|---|---|
| CA | 2444597 | 10/2002 |
| EP | 0407200 | 1/1991 |

(Continued)

OTHER PUBLICATIONS

Abou-Gharbia et al., "Psychotropic Agents: Synthesis and Antipysychotic Activity of Substituted B-Carbolines " *J. Med. Chem.*, 30(6):1100-1115 (1987).

(Continued)

*Primary Examiner* — Bruck Kifle
(74) *Attorney, Agent, or Firm* — Goodwin Procter LLP

(57) ABSTRACT

In part, the present invention is directed to antibacterial compounds.

22 Claims, 7 Drawing Sheets

U.S. PATENT DOCUMENTS

| | | | |
|---|---|---|---|
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,524,843 B2 | 4/2009 | Miller et al. |
| 7,557,125 B2 | 7/2009 | Miller et al. |
| 7,879,872 B2 * | 2/2011 | Berman et al. ................ 514/300 |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |

FOREIGN PATENT DOCUMENTS

| | | |
|---|---|---|
| EP | 1000935 | 5/2000 |
| HU | 0203122 | 1/1988 |
| HU | 210679 | 7/1993 |
| WO | WO-93/04035 | 3/1993 |
| WO | WO-95/18619 | 7/1995 |
| WO | WO-96/00730 | 1/1996 |
| WO | WO-97/48696 | 12/1997 |
| WO | WO-98/57952 | 12/1998 |
| WO | WO-99/24406 | 5/1999 |
| WO | WO-00/27628 | 5/2000 |
| WO | WO-00/57933 | 10/2000 |
| WO | WO-01/26652 | 4/2001 |
| WO | WO-01/26654 | 4/2001 |
| WO | WO-01/27103 | 4/2001 |
| WO | WO-01/41573 | 6/2001 |
| WO | WO-01/48248 | 7/2001 |
| WO | WO-01/70172 | 9/2001 |
| WO | WO-02/10332 | 2/2002 |
| WO | WO-02/42273 | 5/2002 |
| WO | WO-02/48097 | 6/2002 |
| WO | WO-02/064572 | 8/2002 |
| WO | WO-03/086396 | 10/2003 |
| WO | WO-2004/014869 | 2/2004 |
| WO | WO-2004/052890 | 6/2004 |
| WO | WO-2004/082586 | 9/2004 |
| WO | WO-2007/053131 | 5/2007 |
| WO | WO-2007/067416 | 6/2007 |
| WO | WO-2008/009122 | 1/2008 |

OTHER PUBLICATIONS

Ahsan et al., "Reserpine Anlogues: Synthesis of B-Carboline Derivatives," *J. Chem. Soc.*, pp. 3928-3920 (1963).

Bergler, Helmut, et al., "Protein EnvM is the NADH-dependent Enoyl-ACP Reductase (FabI) of *Escherichia coli*," *J. Biological Chemistry*, vol. 269, No. 8, Feb. 25, 1994, pp. 5493-5496.

Claus et al., *Monatsh. Chem.* 97:271-279 (1966).

Database CA on STN, AN 7:66733, Rosenmund et al., "Chemistry of indole II . . . ," *Chem Ber.* 103(2): 496-509 (1970).

Database CAOLD on STN, AN CA51:10524d, Hellman et al., "N-Mannich bases (VI) condensation . . . ," *Direct Submission* (1953).

Database CAPLUS on STN, AN 1977:439214. Misztal et al., "Synthesis and pharmacologic properties of pyridoyl . . . ," *Arch Immuno Ther Exp.* 24(6):851-862 (1976).

Database CAPLUS on STN, AN 1986:68547, Stuetz, et al., "Synthesis and Structure Activity . . . ," *J. Med Chem.*, 29(1): 112-25 (1986).

Database CAPLUS on STN, AN 1991:428908, Fuse et al., "Preparation of cinnamamide derivatives . . . ," EP407200A1 (1991).

Database CAPLUS on STN, AN 1999;325910 Aslanian , et al., "Preparation of phenylalkylimidazoles . . . ," WO99/24406. (1999).

Database Crossfire Beilstein, 1966, Database accession No. 2819049, 2819050, XP002216033.

Grassberger, Maximilian, et al., "Preparation and Antibacterial Activities of New 1,2,3-Diazaborine Derivatives and Analogues," *J. Med. Chemistry*, 1984, 27, 947-953.

Heath, Richard J., et al., "A Triclosan-Resistant Bacterial Enzyme," *Nature*, vol. 406, Jul. 13, 2000, p. 145-146.

Heath, Richard J., et al., "Regulation of Fatty Acid Elongation and Initiation by Acyl-Acyl Carrier Protein in *Escherichia coli*," *J. Biological Chemistry*, vol. 271, No. 4, Jan. 26, 1996, pp. 1833-1836.

Heck, Richard F., *Organic Reactions*, 1982, 27, pp. 345-390.

Himmer et al., "Synthesis and Antibacterial in Vitro Activity of Novel Analogues of Nematophin," *Bioorganic & Medicinal Chemistry Letters*, 8(15): 2045-2050 (Aug. 1998).

Hungarian Search Report dated Dec. 31, 2003.

International Search Report dated Oct. 4, 2000 for PCT/US2000/15154.

International Search Report dated Jan. 25, 2001 for PCT/US2000/27844.

International Search Report dated Jan. 29, 2001 for PCT/US2000/27591.

International Search Report dated Feb. 22, 2001 for PCT/US2000/27619.

International Search Report dated Apr. 21, 2004 for PCT/US2003/38706.

International Search Report dated Oct. 13, 2004 for PCT/IB2004/001261.

International Search Report dated Apr. 20, 2005 for PCT/US2002/10332.

International Search Report dated Jun. 14, 2007 for PCT/US2005/019805.

International Search Report dated Sep. 12, 2007 for PCT/US2006/045903.

International Search Report dated Oct. 26, 2007 for PCT/CA2007/001277.

International Search Report dated Apr. 7, 2008 for PCT/CA2008/000300.

Jianxiong Li et al., "Synthesis and Antistaphylococcal Activity of Nematophin and Its Analogs," *Bioorganic & Medicinal Chemistry Letters* Oxford, GB, 7(10): 1349-1352, (May 20, 1977) XP004136332.

Jossang-Yanagida, Akino, et al., "Tetrahydropyridoazepines and Tetrahydropyridoazepinones from the Corresponding Dihydroquinolones," *J. Heterocyclic Chemistry*, vol. 15, pp. 249-251.

Karlowsky et al. "In Vitro activity of API-1252, a novel Fab1 inhibitor, against clinical isolates of *Staphylococcus aureus* and *Staphylococcus epidermidis*" *Antimicrobial Agents and Chemotherapy*, Apr. 2007, p. 1580-1581 (published on Jan. 12, 2007).

Levy, Colin W., et al., "Molecular Basis of Triclosan Activity," *Nature*, vol. 398, Apr. 1, 1999, pp. 383-384.

McMurray, Laura M., et al., "Triclosan Targets Lipid Synthesis," *Nature*, vol. 394, Aug. 4, 1998, pp. 531-532.

Miller et al., "Discovery of Aminopyridine-Based Inhibitors of Bacterial Enoyl-ACP Reductase (FABI)" *J. Med. Chem.*, 2002, vol. 45, pp. 3246-3256.

Misztal et al., "Synthesis and Pharmacologic Properties of Pyridol Derivatives of 3-Methylaminoindole 2-Methyltryptamine and Isostryptamine," *Archivum Immnologiae et Therapiae Experimentalis*, 24(6): 851-852 (1976.

Pachter et al., "The Chemistry of Hortiamine and 6-Methoxyhetsinine," *J. Amer. Chem.*, 83:635-642 (1961).

Patent Abstract of Japan vol. 2000, No. 02, Feb. 29, 2000, JP 11-302173.

Payne et al., *Drug Discovery Today*, 2008 pp. 537-541.

Rehse et al., "Dopaminanaloge 1,2,3,4-Tetrahydro-B-Carboline," *Arch. Pharm.*, 311(1): 11-18 (1978.

Seefeld et al., "Indole Naphthyridinones as Inhibitors of Bacterial Enoyl-ACP Reductases FabI and FabK" *J. Med. Chem.* 46:1627-1635 (2003).

Shoji et al., "Two Novel Alkaloids from Evodia Rutaecarpa," *J. Natural Products*, 52(5):1160-1162 (1989).

Sladowska et al. "Synthesis and properties of amides of 1-benzyl-3-methyl and 1-butyl-3-phenyl-7-methyl-4-oxo-2-thioxo (2,4-dioxo)-1,2,3,4-tetrahydropyrido-[2,3-d]pyrimidine-6-carboxylic acids" *Farmaco Edizione Scientifica* 1986 41:954-963.

Stutz et al. "Synthesis and Structure-Activity Relationships of Naftifine-Related Allylamine Antimycotics," *Journal of Medicinal Chemistry*, 1986, vol. 29, No. 1, 112-125.

Turnowsky, Friederike, et al., "envM Genes of *Salmonella typhimurium* and *Escherichia coli*," *J. Bacteriology*, vol. 171, No. 12, Dec. 1989, pp. 6555-6565.

Ward, Walter H.J., et al., "Kinetic and Structural Characteristics of the Inhibition of Enoyl (Acyl Carrier Protein) Reductase by Triclosan," *Biochemistry*, 1999, vol. 38, No. 38, pp. 12514-12525.

\* cited by examiner

THERAPEUTIC AGENTS, AND METHODS OF MAKING AND USING THE SAME

CROSS-REFERENCE TO RELATED APPLICATIONS

This application is a national stage entry of International Patent Application Serial No. PCT/US2005/019805, filed Jun. 6, 2005, which claims priority to U.S. Patent Application Ser. No. 60/576,945, filed Jun. 4, 2004, each of which is hereby incorporated by reference in its entirety.

GOVERNMENT SUPPORT

This invention was made with support provided by the National Institute of Health; the government, therefore, has certain rights in the invention.

INTRODUCTION

Infections caused by or related to bacteria are a major cause of human illness worldwide, and the frequency of resistance to standard antibiotics has risen dramatically over the last decade. Hence, there exists an unmet medical need and demand for new agents acting against bacterial targets.

Examples of potential bacterial targets are those enzymes involved in fatty acid biosynthesis. While the overall pathway of saturated fatty acid biosynthesis is similar in all organisms, the fatty acid synthase (FAS) systems vary considerably with respect to their structural organization. It is believed that vertebrates and yeast possess a FAS in which all the enzymatic activities are encoded on one or two polypeptide chains, respectively, and the acyl carrier protein (ACP) is an integral part of the complex. In contrast, in bacterial FAS, it is known that each of the reactions is catalyzed by a distinct, monofunctional enzyme and the ACP is a discrete protein. Therefore, it may be possible to achieve selective inhibition of the bacterial system by appropriate agents.

One such potential bacterial target is the FabI protein. FabI (previously designated EnvM) is believed to function as an enoyl-ACP reductase in the final step of the four reactions involved in each cycle of bacterial fatty acid biosynthesis. It is believed that in this pathway, the first step is catalyzed by β-ketoacyl-ACP synthase, which condenses malonyl-ACP with acetyl-CoA (FabH, synthase III). It is believed that in subsequent rounds, malonyl-ACP is condensed with the growing-chain acyl-ACP (FabB and FabF, synthases I and II, respectively). The second step in the elongation cycle is thought to be ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP. Finally, in step four, trans-2-enoyl-ACP is converted to acyl-ACP by an NADH (or NADPH)-dependent enoyl-ACP reductase (Fab I). Further rounds of this cycle, adding two carbon atoms per cycle, would eventually lead to palmitoyl-ACP (16C), where upon the cycle is stopped largely due to feedback inhibition of Fab I by palmitoyl-ACP. Thus, Fab I is believed to be a major biosynthetic enzyme and is a key regulatory point in the overall synthetic pathway of bacterial fatty acid biosynthesis.

In some bacteria the final step of fatty acid biosynthesis is catalyzed by Fab I only, in others by FabK, an NADH and FMN dependent reductase, still others utilize both FabI and FabK. The present invention provides, in part, compounds and compositions with FabI inhibiting properties.

SUMMARY OF INVENTION

In part, the present invention is directed towards compounds with FabI inhibiting properties as well as other enzymes. Other uses for the subject compounds and compositions will be readily discernable to those of skill in the art.

In part, the present invention is directed towards compounds that will affect multiple species, so-called "wide spectrum" anti-bacterials. Alternatively, subject compounds that are selective for one or more bacterial or other non-mammalian species, and not for one or more mammalian species (especially human), may be identified.

In part, the present invention is directed towards pharmaceutical compositions comprising a compound with FabI inhibiting properties.

The subject compositions may be administered by one of a variety of means known to those of skill in the art. The subject compounds may be prepared as described herein and as known to those of skill in the art.

Whole-cell antimicrobial activity for the antibacterial compositions of the present invention may be determined by broth microdilution using the National Committee for Clinical Laboratory Standards (NCCLS) recommended procedure, Document M7-A5, "Methods for Dilution Susceptibility Tests for Bacteria that Grow Aerobically". The compositions of the present invention may be tested, for example, in serial two-fold dilutions ranging from 0.06 to 32 mcg/mL. A panel of up to 12 or more bacterial strains may be evaluated in the assay. A panel may consist of, for example, the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49619, *Staphylococcus epidermidis* 1024939, *Staphylococcus epidermidis* 1024961, *Escherichia coli* AG100 (AcrAB$^+$), *Escherichia coli* AG100A (AcrAB3$^-$) *Pseudomonas aeruginosa* K767 (MexAB$^+$, OprM$^+$), *Pseudomonas aeruginosa* K1119 (MexAB$^-$, OprM$^-$). The minimum inhibitory concentration (MIC) may then be determined as the lowest concentration of the subject composition that inhibited visible growth. A spectrophotometer may be used to assist in determining the MIC endpoint.)

Non-limiting examples of bacteria that the antibacterial compounds or compositions of the present invention may be used to either destroy or inhibit the growth of include a member of the genus *Streptococcus, Staphylococcus, Bordetella, Corynebacterium, Mycobacterium, Neisseria, Haemophilus, Actinomycetes, Streptomycetes. Nocardia, Enterobacter, Yersinia, Francisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia, Propionibacterium acnes*, and *Mycoplasma*, and further including, but not limited to, a member of the species or group, Group A *Streptococcus*, Group B *Streptococcus*, Group C *Streptococcus*, Group D *Streptococcus*, Group G *Streptococcus*, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis*, coagulase negative Staphylococci, *Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus* ducreyi, *Bordetella*, *Salmonella typhi*, *Citrobacter freundii*, *Proteus mirabilis*, *Proteus vulgaris*, *Yersinia pestis*, *Kleibsiella pneumoniae*, *Serratia marcessens*, *Serratia liquefaciens*, *Vibrio cholera*, *Shigella dysenterii*, *Shigella flexneri*, *Pseudomonas aeruginosa*, *Franscisella tularensis*, *Brucella abortis*, *Bacillus anthracis*, *Bacillus cereus*, *Clostridium perfringens*, *Clostridium tetani*, *Clostridium botulinum*, *Treponema pallidum*, *Rickettsia rickettsii*, *Helicobacter pylori* or *Chlamydia trachomitis*.

In another aspect, the subject compounds or compositions may be used to treat bacterial infections.

In certain embodiments, the present invention provides antibacterial compositions of the present invention, and methods of using the same, for the reduction and abatement of at least one of the bacteria caused disorders or conditions based on a therapeutic regimen. In certain aspects, the present invention contemplates monitoring such disorders or conditions as part of any therapeutic regimen, which may be administered over the short-term and/or long-term. These aspects of the invention may be particularly helpful in preventive care regimes.

In another aspect of the present invention, the antibacterial compounds or compositions of the present invention may be used in the manufacture of a medicament to treat any of the foregoing bacteria related conditions or diseases. In certain embodiments, the present invention is directed to a method for formulating compounds of the present invention in a pharmaceutically acceptable carrier or excipient.

In part, the present invention also relates to inhibitors and compositions comprising inhibitors of enzymes similar to FabI either structurally or functionally, such as, for example, FabK which is also believed to play a role in bacterial fatty acid synthesis.

In another aspect of the present invention, the antibacterial compounds of the present invention may be used to disinfect an inanimate surface by administering the antibacterial compound to the inanimate surface.

For continuous intravenous infusion, e.g., drip or push, the antibacterial agent can be provided in a sterile dilute solution or suspension (collectively hereinafter "i.v. injectable solution"). The i.v. injectable solution may be formulated such that the amount of antibacterial agent (or antibacterial agents) provided in a 1 L solution would provide a dose, if administered over 15 minutes or less, of at least the median effective dose, or less than 100 times the $ED_{50}$, or less than 10 or 5 times the $ED_{50}$. The i.v. injectable solution may be formulated such that the total amount of antibacterial agent (or antibacterial agents) provided in 1 L solution administered over 60, 90, 120 or 240 minutes would provide an $ED_{50}$ dose to a patient, or less than 100 times the $ED_{50}$, or less than 10 or 5 times the $ED_{50}$. In other embodiments, a single i.v. "bag" provides about 0.25 mg to 5000 mg of antibacterial agent per liter i.v. solution, or 0.25 mg to 2500 mg, or 0.25 mg to 1250 mg.

In another embodiment of the invention it will be desirable to include monitoring or diagnostic regimes or kits with subject antibacterial compounds or methods based on FabI inhibitors described herein, and instructions for use of these compositions or methods.

In another aspect, the present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

The dosage may be selected to modulate metabolism of the bacteria in such a way as to inhibit or stop growth of said bacteria or by killing said bacteria. The skilled artisan may identify this amount as provided herein as well as by using other methods known in the art.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

DETAILED DESCRIPTION OF INVENTION

Introduction

The present invention is directed in part towards novel compositions that inhibit bacterial enzymes, and methods of making and using the same. In certain aspects, inhibitors and other compounds of the invention may be found by a structure-guided medicinal chemistry effort.

Figure 1:
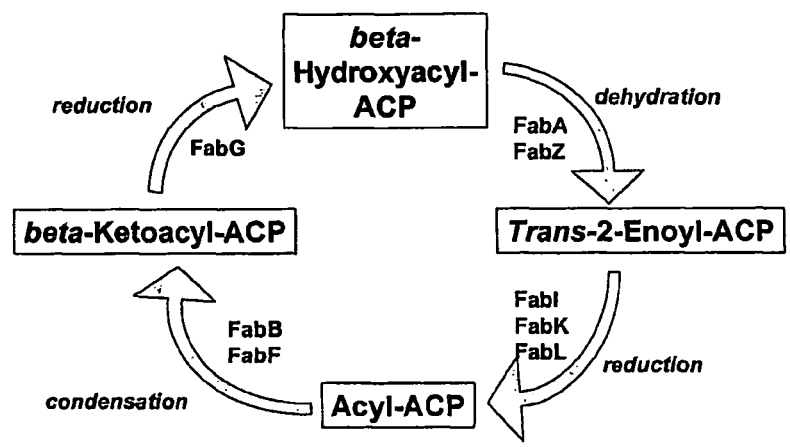
FIG. 1 depicts the bacterial fatty acid biosynthesis cycle via a Type II or dissociated fatty acid synthase system.

Bacterial fatty acid biosynthesis is believed to proceed via a Type II or dissociated fatty acid synthase system, in contrast to the mammalian Type I system. The overall process is believed to proceed in two stages—initiation and cyclical elongation. Enoyl-ACP reductase is part of the elongation cycle, in which malonyl-ACP is condensed with a growing acyl chain by b-ketoacyl-ACP synthase (FabB, FabF, FabH). The β-ketoester is reduced by β-ketoacyl-ACP reductase, which is then dehydrated to the trans-unsaturated acyl-ACP. The trans-unsaturated acyl-ACP is then reduced by enoyl-ACP reductase. (See FIG. 1).

The enoyl-ACP reductase step is believed to be accomplished by FabI in *E. coli* and other gram negative organisms and Staphylococci. In certain gram-positive organisms, FabI paralogs exist. In *Streptococcus pneumoniae*, the enzymatic step is believed to be accomplished by the FabK protein, which has limited homology with the *S. aureus* FabI protein. In *B. subtilis* and *E. faecalis*, genes encoding both FabI and FabK exist. In *Mycobacterium tuberculosis* a FabI paralog termed InhA exists.

Enoyl-ACP reductase is believed to be the enzymatic target of the antimicrobial product triclosan.

Figure 2:
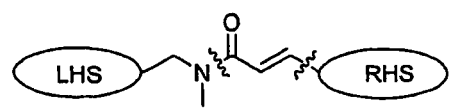
FIG. 2 depicts a simplified view of ene-amide core flanked by LHS (left-hand side) and RHS (right-hand side) moieties.
Figure 3A:
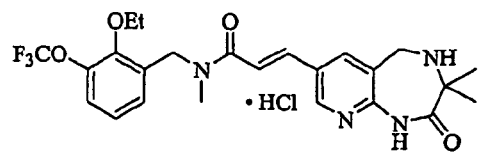
FIGS. 3*a-e* depict non limiting examples of the compounds of the present invention.
Figure 3A:
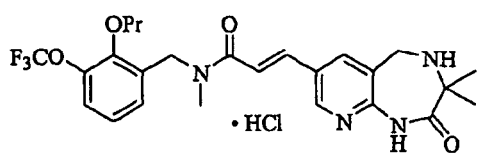
Figure 3A:
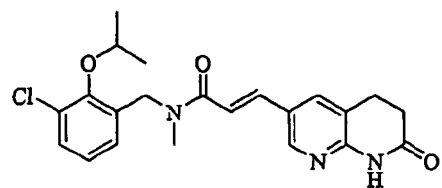
Figure 3A:
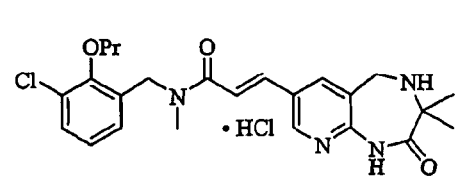
Figure 3A:
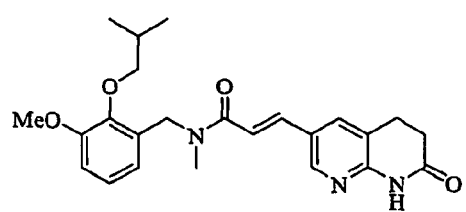
Figure 3A:
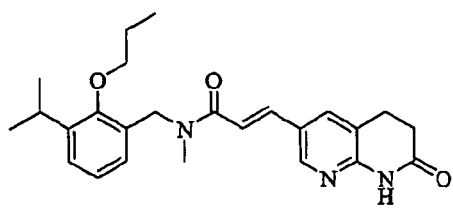
Figure 3A:
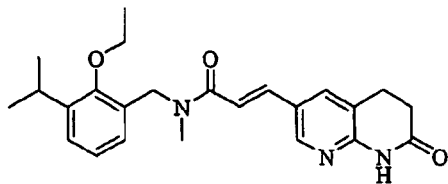
Figure 3A:
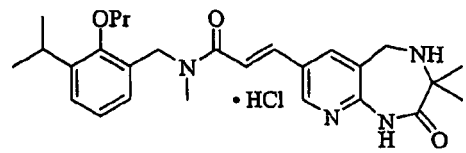
Figure 3A:
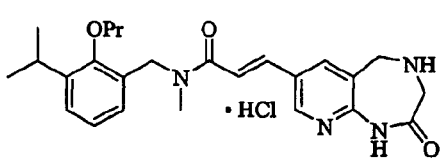
Figure 3A:
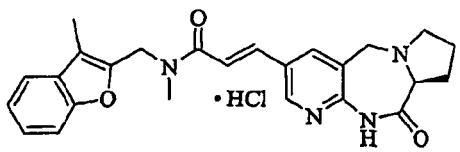
Figure 3A:
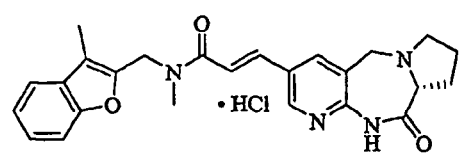
Figure 3A:
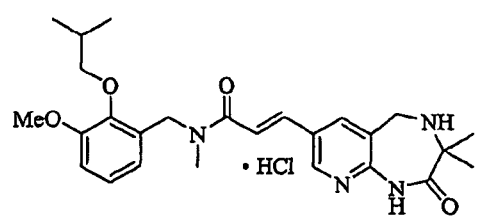
Figure 3B:
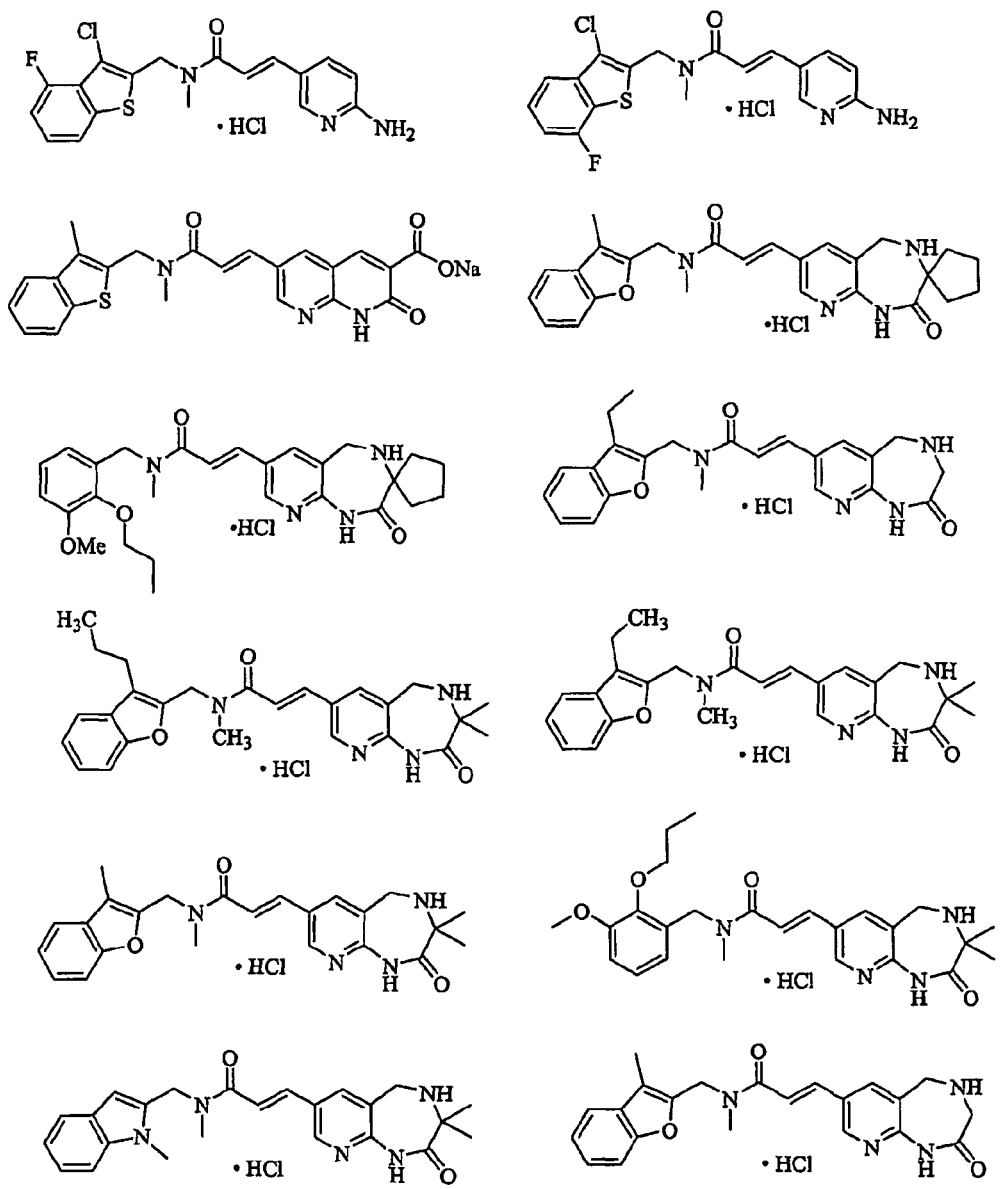
Figure 3C:
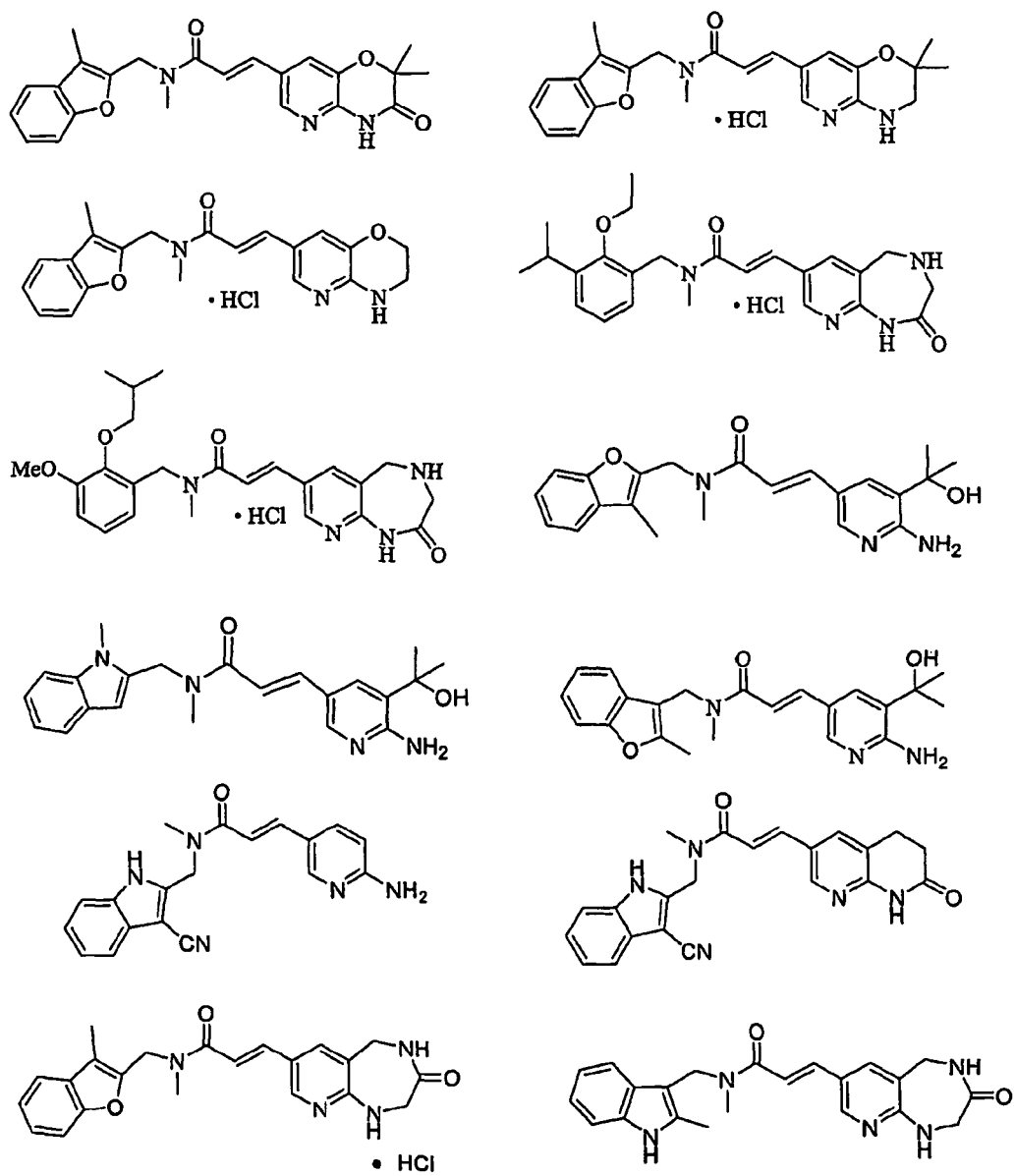
Figure 3D:
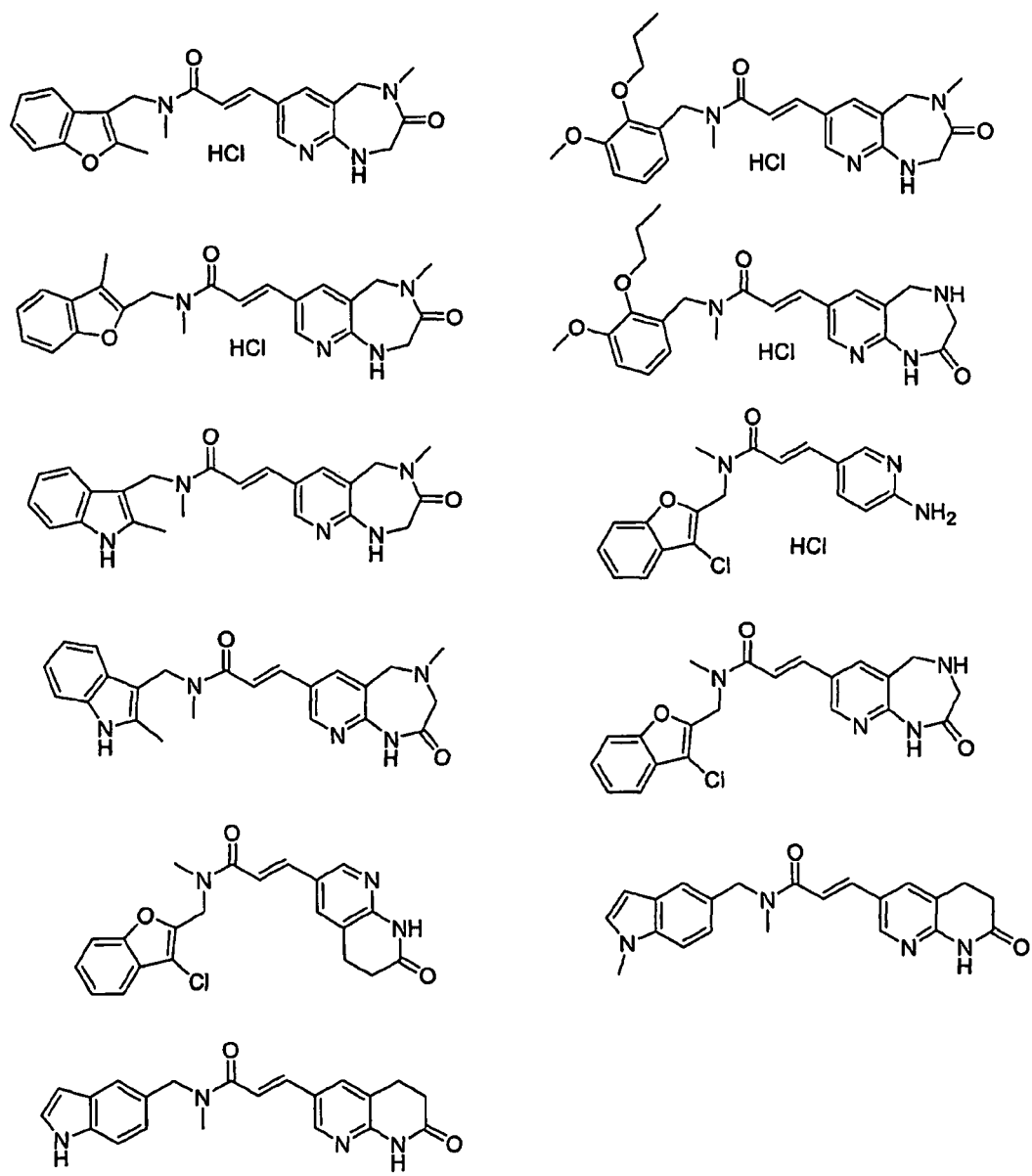
Figure 3E:
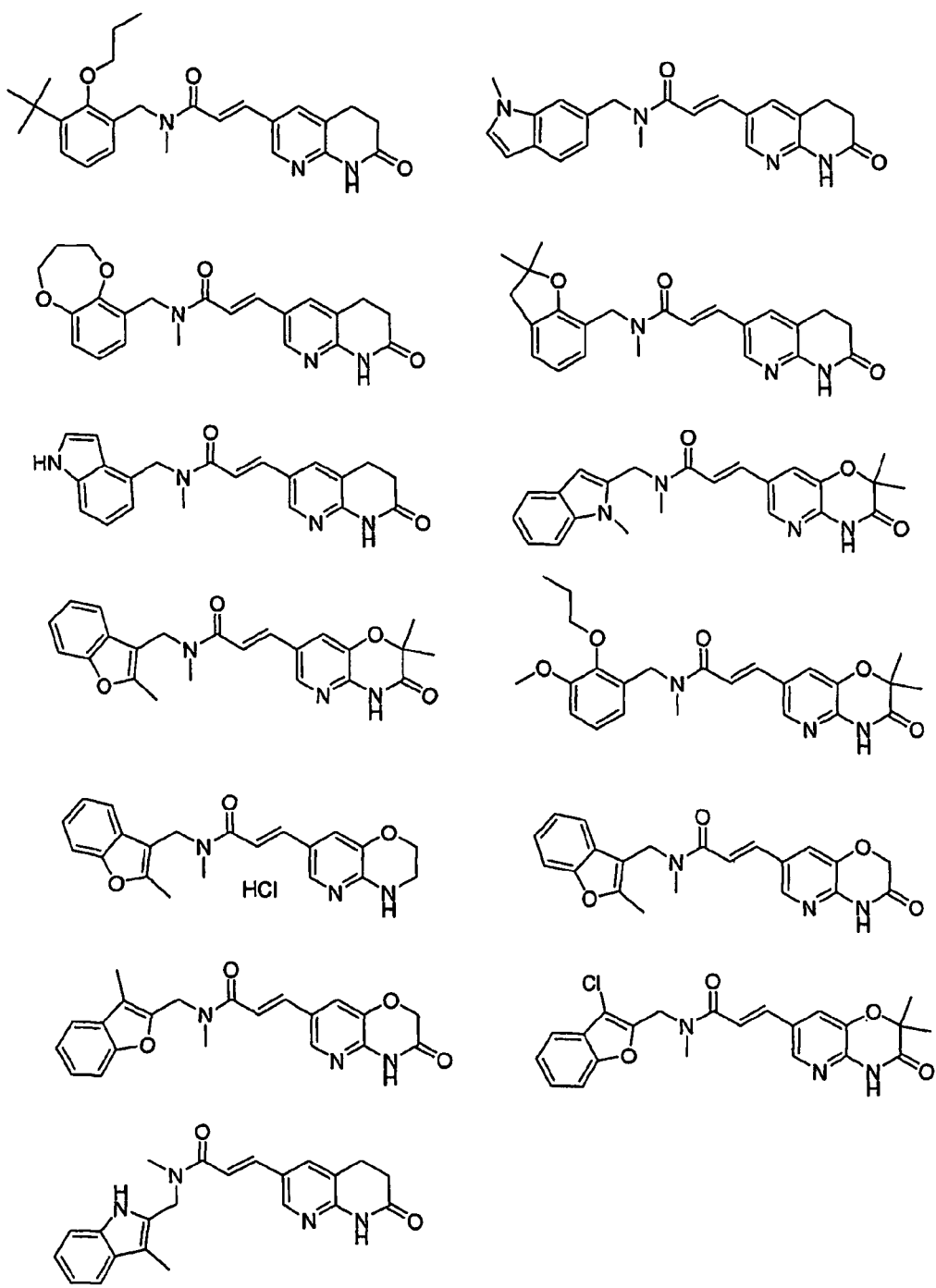

In certain embodiments, the design of new analogs having FabI inhibiting properties is based on viewing the analogs as consisting of a central acrylamide flanked by two relatively hydrophobic groups, conveniently denoted as left-hand side (LHS) and right-hand side (RHS) as put forth in U.S. Provisional Patent Application 60/431,406. Schematically this is depicted in FIG. 2, where a dumbbell like structure provides one way of viewing certain of the subject compositions (the central bond disconnections that is envisioned in a retrosynthetic sense are shown with dashed lines).

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this provisional application.) Other antibiotic agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "synergistic" is art recognized and refers to two or more components working together so that the total effect is greater than the sum of the effect of the components.

The term "illness" as used herein refers to any illness caused by or related to infection by an organism.

The term "bacterial illness" as used herein refers to any illness caused by or related to infection by bacteria.

The term "polynucleotide(s)" is art recognized and refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "polypeptide(s)" is art recognized and refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2$^{nd}$ Ed., T. E. Creighton, W. H. Freeman and Company, New York (1993) and Wold, F., Posttranslational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Antibiotic agents and Fab I/Fab K inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "$K_i$" is art-recognized and refers to the dissociation constant of the enzyme-inhibitor complex.

The term "antimicrobial" is art-recognized and refers to the ability of the compounds of the present invention to prevent, inhibit or destroy the growth of microbes such as bacteria, fungi, protozoa and viruses.

The term "antibacterial" is art-recognized and refers to the ability of the compounds of the present invention to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "structure-activity relationship" or "(SAR)" is art-recognized and refers to the way in which altering the molecular structure of a drug or other compound alters its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

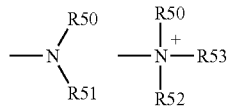

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

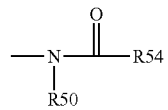

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

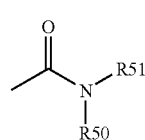

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

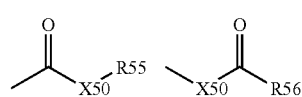

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$), R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

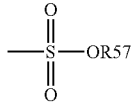

in which R57 is an electron pair, hydrogen, alkyl, cycloalkyl, or aryl.

The term "sulfate" is art recognized and includes a moiety that may be represented by the general formula:

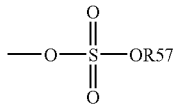

in which R57 is as defined above.

The term "sulfonamido" is art recognized and includes a moiety that may be represented by the general formula:

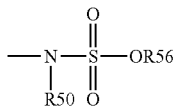

in which R50 and R56 are as defined above.

The term "sulfamoyl" is art-recognized and refers to a moiety that may be represented by the general formula:

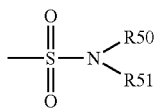

in which R50 and R51 are as defined above.

The term "sulfonyl" is art-recognized and refers to a moiety that may be represented by the general formula:

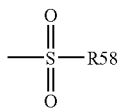

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

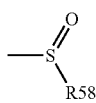

in which R58 is defined above.

The term "phosphoryl" is art-recognized and may in general be represented by the formula:

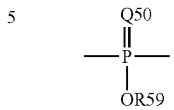

wherein Q50 represents S or O, and R59 represents hydrogen, a lower alkyl or an aryl. When used to substitute, e.g., an alkyl, the phosphoryl group of the phosphorylalkyl may be represented by the general formulas:

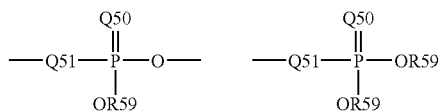

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

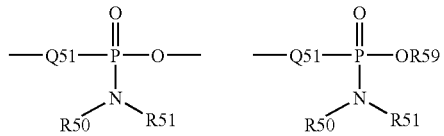

wherein Q51, R50, R51 and R59 are as defined above.

The term "phosphonamidite" is art-recognized and may be represented in the general formulas:

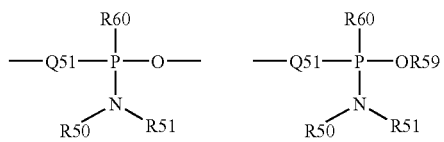

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67$^{th}$ Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59 (McGraw Hill Book Company: New York, 1977). The Hammett constant values are generally negative for electron donating groups ($\sigma(P)$=– 0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives. The terms "amino acid residue" and "peptide residue" are art-recognized and refer to an amino acid or peptide molecule without the —OH of its carboxyl group. The term "amino acid residue" further includes analogs, derivatives and congeners of any specific amino acid referred to herein, as well as C-terminal or N-terminal protected amino acid derivatives (e.g. modified with an N-terminal or C-terminal protecting group). The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl- to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The terms "gene" or "recombinant gene" are art-recognized and refer to a nucleic acid comprising an open reading frame encoding a polypeptide, including both exonic and (optionally) intronic sequences.

The term "gene construct" is art-recognized and refers to a vector, plasmid, viral genome or the like which includes an "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct.

The term "homology" is art-recognized and refers to sequence similarity between two peptides or between two nucleic acid molecules.

The term "operably linked" is art-recognized and refers to the relationship between two nucleic acid regions, means that they are functionally related to each other.

The term "host cell" is art-recognized and refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are art-recognized and are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "regulatory element" is art-recognized and refers to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

The term "transfection" is art-recognized and refers to the introduction of a nucleic acid, e.g., an expression vector, into a recipient cell, which in certain embodiments may be by nucleic acid-mediated gene transfer. "Transformation," as used with respect to transfected nucleic acid, is an art-recognized term and refers to a process in which a cell's genotype is changed as a result of the cellular uptake of exogenous nucleic acid.

The term "transfer vector" is art-recognized and refers to a first nucleic acid molecule to which a second nucleic acid has been linked, and includes for example plasmids, cosmids or phages (as discussed in greater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

The term "transgenic animal" is art-recognized and refers to any animal, often a non-human mammal, a bird or an amphibian, in which one or more of the cells of the animal contain nucleic acid introduced by way of human intervention, such as by transgenic techniques well known in the art. Such nucleic acid may be referred to as a "transgene." The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "antibody" is art-recognized and refers to whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compositions described herein include compositions which otherwise correspond thereto, and which have the same general properties thereof (such as other compositions comprising FabI/Fab K inhibitors), wherein one or more simple variations of substituents or components are made which do not adversely affect the characteristics of the compositions of interest. In general, the components of the compositions of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

FabI Inhibitors

The FabI inhibitor compounds of the present invention include those depicted by

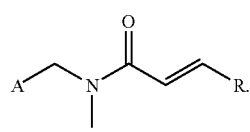

I wherein, independently for each occurrence,

A is a monocyclic ring of 4-7 atoms containing 0-2 heteroatoms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from N, S or O and the rings are optionally substituted with one or more groups selected from $C_{1-4}$ alkyl, OR", CN, $OCF_3$, F, Cl, Br, I; wherein R" is H, alkyl, aralkyl, or heteroaralkyl;

R is

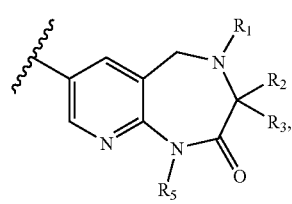

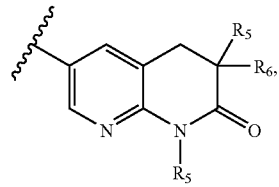 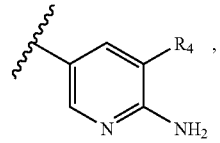

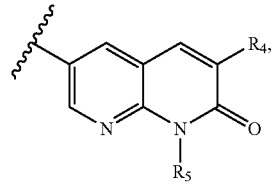

-continued

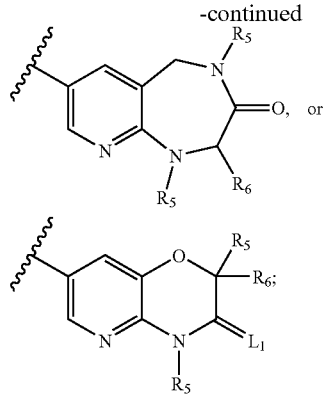

wherein, independently for each occurrence, $R_1$ is H, alkyl, or aryl, or $R_1$ and $R_2$ taken together form a fused ring;

$R_2$ is H, alkyl, or aryl, or $R_2$ and $R_1$ taken together form a fused ring, or $R_2$ and $R_3$ taken together form a spirocyclic ring;

$R_3$ is H, alkyl, or aryl, or $R_3$ and $R_2$ taken together form a spirocyclic ring;

$R_4$ is H, alkyl, aryl, hydroxy substituted alkyl, or —C(O)ONa;

$R_5$ is H, alkyl, or aryl;

$R_6$ is H, alkyl, or aryl; and $L_1$ is O or $H_2$;

In a further embodiment, the present invention includes compounds of formula I and the attendant definitions, wherein A is selected from the following:

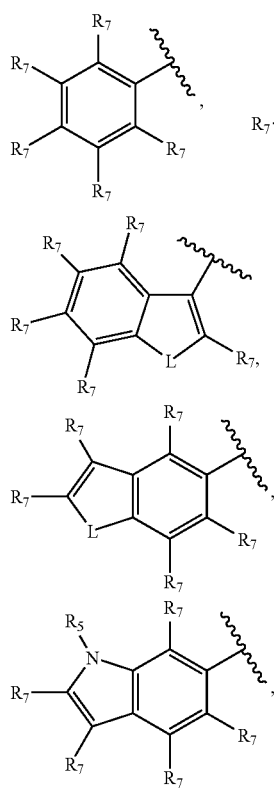

-continued

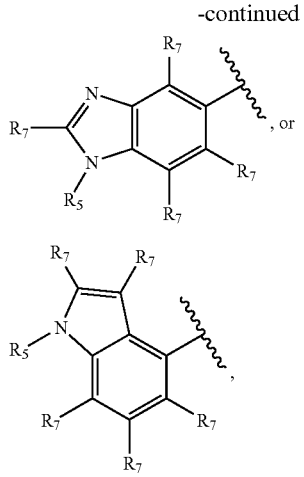

wherein, independently for each occurrence, $R_7$ is H, $C_{1-4}$ alkyl, $C_{1-4}$ haloalkyl, $C_{1-4}$ alkenyl, OR", CN, $OCF_3$, F, Cl, Br, I;

wherein R" is H, alkyl, aralkyl, or heteroaralkyl;

L is O, S, or $NR_5$; and $R_5$ is as defined previously.

In a further embodiment, the present invention includes compounds of formula I and the attendant definitions, wherein A is selected from the following:

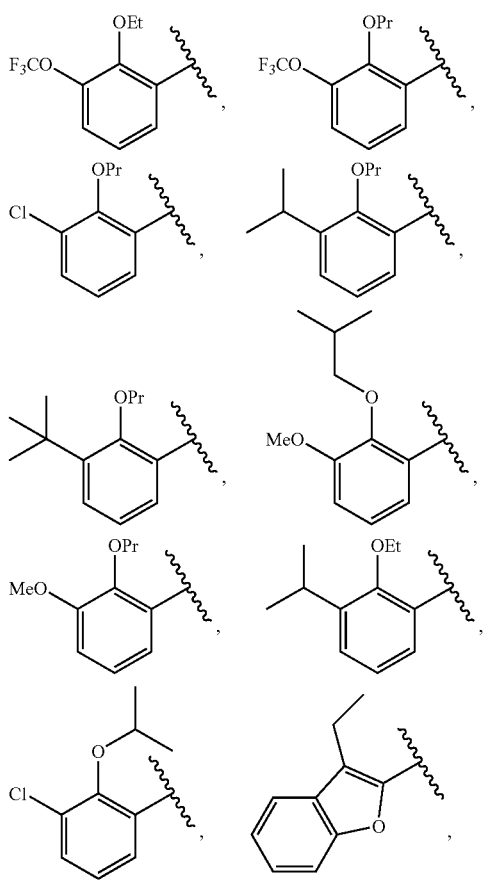

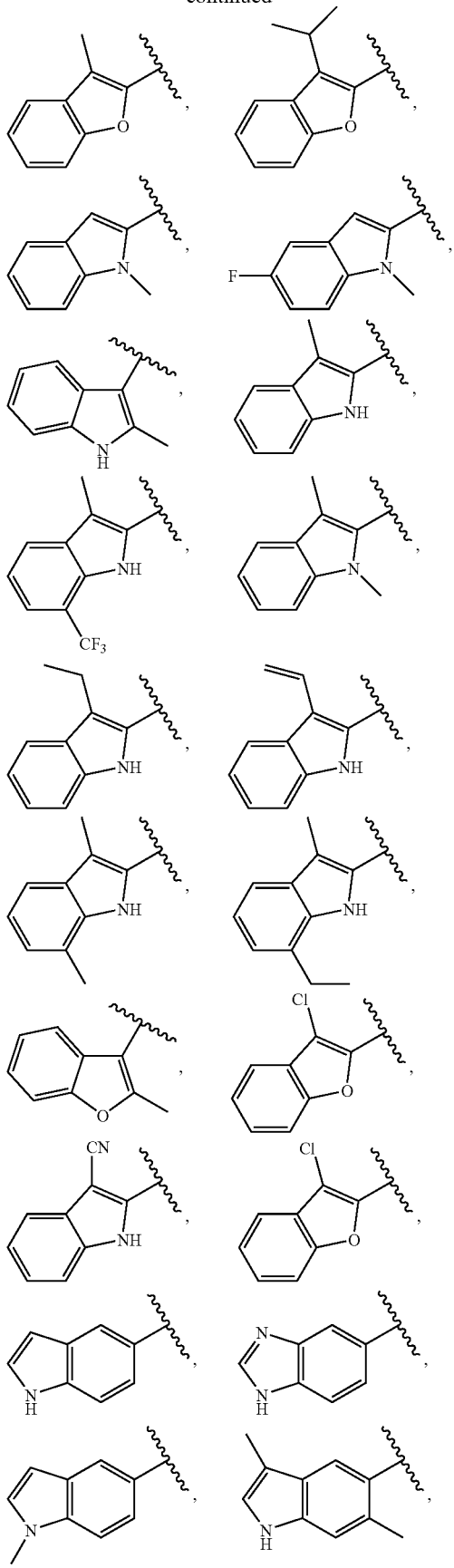
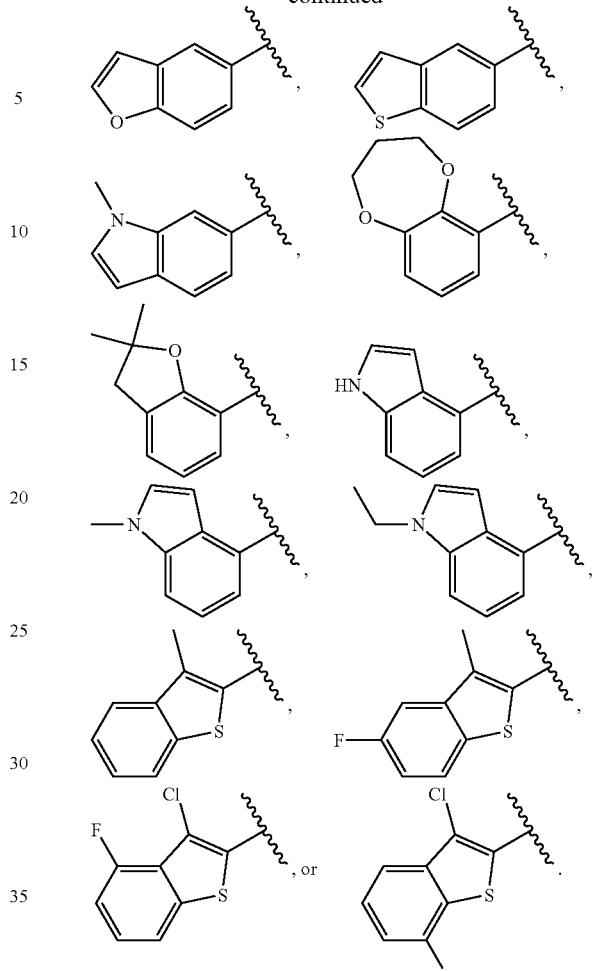
In a further embodiment, the present invention relates to compounds of formula I, wherein the compound has formula Ia:
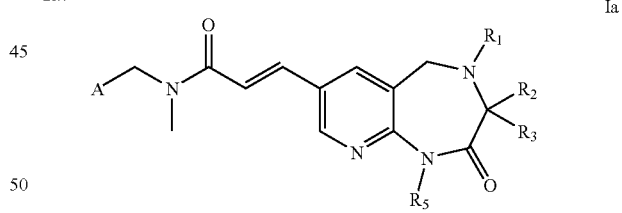
wherein, independently for each occurrence,
$R_1$, $R_2$, and $R_3$ are as previously defined; and
A is selected from the following:
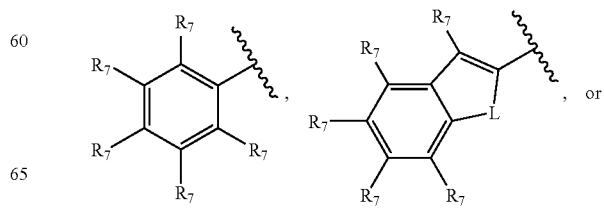

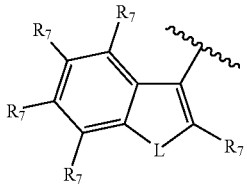

wherein L and R<sub>7</sub> are as previously defined.

In another embodiment, the present invention relates to compounds of formula Ia and the attendant definitions, wherein $R_1$ is H.

In another embodiment, the present invention relates to compounds of formula Ia and the attendant definitions, wherein $R_1$ is phenyl.

In another embodiment, the present invention relates to compounds of formula Ia and the attendant definitions, wherein $R_2$ is methyl and $R_3$ is methyl.

In another embodiment, the present invention relates to compounds of formula Ia and the attendant definitions, wherein $R_1$ and $R_2$ taken together form a five membered ring.

In another embodiment, the present invention relates to compounds of formula Ia and the attendant definitions, wherein $R_2$ and $R_3$ taken together form a five membered ring.

In another embodiment, the present invention relates to compounds of formula Ia and the attendant definitions, wherein A is

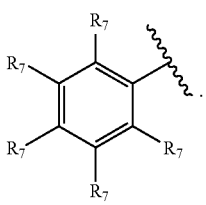

In another embodiment, the present invention relates to compounds of formula Ia and the attendant definitions, wherein A is

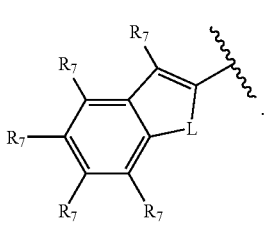

In another embodiment, the present invention relates to compounds of formula Ia and the attendant definitions, wherein A is

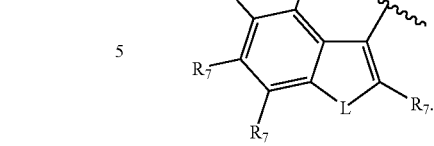

In another embodiment, the present invention relates to compounds of formula Ia and the attendant definitions, wherein A is

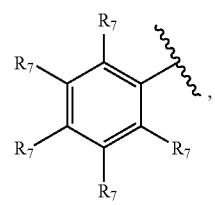

and $R_7$ independently is alkyl or OR".

In another embodiment, the present invention relates to compounds of formula Ia and the attendant definitions, wherein A is

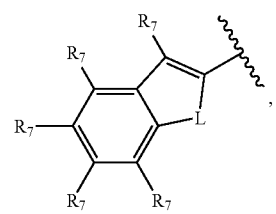

and L is O, and $R_7$ independently is H, alkyl, or Cl.

In another embodiment, the present invention relates to compounds of formula Ia and the attendant definitions, wherein A is

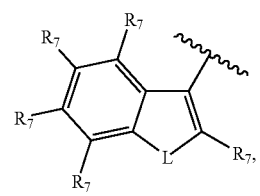

and L is NH.

In another embodiment, the present invention relates to compounds of formula Ia and the attendant definitions, wherein A is

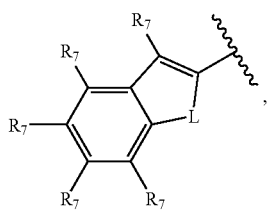

$R_1$ is phenyl, and $R_5$ is H.

In a further embodiment, the present invention relates to compounds of formula I, wherein the compound has formula Ib:

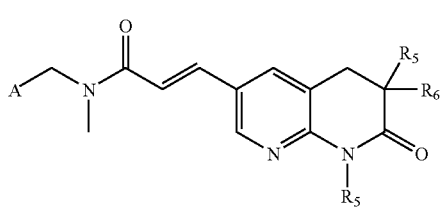

wherein, independently for each occurrence:
A is selected from the following:

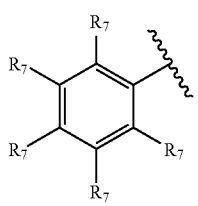 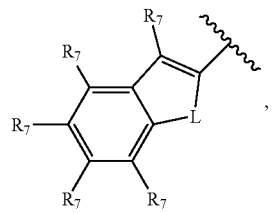

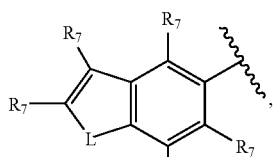

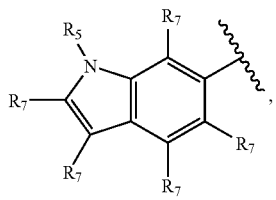

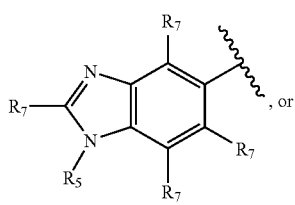, or

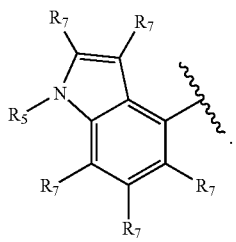

In another embodiment, the present invention relates to compounds of formula Ib and the attendant definitions, wherein A is

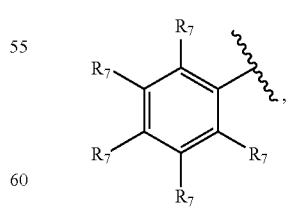

and $R_7$ independently is alkyl, OR", or Cl.

In another embodiment, the present invention relates to compounds of formula Ib and the attendant definitions, wherein A is

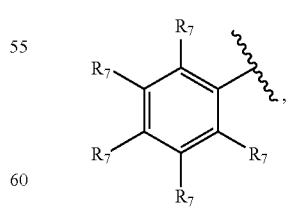

and $R_7$ independently is alkyl or OR".

In another embodiment, the present invention relates to compounds of formula Ib and the attendant definitions, wherein A is

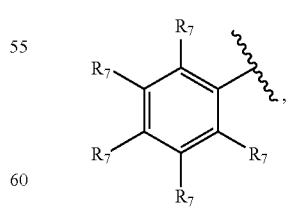

and $R_7$ independently is OR" or Cl.

In another embodiment, the present invention relates to compounds of formula Ib the attendant definitions, wherein A is

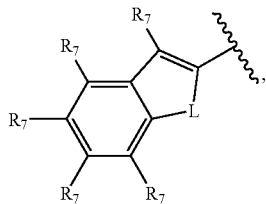

and L is NH.

In another embodiment, the present invention relates to compounds of formula Ib and the attendant definitions, wherein A is

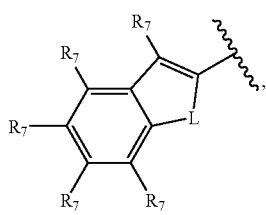

and L is O.

In another embodiment, the present invention relates to compounds of formula Ib and the attendant definitions, wherein A is

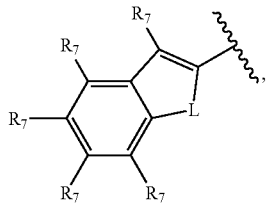

L is NH, and $R_7$ independently is H, CN, or alkyl.

In another embodiment, the present invention relates to compounds of formula Ib and the attendant definitions, wherein A is

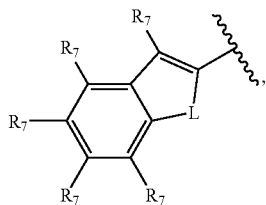

L is O, and $R_7$ independently is H or Cl.

In another embodiment, the present invention relates to compounds of formula Ib and the attendant definitions, wherein A is

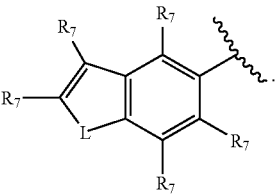

In another embodiment, the present invention relates to compounds of formula Ib and the attendant definitions, wherein A is

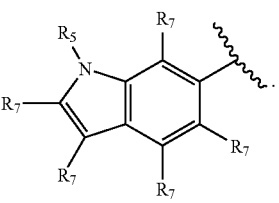

In another embodiment, the present invention relates to compounds of formula Ib and the attendant definitions, wherein A is

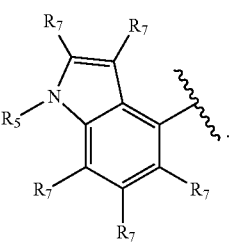

In a further embodiment, the present invention relates to compounds of formula I, wherein the compound has formula Ic:

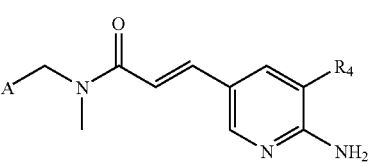

Ic wherein, independently for each occurrence:
$R_4$ is as previously defined, and
A is selected from the following:

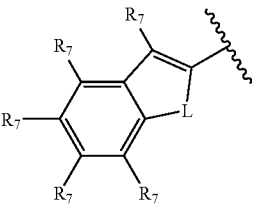 or

-continued

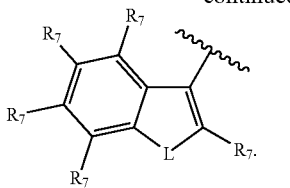

In another embodiment, the present invention relates to compounds of formula Ic and the attendant definitions, wherein $R_4$ is H.

In another embodiment, the present invention relates to compounds of formula Ic and the attendant definitions, wherein $R_4$ is $C(CH_3)_2OH$.

In another embodiment, the present invention relates to compounds of formula Ic and the attendant definitions, wherein A is

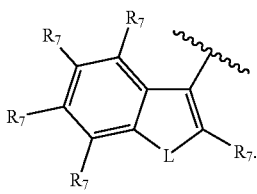

In another embodiment, the present invention relates to compounds of formula Ic and the attendant definitions, wherein A is

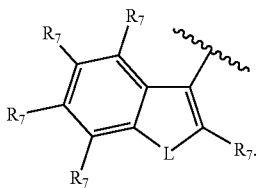

In another embodiment, the present invention relates to compounds of formula Ic and the attendant definitions, wherein A is

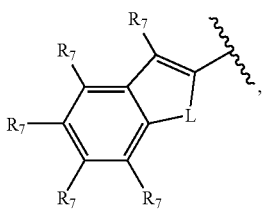

L is O, and $R_7$ independently is H, alkyl or Cl.

In another embodiment, the present invention relates to compounds of formula Ic and the attendant definitions, wherein A is

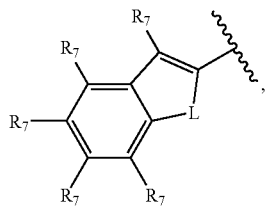

L is $NR_5$, and $R_7$ independently is H or CN.

In another embodiment, the present invention relates to compounds of formula Ic and the attendant definitions, wherein A is

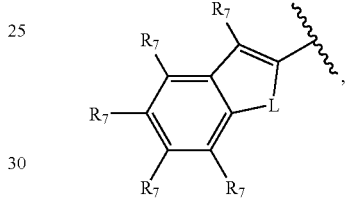

L is S, and $R_7$ independently is H, F, or Cl.

In another embodiment, the present invention relates to compounds of formula Ic and the attendant definitions, wherein A is

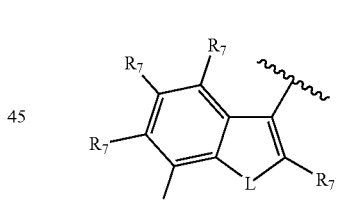

and L is O.

In a further embodiment, the present invention relates to compounds of formula I, wherein the compound has formula Id:

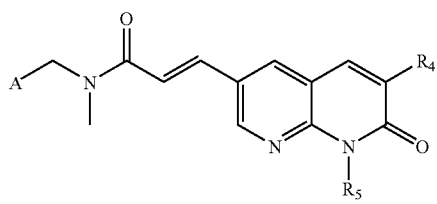

wherein:

A is

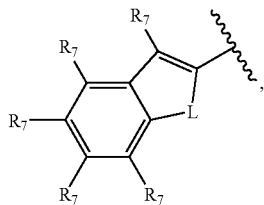

and

L, $R_4$, $R_5$, and $R_7$ are as previously defined.

In another embodiment, the present invention relates to compounds of formula Id and the attendant definitions, wherein L is S.

In another embodiment, the present invention relates to compounds of formula Id and the attendant definitions, wherein $R_7$ independently is H or alkyl.

In another embodiment, the present invention relates to compounds of formula Id and the attendant definitions, wherein $R_4$ is H.

In another embodiment, the present invention relates to compounds of formula Id and the attendant definitions, wherein $R_4$ is —C(O)ONa.

In a further embodiment, the present invention relates to compounds of formula I, wherein the compound has formula Ie:

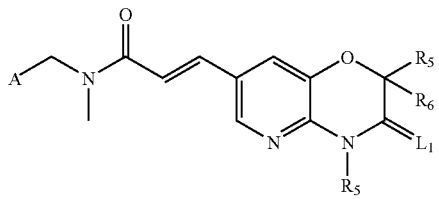

Ie wherein, independently for each occurrence:

$R_5$, $R_6$, and $L_1$ are as previously defined, and

A is selected from the following:

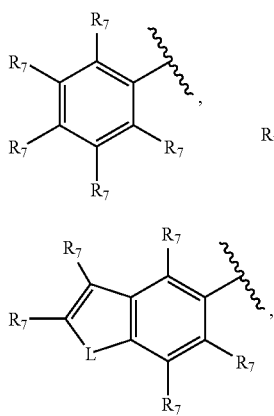

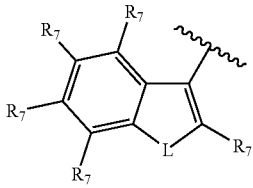

wherein L and $R_7$ are as previously defined.

In another embodiment, the present invention relates to compounds of formula Ie and the attendant definitions, wherein $R_5$ is H and $R_6$ is H.

In another embodiment, the present invention relates to compounds of formula Ie and the attendant definitions, wherein $R_5$ is methyl and $R_6$ is methyl.

In another embodiment, the present invention relates to compounds of formula Ie and the attendant definitions, wherein $L_1$ is O.

In another embodiment, the present invention relates to compounds of formula Ie and the attendant definitions, wherein $L_1$ is $H_2$.

In another embodiment, the present invention relates to compounds of formula Ie and the attendant definitions, wherein A is

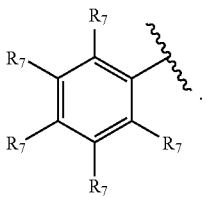

In another embodiment, the present invention relates to compounds of formula Ie and the attendant definitions, wherein A is

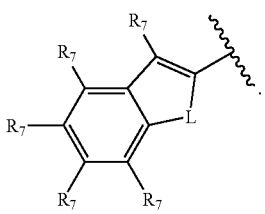

In another embodiment, the present invention relates to compounds of formula Ie and the attendant definitions, wherein A is

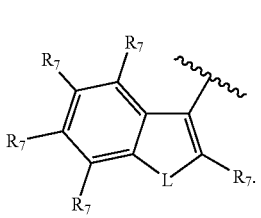

In another embodiment, the present invention relates to compounds of formula Ie and the attendant definitions, wherein A is

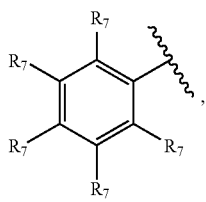

and R$_7$OR".

In another embodiment, the present invention relates to compounds of formula Ie and the attendant definitions, wherein A is

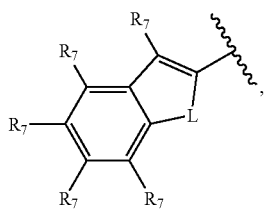

L is O, and R$_7$ independently is H, alkyl, or Cl.

In another embodiment, the present invention relates to compounds of formula Ie and the attendant definitions, wherein A is

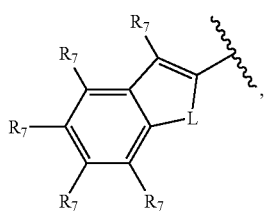

L is NMe, and R$_7$H.

In another embodiment, the present invention relates to compounds of formula Ie and the attendant definitions, wherein A is

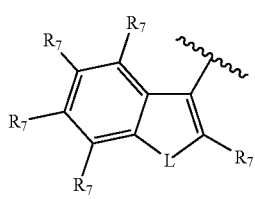

and L is O.

In another embodiment, the present invention relates to compounds of formula Ie and the attendant definitions, wherein A is

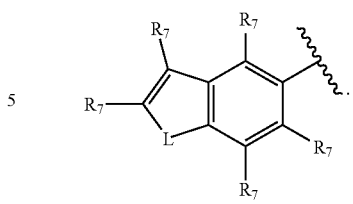

In another embodiment, the present invention relates to compounds of formula Ie and the attendant definitions, wherein A is

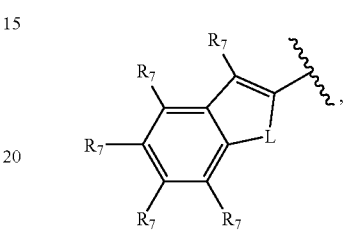

L$_1$ is H$_2$, L is O, and R$_5$ and R$_6$ are Me.

In a further embodiment, the present invention relates to compounds of formula I, wherein the compound has formula If:

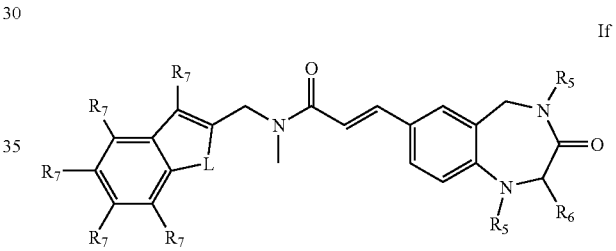

If wherein R$_5$, R$_6$, R$_7$, and L are as previously defined.

In another embodiment, the present invention relates to compounds of formula If and the attendant definitions, wherein R$_5$ is H.

In another embodiment, the present invention relates to compounds of formula If and the attendant definitions, wherein R$_6$ is Me.

In another embodiment, the present invention relates to compounds of formula If and the attendant definitions, wherein R$_6$ is Me and in the S stereochemical configuration.

In another embodiment, the present invention relates to compounds of formula If and the attendant definitions, wherein R$_6$ is Me and in the R stereochemical configuration.

In another embodiment, the present invention relates to compounds of formula If and the attendant definitions, wherein R$_6$ is Me and in the S stereochemical configuration, and R$_5$ is H.

In another embodiment, the present invention relates to compounds of formula If and the attendant definitions, wherein R$_6$ is Me and in the S stereochemical configuration, R$_5$ is H, and L is O.

The present invention relates to, but is not limited to, the compounds of formula I wherein the compound is selected from the following representative list:

(E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide hydrochloride;

(E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide hydrochloride;

(E)-N-(3-Chloro-2-ethoxybenzyl)-N-methyl-3-(7-oxo-5,6,7,8-tetrahydro-[1,8]naphthyridin-3-yl)acrylamide;

(E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide hydrochloride;

(E)-N-(2-Isobutoxy-3-methoxybenzyl)-N-methyl-3-(7-oxo-5,6,7,8-tetrahydro-[1,8]naphthyridin-3-yl)acrylamide;

(E)-N-(3-Isopropyl-2-propoxybenzyl)-N-methyl-3-(7-oxo-5,6,7,8-tetrahydro-[1,8]naphthyridin-3-yl)acrylamide;

(E)-N-(2-Ethoxy-3-isopropylbenzyl)-N-methyl-3-(7-oxo-5,6,7,8-tetrahydro-[1,8]naphthyridin-3-yl)acrylamide;

(E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide hydrochloride;

(E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide;

(S)-(+)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride;

(R)-(−)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride;

(E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide hydrochloride;

(E)-3-(6-amino-pyridin-3-yl)-N-(3-chloro-4-fluoro-benzo[b]thiophen-2-ylmethyl)-N-methylacrylamide hydrochloride;

(E)-3-(6-amino-pyridin-3-yl)-N-(3-chloro-7-fluoro-benzo[b]thiophen-2-ylmethyl)-N-methylacrylamide hydrochloride;

(E)-6-{2-[methyl-(3-methyl-benzo[b]thiophen-2-ylmethyl)-carbamoyl]-vinyl}-2-oxo-1,2-dihydro-[1,8]naphthyridine-3-carboxylic acid sodium salt;

(E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide hydrochloride;

(E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride;

(E)-N-(3-ethyl-benzofuran-2-ylmethyl)-N-methyl-3-(2-oxo-2,3,4,5-tetrahydro-1H-pyrido[2,3-e][1,4]diazepin-7-yl)acrylamide hydrochloride;

(E)-3-(3,3-Dimethyl-2-oxo-2,3,4,5-tetrahydro-1H-pyrido[2,3-e][1,4]dizepin-7-yl)-N-methyl-N-(3-propyl-benzofuran-2-ylmethyl)acrylamide hydrochloride;

(E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide hydrochloride;

(E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide hydrochloride;

(E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide hydrochloride;

(E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide hydrochloride;

(E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide hydrochloride;

(E)-3-(2,2-Dimethyl-3-oxo-3,4-dihydro-2H-pyrido[3,2-b][1,4]oxazin-7-yl)-N-methyl-N-(3-methylbenzofuran-2-ylmethyl)acrylamide;

(E)-3-(2,2-Dimethyl-3,4-dihydro-2H-pyrido[3,2-b][1,4]oxazin-7-yl)-N-methyl-N-(3-methyl-benzofuran-2-ylmethyl)-acrylamide hydrochloride;

(E)-3-(3,4-Dihydro-2H-pyrido[3,2-b][1,4]oxazin-7-yl)-N-methyl-N-(3-methylbenzofuran-2-ylmethyl)acrylamide hydrochloride;

(E)-N-(2-Ethoxy-3-isopropylbenzyl)-N-methyl-3-(2-oxo-2,3,4,5-tetrahydro-1H-pyrido[2,3-e][1,4]diazepin-7-yl)-acrylamide hydrochloride;

(E)-N-(2-Isobutoxy-3-methoxybenzyl)-N-methyl-3-(2-oxo-2,3,4,5-tetrahydro-1H-pyrido[2,3-e][1,4]diazepin-7-yl)acrylamide hydrochloride;

(E)-3-[6-Amino-5-(1-hydroxy-1-methyl-ethyl)-pyridin-3-yl]-N-methyl-N-(3-methyl-benzofuran-2-ylmethyl)-acrylamide;

(E)-3-[6-Amino-5-(1-hydroxy-1-methyl-ethyl)-pyridin-3-yl]-N-methyl-N-(1-methyl-1H-indol-2-ylmethyl)-acrylamide;

(E)-3-[6-Amino-5-(1-hydroxy-1-methyl-ethyl)-pyridin-3-yl]-N-methyl-N-(2-methyl-benzofuran-3-ylmethyl)-acrylamide;

(E)-3-(6-amino-pyridin-3-yl)-N-(3-cyano-1H-indol-2-ylmethyl)-N-methyl-acrylamide;

(E)-N-(3-cyano-1H-indol-2-ylmethyl)-N-methyl-3-(7-oxo-5,6,7,8-tetrahydro-[1,8]naphthyridin-3-yl)-acrylamide;

(E)-N-Methyl-N-(3-methyl-benzofuran-2-ylmethyl)-3-(3-oxo-2,3,4,5-tetrahydro-1H-pyrido[2,3-e][1,4]diazepin-7-yl)-acrylamide hydrochloride;

(E)-N-(1,2-Dimethyl-1H-indol-3-ylmethyl)-N-methyl-3-(3-oxo-2,3,4,5-tetrahydro-1H-pyrido[2,3-e][1,4]diazepin-7-yl)-acrylamide;

(E)-N-Methyl-N-(2-methyl-benzofuran-3-ylmethyl)-3-(4-methyl-3-oxo-2,3,4,5-tetrahydro-1H-pyrido[2,3-e][1,4]diazepin-7-yl)-acrylamide hydrochloride;

(E)-N-Methyl-N-(3-methyl-benzofuran-2-ylmethyl)-3-(4-methyl-3-oxo-2,3,4,5-tetrahydro-1H-pyrido[2,3-e][1,4]diazepin-7-yl)-acrylamide hydrochloride;

(E)-N-(3-Methoxy-2-propoxy-benzyl)-N-methyl-3-(4-methyl-3-oxo-2,3,4,5-tetrahydro-1H-pyrido[2,3-e][1,4]diazepin-7-yl)-acrylamide hydrochloride;

(E)-N-Methyl-N-(2-methyl-1H-indol-3-ylmethyl)-3-(4-methyl-3-oxo-2,3,4,5-tetrahydro-1H-pyrido[2,3-e][1,4]diazepin-7-yl)-acrylamide;

(E)-N-(3-Methoxy-2-propoxy-benzyl)-N-methyl-3-(2-oxo-2,3,4,5-tetrahydro-1H-pyrido[2,3-e][1,4]diazepin-7-yl)-acrylamide;

(E)-N-Methyl-N-(2-methyl-1H-indol-3-ylmethyl)-3-(4-methyl-2-oxo-2,3,4,5-tetrahydro-1H-pyrido[2,3-e][1,4]diazepin-7-yl)-acrylamide;

(E)-3-(6-Amino-pyridin-3-yl)-N-(3-chloro-benzofuran-2-ylmethyl)-N-methyl-acrylamide hydrochloride;

(E)-N-(3-Chloro-benzofuran-2-ylmethyl)-N-methyl-3-(7-oxo-5,6,7,8-tetrahydro-[1,8]naphthyridin-3-yl)-acrylamide;

(E)-N-(3-Chloro-benzofuran-2-ylmethyl)-N-methyl-3-(2-oxo-2,3,4,5-tetrahydro-1H-pyrido[2,3-e][1,4]diazepin-7-yl)-acrylamide hydrochloride;

(E)-N-(1H-Indol-5-ylmethyl)-N-methyl-3-(7-oxo-5,6,7,8-tetrahydro-[1,8]naphthyridin-3-yl)-acrylamide;

(E)-N-Methyl-N-(1-methyl-1H-indol-5-ylmethyl)-3-(7-oxo-5,6,7,8-tetrahydro-[1,8]naphthyridin-3-yl)-acrylamide;

(E)-N-(3-tert-Butyl-2-propoxy-benzyl)-N-methyl-3-(7-oxo-5,6,7,8-tetrahydro-[1,8]naphthyridin-3-yl)-acrylamide;

(E)-N-Methyl-N-(1-methyl-1H-indol-6-ylmethyl)-3-(7-oxo-5,6,7,8-tetrahydro-[1,8]naphthyridin-3-yl)-acrylamide;

(E)-N-(3,4-Dihydro-2H-benzo[b][1,4]dioxepin-6-ylmethyl)-N-methyl-3-(7-oxo-5,6,7,8-tetrahydro-[1,8]naphthyridin-3-yl)-acrylamide;

(E)-N-(2,2-Dimethyl-2,3-dihydro-benzofuran-7-ylmethyl)-N-methyl-3-(7-oxo-5,6,7,8-tetrahydro-[1,8]naphthyridin-3-yl)-acrylamide;

(E)-N-(1H-Indol-4-ylmethyl)-N-methyl-3-(7-oxo-5,6,7,8-tetrahydro-[1,8]naphthyridin-3-yl)-acrylamide;

(E)-3-(2,2-Dimethyl-3-oxo-3,4-dihydro-2H-pyrido[3,2-b][1,4]oxazin-7-yl)-N-methyl-N-(1-methyl-1H-indol-2-ylmethyl)-acrylamide;

(E)-3-(2,2-Dimethyl-3-oxo-3,4-dihydro-2H-pyrido[3,2-b][1,4]oxazin-7-yl)-N-methyl-N-(2-methyl-benzofuran-3-ylmethyl)-acrylamide;

(E)-3-(2,2-Dimethyl-3-oxo-3,4-dihydro-2H-pyrido[3,2-b][1,4]oxazin-7-yl)-N-(3-methoxy-2-propoxy-benzyl)-N-methyl-acrylamide;

(E)-3-(3,4-Dihydro-2H-pyrido[3,2-b][1,4]oxazin-7-yl)-N-methyl-N-(2-methyl-benzofuran-3-ylmethyl)-acrylamide hydrochloride;

(E)-N-Methyl-N-(2-methyl-benzofuran-3-ylmethyl)-3-(3-oxo-3,4-dihydro-2H-pyrido[3,2-b][1,4]oxazin-7-yl)-acrylamide;

(E)-N-Methyl-N-(3-methyl-benzofuran-2-ylmethyl)-3-(3-oxo-3,4-dihydro-2H-pyrido[3,2-b][1,4]oxazin-7-yl)-acrylamide;

(E)-N-(3-Chloro-benzofuran-2-ylmethyl)-3-(2,2-dimethyl-3-oxo-3,4-dihydro-2H-pyrido[3,2-b][1,4]oxazin-7-yl)-N-methyl-acrylamide;

(E)-N-methyl-(1H-indol-2-ylmethyl)-3-(7-oxo-5,6,7,8-tetrahydro-[1,8]napthyridin-3-yl)acrylamide;

(E)-3-(2,2-dimethyl-3,4-dihydro-2H-pyrido[3,2-b][1,4]oxazin-7-yl)-N-methyl-N-((3-methylbenzofuran-2-yl)methyl)acrylamide hydrochloride;

(E)-3-(6-aminopyridin-3-yl)-N-((5-fluoro-3-methylbenzo[b]thiophen-2-yl)methyl)-N-methylacrylamide hydrochloride;

(E)-N-((3-chlorobenzofuran-2-yl)methyl)-N-methyl-3-(3-oxo-3,4-dihydro-2H-pyrido[3,2-b][1,4]oxazin-7-yl)acrylamide;

(E)-N-(3-methoxy-2-propoxybenzyl)-N-methyl-3-(3-oxo-3,4-dihydro-2H-pyrido[3,2-b][1,4]oxazin-7-yl)acrylamide;

(E)-N-((3-isopropylbenzofuran-2-yl)methyl)-N-methyl-3-(3-oxo-3,4-dihydro-2H-pyrido[3,2-b][1,4]oxazin-7-yl)acrylamide;

(E)-N-((3-ethylbenzofuran-2-yl)methyl)-N-methyl-3-(3-oxo-3,4-dihydro-2H-pyrido[3,2-b][1,4]oxazin-7-yl)acrylamide;

(E)-N-((5-fluoro-3-methylbenzo[b]thiophen-2-yl)methyl)-N-methyl-3-(3-oxo-3,4-dihydro-2H-pyrido[3,2-b][1,4]oxazin-7-yl)acrylamide;

(E)-N-((5-fluoro-3-methylbenzo[b]thiophen-2-yl)methyl)-N-methyl-3-(7-oxo-5,6,7,8-tetrahydro-1,8-naphthyridin-3-yl)acrylamide;

(E)-N-((5-fluoro-1-methyl-1H-indol-2-yl)methyl)-N-methyl-3-(7-oxo-5,6,7,8-tetrahydro-1,8-naphthyridin-3-yl)acrylamide;

(E)-N-((3-ethylbenzofuran-2-yl)methyl)-N-methyl-3-(7-oxo-5,6,7,8-tetrahydro-1,8-naphthyridin-3-yl)acrylamide;

(E)-N-((3-isopropylbenzofuran-2-yl)methyl)-N-methyl-3-(7-oxo-5,6,7,8-tetrahydro-1,8-naphthyridin-3-yl)acrylamide;

(E)-N-(benzofuran-5-ylmethyl)-N-methyl-3-(7-oxo-5,6,7,8-tetrahydro-1,8-naphthyridin-3-yl)acrylamide;

(E)-N-(benzo[b]thiophen-5-ylmethyl)-N-methyl-3-(7-oxo-5,6,7,8-tetrahydro-1,8-naphthyridin-3-yl)acrylamide;

(E)-N-methyl-N-((1-methyl-1H-indol-4-yl)methyl)-3-(7-oxo-5,6,7,8-tetrahydro-1,8-naphthyridin-3-yl)acrylamide;

(E)-N-((1-ethyl-1H-indol-4-yl)methyl)-N-methyl-3-(7-oxo-5,6,7,8-tetrahydro-1,8-naphthyridin-3-yl)acrylamide;

(E)-N-((1H-benzo[d]imidazol-5-yl)methyl)-N-methyl-3-(7-oxo-5,6,7,8-tetrahydro-1,8-naphthyridin-3-yl)acrylamide;

(E)-N-methyl-N-((3-methylbenzofuran-2-yl)methyl)-3-(8-oxo-6,7,8,9-tetrahydro-5H-pyrido[2,3-b]azepin-3-yl)acrylamide;

(E)-N-((3,6-dimethyl-1H-indol-5-yl)methyl)-N-methyl-3-(8-oxo-6,7,8,9-tetrahydro-5H-pyrido[2,3-b]azepin-3-yl)acrylamide;

(E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride;

(E)-3-(6-aminopyridin-3-yl)-N-methyl-N-((3-methyl-1H-indol-2-yl)methyl)acrylamide;

(E)-N-methyl-N-((3-methyl-1H-indol-2-yl)methyl)-3-(3-oxo-3,4-dihydro-2H-pyrido[3,2-b][1,4]oxazin-7-yl)acrylamide;

(E)-N-((3,7-dimethyl-1H-indol-2-yl)methyl)-N-methyl-3-(3-oxo-3,4-dihydro-2H-pyrido[3,2-b][1,4]oxazin-7-yl)acrylamide;

(E)-N-methyl-N-((3-methyl-7-(trifluoromethyl)-1H-indol-2-yl)methyl)-3-(7-oxo-5,6,7,8-tetrahydro-1,8-naphthyridin-3-yl)acrylamide;

(E)-N-((3,7-dimethyl-1H-indol-2-yl)methyl)-N-methyl-3-(8-oxo-6,7,8,9-tetrahydro-5H-pyrido[2,3-b]azepin-3-yl)acrylamide;

(E)-N-((3-ethyl-1H-indol-2-yl)methyl)-N-methyl-3-(7-oxo-5,6,7,8-tetrahydro-1,8-naphthyridin-3-yl)acrylamide;

(E)-N-((3-ethyl-1H-indol-2-yl)methyl)-N-methyl-3-(3-oxo-3,4-dihydro-2H-pyrido[3,2-b][1,4]oxazin-7-yl)acrylamide;

(E)-N-methyl-3-(3-oxo-3,4-dihydro-2H-pyrido[3,2-b][1,4]oxazin-7-yl)-N-((3-vinyl-1,1-indol-2-yl)methyl)acrylamide;

(E)-N-((1,3-dimethyl-1H-indol-2-yl)methyl)-N-methyl-3-(3-oxo-3,4-dihydro-2H-pyrido[3,2-b][1,4]oxazin-7-yl)acrylamide;

(E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide;

(E)-N-methyl-N-((3-methyl-7-(trifluoromethyl)-1H-indol-2-yl)methyl)-3-(3-oxo-3,4-dihydro-2H-pyrido[3,2-b][1,4]oxazin-7-yl)acrylamide;

(E)-N-methyl-N-((3-methyl-7-(trifluoromethyl)-1H-indol-2-yl)methyl)-3-(7-oxo-5,6,7,8-tetrahydro-1,8-naphthyridin-3-yl)acrylamide;

(E)-N-((7-ethyl-3-methyl-1H-indol-2-yl)methyl)-N-methyl-3-(3-oxo-3,4-dihydro-2H-pyrido[3,2-b][1,4]oxazin-7-yl)acrylamide;

(E)-N-((7-ethyl-3-methyl-1H-indol-2-yl)methyl)-N-methyl-3-(7-oxo-5,6,7,8-tetrahydro-1,8-naphthyridin-3-yl)acrylamide;

(E)-N-((3,6-dimethyl-1H-indol-5-yl)methyl)-N-methyl-3-(7-oxo-5,6,7,8-tetrahydro-1,8-naphthyridin-3-yl)acrylamide;

(E)-N-((3,6-dimethyl-1H-indol-5-yl)methyl)-N-methyl-3-(3-oxo-3,4-dihydro-2H-pyrido[3,2-b][1,4]oxazin-yl)acrylamide;

(E)-N-methyl-N-((3-methylbenzofuran-2-yl)methyl)-3-(7-oxo-7,8-dihydro-1,8-naphthyridin-3-yl)acrylamide; or (E)-3-(6,6-dimethyl-7-oxo-5,6,7,8-tetrahydro-1,8-naphthyridin-3-yl)-N-methyl-N-((3-methylbenzo furan-2-yl)methyl)acrylamide.

Also included in the antibacterial compositions of the present invention are pharmaceutically acceptable addition salts and complexes of the FabI inhibitors. In cases wherein the inhibitors may have one or more chiral centers, unless specified, the present invention comprises each unique racemic compound, as well as each unique nonracemic compound.

In cases in which the inhibitors have unsaturated carbon-carbon double bonds, both the cis (Z) and trans (E) isomers are within the scope of this invention. In cases wherein inhibitors may exist in tautomeric forms, such as keto-enol tautomers, such as

and

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in the antibiotic compounds of the present invention are prodrugs of the FabI inhibitors.

A variety of subject compounds and intermediates of them may be made by a person of ordinary skill in the art using conventional reaction techniques. Non-limiting examples of compounds and methods of making them may be found in U.S. patent application Ser. Nos. 08/790,043, 10/009,219, 10/089,019, 09/968,129, 09/968,123, 09/968,236, 09/959,172, 09/979,560, 09/980,369, 10/089,755, 10/089,739, 10/089,740, and PCT Application Nos. PCT/US03/38706, WO 0027628 and WO 0210332.

Synthetic Routes to Compounds of Formula I

A generalized chemical approach to assembling compounds of formula I is based on viewing the analogs as consisting of a central ene-amide flanked by left-hand side (LHS) and right-hand side (RHS) moieties. Schematically, this is depicted in FIG. 2. Two possible bond disconnections envisioned in a retrosynthetic sense are shown with dashed lines. Schemes 1 to 22 illustrate some of the general methods that can be used in the synthesis of compounds of formula I wherein the final covalent bond formed is via a Heck coupling between an alkene and a suitably halogenated right hand side moiety. Schemes 23 to 30 illustrate some of the general methods that can be used in the synthesis of compounds of formula I wherein the final covalent bond formed is via a dehydrative coupling between a left hand side alkyl amine and an ene-carboxylic acid. It will be recognized by one skilled in the art that other disconnections are possible resulting in alternative modes of assembly of the compounds of the invention.

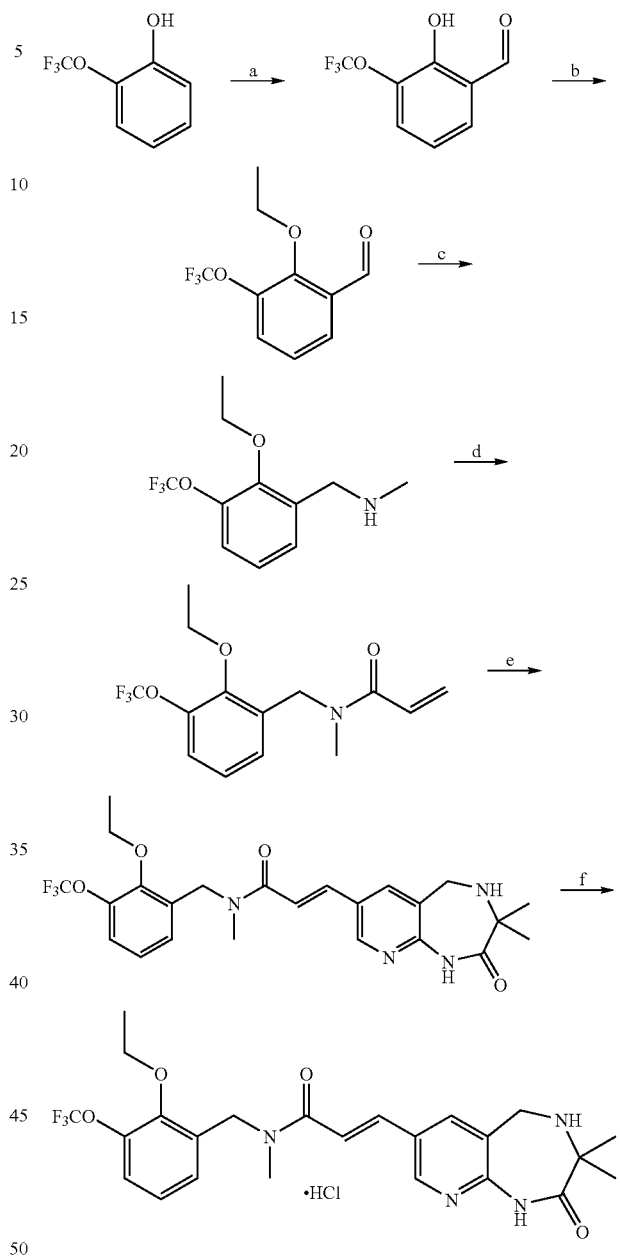

a) (CH$_2$O)$_n$, MgCl$_2$, Et$_3$N, MeCN, reflux;
b) iodoethane, K$_2$CO$_3$, DMF;
c) i. MeNH$_2$, MeOH, ii. NaBH$_4$, EtOH;
d) acryloyl chloride, Et$_3$N, CH$_2$Cl$_2$;
e) 7-bromo-3,3-dimethyl-1,3,4,5-tetrahydro-pyrido[2,3-E][1,4]diazepin-2-one, Pd(OAc)$_2$, P(o-tol)$_3$, (i-Pr)$_2$EtN, EtCN, DMF, reflux;
f) HCl in ether, CH$_2$Cl$_2$.

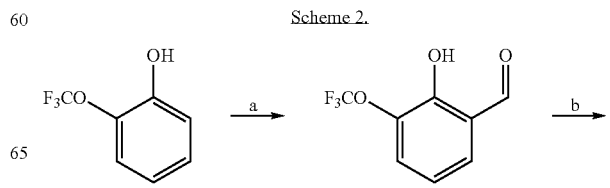

45
-continued

46
-continued

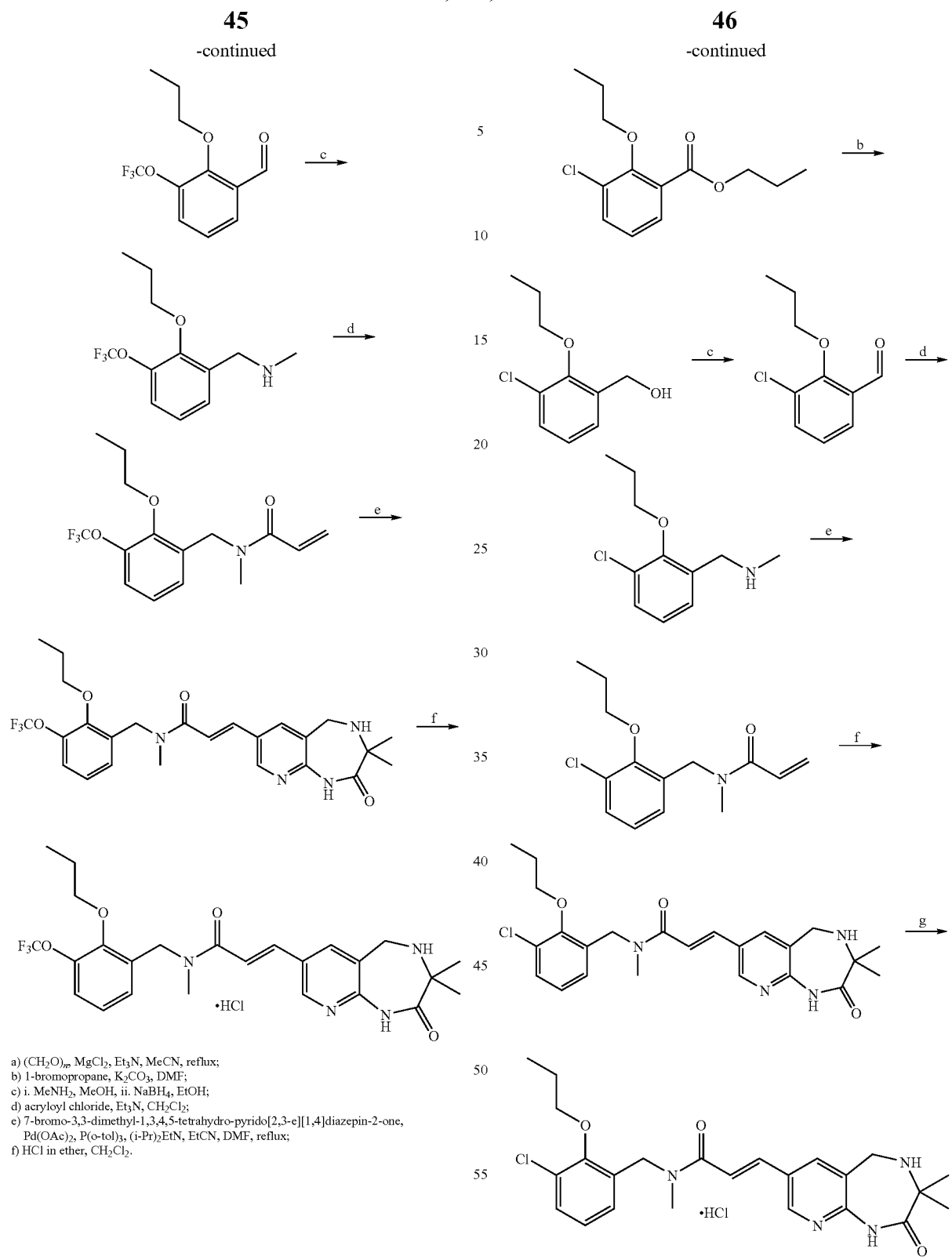

a) (CH₂O)ₙ, MgCl₂, Et₃N, MeCN, reflux;
b) 1-bromopropane, K₂CO₃, DMF;
c) i. MeNH₂, MeOH, ii. NaBH₄, EtOH;
d) acryloyl chloride, Et₃N, CH₂Cl₂;
e) 7-bromo-3,3-dimethyl-1,3,4,5-tetrahydro-pyrido[2,3-e][1,4]diazepin-2-one, Pd(OAc)₂, P(o-tol)₃, (i-Pr)₂EtN, EtCN, DMF, reflux;
f) HCl in ether, CH₂Cl₂.

Scheme 3.

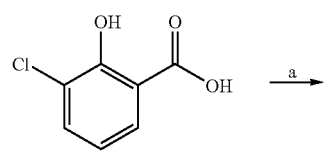

a) 1-bromopropane, K₂CO₃, DMF;
b) DIBAL-H, THF;
c) MnO₂, benzene;
d) i. MeNH₂, MeOH, ii. NaBH₄, EtOH;
e) acryloyl chloride, Et₃N, CH₂Cl₂;
f) 7-bromo-3,3-dimethyl-1,3,4,5-tetrahydro-pyrido[2,3,-e][1,4]diazepin-2-one, Pd(OAc)₂, P(o-tol)₃, (i-Pr)₂EtN, EtCN, DMF, reflux;
g) HCl in ether, CH₂Cl₂.

Scheme 4.

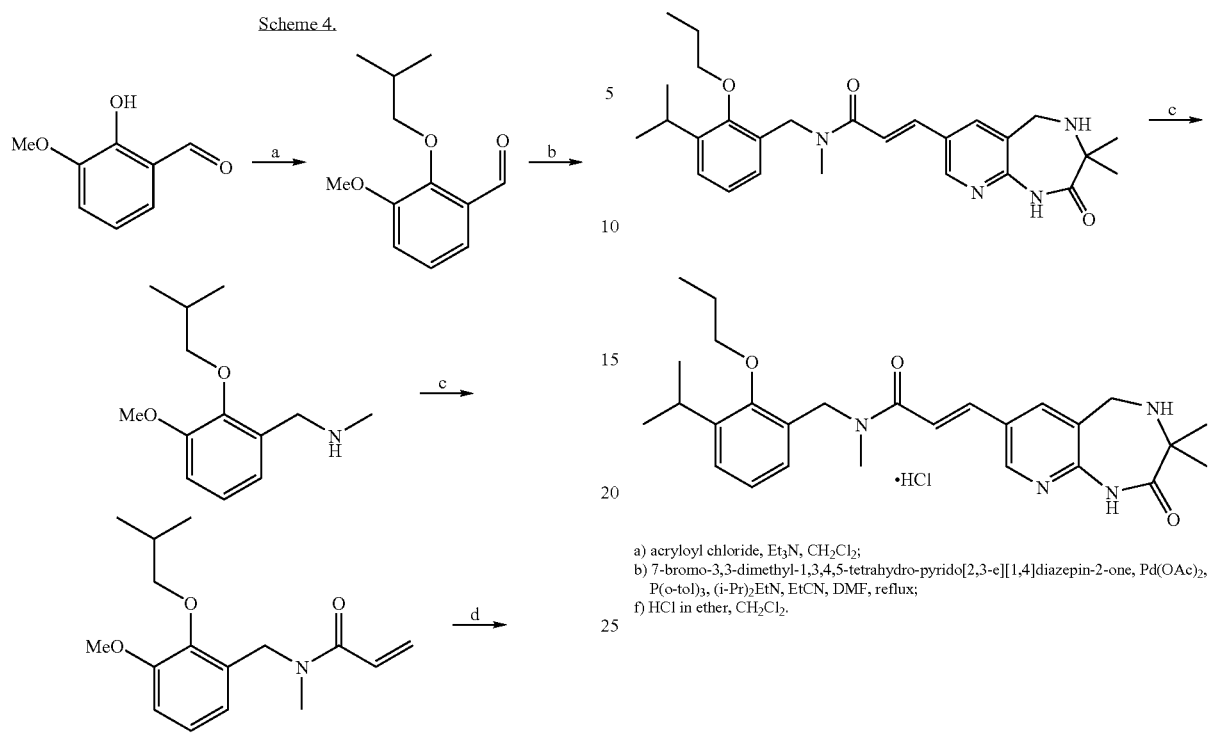

a) Iodoisobutane, K₂CO₃, DMF;
b) i. MeNH₂, MeOH; ii. NaBH₄, EtOH;
c) acryloyl chloride, Et₃N, CH₂Cl₂;
d) 6-bromo-3,4-dihydro-1H-[1,8]naphthyridin-2-one, Pd(OAc)₂, P(o-tol)₃, (i-Pr)₂EtN, EtCN, DMF, reflux.

Scheme 5.

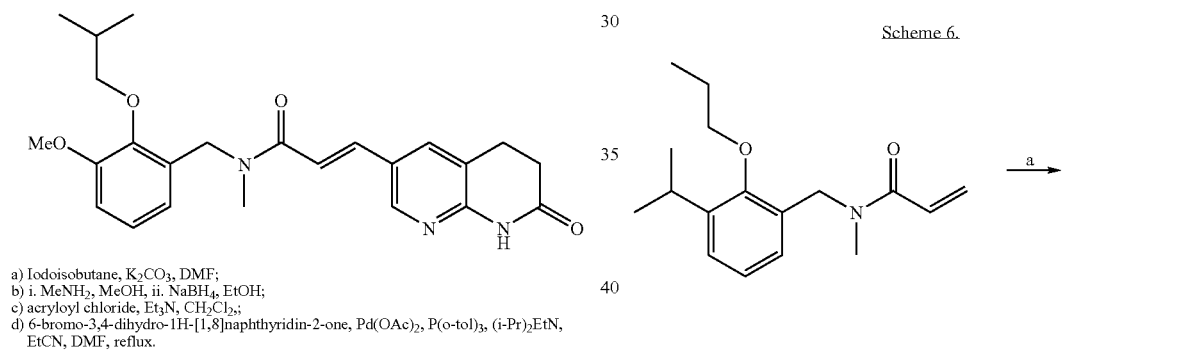

a) acryloyl chloride, Et₃N, CH₂Cl₂;
b) 7-bromo-3,3-dimethyl-1,3,4,5-tetrahydro-pyrido[2,3-e][1,4]diazepin-2-one, Pd(OAc)₂, P(o-tol)₃, (i-Pr)₂EtN, EtCN, DMF, reflux;
f) HCl in ether, CH₂Cl₂.

Scheme 6.

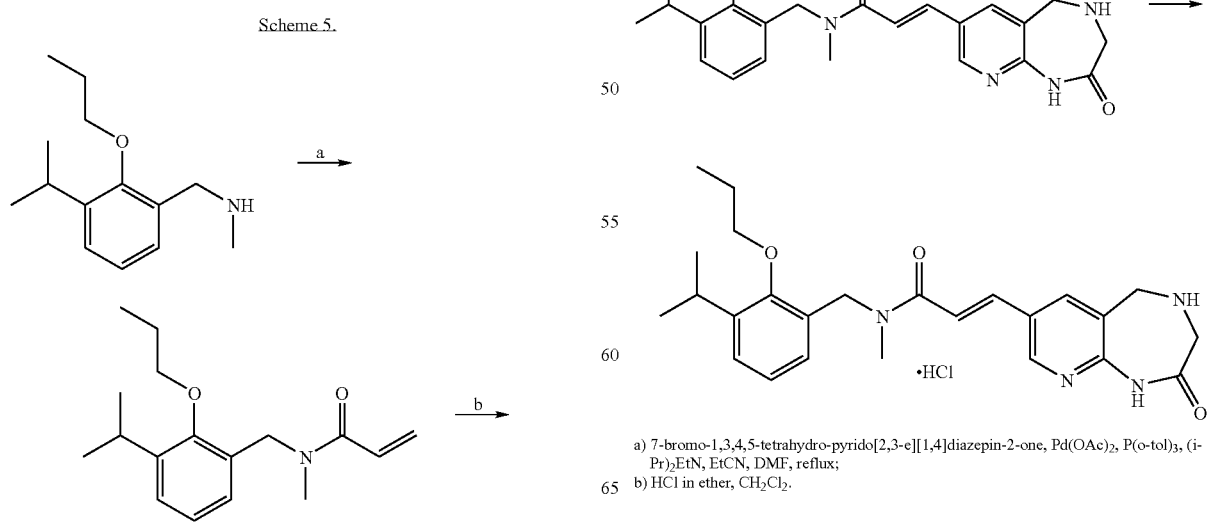

a) 7-bromo-1,3,4,5-tetrahydro-pyrido[2,3-e][1,4]diazepin-2-one, Pd(OAc)₂, P(o-tol)₃, (i-Pr)₂EtN, EtCN, DMF, reflux;
b) HCl in ether, CH₂Cl₂.

Scheme 7.

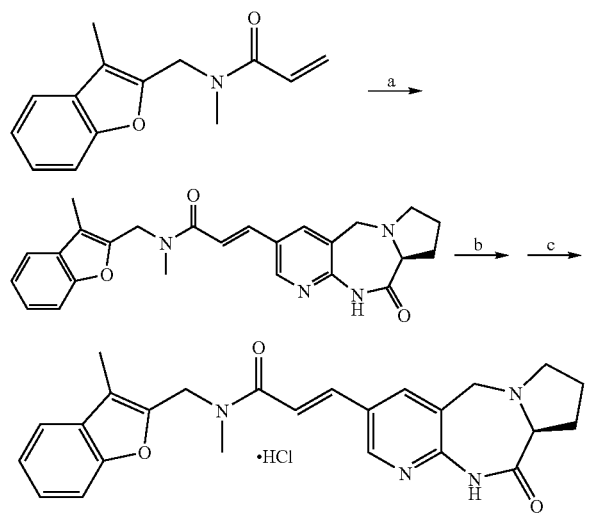

a) (S)-6-bromo-1,2,3,4,9,10a-hexahydro-3a,8,9-triazabenzo[f]azulen-10-one, Pd(OAc)₂, P(o-tol)₃, (i-Pr)₂EtN, EtCN, DMF, reflux;
b) HCl in ether, CH₂Cl₂.

Scheme 8.

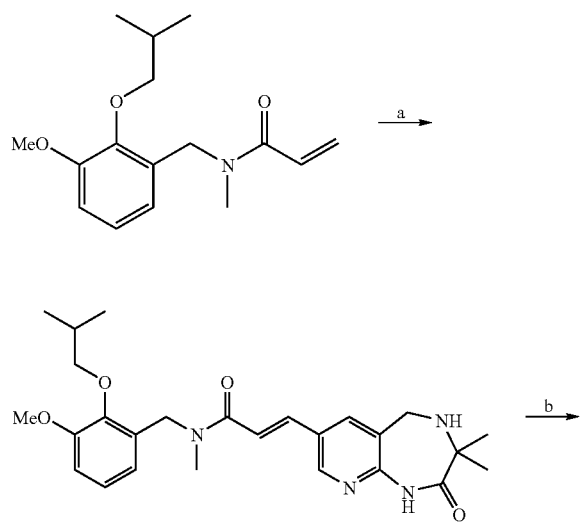

a) 7-bromo-3,3-dimethyl-1,3,4,5-tetrahydro-pyrido[2,3-e][1,4]diazepin-2-one, Pd(OAc)₂, P(o-tol)₃, (i-Pr)₂EtN, EtCN, DMF, reflux;
b) HCl in ether, CH₂Cl₂.

Scheme 9.

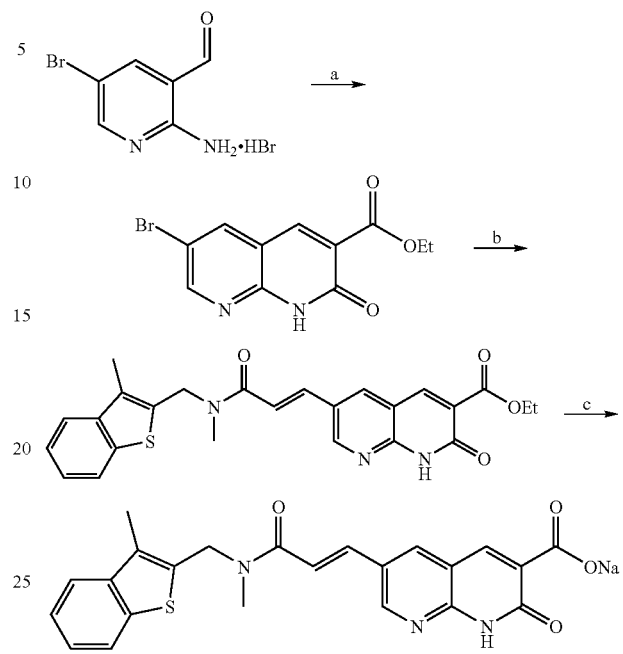

a) diethyl malonate, piperidine, EtOH;
b) N-methyl-N-(3-methyl-benzo[b]thiopen-2-ylmethyl)acrylamide, Pd(OAc)₂, P(o-tol)₃, (i-Pr)₂EtN, EtCN, DMF;
c) NaOH, MeOH, CH₂Cl₂.

Scheme 10.

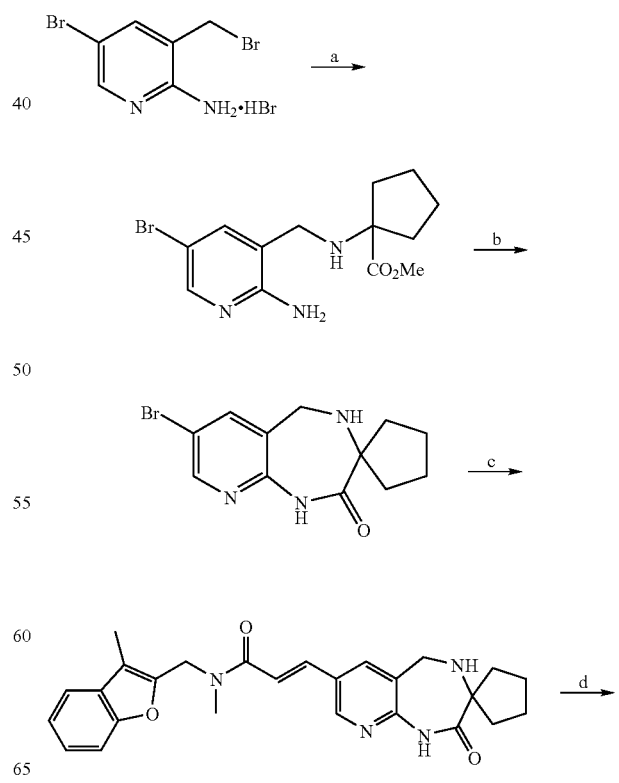

51
-continued

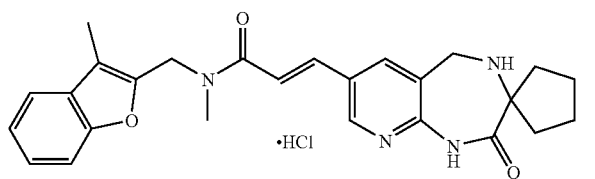

a) 1-amino-cyclopentanecarboxylic acid methyl ester, Et₃N, DMF;
b) NaH, DMSO;
c) N-methyl-N-(3-methyl-benzofuran-2-ylmethyl)acrylamide, Pd(OAc)₂, P(o-tol)₃, (i-Pr)₂EtN, EtCN, DMF;
d) HCl, CH₂Cl₂.

Scheme 11.

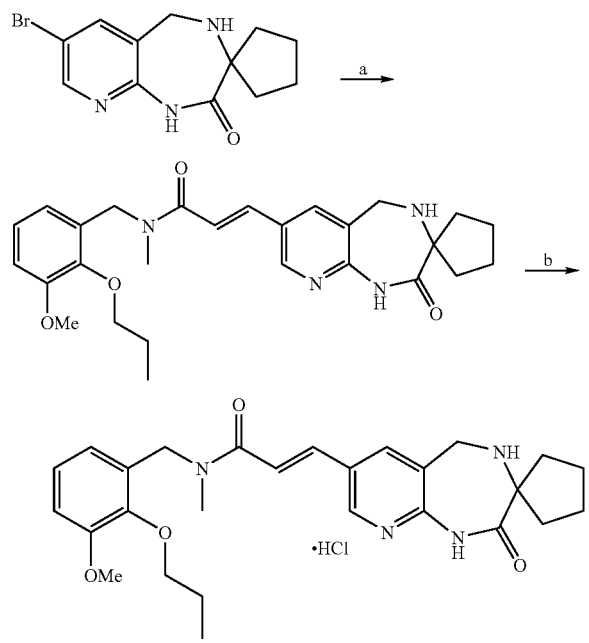

a) N-(3-methoxy-2-propoxybenzyl)-N-methylacrylamide, Pd(OAc)₂, P(o-tol)₃, (i-Pr)₂EtN, EtCN, DMF;
d) HCl, CH₂Cl₂.

Scheme 12.

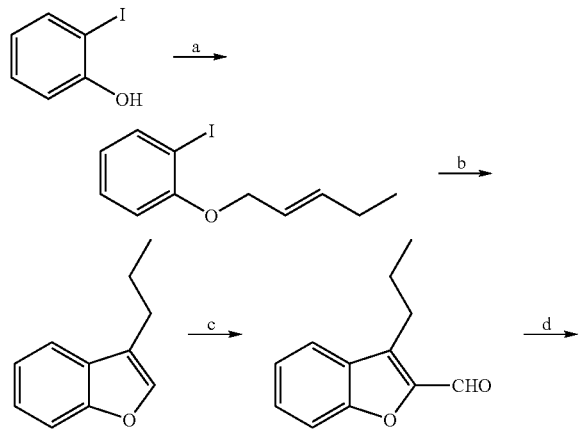

52
-continued

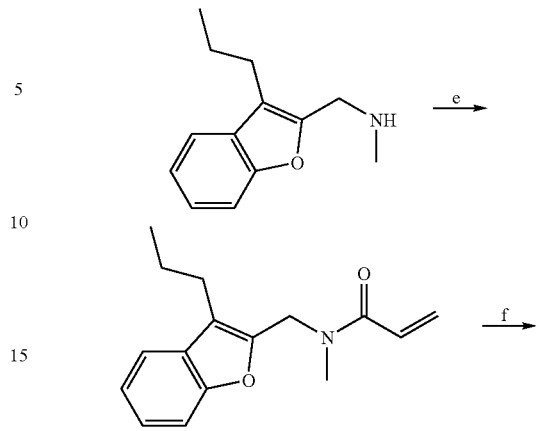

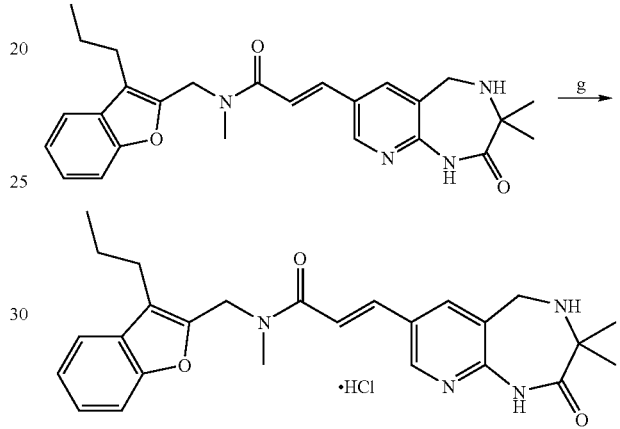

a) 1-Bromo-pent-2-ene, NaH, DMF;
b) n-Bu₄NCl, Pd(OAc)₂, Na₂CO₃, NaOAc, DMF, reflux;
c) i. n.butyllithium, THF, ii. DMF;
d) i. CH₃NH₂/MeOH, ii. NaBH₄/EtOH;
e) methyl-(3-propyl-benzofuran-2-ylmethyl)amine, CH₂Cl₂, acryloyl chloride, Et₃N;
f) N-Methyl-N-(3-propyl-benzofuran-2-ylmethyl)acrylamide, Pd(OAc)₂, P(o-tol)₃, (i-Pr)₂EtN, EtCN, DMF;
g) HCl in Et₂O, CH₂Cl₂.

Scheme 13.

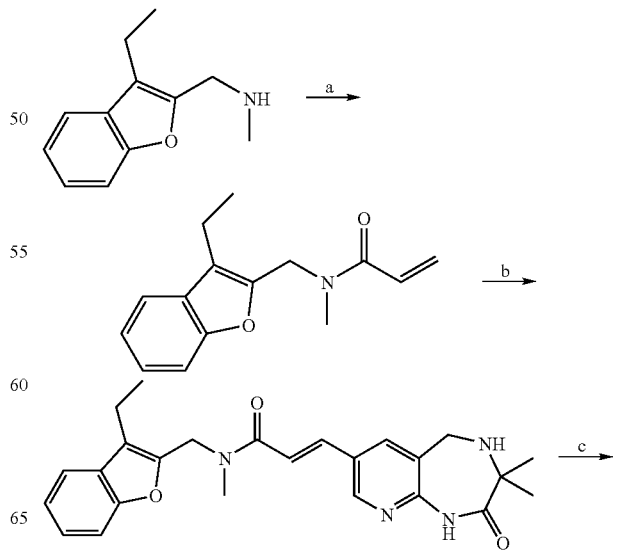

53

-continued

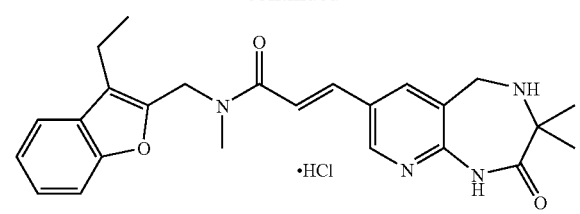

a) N-(3-ethyl-benzofuran-2-ylmethyl)methylamine, CH$_2$Cl$_2$, acryloyl chloride, Et$_3$N;
(b) N-(3-ethyl-benzofuran-2-ylmethyl)-N-methylacrylamide, Pd(OAc)$_2$, P(o-tol)$_3$, (i-Pr)$_2$EtN, EtCN, DMF;
c) HCl in Et$_2$O, CH$_2$Cl$_2$.

Scheme 14.

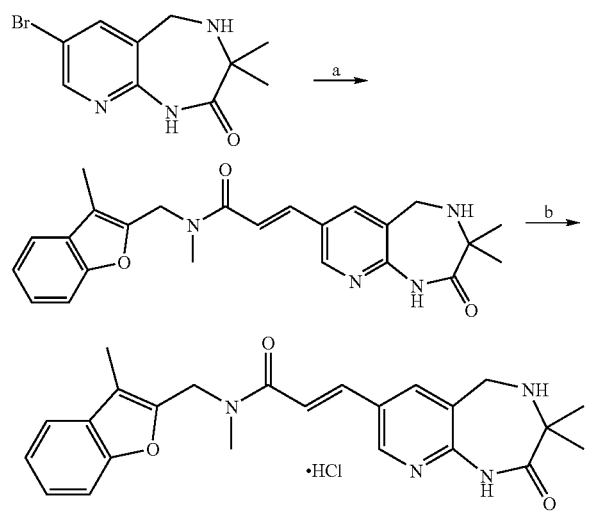

a) N-methyl-N-(3-methylbenzofuran-2-ylmethyl)acrylamide, Pd(OAc)$_2$, P(o-tol)$_3$, (i-Pr)$_2$EtN, EtCN, DMF;
b) HCl in Et$_2$O, CH$_2$Cl$_2$.

Scheme 15.

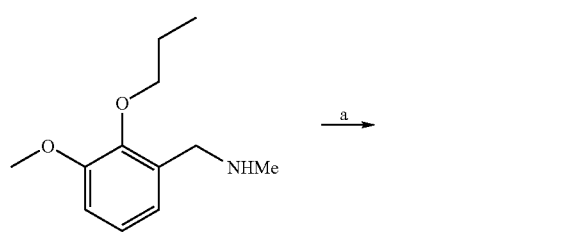

54

-continued

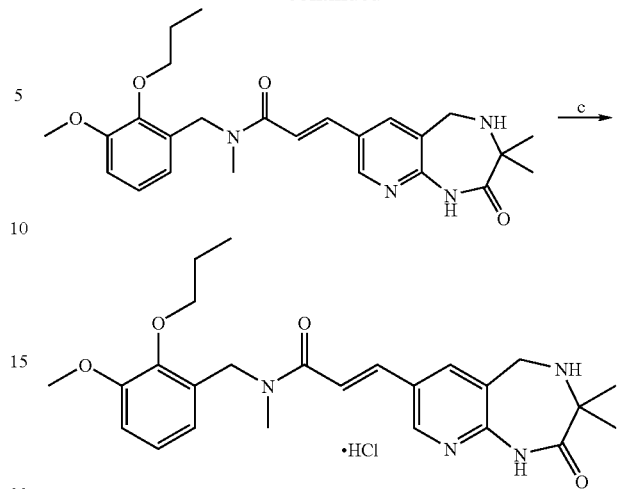

a) acryloyl chloride, Et$_3$N, CH$_2$Cl$_2$;
b) 7-bromo-3,3-dimethyl-1,3,4,5-tetrahydro-pyrido[2,3-e][1,4]diazepin-2-one, Pd(OAc)$_2$, P(o-tol)$_3$, (i-Pr)$_2$EtN, EtCN, DMF;
c) HCl in Et$_2$O, CH$_2$Cl$_2$.

Scheme 16.

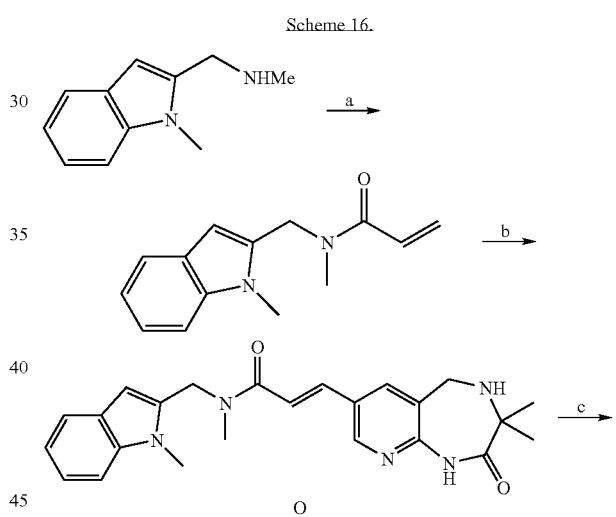

a) acryloyl chloride, Et$_3$N, CH$_2$Cl$_2$;
b) 7-bromo-3,3-dimethyl-1,3,4,5-tetrahydro-pyrido[2,3-e][1,4]diazepin-2-one, Pd(OAc)$_2$, P(o-tol)$_3$, (i-Pr)$_2$EtN, EtCN, DMF;
c) HCl in Et$_2$O, CH$_2$Cl$_2$.

Scheme 17.

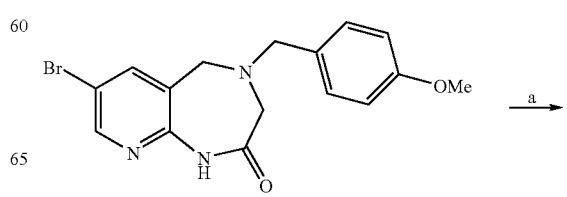

55
-continued

56
-continued

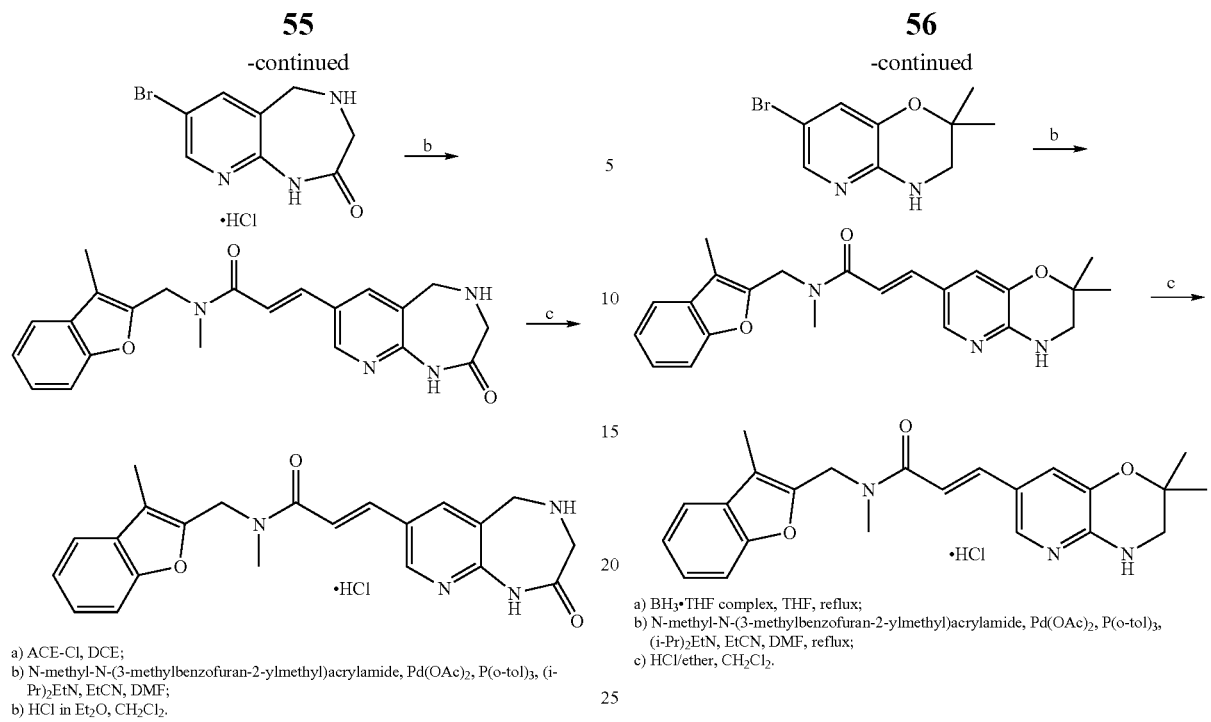

a) ACE-Cl, DCE;
b) N-methyl-N-(3-methylbenzofuran-2-ylmethyl)acrylamide, Pd(OAc)$_2$, P(o-tol)$_3$, (i-Pr)$_2$EtN, EtCN, DMF;
b) HCl in Et$_2$O, CH$_2$Cl$_2$.

a) BH$_3$•THF complex, THF, reflux;
b) N-methyl-N-(3-methylbenzofuran-2-ylmethyl)acrylamide, Pd(OAc)$_2$, P(o-tol)$_3$, (i-Pr)$_2$EtN, EtCN, DMF, reflux;
c) HCl/ether, CH$_2$Cl$_2$.

Scheme 18.

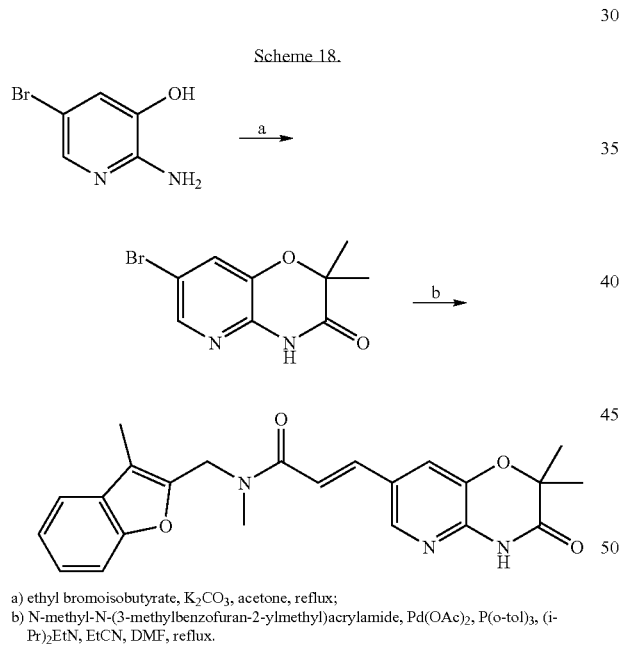

a) ethyl bromoisobutyrate, K$_2$CO$_3$, acetone, reflux;
b) N-methyl-N-(3-methylbenzofuran-2-ylmethyl)acrylamide, Pd(OAc)$_2$, P(o-tol)$_3$, (i-Pr)$_2$EtN, EtCN, DMF, reflux.

Scheme 20.

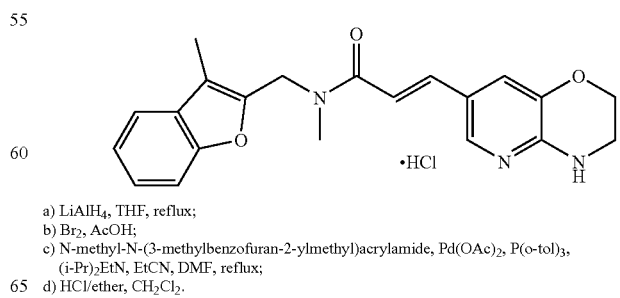

a) LiAlH$_4$, THF, reflux;
b) Br$_2$, AcOH;
c) N-methyl-N-(3-methylbenzofuran-2-ylmethyl)acrylamide, Pd(OAc)$_2$, P(o-tol)$_3$, (i-Pr)$_2$EtN, EtCN, DMF, reflux;
d) HCl/ether, CH$_2$Cl$_2$.

Scheme 19.

Scheme 21.
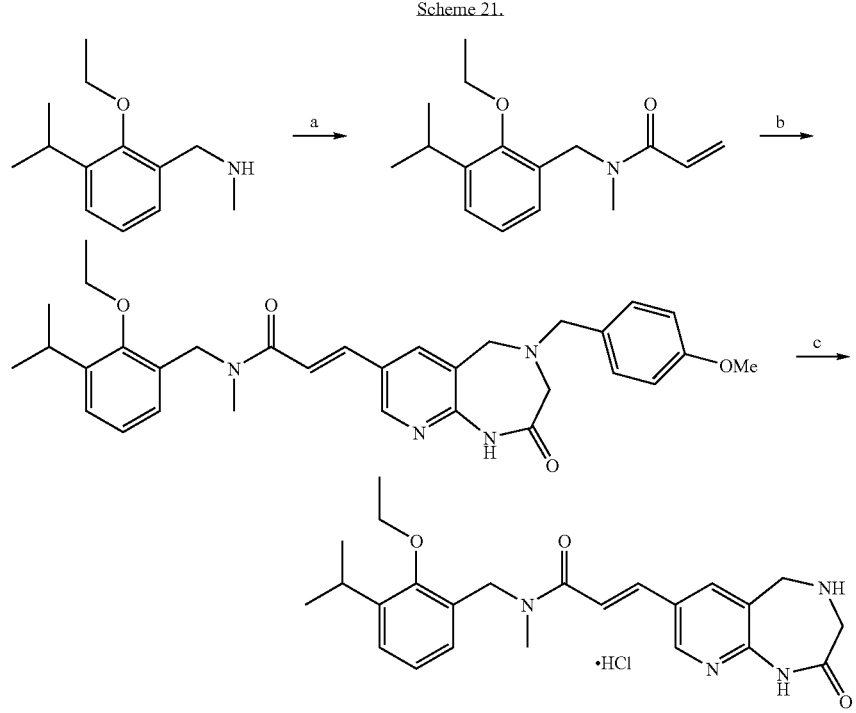
a) acryloyl chloride, Et₃N, CH₂Cl₂;
b) 7-bromo-4-(4-methoxybenzyl)-1,3,4,5-tetrahydro-pyrido[2,3-e][1,4]diazepin-2-one, Pd(OAc)₂, P(o-tol)₃, (i-Pr)₂EtN, EtCN, DMF, reflux;
c) i.ACE-Cl, C₂H₄Cl₂; ii. MeOH, reflux.
Scheme 22.
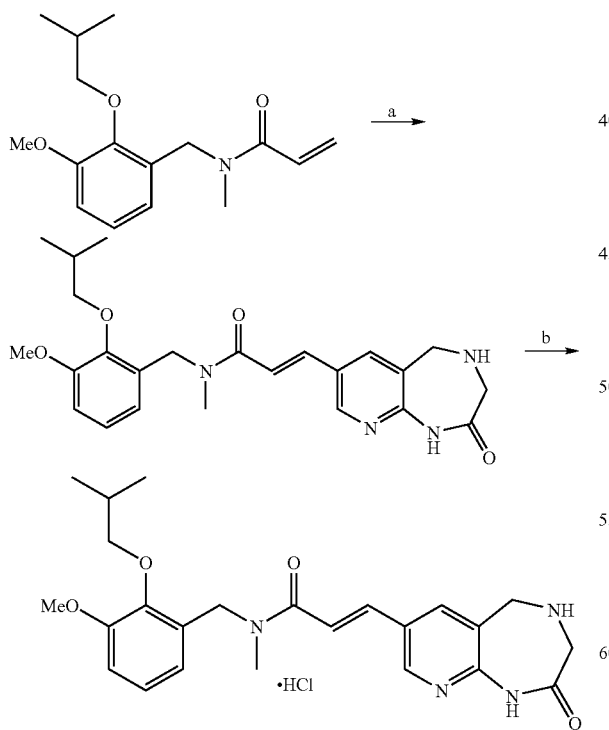
a) 7-bromo-1,3,4,5-tetrahydro-pyrido[2,3-e][1,4]diazepin-2-one, Pd(OAc)₂, P(o-tol)₃, (i-Pr)₂EtN, EtCN, DMF, reflux;
b) HCl in ether, CH₂Cl₂.
Scheme 23.
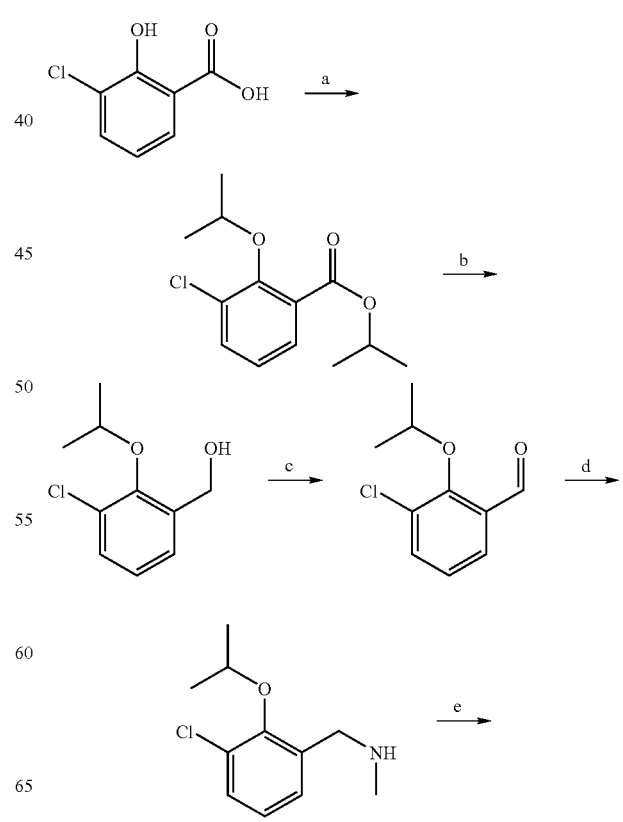

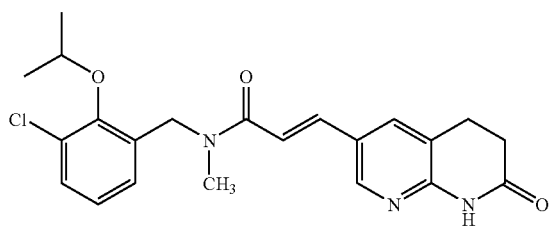
a) 2-iodopropane, K$_2$CO$_3$, DMF;
b) DIBAL-H, THF;
c) MnO$_2$, benzene;
d) i. MeNH$_2$, MeOH, ii. NaBH$_4$, EtOH;
e) EDC, HOBt, (i-Pr)$_2$EtN, (E)-3-(7-oxo-5,6,7,8-tetrahydro-[1,8]naphthyridin-3-yl)acrylic acid hydrochloride, DMF.
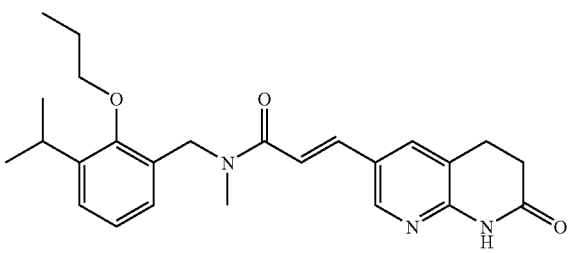
a) 1-bromopropane, K$_2$CO$_3$, DMF;
b) DIBAL-H, THF;
c) MnO$_2$, benzene;
d) i. MeNH$_2$, MeOH, ii. NaBH$_4$, EtOH;
e) EDC, HOBt, (i-Pr)$_2$EtN, (E)-3-(7-oxo-5,6,7,8-tetrahydro-[1,8]naphthyridin-3-yl)acrylic acid hydrochloride, DMF.
Scheme 24.
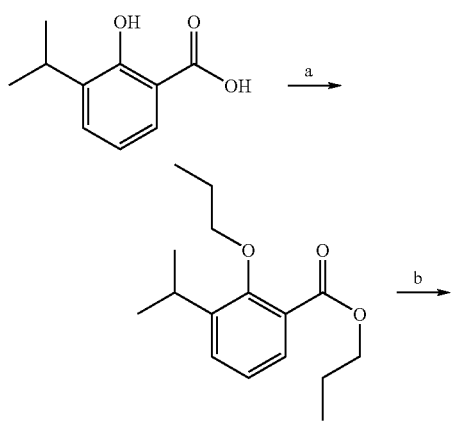
Scheme 25.
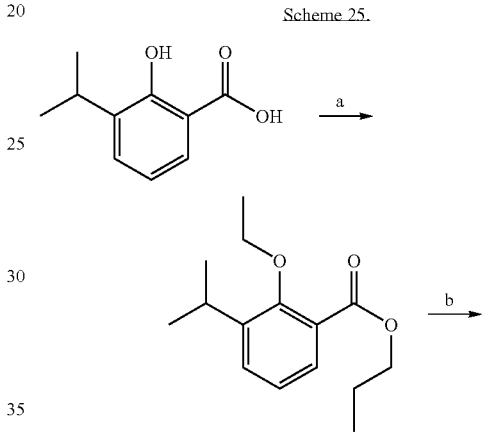

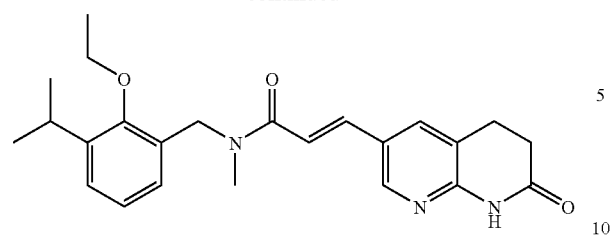

a) 1-bromopropane, K$_2$CO$_3$, DMF;
b) DIBAL-H, THF;
c) MnO$_2$, benzene;
d) i. MeNH$_2$, MeOH, ii. NaBH$_4$, EtOH;
e) EDC, HOBt, (i-Pr)$_2$EtN, (E)-3-(7-oxo-5,6,7,8-tetrahydro-[1,8]naphthyridin-3-yl)acrylic acid hydrochloride, DMF.

Scheme 26.

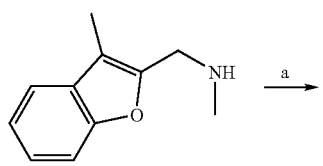

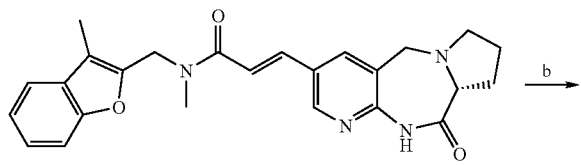

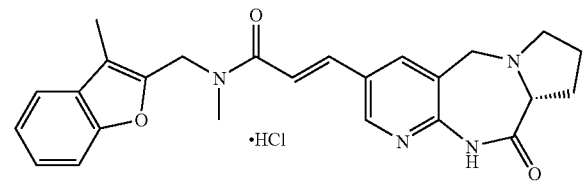

a) EDC, HOBt, (i-Pr)$_2$EtN, (E)-3-(7-oxo-5,6,7,8-tetrahydro-[1,8]naphthyridin-3-yl)acrylic acid hydrochloride, DMF;
b) HCl in ether, CH$_2$Cl$_2$.

Scheme 27.

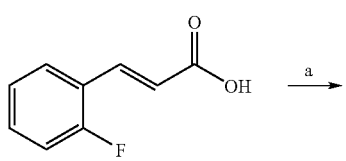

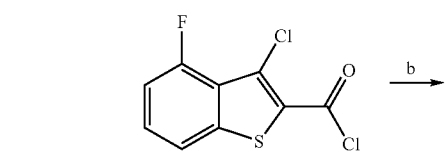

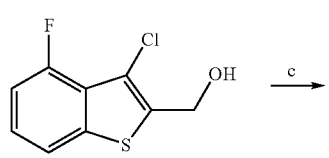

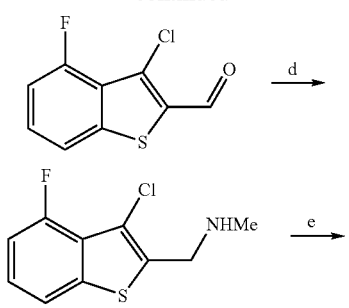

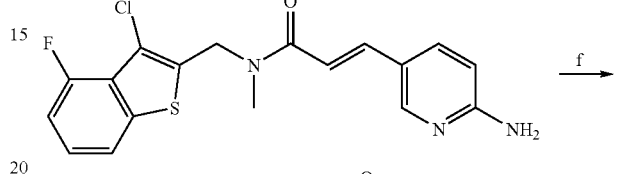

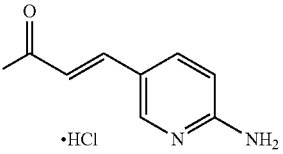

a) SOCl$_2$, pyridine, chlorobenzene;
b) LiAlH$_4$, THF;
c) MnO$_2$, benzene;
d) i. MeNH$_2$, MeOH, ii. NaBH$_4$, EtOH;
e) 3-(6-amino-pyridin-3-yl)acrylic acid trifluoroacetic acid salt, EDC, HOBt, DIEA, DMF;
f) HCl, CH$_2$Cl$_2$.

Scheme 28.

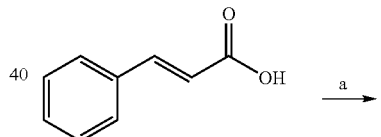

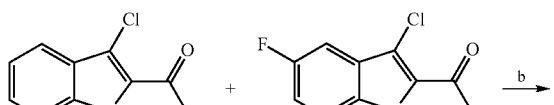

1:6

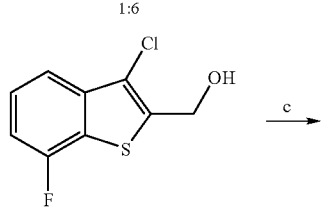

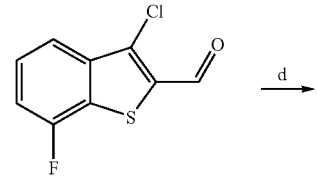

63 -continued

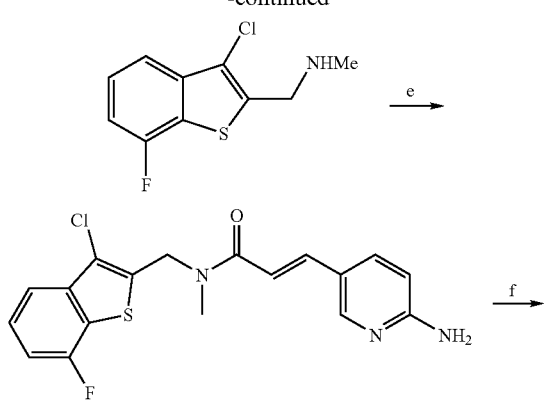

a) SOCl$_2$, pyridine, chlorobenzene;
b) i. LiAlH$_4$, THF; ii. silica gel chromatography;
c) MnO$_2$, benzene;
d) i. MeNH$_2$, MeOH, ii. NaBH$_4$, EtOH;
e) 3-(6-amino-pyridin-3-yl)acrylic acid trifluoroacetic acid salt, EDC, HOBt, DIEA, DMF;
f) HCl, CH$_2$Cl$_2$.

64 -continued

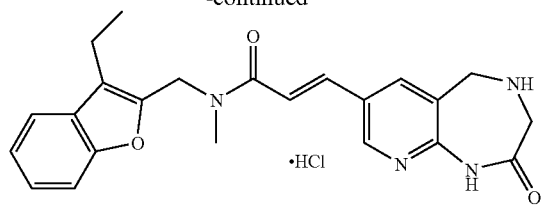

a) crotylbromide, NaH, DMF;
b) n-Bu$_4$NCl, Pd(OAc)$_2$, Na$_2$CO$_3$, NaOAc, DMF, reflux;
c) i. n-butyllithium, THF, ii. DMF;
d) i. CH$_3$NH$_2$/MeOH, ii. NaBH$_4$/EtOH;
e) EDC, HOBt, (i-Pr)$_2$EtN, DMF, 3-(2-oxo-2,3,4,5,-tetrahydro-1H-pyrido[2,3-e][1,4]diazepin-7-yl)-acrylic acid hydrochloride;
f) HCl/Et$_2$O, CH$_2$Cl$_2$.

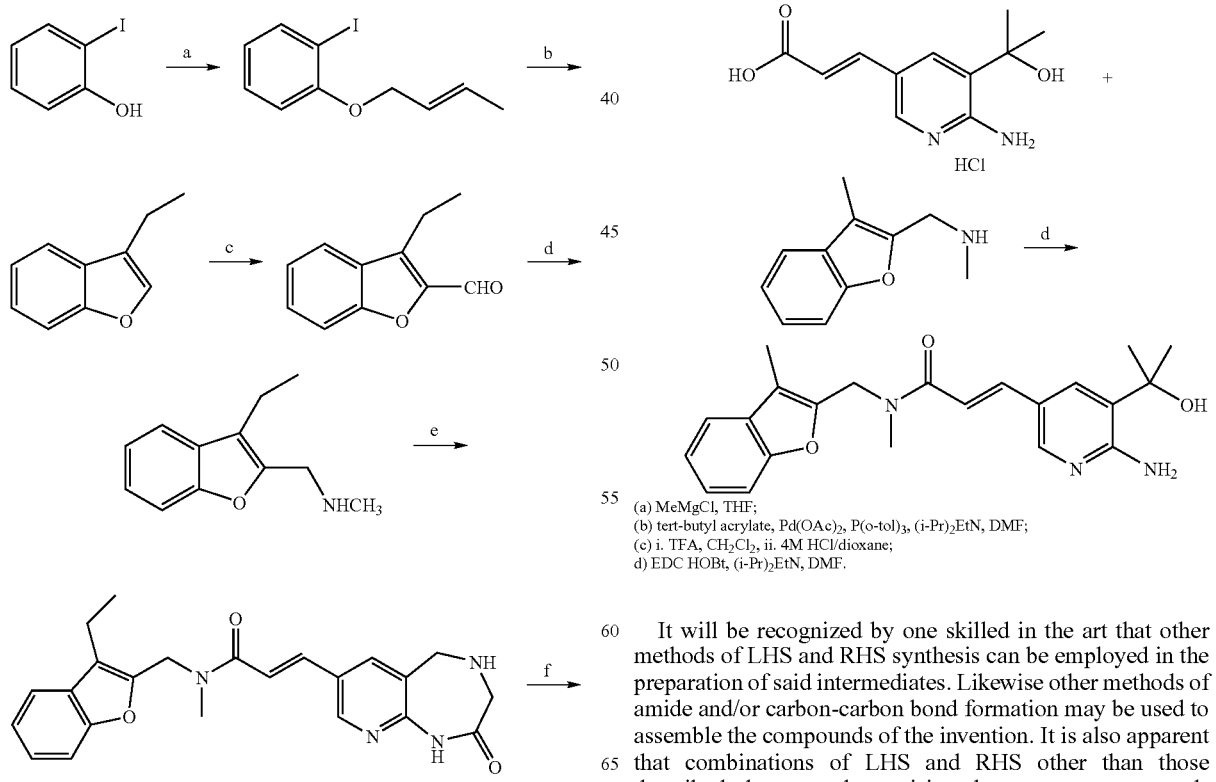

(a) MeMgCl, THF;
(b) tert-butyl acrylate, Pd(OAc)$_2$, P(o-tol)$_3$, (i-Pr)$_2$EtN, DMF;
(c) i. TFA, CH$_2$Cl$_2$, ii. 4M HCl/dioxane;
d) EDC HOBt, (i-Pr)$_2$EtN, DMF.

It will be recognized by one skilled in the art that other methods of LHS and RHS synthesis can be employed in the preparation of said intermediates. Likewise other methods of amide and/or carbon-carbon bond formation may be used to assemble the compounds of the invention. It is also apparent that combinations of LHS and RHS other than those described above can be envisioned to prepare compounds falling within the scope of the invention as represented by formula I. These possibilities are further detailed in the preparations and examples section to follow.

Acid addition salts of the compounds of formula I can be prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. This is illustrated by the preparation of hydrochloric acid salts as a final step in several of the general schemes shown above. Certain of the compounds form inner salts or zwitterions which may be acceptable. Cationic salts may be prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are some non-limiting examples of cations present in pharmaceutically acceptable salts.

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organs of toxicity. As candidate selection nears, these studies may provide guidance for the selection of proper doses in multi-dose studies, as well as establish any species specific differences in toxicities. These studies may be combined with routine PK measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

Resistance Frequencies and Mechanisms of Compounds

In vitro resistance frequencies in bacteria of interest can be estimated for compounds of formula I. Experiments can determine whether resistant isolates arise when challenged to grow on solid media at 1×, 2× and 4×MIC concentrations. For example with respect to S. aureus or E. coli, the experiments may use several recent clinical isolates of methicillin-sensitive and methicillin-resistant S. aureus and a laboratory strain of E. coli with acrA efflux pump defect. In addition, experiments may use several characterized triclosan-resistant S. aureus strains. The MICs of resistant strains isolated in this manner can then be determined. Subsequent experiments can determine whether resistant strains arise after serial passage of the strains in 0.5×MIC concentrations of each lead compound.

Mechanism of resistance may be determined in S. aureus laboratory strain, RN450 and in an E. coli laboratory strain carrying an acrA efflux pump mutation. Both high dose challenge (4×MIC) and sub-MIC serial passage may be used to obtain spontaneously arising resistant isolates. If no isolates are obtained with reasonable frequencies, chemical and physical mutagenesis methods can be used to obtain resistant isolates. The fabI gene from the chromosome of resistant isolates may be PCR amplified, then may be sequenced to determine whether changes in the FabI protein caused resistance. Triplicate PCR amplifications and sequences may be performed to assure that the observed sequence changes are correct, and did not arise from PCR errors during amplification. Strains carrying resistance mutations outside of the gene of interest may be documented and saved, characterized for their effects on susceptibilities of other antibiotics as evidence of possible efflux-mediated resistance mechanisms, characterized for their ability to alter compounds characterized for their effects on the expression of the specific mRNA and FabI protein.

Assays

Many different assay methods can be used to determine the activity of the compounds of the present invention. These assay methods include, for example, the following but also include other methods known to one of ordinary skill in the art.

S. aureus FabI Enzyme Inhibition Assay (NADH)

Assays are carried out in half-area, 96-well microtitre plates. Compounds are evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, may be included in an assay as a positive control. Compounds of this invention may have $IC_{50}$'s from about 5.0 micromolar to about 0.05 micromolar.

S. aureus FabI Enzyme Inhibition Assay (NADPH) (Modified)

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors are typically varied over the range of 0.01-10 uM. The consumption of NADPH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

H. influenzae FabI Enzyme Inhibition Assay

Assays are carried out in half-area, 96-well microtiter plates. Compounds are evaluated in 150-uL assay mixtures containing 100 mM MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of H. influenzae FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves. $IC_{50}$'s are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is currently included in all assays as a positive control.

E. coli FabI Enzyme Inhibition Assay

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of *E. coli* FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP

Reactions contain 5 mg/mL *E. coli* apo-ACP, 0.8 mM crotonoyl-CoA (Fluka), 10 mM $MgCl_2$, and 30 uM *S. pneumoniae* ACP synthase in 50 mM NaHEPES, pH 7.5. The mixture is gently mixed on a magnetic stirrer at 23° C. for 2 hr, and the reaction is terminated by the addition of 15 mM EDTA and cooling on ice. The reaction mixture is filtered through a 0.2 micron filter (Millipore) and applied to a MonoQ column (Pharmacia) equilibrated with 20 mM Tris-Cl, pH 7.5. The column is washed with buffer until all non-adherent material is removed (as observed by UV detection), and the crotonoyl-ACP is eluted with a linear gradient of 0 to 400 mM NaCl.

*S. aureus* FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of *S. aureus* Fab I (approximately 20 nM). Inhibitors are typically varied over the range of 0.01-30 uM. The consumption of NADPH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent Ki is calculated from Equation 2 assuming the inhibition is competitive with crotonoyl-ACP. More specifically, measured $IC_{50}$ values for 24 compounds of the present invention, as provided in the representative list above, ranged from less than about 0.02 μM to about 25 μM with 11 of these compounds having an $IC_{50}$ of less than 1.

*H. pylori* FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 10 uM crotonoyl-ACP, 50 uM NADH, 100 mM ammonium acetate, and an appropriate dilution of *H. pylori* Fab I (approximately 15 nM). Inhibitors are typically varied over the range of 0.025-30 uM. The consumption of NADH is monitored for 30 minutes at 25° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar.

The apparent IC; is calculated from Equation 2 assuming the inhibition is competitive with crotonoyl-ACP.

$$v=\text{Range}/(1+[I]/IC50)s+\text{Background} \qquad \text{Equation 1}$$

$$Ki(app)=IC50/(1+[S]/Ks) \qquad \text{Equation 2:}$$

*S. pneumoniae* FabK Enzyme Inhibition Assay Using Crotonoyl-ACP

Assays are carried out in half-area, 96-well microtitre plates. Compounds are evaluated in 100 uL assay mixtures containing 100 mM MES, 51 mM diethanolamine, 51 mM triethanolamine, pH 6.5 [MES=2-(N-morpholino)ethanesulfonic acid], 4% glycerol buffer, 100 mM $NH_4Cl$, 25 μM crotonoyl-ACP, 50 μM NADH, and 15 nM *S. pneumoniae* FabK. Inhibitors are typically varied over the range of 0.025-30 uM. The consumption of NADH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent $K_i$ is calculated from Equation 2 assuming the inhibition is competitive with crotonoyl-ACP.

Antimicrobial Activity Assay

Whole-cell antimicrobial activity is determined by broth microdilution using the National Committee for Clinical Laboratory Standards (NCCLS) recommended procedure, Document M7-A5, "Methods for Dilution Susceptibility Tests for Bacteria that Grow Aerobically". The compound is tested in serial two-fold dilutions ranging from 0.06 to 64 mcg/mL A panel of 12 strains are evaluated in the assay. This panel consists of the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49619, *Staphylococcus epidermidis* 1024939, *Staphylococcus epidermidis* 1024961, *Escherichia coli* AG100 ($AcrAB^+$), *Escherichia coli* AG100A ($AcrAB^-$) *Pseudomonas aeruginosa* K767 ($MexAB^+$, $OprM^+$), *Pseudomonas aeruginosa* K1119 ($MexAB^-$, $OprM^-$). The minimum inhibitory concentration (MIC) is determined as the lowest concentration of compound that inhibited visible growth. A spectrophotometer is used to assist in determining the MIC endpoint.

MIC assays may be performed using the microdilution method in a 96 well format. The assays may be performed in 96 well plates with a final volume of 100 μl cation-adjusted Mueller Hinton broth containing 2 fold serial dilutions of compounds ranging from 32 to 0.06 μg/ml. Bacterial growth may be measured at 600 nm using a Molecular Devices SpectraMax 340PC spectrophotometer. MICs can then be determined by an absorbance threshold algorithm and confirmed in some cases by inspecting the plates over a light box.

Minimum Bactericidal Concentration (MBC) may be determined by plating aliquots of MIC dilution series that did not show bacterial growth onto Petri plates containing appropriate semi-solid growth media. The lowest compound concentration that resulted in >99% killing of bacterial cells (relative to initial bacterial inocula in MIC test) is defined as the MBC.

Several strain panels may be used at various points in the compound progression scheme. The primary panel may include single prototype strains of both community- and hospital-acquired pathogens for determining initial activities and spectra of activity. Secondary panel compositions will depend on the results of the primary panels, and will include 10-20 strains of relevant species that will include community acquired and antibiotic-resistant hospital acquired strains of *Staphylococcus aureus* and coagulase negative Staphylococci together with other strains that are sensitive to the new compounds, and negative control strains. The secondary panels will be used during optimization of lead chemical series. Tertiary panels will include 100-200 clinical strains of *S. aureus* and coagulase negative Staphylococci together with other relevant strains as for the secondary panels. The tertiary panels will be utilized during the compound candidate selection stage and preclinical studies to generate bacterial population efficacy parameters such as $MIC_{so}$ and $MIC_{90}$.

Using the assay described above, measured MIC values against *Staphylococcus aureus* 29213 for 24 compounds of the present invention, as provided in the representative list above, ranged from less than about 0.06 µg/ml to greater than about 30 µg/ml with 9 of these compounds having an MIC of less than 1.

*Franciscella tularensis* In Vitro Efficacy Studies

Routine MIC testing of *F. tularensis* may be undertaken on compounds that have demonstrated enzymatic activity inhibition against the *F. tularensis* FabI protein. The MIC testing of *F. tularensis* may be outsourced to a facility with BL3 capabilities, and with experience in handling *F. tularensis* cultures in the laboratory. The studies may be undertaken with the recommended methods for antimicrobial susceptibility testing of *F. tularensis*.

*Helicobacter pylori* In Vitro Efficacy Studies

Routine MIC testing of *H. pylori* may be undertaken on compounds that have demonstrated enzymatic activity inhibition against the *H. pylori* FabI protein. The studies may be undertaken with the recommended methods for antimicrobial susceptibility testing of *H. pylori*.

Cytotoxicity Assays

Cytotoxicity of the new compounds may be evaluated by the Alamar Blue assay according the manufacturers instructions. Human cell lines (e.g. Jurkat) grown in 96 well plates may be exposed to serial dilutions of the tested compounds. After adding Alamar Blue, cell viability may be determined by measuring the absorbance of the reduced and oxidized forms of Alamar Blue at 570 nm and 600 nm. Cytotoxicity may be reported as $LD_{50}$, the concentration that causes a 50% reduction in cell viability.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored y measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the FabI inhibitor) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The antibacterial compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In certain embodiments, the subject compounds may be formulated as a tablet, pill capsule or other appropriate ingestible formulation (collectively hereinafter "tablet"), to provide a therapeutic dose in 10 tablets or fewer. In another example, a therapeutic dose is provided in 50, 40, 30, 20, 15, 10, 5 or 3 tablets.

In a certain embodiment, the antibacterial agent is formulated for oral administration as a tablet or an aqueous solution or suspension. In another embodiment of the tablet form of the antibacterial agent, the tablets are formulated such that the amount of antibacterial agent (or antibacterial agents) provided in 20 tablets, if taken together, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, the tablets are formulated such that the total amount of antibacterial agent (or antibacterial agents) provided in 10, 5, 2 or 1 tablets would provide at least an $ED_{50}$ dose to a patient (human or non-human mammal). In other embodiments, the amount of antibacterial agent (or antibacterial agents) provided in 20, 10, 5 or 2 tablets taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the ED50 is provided. In other embodiments, a single dose of tablets (1-20 tablets) provides about 0.25 mg to 1250 mg of an antibacterial agent(s).

Likewise, the antibacterial agents can be formulated for parenteral administration, as for example, for subcutaneous, intramuscular or intravenous injection, e.g., the antibacterial agent can be provided in a sterile solution or suspension (collectively hereinafter "injectable solution"). The injectable solution is formulated such that the amount of antibacterial agent (or antibacterial agents) provided in a 200 cc bolus injection would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided in 100, 50, 25, 10, 5, 2.5, or 1 cc injections would provide an $ED_{50}$ dose to a patient, or less than 100 times the $ED_{50}$, or less than 10 or 5 times the $ED_{50}$. In other embodiments, the amount of antibacterial agent (or antibacterial agents) provided in a total volume of 100 cc, 50, 25, 5 or 2 cc to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg of antibacterial agent.

Efficacy of Treatment

The efficacy of treatment with the subject compositions may be determined in a number of fashions known to those of skill in the art.

In one exemplary method, the median survival rate of the bacteria or bacteria median survival time or life span for treatment with a subject composition may be compared to other forms of treatment with the particular FabI inhibitor, or with other antibiotic agents. The decrease in median bacteria survival rate or time or life span for treatment with a subject composition as compared to treatment with another method may be 10, 25, 50, 75, 100, 150, 200, 300, 400% even more. The period of time for observing any such decrease may be about 3, 5, 10, 15, 30, 60 or 90 or more days. The comparison may be made against treatment with the particular FabI inhibitor contained in the subject composition, or with other antibiotic agents, or administration of the same or different agents by a different method, or administration as part of a different drug delivery device than a subject composition. The comparison may be made against the same or a different effective dosage of the various agents. The different regiments compared may use measurements of bacterial levels to assess efficacy.

Alternatively, a comparison of the different treatment regimens described above may be based on the effectiveness of the treatment, using standard indicies for bacterial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different FabI inhibitor.

As a non-limiting example, to determine if compounds are bactericidal or bacteriostatic at relevant concentrations, and to examine the kinetics of bacterial killing the following experiment may be performed with S. aureus, S. epidermidis and appropriate control strains and antibiotics. To fresh logarithmic cultures at $10^7$ viable cells/ml, compound may be added to reach concentrations of ×1, ×2 or ×4 the MIC. Control cultures will receive no compound. At 1 hour intervals, aliquots will be diluted and plated for determining viable counts. Plots of viable cells vs. time for up to 24 hours will reveal bactericidal/bacteriostatic properties of the compounds, and also show the kill kinetics. These experiments are important to determine whether these inhibitors have time-dependent or concentration-dependent effects, and will be used to help set appropriate dosages in vivo in combination with pharmacokinetic and pharmacodynamic measurements.

In the practice of the instant methods, the antibacterial compositions of the present invention inhibit bacterial FabI with a $K_i$ of 5 µM or less, 1 µM or less, 100 nM or less, 10 nM or less or even 1 nM or less. In treatment of humans or other animals, the subject method may employ FabI inhibitors which are selective for the bacterial enzyme relative to the host animals enoyl CoA hydratase, e.g., the $K_i$ for inhibition of the bacterial enzyme is at least one order, two orders, three orders, or even four or more orders of magnitude less than the $K_i$ for inhibition of enoyl CoA hydratase from the human (or other animal). That is, the practice of the subject method in vivo in animals utilizes FabI inhibitors with therapeutic indexes of at least 10, 100 or 1000.

Similarly, in the practice of the instant method, the antibacterial compounds of the present invention inhibit FabI with an $IC_{50}$ of 30 µM or less, 10 µM or less, 100 nM or less, or even 10 nM or less. In treatment of humans or other animals, the subject method may employ FabI inhibitors which are selective for the bacterial enzyme relative to the host animals' enoyl CoA hydratase, e.g., the $IC_{50}$ for inhibition of the bacterial enzyme is at least one order, two orders, three orders, or even four orders of magnitude less than the $IC_{50}$ for inhibition of enoyl CoA hydratase from the human (or other animal). That is, in preferred embodiments, the practice of the subject method in vivo in animals utilizes FabI inhibitors with therapeutic indexes of at least 10, 100 or 1000.

Alternatively, bacterial inhibition by an antibacterial compound of the present invention may also be characterized in terms of the minimum inhibitory concentration (MIC), which is the highest concentration of compound required to achieve complete inhibition of bacterial cell growth. Such values are well known to those in the art as representative of the effectiveness of a particular antibacterial agent against a particular organism or group of organisms. In the practice of the instant methods, the antibacterial compositions of the present invention inhibit bacterial growth with MIC values of about 32 mg/mL, less than about 16 µg/mL, less than about 8 µg/mL, less than about 4 µg/mL, less than about 2 µg/mL, less than about 1 µg/mL, less than about 0.5 µg/mL, less than about 0.25 µg/mL, or even less than about 0.125 µg/mL. The value of MIC90, defined as the concentration of a compound required to inhibit the growth of 90% of bacterial strains within a given bacterial strain population, can also be used. In certain embodiments, the compounds of the present invention are selected for use based, inter alia, on having MIC90 values of less than about 32 µg/mL, less than about 16 µg/mL, less than about 8 µg/mL, less than about 4 µg/mL, less than about 2 µg/mL, less than about 1 µg/mL, less than about 0.5 µg/mL, less than about 0.25 µg/mL, or even less than about 0.125 µg/mL.

In other embodiments, the subject compounds are selected for use in animals, or animal cell/tissue culture based at least in part on having $LD_{50}$'s at least one order, or two orders, or three orders, or even four orders or more of magnitude greater than the $ED_{50}$. That is, in certain embodiments where the subject compounds are to be administered to an animal, a suitable therapeutic index is preferably greater than 10, 100, 1000 or even 10,000.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

The examples which follow are intended in no way to limit the scope of this invention but are provided to illustrate how to prepare and use compounds of the present invention. Many other embodiments of this invention will be apparent to one skilled in the art.

EXEMPLIFICATION

General

Proton nuclear magnetic resonance ($^1$H NMR) spectra were recorded at either 300 or 500 MHz, and chemical shifts are reported in parts per million (δ) downfield from the internal standard tetramethylsilane (TMS) or from deuterated solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, DMSO-$d_6$ is hexadeuteriodimethylsulfoxide, $CD_3OD$ is tetradeuteriomethanol and $D_2O$ is deuterated oxide. Mass spectra were obtained using electrospray (ESI) ionization techniques. Flash chromatography was carried out on E. Merck Kieselgel 60 (230-400 mesh) silica gel. Analytical HPLC was performed on Varian chromatography systems. Celite® is a filter aid composed of acid-washed diatomaceous silica, and is a registered trademark of Manville Corp., Denver, Colo. General abbreviations are as follows: EDC=1-(3-dimethylaminopropyl)-3-ethylcarbodiimide hydrochloride, HOBt=1-hydroxybenzotriazole hydrate, (i-Pr)$_2$EtN=N,N-diisopropylethylamine, DMF=N,N-dimethylformamide, MeOH=methanol, EtOH=ethanol, THF=tetrahydrofuran, DMSO=dimethylsulfoxide, Et$_2$O=diethyl ether, Ar=argon, Pd(OAc)$_2$=palladium(II) acetate, P(o-tol)$_3$=tri-ortho-tolylphoshine, EtOAc=ethyl acetate, ACE-Cl=1-chloroethyl chloroformate, satd=saturated, Et$_3$N=triethylamine, TFA=trifluoroacetic acid, NaBH(OAc)$_3$=sodium triacetoxyborohydride, HOAc=acetic acid, EtCN=proprionitrile, CBzCl=benzyl chloroformate, MeCN=acetonitrile.

Example 1

Preparation of (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide hydrochloride

$C_8H_5F_3O_3$
Exact Mass: 206.02 a) 2-Hydroxy-3-trifluoromethoxybenzaldehyde

A solution of 2-trifluoromethoxyphenol (5.13 g, 28.8 mmol) in anhydrous acetonitrile (150 mL) in oven-dried glassware was treated with triethylamine (15.0 mL, 108 mmol) and MgCl$_2$ (4.11 g, 43.2 mmol) which had been dried under vacuum with heat. Paraformaldehyde (5.18 g, 172 mmol), which had been dried under vacuum with P$_2$O$_5$, was added and the solution was heated to reflux. After 5 days, the reaction was quenched with 1 N HCl (200 mL) and the mixture was extracted using Et₂O (2×100 mL). The combined organics were washed with brine (2×150 mL), dried (Na₂SO₄) and concentrated to a yellow solid. Purification by column chromatography (silica gel, 98:2 to 95:5 hexanes/EtOAc) gave the title compound (2.45 g, 41%) as a yellow powder: ¹H NMR (300 MHz, DMSO-d₆) δ 10.24 (s, 1H), 7.75-7.65 (m, 2H), 7.08 (t, J=7.9 Hz, 1H).

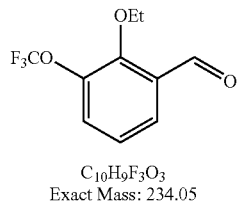 [SMILES: CCOc1c(C=O)cccc1OC(F)(F)F]

C₁₀H₉F₃O₃
Exact Mass: 234.05 b) 2-Ethoxy-3-trifluoromethoxybenzaldehyde

To a solution of 2-hydroxy-3-trifluoromethoxybenzaldehyde (1.00 g, 4.82 mmol) in DMF (10 mL), was added K₂CO₃ (1.46 g, 10.6 mmol) followed by iodoethane (0.57 mL, 7.24 mmol) and the mixture was heated to 37° C. for 6 h. The reaction was quenched by the addition of H₂O (40 mL) and the mixture was extracted with EtOAc (3×100 mL). The combined organics were washed with brine (2×100 mL), dried (Na₂SO₄) and concentrated to yield the title compound (1.17 g, quant.) as an orange oil: ¹H NMR (300 MHz, DMSO-d₆) δ 10.31 (s, 1H), 7.77 (m, 2H), 7.38 (t, J=8.1 Hz, 1H), 4.19 (q, J=6.9 Hz, 2H), 1.36 (t, J=6.9 Hz, 3H).

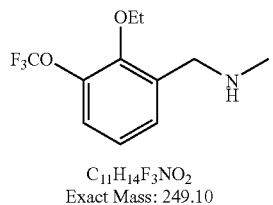 [SMILES: CCOc1c(CNC)cccc1OC(F)(F)F]

C₁₁H₁₄F₃NO₂
Exact Mass: 249.10 c) (2-Ethoxy-3-trifluoromethoxybenzyl)methylamine

A solution of methylamine (20 mL of a 2.0 M solution if MeOH, 40 mmol) was added to 2-ethoxy-3-trifluoromethoxybenzaldehyde (1.17 g, 4.95 mmol) under N₂ and the solution was stirred for 18 h. The solution was concentrated under reduced pressure. The resulting clear oil was dissolved in EtOH (20 mL) and treated with NaBH₄ (0.187 g, 4.95 mmol). After stirring for 5.5 h, the reaction mixture was concentrated under reduced pressure, then dissolved in 1 N NaOH (20 mL) and extracted with Et₂O (3×50 mL). The combined organics were collected, washed with brine (2×100 mL), dried (Na₂SO₄) and concentrated to yield the title compound (0.72 g, 58%) as a clear oil: ¹H NMR (500 MHz, DMSO-d₆) δ 7.40 (dd, J=7.7, 1.55 Hz, 1H), 7.25 (d, J=9.5 Hz, 1H), 7.16 (t, J=7.7 Hz, 1H), 3.97 (t, J=7.0 Hz, 2H), 3.68 (s, 2H), 2.28 (s, 3H), 2.02 (br s, 1H), 1.35-1.30 (m, 3H).

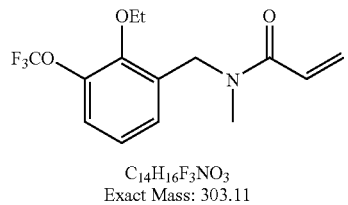 [SMILES: C=CC(=O)N(C)Cc1cccc(OC(F)(F)F)c1OCC]

C₁₄H₁₆F₃NO₃
Exact Mass: 303.11 d) N-(2-Ethoxy-3-trifluoromethoxybenzyl)-N-methylacrylamide

To a solution of (2-ethoxy-3-trifluoromethoxybenzyl)methylamine (0.720 g, 2.08 mmol) in CH₂Cl₂ (25 mL), was added acryloyl chloride (0.25 mL, 3.15 mmol) drop-wise. After stirring for five minutes, triethylamine (0.43 mL, 3.15 mmol) was added. The solution was allowed to stir under N₂ for 3 h. The solution was diluted with CH₂Cl₂ (30 mL) and then washed with H₂O (3×50 mL) and brine (2×100 mL), dried (Na₂SO₄) and concentrated to yield the title compound (0.746 g, 86%) as a yellow oil and as a mixture of amide rotamers: ¹H NMR (500 MHz, CDCl₃) δ 7.21-7.02 (m, 3H), 6.67-6.50 (m, 1H), 6.41-6.36 (m, 1H), 5.75-5.58 (m, 1H), 4.75-4.65 (m, 2H), 4.14-4.05 (m, 2H), 3.03-2.99 (m, 3H), 1.43-141 (m, 3H).

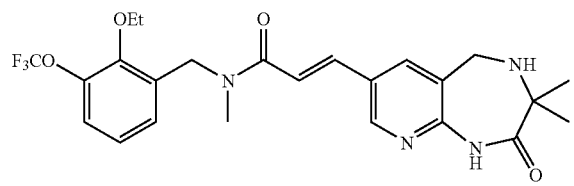

C₂₄H₂₇F₃N₄O₄
Exact Mass: 492.20 e) (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide A solution of N-(2-ethoxy-3-trifluoromethoxybenzyl)-N-methylacrylamide (0.447 g, 1.47 mmol) in propionitrile (5 mL) and DMF (1 mL) was deoxygenated with Ar for 20 min and then treated with diisopropylethylamine (0.40 mL, 2.3 mmol) and 7-bromo-3,3-dimethyl-1,3,4,5-tetrahydro-pyrido [2,3-e][1,4]diazepin-2-one (0.300 g, 1.11 mmol). The solution was deoxygenated with Ar for 20 minutes. Pd(OAc)₂ (0.024 g, 0.111 mmol) and P(o-tol)₃ (0.067 g, 0.222 mmol) were added and the solution deoxygenated with Ar for 20 min. The mixture was heated to reflux for 18 h then, allowed to cool. The mixture was diluted with EtOAc (30 mL) and was washed with H₂O (3×50 mL) and brine (2×50 mL), dried (Na₂SO₄) and concentrated to a yellow-orange solid. Purification by column chromatography (silica gel, CH₂Cl₂/MeOH, 100 to 98:2) gave the title compound (0.25 g, 31%) as an off-white solid and as a mixture of amide rotamers: ¹H NMR (300 MHz, DMSO-d₆) δ 9.80-9.78 (m, 1H), 8.40-8.37

(m, 1H), 8.01-7.93 (m, 1H), 7.56-7.49 (m, 1H), 7.36-7.09 (m, 4H), 4.87-4.68 (m, 2H), 4.06-3.83 (m, 4H), 3.31-2.88 (m, 4H), 1.36-1.29 (m, 9H).

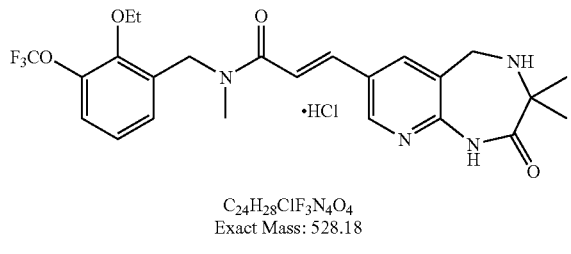 [SMILES: CCOc1c(CN(C)C(=O)/C=C/c2cnc3c(c2)CNC(C)(C)C(=O)N3)cccc1OC(F)(F)F ; Cl]

C$_{24}$H$_{28}$ClF$_3$N$_4$O$_4$
Exact Mass: 528.18 f) (E)-3-(3,3-Dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide hydrochloride A stirring solution of (E)-3-(3,3-dimethyl-2-oxo-2,3,4,5-tetrahydro-1H-pyrido[2,3-e][1,4]diazepin-7-yl)-N-methyl-N-(2-ethoxy-3-trifluoromethoxybenzyl)acrylamide (0.172 g, 0.349 mmol) in CH$_2$Cl$_2$ (4 mL) under N$_2$ was treated with anhydrous HCl (0.17 mL of a 2 M solution in diethyl ether, 0.34 mmol). After stirring for 18 h, the resulting solid was collected by filtration, washed with Et$_2$O (100 mL) and dried to yield the title compound (0.11 g, 62%) as an off white solid and as a mixture of amide rotamers: $^1$H NMR (300 MHz, DMSO-d$_6$) δ 10.94 (br s, 1H), 10.38 (br s, 2H), 8.67-8.64 (m, 1H), 8.38-8.30 (m, 1H), 7.62-7.54 (m, 1H), 7.41-7.10 (m, 4H), 4.89-4.70 (m, 2H), 4.41-4.36 (m, 2H), 4.06-4.00 (m, 2H), 3.17-2.87 (m, 3H), 1.61-1.59 (m, 6H), 1.37-1.31 (m, 3H); MS (ESI) m/e 493 (M+H)$^+$.

Example 2

Preparation of (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide hydrochloride

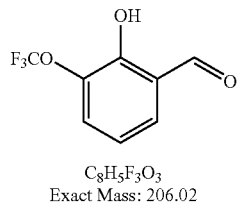 [SMILES: O=Cc1cccc(OC(F)(F)F)c1O]

C$_8$H$_5$F$_3$O$_3$
Exact Mass: 206.02 a) 2-Hydroxy-3-trifluoromethoxybenzaldehyde

A solution of 2-trifluoromethoxyphenol (5.13 g, 28.8 mmol) in anhydrous acetonitrile (150 mL) in oven-dried glassware was treated with triethylamine (15.0 mL, 108 mmol) and MgCl$_2$ (4.11 g, 43.2 mmol) which had been dried under vacuum with heating. Paraformaldehyde (5.18 g, 172 mmol), which had been dried under vacuum with P$_2$O$_5$, was then added and the solution was heated to reflux. After 5 days, the reaction was quenched with 1 N HCl (200 mL). The mixture was extracted using Et$_2$O (2×100 mL). The combined organics were washed with brine (2×150 mL), dried (Na$_2$SO$_4$) and concentrated to a yellow solid. Purification by column chromatography (silica gel, 98:2 to 95:5 hexanes/EtOAc) gave the title compound (2.45 g, 41%) as a yellow powder: $^1$H NMR (300 MHz, DMSO-d$_6$) δ 10.24 (s, 1H), 7.75-7.65 (m, 2H), 7.08 (t, J=7.9 Hz, 1H).

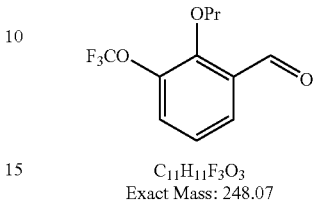

C$_{11}$H$_{11}$F$_3$O$_3$
Exact Mass: 248.07 b) 2-Propoxy-3-trifluoromethoxybenzaldehyde

To a solution of 2-hydroxy-3-trifluoromethoxybenzaldehyde (1.00 g, 4.82 mmol) in DMF (10 mL) was added K$_2$CO$_3$ (1.46 g, 10.6 mmol) followed by 1-bromopropane (0.65 mL, 7.2 mmol). The solution was heated to 37° C. for 6 h. The reaction was quenched with H$_2$O (40 mL) and the mixture was extracted with EtOAc (3×50 mL). The combined organics were washed with brine (2×100 mL), dried (Na$_2$SO$_4$) and concentrated to yield the title compound (1.15 g, 96%) as a yellow oil: $^1$H NMR (300 MHz, DMSO-d$_6$) δ 10.30 (s, 1H), 7.77 (d, J=8.0 Hz, 2H), 7.38 (t, J=7.9 Hz, 1H), 4.09 (t, J=6.4 Hz, 2H), 1.81-1.72 (m, 2H), 1.01 (t, J=7.4 Hz, 3H).

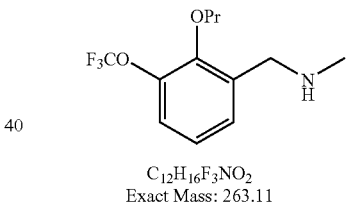

C$_{12}$H$_{16}$F$_3$NO$_2$
Exact Mass: 263.11 c) Methyl-(2-propoxy-3-trifluoromethoxybenzyl)amine

A solution of methylamine (19 mL of a 2.0 M solution in MeOH, 38 mmol) was added to 2-propoxy-3-trifluoromethoxybenzaldehyde (1.15 g, 4.60 mmol). The mixture was stirred for 18 h. The solution was concentrated under reduced pressure. The resulting clear oil was dissolved in EtOH (19 mL) and treated with NaBH$_4$ (0.174 g, 4.60 mmol). After stirring for 5.5 h, the reaction mixture was concentrated under reduced pressure, then dissolved in 1 N NaOH (19 mL). The mixture was extracted with Et$_2$O (3×50 mL). The organics were collected, washed with brine (2×100 mL), dried (Na$_2$SO$_4$) and concentrated to yield the title compound (0.89 g, 73%) as an orange oil: $^1$H NMR (300 MHz, DMSO-d$_6$) δ 7.41 (dd, J=7.7, 1.6 Hz, 1H), 7.25 (dd, J=6.7, 1.3 Hz, 1H), 7.16 (t, J=7.7 Hz, 1H), 3.87 (t, J=6.3 Hz, 2H), 3.68 (s, 2H), 2.27 (s, 3H), 2.07 (br s, 1H), 1.74 (q, J=6.4 Hz, 2H), 1.02 (t, J=3.1 Hz, 3H).

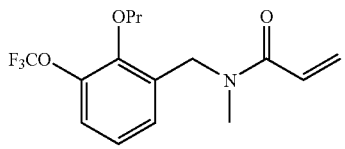

C<sub>15</sub>H<sub>18</sub>F<sub>3</sub>NO<sub>3</sub>
Exact Mass: 317.12 d) N-Methyl-N-(2-propoxy-3-trifluoromethoxybenzyl)acrylamide

To a solution of methyl-(2-propoxy-3-trifluoromethoxybenzyl)amine (0.890 g, 3.35 mmol) in CH$_2$Cl$_2$ (30 mL) was added acryloyl chloride (0.30 mL, 3.6 mmol) drop-wise. After stirring for five minutes, triethylamine (0.51 mL, 3.6 mmol) was added. The solution was allowed to stir under N$_2$ for 3 h. The solution was diluted with CH$_2$Cl$_2$ (30 mL), washed with H$_2$O (3×50 mL) and brine (2×50 mL), dried (Na$_2$SO$_4$) filtered and concentrated to yield the title compound (0.95 g, 90%) as a yellow oil and as a mixture of amide rotamers: $^1$H NMR (500 MHz, CDCl$_3$) δ 7.21-7.00 (m, 3H), 6.67-6.48 (m, 1H), 6.41-6.36 (m, 1H), 5.76-5.66 (m, 1H), 4.75-4.65 (m, 2H), 3.99-3.93 (m, 2H), 3.03 (s, 3H), 1.83-1.78 (m, 2H), 1.07-1.03 (m, 3H).

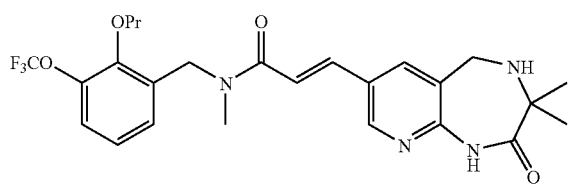

C$_{25}$H$_{29}$F$_3$N$_4$O$_4$
Exact Mass: 506.21 e) (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide A solution of N-methyl-N-(2-propoxy-3-trifluoromethoxybenzyl)acrylamide (0.468 g, 1.47 mmol) in propionitrile (5 mL) and DMF (1 mL) was deoxygenated with Ar for 20 min. The solution was treated sequentially with diisopropylethylamine (0.40 mL, 2.3 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. Pd(OAc)$_2$ (0.024 g, 0.111 mmol) and P(o-tol)$_3$ (0.067 g, 0.222 mmol) were added and the solution was deoxygenated with Ar for 20 minutes. The mixture was heated to reflux for 18 h, then allowed to cool. The mixture was diluted with EtOAc (30 mL) and then washed with H$_2$O (3×50 mL) and brine (2×100 mL), dried (Na$_2$SO$_4$) and concentrated to a yellow-orange solid. Purification by column chromatography (silica gel, CH$_2$Cl$_2$/MeOH, 100 to 98:2) gave the title compound (0.25 g, 31%) as an off-white solid and as a mixture of amide rotamers: $^1$H NMR (300 MHz, DMSO-d$_6$) δ 9.80-9.78 (m, 1H), 8.41-8.36 (m, 1H), 8.01-7.92 (m, 1H), 7.56-7.49 (m, 1H), 7.36-7.08 (m, 4H), 4.87-4.69 (m, 2H), 3.96-3.83 (m, 4H), 3.16-2.88 (m, 4H), 1.78-1.71 (m, 2H), 1.31-1.29 (m, 6H), 1.03-0.98 (m, 3H); MS (ESI) m/e 507 (M+H)$^+$.

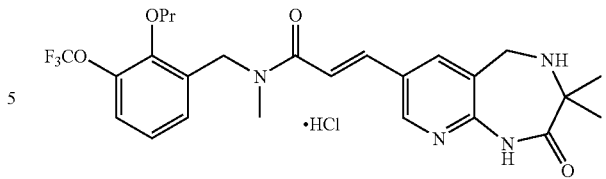

C$_{25}$H$_{30}$ClF$_3$N$_4$O$_4$
Exact Mass: 542.19 f) (E)-3-(3,3-Dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide hydrochloride A stirring solution of (E)-3-(3,3-dimethyl-2-oxo-2,3,4,5-tetrahydro-1H-pyrido[2,3-e][1,4]diazepin-7-yl)-N-methyl-N-(2-propoxy-3-trifluoromethoxybenzyl)acrylamide (0.255 g, 0.503 mmol) in CH$_2$Cl$_2$ (5 mL) under N$_2$, was treated with anhydrous HCl (0.25 mL of a 2 M solution in diethyl ether, 0.5 mmol). After stirring for 18 h, the resulting solid was collected by filtration and washed with Et$_2$O (150 mL). The solid was dried under vacuum to yield the target compound (0.21 g, 82%) as an off white solid and as a mixture of amide rotamers: $^1$H NMR (300 MHz, DMSO-d$_6$) δ 10.93-10.91 (m, 1H), 10.51 (br s, 2H), 8.66-8.64 (m, 1H), 8.40-8.32 (m, 1H), 7.63-7.54 (m, 1H), 7.40-7.09 (m, 4H), 4.89-4.70 (m, 2H), 4.41-4.36 (m, 2H), 3.96-3.90 (m, 2H), 3.18-2.87 (m, 3H), 1.79-1.70 (m, 2H), 1.63-1.61 (m, 6H), 1.09-0.97 (m, 3H); MS (ESI) m/e 507 (M+H)$^+$.

Example 3

Preparation of (E)-N-(3-Chloro-2-ethoxybenzyl)-N-methyl-3-(7-oxo-5,6,7,8-tetrahydro-[1,8]naphthyridin-3-yl)acrylamide

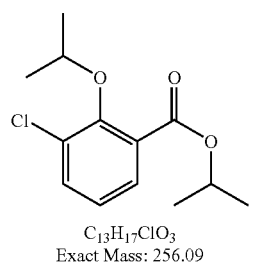 [SMILES: CC(C)OC(=O)c1cccc(Cl)c1OC(C)C]

C$_{13}$H$_{17}$ClO$_3$
Exact Mass: 256.09 a) 3-Chloro-2-isopropoxybenzoic acid isopropyl ester

2-Iodopropane (1.73 mL, 17.3 mmol) was added to a stirring solution of 3-chloro-2-hydroxybenzoic acid (2.00 g, 11.5 mmol) and K$_2$CO$_3$ (3.52 g, 25.4 mmol) in DMF (25 mL) under N$_2$. After stirring at 70° C. for 18 h, additional 2-iodopropane (1.73 mL, 17.3 mmol) was added. The solution was allowed to stir for an additional 48 h. The reaction was quenched with H$_2$O (70 mL) and the mixture was extracted with Et$_2$O (2×100 mL). The combined organics were washed with brine (100 mL), dried (Na$_2$SO$_4$) and concentrated to yield the title compound (2.29 g, 77%) as a clear oil: $^1$H NMR (300 MHz, DMSO-d$_6$) δ 7.68 (dd, J=8.1, 1.8 Hz, 1H), 7.58 (dd, J=7.8, 1.8 Hz, 1H), 7.20 (t, J=7.8 Hz, 1H), 5.16-5.50 (m, 1H), 4.39-4.30 (m, 1H), 1.29 (d, J=7.2 Hz, 6H), 1.22 (d, J=6.0 Hz, 6H).

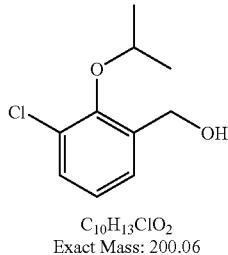

C$_{10}$H$_{13}$ClO$_2$
Exact Mass: 200.06 b) (3-Chloro-2-isopropoxyphenyl)methanol

Diisobutylaluminum lithium hydride (26.8 mL of a 1.0 M in hexanes, 26.8 mmol) was added dropwise to a solution of 3-chloro-2-isopropoxybenzoic acid isopropyl ester (2.29 g, 8.94 mmol) in THF (20 mL) under N$_2$ at 0° C. After the addition was complete, the ice bath was removed, the solution warmed to ambient temperature, and the reaction mixture stirred for 5 d. The reaction was cooled to 0° C. and quenched using 1N HCl (100 mL) until all the solids dissolved. The solution was extracted with Et$_2$O (3×50 mL). The combined organics were washed with brine (2×100 mL), dried (Na$_2$SO$_4$) and concentrated to yield the title compound (1.60 g, 89%) as an off-white solid: $^1$H NMR (500 MHz, DMSO-d$_6$) δ 7.41 (d, J=4.5 Hz, 1H), 7.33 (dd, J=8.0, 1.5 Hz, 1H), 7.11 (t, J=8.0 Hz, 1H), 5.19 (t, J=5.7 Hz, 1H), 4.53 (d, J=5.5 Hz, 1H), 4.44-4.36 (m, 1H), 1.24 (d, J=6.1 Hz, 6H).

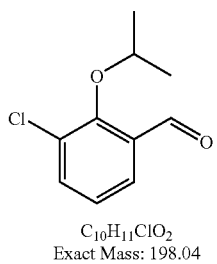

C$_{10}$H$_{11}$ClO$_2$
Exact Mass: 198.04 c) 3-Chloro-2-isopropoxybenzaldehyde

MnO$_2$ (4.86 g, 56.0 mmol) was added to a stirring solution of (3-chloro-2-isopropoxyphenyl)methanol (1.60 g, 8.00 mmol) in benzene (75 mL), under N$_2$. After stirring for 48 h, the solution was filtered over diatomaceous earth, the pad was rinsed with CH$_2$Cl$_2$ (100 mL), and the solution was concentrated to a yellow oil. Purification by column chromatography (silica gel hexanes/EtOAc, 98:2) gave the title compound (0.50 g, 31%) as a clear oil: $^1$H NMR (300 MHz, DMSO-d$_6$) δ 10.28 (s, 1H), 7.84 (dd, J=7.8, 1.5 Hz, 1H), 7.72 (dd, J=7.8, 1.5 Hz, 1H), 7.31 (t, J=8.1 Hz, 1H), 4.53-4.48 (m, 1H), 1.32 (d, J=6.0 Hz, 6H).

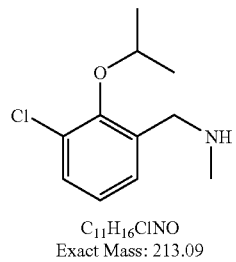

C$_{11}$H$_{16}$ClNO
Exact Mass: 213.09 d) (3-chloro-2-isopropoxybenzyl)methylamine

Methylamine (10.3 mL of a 2.0 M solution in MeOH, 20.6 mmol) was added to 3-chloro-2-isopropoxybenzaldehyde (0.500 g, 2.52 mmol) and the mixture was stirred for 72 h. The solution was concentrated under reduced pressure. The resulting light yellow oil was dissolved in EtOH (10.3 mL) and treated with NaBH$_4$ (0.095 g, 2.52 mmol). After stirring for 18 h, the reaction mixture was concentrated under reduced pressure, dissolved in 1 N NaOH (20 mL) and extracted with Et$_2$O (3×50 mL). The combined organics were washed with brine (2×75 mL), dried (Na$_2$SO$_4$) and concentrated to give the title compound (0.50 g, 93%) as a yellow oil: $^1$H NMR (300 MHz, DMSO-d$_6$) δ 7.40-7.31 (m, 2H), 7.08 (t, J=7.8 Hz, 1H), 4.42 (q, J=6.1 Hz, 1H), 3.66 (s, 2H), 2.25 (s, 3H), 2.02 (br s, 1H), 1.25 (d,

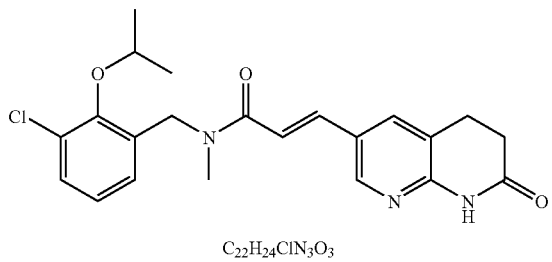

C$_{22}$H$_{24}$ClN$_3$O$_3$
Exact Mass: 413.15 e) (E)-N-(3-Chloro-2-ethoxybenzyl)-N-methyl-3-(7-oxo-5,6,7,8-tetrahydro-[1,8]naphthyridin-3-yl)acrylamide A stirring solution of (3-chloro-2-isopropoxybenzyl)methylamine (0.229 g, 1.07 mmol) and diisopropylethylamine (0.51 mL, 2.9 mmol) in DMF (20 mL) under N$_2$ was treated sequentially with (E)-3-(7-oxo-5,6,7,8-tetrahydro-[1,8]naphthyridin-3-yl)acrylic acid hydrochloride (0.250 g, 0.980 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with H$_2$O (30 mL). The resulting solids were collected by filtration and washed with Et$_2$O (100 mL), suspended in MeOH (30 mL) and sonicated for 30 minutes. The solids were then collected by filtration, washed with MeOH and dried to yield the title compound (0.085 g, 21%) as a white solid and as a mixture of amide rotamers: $^1$H NMR (300 MHz, DMSO-d$_6$) δ 10.67-10.64 (m, 1H), 8.37-8.32 (m, 1H), 8.09-7.91 (m, 1H), 7.53-7.48 (m, 1H), 7.42-7.37 (m, 1H), 7.28-7.02 (m, 3H), 4.83-4.68 (m, 2H), 4.53-4.45 (m, 1H), 2.94-2.85 (m, 5H), 2.56-2.49 (m, 2H), 1.33-1.28 (m, 6H); MS (ESI) m/e 414 (M+H)+.

Example 4

Preparation of (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide hydrochloride

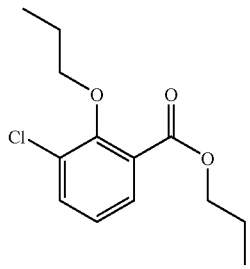

C$_{13}$H$_{17}$ClO$_3$
Exact Mass: 256.09 a) 3-Chloro-2-propoxybenzoic acid propyl ester

To a solution of 3-chlorosalicylic acid (3.42 g, 19.8 mmol) in DMF (45 mL) was added K$_2$CO$_3$ (6.02 g, 43.5 mmol) followed by 1-bromopropane (5.39 mL, 59.4 mmol). The mixture was heated to 30° C. After 18 h, additional 1-bromopropane (1.79 mL, 19.6 mmol) was added to ensure the dialkylated product. After stirring for an additional 48 h, the reaction was quenched with H$_2$O (75 mL) and the mixture was extracted with Et$_2$O (3×100 mL). The combined organics were washed with brine (2×100 mL), dried (Na$_2$SO$_4$) and concentrated to yield the title compound (2.62 g, 51%) as a yellow oil: $^1$H NMR (300 MHz, DMSO-d$_6$) δ 7.71 (dd, J=7.9, 1.5 Hz, 1H), 7.64 (dd, J=7.8, 1.6 Hz, 1H), 7.24 (t, J=7.8 Hz, 1H), 4.22 (t, J=6.6 Hz, 2H), 3.92 (t, J=6.5 Hz, 2H), 1.78-1.67 (m, 4H), 1.01-0.93 (m, 6H).

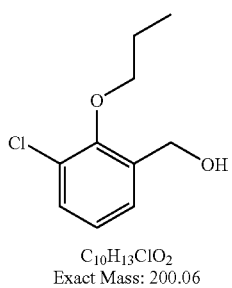

C$_{10}$H$_{13}$ClO$_2$
Exact Mass: 200.06 b) (3-Chloro-2-propoxyphenyl)methanol

Diisobutylaluminum lithium hydride (30.7 mL of a 1.0 M in hexanes, 30.7 mmol) was added dropwise to an ice-cold solution of 3-chloro-2-propoxybenzoic acid propyl ester (2.63 g, 10.2 mmol) in THF (20 mL). After the addition was complete, the ice bath was removed and the mixture stirred at ambient temperature for 18 h. The reaction was cooled to 0° C. and HCl (1N, 100 mL) was added until all the resulting solids returned to solution. The solution was extracted with Et$_2$O (3×100 mL). The combined organics were washed with brine (2×100 mL), dried (Na$_2$SO$_4$) filtered and concentrated to yield the title compound (1.12 g, 56%) as a light yellow oil: $^1$H NMR (500 MHz, DMSO-d$_6$) δ 7.40-7.33 (m, 2H), 7.13 (t, J=7.7 Hz, 1H), 5.22 (t, J=5.6 Hz, 1H), 5.56 (d, J=5.6 Hz, 2H), 3.84 (t, J=6.4 Hz, 2H), 1.76-1.71 (m, 2H), 1.01 (t, J=7.3 Hz, 3H).

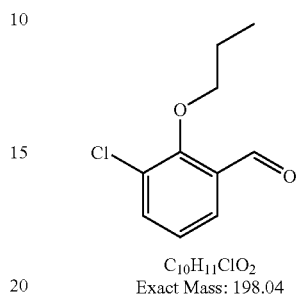

C$_{10}$H$_{11}$ClO$_2$
Exact Mass: 198.04 c) 3-Chloro-2-propoxybenzaldehyde

MnO$_2$ (3.40 g, 39.2 mmol) was added to a stirring solution of (3-chloro-2-propoxyphenyl)methanol (1.12 g, 5.60 mmol) in benzene (54 mL) under N$_2$. After stirring for 48 h, the solution was filtered over diatomaceous earth, the pad rinsed with CH$_2$Cl$_2$ (100 mL), and the solution concentrated to a clear oil. Purification by column chromatography (silica gel, hexanes/EtOAc, 98:2) gave the title compound (0.42 g, 38%) as a clear oil: $^1$H NMR (300 MHz, DMSO-d$_6$) δ 10.27 (s, 1H), 7.85 (d, J=1.6 Hz, 1H), 7.73 (d, J=1.6 Hz, 1H), 7.32 (t, J=7.8 Hz, 1H), 4.04 (t, J=6.4 Hz, 2H), 1.85-1.78 (m, 2H), 1.03 (t, J=7.3

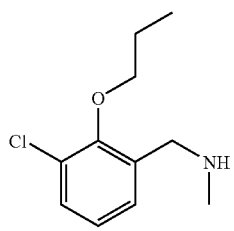

C$_{11}$H$_{16}$ClNO
Exact Mass: 213.09 d) (3-Chloro-2-propoxybenzyl)methylamine

A solution of methylamine (8.5 mL of a 2.0 M solution in MeOH, 17 mmol) was added to 3-chloro-2-propoxybenzaldehyde (0.425 g, 2.14 mmol) and the mixture was stirred for 72 h. The solution was concentrated under reduced pressure. The resulting clear oil was dissolved in EtOH (8.5 mL) and treated with NaBH$_4$ (0.080 g, 2.1 mmol). After stirring for 18 h, the reaction mixture was concentrated under reduced pressure and then dissolved in 1 N NaOH (10 mL). The mixture was extracted with Et$_2$O (3×50 mL). The combined organics were washed with brine (2×100 mL), dried (Na$_2$SO$_4$) and concentrated to yield the title compound (0.441 g, 96%) as a light yellow oil: $^1$H NMR (300 MHz, DMSO-d$_6$) δ 7.37-7.31 (m, 2H), 7.08 (t, J=7.7 Hz, 1H), 3.85 (t, J=6.4 Hz, 2H), 3.67 (s, 2H), 2.26 (s, 3H), 2.04 (br s, 1H), 1.82-1.70 (m, 2H), 1.02 (t, J=7.3 Hz, 3H).

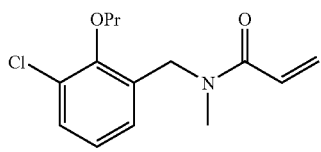

C₁₄H₁₈ClNO₂
Exact Mass: 267.10

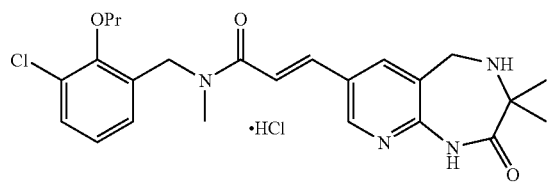

C₂₄H₃₀Cl₂N₄O₃
Exact Mass: 492.17 d) N-(3-Chloro-2-propoxybenzyl)-N-methylacrylamide

To a solution of (3-chloro-2-propoxybenzyl)methylamine (0.435 g, 2.04 mmol) in CH₂Cl₂ (18 mL) was added acryloyl chloride (0.18 mL, 2.24 mmol) drop-wise. After stirring for five minutes, triethylamine (0.531 mL, 2.24 mmol) was added. The solution was stirred under N₂ for 18 h. The solution was diluted with CH₂Cl₂ (30 mL) and then washed with H₂O (3×50 mL) and brine (2×100 mL), dried over Na₂SO₄, filtered and concentrated to yield the title compound (0.48 g, 89%) as a light yellow oil and as a mixture of amide rotamers: ¹H NMR (500 MHz, CDCl₃) δ 7.31-7.26 (m, 1H), 7.10-6.98 (m, 2H), 6.63-6.37 (m, 2H), 5.77-5.73 (m, 1H), 4.76-4.65 (m, 2H), 3.94-3.89 (m, 2H), 3.01 (s, 3H), 1.89-1.82 (m, 2H), 1.11-1.05 (m, 3H).

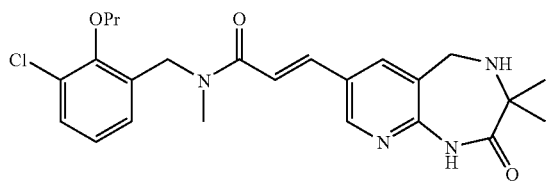

e) (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide A solution of N-(3-chloro-2-propoxybenzyl)-N-methylacrylamide (0.392 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydropyrido[2,3-e][1,4]diazepin-2-one (0.300 g, 1.11 mmol). The solution was deoxygenated with Ar for 20 min. Pd(OAc)₂ (0.024 g, 0.111 mmol) and P(o-tol)₃ (0.067 g, 0.222 mmol) were then added and the solution was deoxygenated again with Ar for 20 min. The mixture was heated to reflux for 18 h, then allowed to cool. The mixture was diluted with EtOAc (30 mL) and was washed with H₂O (3×50 mL). The organic layer was washed with brine (1×100 mL), dried (Na₂SO₄) and concentrated to an orange oil. Purification by column chromatography (silica gel, CH₂Cl₂/MeOH, 100 to 98:2) gave the title compound (0.30 g, 59%) as a light yellow solid and as a mixture of amide rotamers: ¹H NMR (300 MHz, DMSO-d₆) δ 9.80-9.78 (m, 1H), 8.40-8.37 (m, 1H), 8.01-7.92 (m, 1H), 7.54-7.49 (m, 1H), 7.41-7.25 (m, 2H), 7.15-7.05 (m, 2H), 4.86-4.68 (m, 2H), 3.91-3.84 (m, 4H), 3.14-2.95 (m, 4H), 1.83-1.76 (m, 2H), 1.31-1.29 (m, 6H), 1.05-0.99 (m, 3H).

f) (E)-N-(3-Chloro-2-propoxybenzyl)-3-(3,3-dimethyl-2-oxo-2,3,4,5-tetrahydro-1H-pyrido[2,3-e][1,4]diazepin-7-yl)-N-methylacrylamide hydrochloride A stirring solution of (E)-N-(3-chloro-2-propoxybenzyl)-3-(3,3-dimethyl-2-oxo-2,3,4,5-tetrahydro-1H-pyrido[2,3-e][1,4]diazepin-7-yl)-N-methylacrylamide (0.300 g, 0.656 mmol) in CH₂Cl₂ (7 mL) under N₂ was treated with anhydrous HCl (0.32 mL of a 2 M solution in diethyl ether, 0.64 mmol) After stirring for 7 h, the resulting solid was collected by filtration, washed with Et₂O (100 mL) and then dried to yield the target compound (0.25 g, 79%) as an off white solid and as a mixture of amide rotamers: ¹H NMR (300 MHz, DMSO-d₆) δ 10.93 (br s, 1H), 10.38 (br s, 2H), 8.66-8.63 (m, 1H), 8.37-8.28 (m, 1H), 7.62-7.54 (m, 1H), 7.44-7.32 (m, 2H), 7.19-7.02 (m, 2H), 4.87-4.69 (m, 2H), 4.41-4.37 (m, 2H), 3.94-3.87 (m, 2H), 3.16-2.89 (m, 3H), 1.83-1.76 (m, 2H), 1.61-1.59 (m, 6H), 1.05-0.99 (m, 3H); MS (APCI) m/e 457 (M+H)⁺.

Example 5

Preparation of (E)-N-(2-Isobutoxy-3-methoxybenzyl)-N-methyl-3-(7-oxo-5,6,7,8-tetrahydro-[1,8]naphthyridin-3-yl)acrylamide

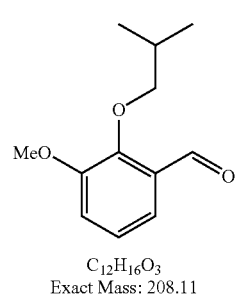

C₁₂H₁₆O₃
Exact Mass: 208.11 a) 2-Isobutoxy-3-methoxybenzaldehyde

A solution of 2-hydroxy-3-methoxybenzaldehyde (4.00 g, 26.2 mmol) in DMF (50 mL) was treated with K₂CO₃ (8.00 g, 57.9 mmol) followed by iodoisobutane (4.53 mL, 39.4 mmol). The resulting slurry was stirred for at ambient temperature for 18 h. Additional DMF (70 mL) was added to help aid stirring, and the mixture was heated to 40° C. for 18 h. Additional iodoisobutane (2.26 mL, 19.7 mmol) was added and the mixture was stirred at ambient temperature for 48 h. The reaction was quenched with H₂O (100 mL) and the mixture was extracted with EtOAc (3×100 mL). The combined organics were washed with H₂O (2×100 mL) and brine (2×100 mL), dried (Na$_2$SO$_4$) and concentrated to an orange oil. Purification by column chromatography (silica gel, hexanes/EtOAc, 90:10) gave the title compound (2.46 g, 62%) as a clear oil: $^1$H NMR (300 MHz, DMSO-d$_6$) δ 10.34 (s, 1H), 7.36 (dd, J=7.9, 1.7 Hz, 1H), 7.27 (dd, J=7.8, 1.7 Hz, 1H), 7.19 (dt, J=7.8, 0.6 Hz, 1H), 3.85 (m, 5H), 2.09-2.00 (m, 1H), 0.99 (d, J=6.7 Hz, 6H).

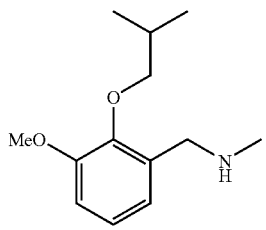

C$_{13}$H$_{21}$NO$_2$
Exact Mass: 223.16 b) (2-Isobutoxy-3-methoxybenzyl)methylamine

A solution of methylamine (64 mL of a 2.0 M solution in MeOH, 128 mmol) was added to 2-isobutoxy-3-methoxybenzaldehyde (2.45 g, 11.9 mmol) and the solution was stirred for 18 h. The solution was concentrated under reduced pressure. The resulting clear oil was dissolved in EtOH (64 mL) and treated with NaBH$_4$ (0.616 g, 16.3 mmol). After stirring for 7 h, the mixture was concentrated under reduced pressure and then dissolved in 1 N NaOH (57 mL). The mixture was extracted with Et$_2$O (3×75 mL). The combined organics were washed with brine (2×100 mL), dried (Na$_2$SO$_4$) and concentrated to yield the title compound (2.43 g, 91%) as a light yellow oil: $^1$H NMR (300 MHz, DMSO-d$_6$) δ 7.01-6.88 (m, 3H), 3.76 (s, 3H), 3.63 (t, J=6.4 Hz, 3H), 2.25 (s, 3H), 2.00-1.93 (m, 1H), 1.84 (br s, 1H), 0.98 (d, J=6.6 Hz, 6H).

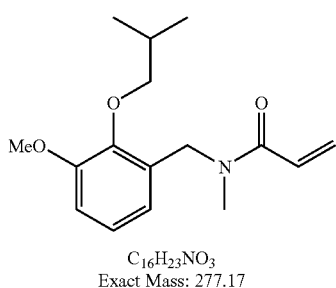 [SMILES: C=CC(=O)N(C)Cc1cccc(OC)c1OCC(C)C]

C$_{16}$H$_{23}$NO$_3$
Exact Mass: 277.17 c) N-(2-Isobutoxy-3-methoxybenzyl)-N-methylacrylamide

To a solution of (2-isobutoxy-3-methoxybenzyl)methylamine (2.00 g, 8.96 mmol) in CH$_2$Cl$_2$ (80 mL) was added acryloyl chloride (0.85 mL, 9.8 mmol) drop-wise. After stirring for five minutes, triethylamine (1.37 mL, 9.86 mmol) was added. The solution was stirred for 6 hours. The solution was diluted with CH$_2$Cl$_2$ (30 mL) and then washed with H$_2$O (3×100 mL) and brine (2×100 mL), dried (Na$_2$SO$_4$) and concentrated to yield the title compound (2.30 g, 92%) as a light yellow oil and as a mixture of amide rotamers: $^1$H NMR (500 MHz, DMSO-d$_6$) δ 7.06-6.93 (m, 2H), 6.85-6.62 (m, 1H), 6.57-6.53 (m, 1H), 6.17-6.13 (m, 1H), 5.73-5.63 (m, 1H), 4.64-4.58 (m, 2H), 3.79-3.78 (m, 3H), 3.69-3.66 (m, 2H), 2.95-2.87 (m, 3H), 2.01-1.98 (m, 1H), 0.99-0.97 (m, 6H).

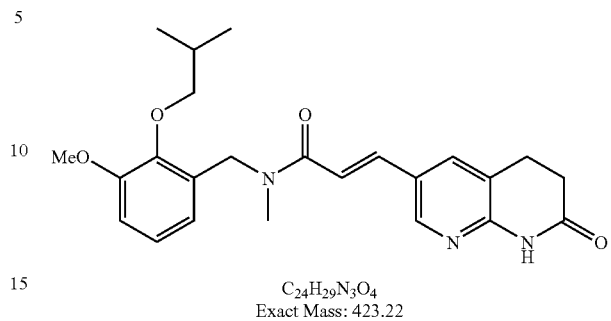

C$_{24}$H$_{29}$N$_3$O$_4$
Exact Mass: 423.22 d) (E)-N-(2-Isobutoxy-3-methoxybenzyl)-N-methyl-3-(7-oxo-5,6,7,8-tetrahydro-[1,8]naphthyridin-3-yl)acrylamide A solution of N-(2-isobutoxy-3-methoxybenzyl)-N-methyl-acrylamide (0.475 g, 1.71 mmol) in propionitrile (6 mL) and DMF (1.2 mL) was deoxygenated with Ar for 20 min. The solution was treated with diisopropylethylamine (0.48 mL, 2.77 mmol) and 6-bromo-3,4-dihydro-1H-[1,8]naphthyridin-2-one (0.300 g, 1.32 mmol). The solution was deoxygenated with Ar for 20 min. Pd(OAc)$_2$ (0.029 g, 0.13 mmol) and P(o-tol)$_3$ (0.080 g, 0.26 mmol) were then added and the mixture was deoxygenated with Ar for 20 min. The mixture was heated to reflux for 18 h. Upon cooling, a precipitate formed. The solids were collected by filtration and washed with water. Purification by column chromatography (silica gel, CH$_2$Cl$_2$/MeOH 9:1) gave an orange solid. The solid was dissolved in CH$_2$Cl$_2$ and the solution was diluted with hexanes. The resulting precipitate was collected by filtration, washed with Et$_2$O (50 mL) and dried to yield the title compound (0.18 g, 32%) as an off-white solid and as a mixture of amide rotamers: $^1$H NMR (300 MHz, DMSO-d$_6$) δ 10.66-10.64 (m, 1H), 8.36-8.32 (m, 1H), 8.09-8.00 (m, 1H), 7.53-7.47 (m, 1H), 7.27-7.20 (m, 1H), 7.04-7.96 (m, 2H), 6.66-6.60 (m, 1H), 4.79-4.64 (m, 2H), 3.79 (s, 3H), 3.72-3.67 (m, 2H), 3.10-2.85 (m, 5H), 2.56-2.49 (m, 2H), 2.03-1.97 (m, 1H), 1.00-0.97 (m, 6H); MS (ESI) m/e 424 (M+H)$^+$.

Example 6

Preparation of (E)-N-(3-Isopropyl-2-propoxybenzyl)-N-methyl-3-(7-oxo-5,6,7,8-tetrahydro-[1,8]naphthyridin-3-yl)acrylamide

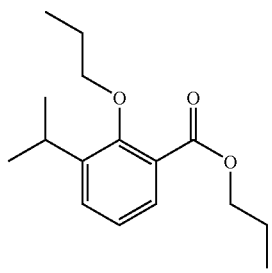

C$_{16}$H$_{24}$O$_3$
Exact Mass: 264.17 a) 3-Isopropyl-2-propoxybenzoic acid propyl ester

1-Bromopropane (7.55 mL, 83.1 mmol) was added to a stirring solution of 2-hydroxy-3-isopropylbenzoic acid (5.00 g, 27.7 mmol) and $K_2CO_3$ (11.48 g, 83.1 mmol) in DMF (60 mL). After stirring at 30° C. for 18 h, the reaction was quenched with $H_2O$ (100 mL) and the mixture extracted with EtOAc (3×100 mL). The combined organics were washed with brine (3×200 mL), dried ($Na_2SO_4$) and concentrated to a clear oil. Purification by column chromatography (silica gel, hexanes/EtOAc, 100 to 95:5) gave the title compound (3.96 g, 54%) as a clear oil: $^1$H NMR (300 MHz, $CDCl_3$) δ 7.60 (dd, J=7.6, 1.7 Hz, 1H), 7.41 (dd, J=7.7, 1.7 Hz, 1H), 7.10 (t, J=7.7 Hz, 1H), 4.26 (t, J=6.7 Hz, 2H), 3.83 (t, J=6.7 Hz, 2H), 3.46-3.37 (m, 1H), 1.87-1.75 (m, 4H), 1.22 (d, J=6.9 Hz, 6H), 1.06-0.99 (m, 6H).

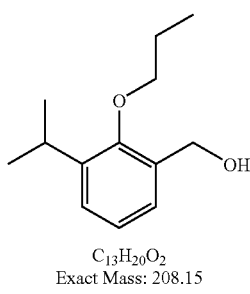

$C_{13}H_{20}O_2$
Exact Mass: 208.15 b) (3-Isopropyl-2-propoxyphenyl)methanol

Diisobutylaluminum lithium hydride (40.8 mL of a 1.0 M in hexanes, 40.8 mmol) was added dropwise to an ice-cold solution of 3-isopropyl-2-propoxybenzoic acid propyl ester (3.60 g, 13.6 mmol) in THF (30 mL). After the addition was complete, the ice bath was removed and the reaction mixture was stirred at ambient temperature for 18 h. The reaction was cooled to 0° C. and HCl (1N, 180 mL) was added until all the resulting solids returned to solution. The mixture was extracted with EtOAc (3×150 mL). The combined organics were washed with brine (2×200 mL), dried ($Na_2SO_4$) and concentrated to yield the title compound (2.76 g, 97%) as a yellow oil: $^1$H NMR (300 MHz, DMSO-$d_6$) δ 7.25 (d, J=6.3 Hz, 1H), 7.17 (d, J=5.9 Hz, 1H), 7.10 (t, J=7.5 Hz, 1H), 5.02 (t, J=5.6 Hz, 1H), 4.52 (d, J=5.5 Hz, 2H), 3.68 (t, J=6.4 Hz, 2H), 3.32-3.25 (m, 1H), 1.77-1.70 (m, 2H), 1.16 (d, J=6.9, 6H), 1.02 (t, J=7.3 Hz, 3H).

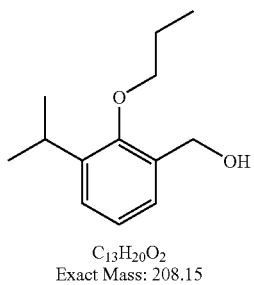

$C_{13}H_{20}O_2$
Exact Mass: 208.15 c) 3-Isopropyl-2-propoxybenzaldehyde $MnO_2$ (6.88 g, 79.2 mmol) was added to a stirring solution of (3-isopropyl-2-propoxyphenyl)methanol (2.75 g, 13.2 mmol) in benzene (130 mL) under $N_2$. After stirring for 48 h, the solution was filtered over diatomaceous earth, the pad rinsed with $CH_2Cl_2$ (200 mL) and the solution concentrated to a yellow oil. Purification by column chromatography (silica gel, hexanes/EtOAc, 100 to 98:2) gave the title compound (1.49 g, 54%) as a light yellow oil: $^1$H NMR (300 MHz, DMSO-$d_6$) δ 10.26 (s, 1H), 7.67 (dd, J=7.6, 1.7 Hz, 1H), 7.59 (dd, J=7.6, 1.7 Hz, 1H), 7.28 (t, J=7.6 Hz, 1H), 3.87 (t, J=6.4 Hz, 2H), 3.35-3.30 (m, 2H), 1.85-1.78 (m, 2H), 1.21 (t, J=6.9 Hz, 7H), 1.03 (t, J=7.3 Hz, 3H).

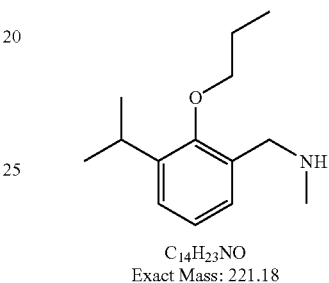

$C_{14}H_{23}NO$
Exact Mass: 221.18 d) (3-Isopropyl-2-propoxybenzyl)methylamine

A solution of methylamine (30 mL of a 2.0 M solution in MeOH, 60 mmol) was added to 3-isopropyl-2-propoxybenzaldehyde (1.49 g, 7.22 mmol) and the mixture was stirred for 72 h. The solution was concentrated under reduced pressure. The resulting dark yellow oil was dissolved in EtOH (30 mL) and treated with $NaBH_4$ (0.273 g, 7.22 mmol). After 18 h, the reaction mixture was concentrated under reduced pressure and dissolved in 1 N NaOH (30 mL). The mixture was extracted with $Et_2O$ (3×75 mL). The combined organics were dried ($Na_2SO_4$) and concentrated to yield the title compound (1.52 g, 95%) as an orange oil: $^1$H NMR (300 MHz, DMSO-$d_6$) δ 7.21-7.14 (m, 2H), 7.04 (t, J=7.5 Hz, 1H), 3.70 (t, J=6.3 Hz, 2H), 3.63 (s, 2H), 3.32-3.23 (m, 1H), 2.28 (s, 3H), 1.78 (br s, 1H), 1.76-1.71 (m, 2H), 1.16 (d, J=6.9 Hz, 6H), 1.03 (t, J=7.3 Hz, 3H).

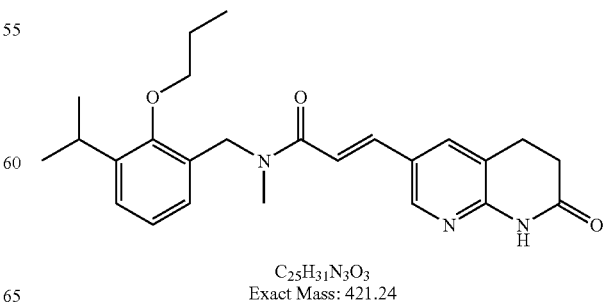

$C_{25}H_{31}N_3O_3$
Exact Mass: 421.24 e) (E)-N-(3-Isopropyl-2-propoxybenzyl)-N-methyl-3-(7-oxo-5,6,7,8-tetrahydro-[1,8]naphthyridin-3-yl)acrylamide A solution of (3-isopropyl-2-propoxybenzyl)methylamine (0.238 g, 1.07 mmol) and diisopropyl-ethylamine (0.51 mL, 2.9 mmol) in DMF (20 mL) under $N_2$ was treated sequentially with (E)-3-(7-oxo-5,6,7,8-tetrahydro-[1,8]naphthyridin-3-yl)acrylic acid hydrochloride (0.250 g, 0.981 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with $H_2O$ (30 mL). The resulting solids were collected by filtration and when washed with $Et_2O$ (50 mL) were unexpectedly dissolved. The filtrate was extracted with EtOAc (3×50 mL). The combined organics were washed with brine (2×100 mL), dried ($Na_2SO_4$) and concentrated to a light yellow solid. Purification by column chromatography (silica gel, $CH_2Cl_2$/MeOH, 100 to 99.5:0.5) gave the title compound (0.26 g, 63%) as a white solid and as a mixture of amide rotamers: $^1$H NMR (500 MHz, DMSO-$d_6$) δ 10.64-10.62 (m, 1H), 8.37-8.31 (m, 1H), 8.09-7.98 (m, 1H), 7.52-7.49 (m, 1H), 7.28-7.19 (m, 2H), 7.10-7.06 (m, 1H), 6.89-6.87 (m, 1H), 4.80-4.66 (m, 2H), 3.76-3.70 (m, 2H), 3.31-3.26 (m, 1H), 3.12-2.85 (m, 5H), 2.55-2.49 (m, 2H), 1.82-1.76 (m, 2H), 1.19-1.17 (m, 6H), 1.05-1.02 (m, 3H); MS (ESI) m/e 422 (M+H)$^+$.

Example 7

Preparation of (E)-N-(2-Ethoxy-3-isopropylbenzyl)-N-methyl-3-(7-oxo-5,6,7,8-tetrahydro-[1,8]naphthyridin-3-yl)acrylamide

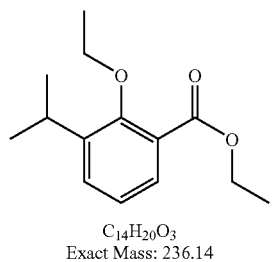 [SMILES: CCOC(=O)c1cccc(C(C)C)c1OCC]

$C_{14}H_{20}O_3$
Exact Mass: 236.14 a) Preparation of 2-Ethoxy-3-isopropylbenzoic acid propyl ester

Iodoethane (6.64 mL, 83.1 mmol) was added to a stirring solution of 2-hydroxy-3-isopropylbenzoic acid (5.00 g, 27.7 mmol) and $K_2CO_3$ (11.48 g, 83.1 mmol) in DMF (60 mL). After stirring at 30° C. for 18 h, the reaction was quenched with $H_2O$ (100 mL) and the mixture was extracted with EtOAc (3×100 mL). The combined organics were washed with brine (3×250 mL), dried ($Na_2SO_4$) and concentrated to a clear oil. Purification by column chromatography (silica gel, hexanes/EtOAc, 100 to 98:2) gave the title compound (4.54 g, 69%) as an orange oil: $^1$H NMR (300 MHz, CDCl$_3$) δ 7.60 (dd, J=7.6, 1.7 Hz, 1H), 7.41 (dd, J=7.7, 1.7 Hz, 1H), 7.11 (t, J=7.7 Hz, 1H), 4.37 (q, J=7.1 Hz, 2H), 3.95 (q, J=7.0 Hz, 2H), 3.43-3.39 (m, 1H), 1.45-1.39 (m, 6H), 1.22 (d, J=6.9 Hz, 6H).

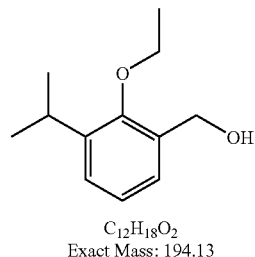

$C_{12}H_{18}O_2$
Exact Mass: 194.13 b) Preparation of (2-Ethoxy-3-isopropylphenyl)methanol

Diisobutylaluminum lithium hydride (55.0 mL of a 1.0 M in hexanes, 55.0 mmol) was added drop-wise to an ice-cold solution of 2-ethoxy-3-isopropylbenzoic acid propyl ester (4.34 g, 18.3 mmol) in THF (40 mL). After the addition was complete, the ice bath was removed and reaction mixture was stirred for 18 h. The reaction was cooled to 0° C. and HCl (1N, 275 mL) was added until all the resulting solids returned to solution. The mixture was extracted with EtOAc (3×150 mL). The combined organics were washed with brine (2×200 mL), dried ($Na_2SO_4$) and concentrated to yield the title compound (3.73 g, quantitative) as a light yellow oil: $^1$H NMR (300 MHz, DMSO-$d_6$) δ 7.24 (d, J=5.7 Hz, 1H), 7.16 (d, J=1.7 Hz, 1H), 7.07 (t, J=7.5 Hz, 1H), 5.02 (t, J=5.6 Hz, 1H), 4.52 (d, J=-5.6 Hz, 2H), 3.77 (q, J=7.0 Hz, 2H), 3.32-3.25 (m, 1H), 1.33 (t, J=6.9 Hz, 3H), 1.16 (d, J=6.9, 6H).

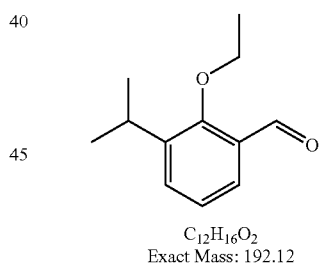

$C_{12}H_{16}O_2$
Exact Mass: 192.12 c) 2-Ethoxy-3-isopropyl-benzaldehyde $MnO_2$ (9.49 g, 109 mmol) was added to a stirring solution of (2-ethoxy-3-isopropylphenyl)methanol (3.54 g, 18.2 mmol) in benzene (175 mL) under $N_2$. After stirring for 48 h, the solution was filtered over diatomaceous earth and the pad rinsed with $CH_2Cl_2$ (200 mL), and the solution was concentrated to a clear oil. Purification by column chromatography (silica gel, hexanes/EtOAc, 100 to 98:2) gave the title compound (1.49 g, 42%) as a light yellow oil: $^1$H NMR (300 MHz, DMSO-$d_6$) δ 10.26 (s, 1H), 7.67 (dd, J=7.6, 1.7 Hz, 1H), 7.59 (dd, J=7.6, 1.7 Hz, 1H), 7.28 (t, J=7.6 Hz, 1H), 3.97 (q, J=6.9 Hz, 2H), 3.32-3.30 (m, 1H), 1.39 (t, J=6.9 Hz, 3H), 1.21 (d, J=6.9 Hz, 6H).

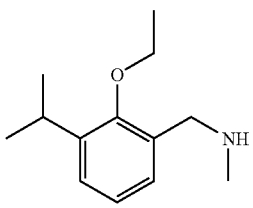

C₁₃H₂₁NO
Exact Mass: 207.16 d) (2-Ethoxy-3-isopropylbenzyl)methylamine

A solution of methylamine (30 mL of a 2.0 M solution, 60 mmol) was added to 2-ethoxy-3-isopropylbenzaldehyde (1.49 g, 7.75 mmol) and the mixture was stirred for 72 h. The solution was concentrated under reduced pressure. The residue was dissolved in EtOH (30 mL) and treated with NaBH₄ (0.293 g, 7.75 mmol). After stirring for 18 h, the reaction mixture was concentrated under reduced pressure and then dissolved in 1 N NaOH (30 mL). The mixture was extracted with Et₂O (3×50 mL). The combined organics were collected, washed with brine (2×100 mL), dried (Na₂SO₄) and concentrated to yield the title compound (1.51 g, 94%) as a light yellow oil: ¹H NMR (300 MHz, DMSO-d₆) δ 7.21-7.13 (m, 2H), 7.04 (t, J=7.5 Hz, 1H), 3.79 (q, J=7.0 Hz, 2H), 3.63 (s, 2H), 3.28-3.23 (m, 1H), 2.29 (s, 3H), 1.93 (br s, 1H), 1.35 (t, J=3.8 Hz, 3H), 1.16 (d, J=6.9 Hz, 6H).

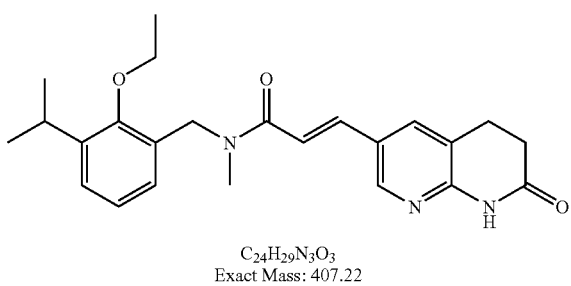 [SMILES: CCOc1c(CN(C)C(=O)/C=C/c2cnc3c(c2)CCC(=O)N3)cccc1C(C)C]

C₂₄H₂₉N₃O₃
Exact Mass: 407.22 e) (E)-N-(2-Ethoxy-3-isopropylbenzyl)-N-methyl-3-(7-oxo-5,6,7,8-tetrahydro-[1,8]naphthyridin-3-yl)acrylamide A solution of (2-ethoxy-3-isopropylbenzyl)methylamine (0.223 g, 1.07 mmol) and diisopropyl-ethylamine (0.51 mL, 2.94 mmol) in DMF (20 mL) was treated sequentially with (E)-3-(7-oxo-5,6,7,8-tetrahydro-[1,8]naphthyridin-3-yl)acrylic acid hydrochloride (0.250 g, 0.981 mmol), 1-hydroxybenzotriazole hydrate (0.144 g, 1.07 mmol) and 1-(3-dimethylaminopropyl)-3-ethylcarbodiimide hydrochloride (0.205 g, 1.07 mmol). After stirring for 18 h, the reaction mixture was diluted with H₂O (30 mL). The resulting solids were collected by filtration, and when washed with Et₂O (50 mL), unexpectedly dissolved. The filtrate was extracted with EtOAc (3×50 mL). The combined organics were washed with brine (2×100 mL), dried over Na₂SO₄, filtered and concentrated to a light orange solid. Purification by column chromatography (silica gel, CH₂Cl₂/MeOH, 100 to 99.5:0.5) gave the title compound (0.20 g, 52%) as a white solid and as a mixture of amide rotamers: ¹H NMR (500 MHz, DMSO-d₆) δ 10.64-10.61 (m, 1H), 8.37-8.31 (m, 1H), 8.09-7.99 (m, 1H), 7.52-7.49 (m, 1H), 7.28-7.20 (m, 2H), 7.11-7.05 (m, 1H), 6.89-6.86 (m, 1H), 4.81-4.66 (m, 2H), 3.86-3.79 (m, 2H), 3.28-3.25 (m, 1H), 3.11-2.85 (m, 5H), 2.55-2.49 (m, 2H), 1.39-1.35 (m, 3H), 1.19-1.17 (m, 6H); MS (ESI) m/e 408 (M+H)⁺.

Example 8

Preparation of (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide hydrochloride

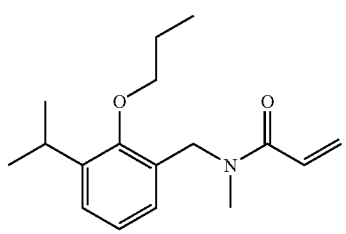

C₁₇H₂₅NO₂
Exact Mass: 275.19 a) N-(3-Isopropyl-2-propoxybenzyl)-N-methylacrylamide

To a solution of (3-isopropyl-2-propoxybenzyl)methylamine (1.00 g, 4.51 mmol) in CH₂Cl₂ (40 mL) was added acryloyl chloride (0.43 mL, 4.96 mmol) drop-wise. After stirring for five minutes, triethylamine (0.69 mL, 4.96 mmol) was added and the solution was stirred for 5 hours. The solution was diluted with CH₂Cl₂ (50 mL), washed with H₂O (3×50 mL) and brine (2×100 mL), dried (Na₂SO₄) and concentrated to yield the title compound (1.10 g, 88%) as a light yellow oil and a mixture of amide rotamers: ¹H NMR (300 MHz, DMSO-d₆) δ 7.23-7.19 (m, 1H), 7.10-7.06 (m, 1H), 6.86-6.80 (m, 2H), 6.20-6.13 (m, 1H), 5.61-5.79 (m, 1H), 4.68-4.61 (m, 2H), 3.71-3.67 (m, 2H), 3.34-3.26 (m, 1H), 3.01-2.88 (m, 3H), 1.78-1.76 (m, 2H), 1.19-1.17 (m, 6H), 1.06-1.00 (m, 3H).

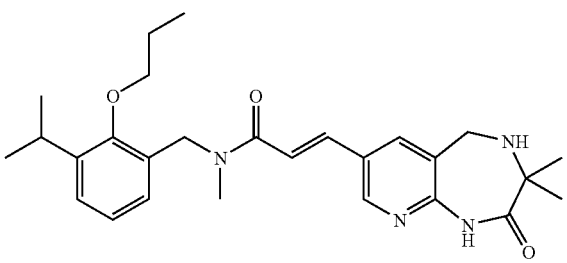

C₂₇H₃₆N₄O₃
Exact Mass: 464.28 b) (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide A solution of N-(3-isopropyl-2-propoxybenzyl)-N-methylacrylamide (0.397 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. Pd(OAc)$_2$ (0.024 g, 0.111 mmol) and P(o-tol)$_3$ (0.067 g, 0.222 mmol) were then added and the mixture deoxygenated with Ar for 20 min. The mixture was heated to reflux for 18 h, then allowed to cool. The solution was diluted with EtOAc (30 mL) and H$_2$O (50 mL). The aqueous layer was extracted with EtOAc (3×50 mL). The combined organics were washed with brine (2×100 mL), dried over Na$_2$SO$_4$, filtered and concentrated to an orange oil. Purification by column chromatography (silica gel, CH$_2$Cl$_2$/MeOH, 100 to 95:5) gave the title compound (0.16 g, 31%) as an off-white solid and as a mixture of amide rotamers: $^1$H NMR (300 MHz, DMSO-d$_6$) δ 9.80-9.77 (m, 1H), 8.40-8.35 (m, 1H), 8.01-7.91 (m, 1H), 7.55-7.48 (m, 1H), 7.31-7.20 (m, 2H), 7.10-7.03 (m, 1H), 6.88-6.85 (m, 1H), 4.81-4.66 (m, 2H), 3.90-3.83 (m, 2H), 3.77-3.69 (m, 2H), 3.32-3.25 (m, 1H), 3.12-2.90 (m, 4H), 1.81-1.77 (m, 2H), 1.31-1.28 (m, 6H), 1.19-1.17 (m, 6H), 1.06-1.01 (3H).

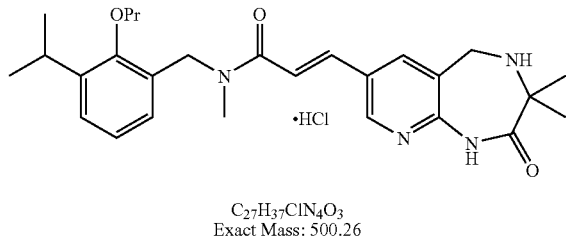

C$_{27}$H$_{37}$ClN$_4$O$_3$
Exact Mass: 500.26 c) (E)-3-(3,3-Dimethyl-2-oxo-2,3,4,5-tetrahydro-1H-pyrido[2,3-e][1,4]diazepin-7-yl)-N-(3-isopropyl-2-propoxybenzyl)-N-methylacrylamide hydrochloride A stirring solution of (E)-3-(3,3-dimethyl-2-oxo-2,3,4,5-tetrahydro-1H-pyrido[2,3-e][1,4]diazepin-7-yl)-N-(3-isopropyl-2-propoxybenzyl)-N-methylacrylamide (0.164 g, 0.352 mmol) in CH$_2$Cl$_2$ (4 mL) under N$_2$ was treated with anhydrous HCl (0.17 mL of a 2.0 M solution in diethyl ether, 0.34 mmol) After stirring for 18 h, the resulting solid was collected by filtration, washed with Et$_2$O (100 mL) and dried to yield the title compound (0.12 g, 71%) as an off white solid and as a mixture of amide rotamers: $^1$H NMR (300 MHz, DMSO-d$_6$) δ 10.95 (br s, 1H), 10.25 (br s, 2H), 8.67-8.63 (m, 1H), 8.36-8.26 (m, 1H), 7.62-7.54 (m, 1H), 7.39-7.31 (m, 1H), 7.26-7.20 (m, 1H), 7.13-7.05 (m, 1H), 6.90-6.84 (m, 1H), 4.82-4.67 (m, 2H), 4.41-4.36 (m, 2H), 3.77-3.69 (m, 2H), 3.30-3.25 (m, 1H), 3.16-2.89 (m, 3H), 1.82-1.75 (m, 2H), 1.60-1.58 (m, 6H), 1.23-1.13 (m, 6H), 1.06-1.01 (m, 3H); MS (ESI) m/e 465 (M+H)$^+$.

Example 9

Preparation of (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide

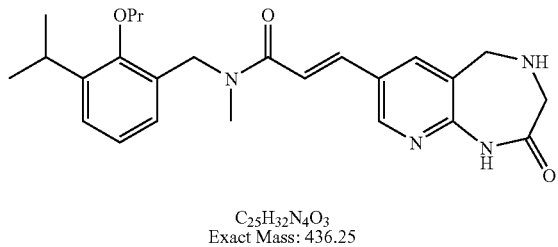

C$_{25}$H$_{32}$N$_4$O$_3$
Exact Mass: 436.25 a) (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide A solution of N-(3-isopropyl-2-propoxybenzyl)-N-methylacrylamide (0.385 g, 1.40 mmol) in propionitrile (5 mL) and DMF (1 mL) was deoxygenated with Ar for 20 min. The solution was treated with diisopropylethylamine (0.39 mL, 2.25 mmol) and 7-bromo-1,3,4,5-tetrahydro-pyrido[2,3-e][1,4]diazepin-2-one (0.300 g, 1.07 mmol). The solution was deoxygenated with Ar for 20 min. Pd(OAc)$_2$ (0.024 g, 0.10 mmol) and P(o-tol)$_3$ (0.065 g, 0.21 mmol) were then added and the solution deoxygenated with Ar for 20 min. The solution was heated to reflux for 18 h, then allowed to cool. The solution was diluted with H$_2$O (30 mL) and the mixture was washed with EtOAc (3×50 mL). The combined organics were washed with brine (2×100 mL), dried (Na$_2$SO$_4$) and concentrated. Purification by column chromatography (silica gel, CH$_2$Cl$_2$/MeOH, 100 to 95:5) gave the title compound (0.15 g, 33%) as an off-white solid and as a mixture of amide rotamers: $^1$H NMR (300 MHz, DMSO-d$_6$) δ 10.08-10.05 (m, 1H), 8.45-8.39 (m, 1H), 8.03-7.93 (m, 1H), 7.55-7.49 (m, 1H), 7.32-7.20 (m, 2H), 7.13-7.04 (m, 1H), 6.88-6.86 (m, 1H), 4.81-4.66 (m, 2H), 3.91-3.86 (m, 2H), 3.76-3.69 (m, 2H), 3.63-3.60 (m, 2H), 3.30-3.25 (m, 1H), 3.12-2.90 (m, 4H), 1.83-1.75 (m, 2H), 1.24-1.17 (m, 6H), 1.06-1.01 (m, 3H).

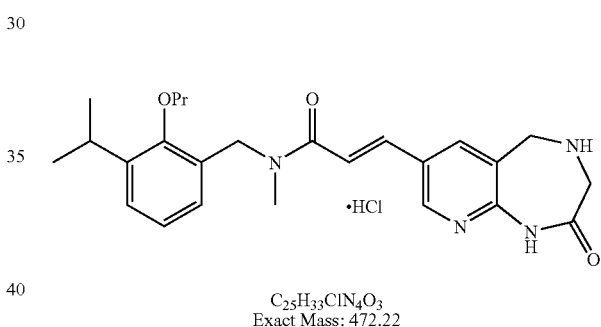

C$_{25}$H$_{33}$ClN$_4$O$_3$
Exact Mass: 472.22 b) (E)-N-(3-Isopropyl-2-propoxybenzyl)-N-methyl-3-(2-oxo-2,3,4,5-tetrahydro-1H-pyrido[2,3-e][1,4]diazepin-7-yl)acrylamide hydrochloride A stirring solution of (E)-N-(3-isopropyl-2-propoxybenzyl)-3-(3,3-dimethyl-2-oxo-2,3,4,5-tetrahydro-1H-pyrido[2,3-e][1,4]diazepin-7-yl)-N-methylacrylamide (0.158 g, 0.362 mmol) in CH$_2$Cl$_2$ (4 mL) under N$_2$ was treated with anhydrous HCl (0.18 mL of a 2.0 M solution in diethyl ether, 0.36 mmol) After stirring for 18 h, the resulting solid was collected by filtration, washed with Et$_2$O (100 mL) and dried to yield the title compound (0.15 g, 91%) as an off white solid and as a mixture of amide rotamers: $^1$H NMR (300 MHz, DMSO-d$_6$) δ 11.10-11.07 (m, 1H), 10.07 (br s, 2H), 8.77-8.72 (m, 1H), 8.33-8.24 (m, 1H), 7.63-7.55 (m, 1H), 7.40-7.31 (m, 1H), 7.26-7.21 (m, 1H), 7.13-7.05 (m, 1H), 6.90-6.83 (m, 1H), 4.83-4.67 (m, 2H), 4.28-4.22 (m, 2H), 3.85-3.69 (m, 4H), 3.30-3.25 (m, 1H), 3.14-2.89 (m, 3H), 1.81-1.75 (m, 2H), 1.20-1.17 (m, 6H), 1.06-1.01 (m, 3H); MS (ESI) m/e 437 (M+H)$^+$.

Example 10

Preparation of (S)-(+)-(E)-N-Methyl-N-(3-methyl-benzofuran-2-ylmethyl)-3-(10-oxo-2,3,4,9,10,10a-hexahydro-1H-3a,8,9-triazabenzo[f]azulen-6-yl)acrylamide hydrochloride

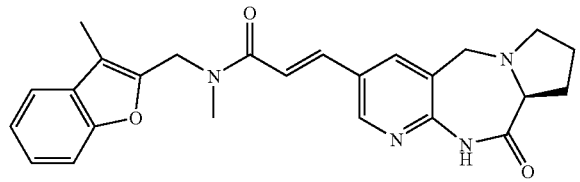

C$_{25}$H$_{26}$N$_4$O$_3$
Exact Mass: 430.20 a) (S)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide A solution of N-methyl-N-(3-methylbenzofuran-2-ylmethyl)acrylamide (0.210 g, 0.920 mmol) in propionitrile (3 mL) and DMF (0.65 mL) was deoxygenated with Ar for 20 min. The solution was treated with diisopropylethylamine (0.24 mL, 1.4 mmol) and (S)-6-bromo-1,2,3,4,9,10a-hexahydro-3a,8,9-triazabenzo[f]azulen-10-one (0.200 g, 0.708 mmol). The solution was deoxygenated with Ar for 20 min. Pd(OAc)$_2$ (0.015 g, 0.070 mmol) and P(o-tol)$_3$ (0.067 g, 0.14 mmol) were then added and the solution was deoxygenated with Ar for 20 min. The solution was heated to reflux for 18 h, then allowed to cool. The solution was diluted with CH$_2$Cl$_2$ (50 mL) and was washed with H$_2$O (3×100 mL). The combined organics were washed with brine (2×100 mL), dried (Na$_2$SO$_4$) and concentrated. Purification by column chromatography (silica gel, CH$_2$Cl$_2$/MeOH, 98:2) gave the title compound (0.25 g, 77%) as a glassy yellow solid and as a mixture of amide rotamers: $^1$H NMR (300 MHz, CDCl$_3$) δ 8.74 (s, 1H), 8.60-8.50 (m, 1H), 7.75-7.67 (m, 2H), 7.49-7.48 (m, 1H), 7.42-7.40 (m, 1H), 7.28-7.16 (m, 3H), 4.83-4.71 (m, 2H), 3.99-3.82 (m, 2H), 3.59-2.57 (m, 1H), 3.23-3.08 (m, 3H), 2.89-2.86 (m, 2H), 2.53-2.44 (m, 1H), 2.31-2.30 (m, 3H), 2.04-1.68 (m, 3H).

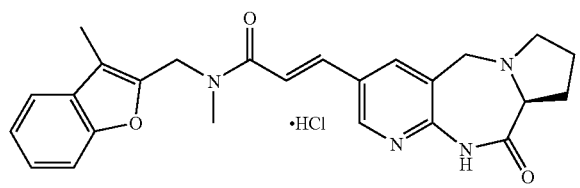

C$_{25}$H$_{27}$ClN$_4$O$_3$
Exact Mass: 466.18 b) (S)-(+)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride A stirring solution of (S)-(E)-N-methyl-N-(3-methylbenzofuran-2-ylmethyl)-3-(10-oxo-2,3,4,9,10,10a-hexahydro-1H-3a,8,9-triazabenzo[f]azulen-6-yl)acrylamide (0.235 g, 0.545 mmol) in CH$_2$Cl$_2$ (5 mL) under N$_2$ was treated with anhydrous HCl (0.27 mL of a 2.0 M solution in diethyl ether, 0.54 mmol) After stirring for 18 h, the resulting solid was collected by filtration, washed with Et$_2$O (100 mL) and dried to yield the title compound (0.22 g, 89%) as a yellow solid and as a mixture of amide rotamers: $^1$H NMR (300 MHz, DMSO-d$_6$) δ 12.15 (br s, 1H), 11.30 (br s, 1H), 8.87-8.83 (m, 1H), 8.36-8.31 (m, 1H), 7.63-7.55 (m, 2H), 7.50-7.48 (m, 1H), 7.35-7.22 (m, 3H), 5.07-4.95 (m, 2H), 4.47-4.26 (m, 3H), 3.63 (br s, 2H), 3.20-2.93 (m, 3H), 2.27 (s, 4H), 2.10 (br s, 1H), 1.88 (m, 2H); [α]$^{25}_D$ +66.3° (c 0.90, methanol); MS (ESI) m/e 431 (M+H)$^+$.

Example 11

Preparation of (R)-(−)-(E)-N-Methyl-N-(3-methyl-benzofuran-2-ylmethyl)-3-(10-oxo-2,3,4,9,10,10a-hexahydro-1H-3a,8,9-triazabenzo[f]azulen-6-yl)acrylamide hydrochloride

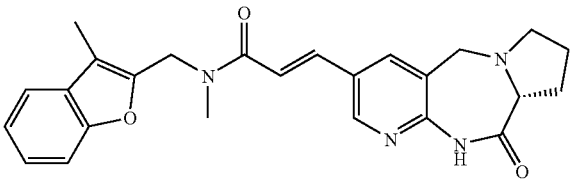

C$_{25}$H$_{26}$N$_4$O$_3$
Exact Mass: 430.20 a) (R)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide A solution of methyl-(3-methylbenzofuran-2-ylmethyl)amine (0.166 g, 0.953 mmol) and diisopropylethylamine (0.45 mL, 2.59 mmol) in DMF (20 mL) under N$_2$ was treated sequentially with (R)-6-bromo-1,2,3,4,9,10a-hexahydro-3a,8,9-triazabenzo[f]azulen-10-one (0.300 g, 0.866 mmol), 1-hydroxybenzotriazole hydrate (0.128 g, 0.953 mmol) and 1-(3-dimethylaminopropyl)-3-ethylcarbodiimide hydrochloride (0.182 g, 0.953 mmol). After stirring for 18 h, the reaction mixture was diluted with H$_2$O (30 mL). The resulting solids were collected by filtration, washed with Et$_2$O and dried to give the title compound (0.93 g, 31%) as a white solid and as a mixture of amide rotamers: $^1$H NMR (300 MHz, DMSO-d$_6$) δ 10.38 (s, 1H), 8.59-8.56 (m, 1H), 8.23-8.21 (m, 1H), 7.58-7.21 (m, 6H), 5.00-4.79 (m, 2H), 3.96-3.92 (m, 1H), 3.55-3.47 (m, 2H), 3.19-2.84 (m, 4H), 2.61-2.59 (m, 1H), 2.26 (m, 4H), 1.76-1.74 (m, 3H).

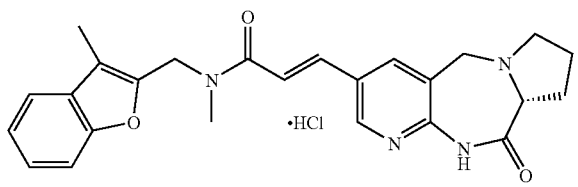

C$_{25}$H$_{27}$ClN$_4$O$_3$
Exact Mass: 466.18 b) (R)-(−)-(E)-N-Methyl-N-(3-methylbenzofuran-2-ylmethyl)-3-(10-oxo-2,3,4,9,10,10a-hexahydro-1H-3a,8,9-triazabenzo[f]azulen-6-yl)acrylamide hydrochloride A stirring solution of (R)-(E)-N-methyl-N-(3-methylbenzofuran-2-ylmethyl)-3-(10-oxo-2,3,4,9,10,10a-hexahydro-1H-3a,8,9-triazabenzo[f]azulen-6-yl)acrylamide (0.090 g, 0.20 mmol) in CH$_2$Cl$_2$ (3 mL) under N$_2$ was treated with anhydrous HCl (0.10 mL of a 2.0 M solution in diethyl ether, 0.20 mmol) After stirring for 18 h, the resulting solid was collected by filtration, washed with Et$_2$O (50 mL) and dried to yield the target compound (0.066 g, 67%) as an off white solid and as a mixture of amide rotamers: $^1$H NMR (300 MHz, DMSO-d$_6$) δ 12.31 (br s, 1H), 11.29 (br s, 1H), 8.85-8.83 (m, 1H), 8.33-8.31 (m, 1H), 7.62-7.56 (m, 2H), 7.451-7.48 (m, 1H), 7.35-7.22 (m, 3H), 5.07-4.81 (m, 2H), 4.51-4.16 (m, 3H), 3.58 (br s, 3H), 3.20-2.94 (m, 3H), 2.27 (m, 3H), 2.10-1.89 (m, 3H); [α]$^{25}_D$ −52.4° (c 0.86, methanol); MS (ESI) m/e 431 (M+H)$^+$.

Example 12

Preparation of (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide hydrochloride

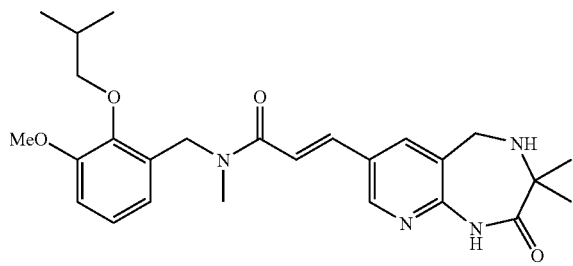

C$_{26}$H$_{34}$N$_4$O$_4$
Exact Mass: 466.26 a) (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide A solution of N-(2-isobutoxy-3-methoxybenzyl)-N-methylacrylamide (0.407 g, 1.47 mmol) in propionitrile (5 mL) and DMF (1 mL) was deoxygenated with Ar for 20 min. The solution was treated with diisopropylethylamine (0.40 mL, 2.33 mmol) and 7-bromo-3,3-dimethyl-1,3,4,5-tetrahydro-pyrido[2,3-e][1,4]diazepin-2-one (0.300 g, 1.11 mmol). The solution was deoxygenated with Ar for 20 min. Pd(OAc)$_2$ (0.024 g, 0.11 mmol) and P(o-tol)$_3$ (0.067 g, 0.22 mmol) were then added and the solution was deoxygenated with Ar for 20 min. The solution was heated to reflux for 18 h, then allowed to cool. The solution was diluted with EtOAc (30 mL) and was washed with H$_2$O (3×50 mL). The organic layer was washed with brine (2×50 mL), dried (Na$_2$SO$_4$) and concentrated to an orange oil. Purification by column chromatography (silica gel, CH$_2$Cl$_2$/MeOH, 100 to 98:2) gave the title compound (0.19 g, 32%) as an off-white solid and as a mixture of amide rotamers: $^1$H NMR (300 MHz, DMSO-d$_6$) δ 9.79-9.77 (m, 1H), 8.40-8.35 (m, 1H), 8.00-7.92 (m, 1H), 7.54-7.48 (m, 1H), 7.29-7.22 (m, 1H), 7.04-6.96 (m, 2H), 6.66-6.63 (m, 1H), 4.79-4.64 (m, 2H), 3.89-3.83 (m, 2H), 3.79 (s, 3H), 3.72-3.67 (m, 2H), 3.11-2.87 (m, 4H), 2.04-1.99 (m, 1H), 1.31-1.29 (m, 6H), 1.00-0.97 (m, 6H).

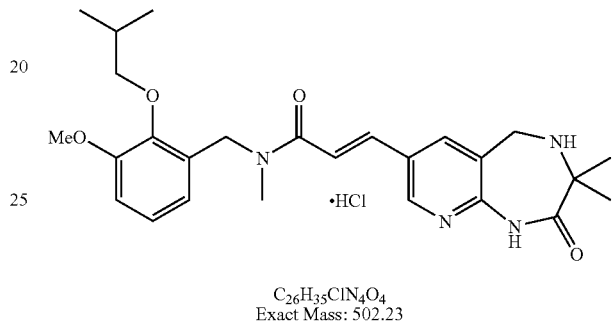

C$_{26}$H$_{35}$ClN$_4$O$_4$
Exact Mass: 502.23 b) (E)-3-(3,3-Dimethyl-2-oxo-2,3,4,5-tetrahydro-1H-pyrido[2,3-e][1,4]diazepin-7-yl)-N-(2-isobutoxy-3-methoxybenzyl)-N-methylacrylamide hydrochloride A stirring solution of (E)-3-(3,3-dimethyl-2-oxo-2,3,4,5-tetrahydro-1H-pyrido[2,3-e][1,4]diazepin-7-yl)-N-(2-isobutoxy-3-methoxybenzyl)-N-methylacrylamide (0.196 g, 0.426 mmol) in CH$_2$Cl$_2$ (4 mL) under N$_2$ was treated with anhydrous HCl (0.21 mL of a 2.0 M solution in diethyl ether, 0.42 mmol) After stirring for 7 h, the resulting solid was collected by filtration, washed with Et$_2$O (100 mL) and dried to yield the title compound (0.10 g, 47%) as an off white solid and as a mixture of amide rotamers: $^1$H NMR (300 MHz, DMSO-d$_6$) δ 10.93-10.92 (m, 1H), 10.51 (br s, 2H), 8.66-8.62 (m, 1H), 8.40-8.32 (m, 1H), 7.60-7.53 (m, 1H), 7.38-7.33 (m, 1H), 7.05-6.94 (m, 2H), 6.68-6.61 (m, 1H), 4.80-4.65 (m, 2H), 4.42-4.37 (m, 2H), 3.79 (s, 3H), 3.72-3.68 (m, 2H), 3.12-2.86 (m, 3H), 2.04-1.97 (m, 1H), 1.63-1.61 (m, 6H), 1.00-0.97 (m, 6H); MS (ESI) m/e 467 (M+H)$^+$.

Example 13

Preparation of (E)-3-(6-amino-pyridin-3-yl)-N-(3-chloro-4-fluoro-benzo[b]thiophen-2-ylmethyl)-N-methylacrylamide hydrochloride

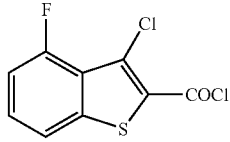

C$_9$H$_3$Cl$_2$FOS
Exact Mass: 247.93 a) 3-chloro-4-fluoro-benzo[b]thiophene-2-carbonyl chloride

A mixture of 3-(2-fluoro-phenyl)acrylic acid (15.0 g, 90.3 mmol), SOCl$_2$ (40 mL, 542 mmol) and pyridine (0.72 mL, 9.00 mmol) in chlorobenzene (90 mL) was heated to reflux for 3 d. The mixture was cooled to room temperature and concentrated. The residue was triturated with hexanes to give the title compound (5.46 g, 26%) as a yellow solid: $^1$H NMR (500 MHz, CDCl$_3$) δ 7.63 (dd, J=8.2, 0.8 Hz, 1H), 7.56 (ddd, J=8.0, 8.0, 4.5 Hz, 1H), 7.16 (ddd, J=11.2, 7.9, 0.8 Hz, 1H).

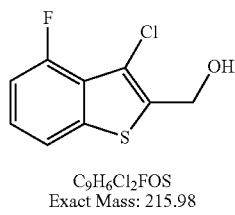 [SMILES: OCc1sc2cccc(F)c2c1Cl]

C$_9$H$_6$Cl$_2$FOS
Exact Mass: 215.98 b) (3-chloro-4-fluoro-benzo[b]thiophen-2-yl)methanol

To an ice-cold suspension of 3-chloro-4-fluoro-benzo[b]thiophene-2-carbonyl chloride (5.46 g, 23.6 mmol) in THF (120 mL) was added lithium aluminum hydride (11.8 mL of a 1.0 M solution in THF, 11.8 mmol) dropwise. The mixture was stirred for 2 h then quenched with NaOH (0.35 N solution in H$_2$O). The mixture was diluted with Et$_2$O and the solution filtered. The filtrate was dried (Na$_2$SO$_4$) and concentrated. Purification by flash column chromatography (silica gel, hexanes/EtOAc, 8:2) gave the title compound (4.52 g, 96%) as an off-white solid: $^1$H NMR (300 MHz, CDCl$_3$) δ 7.57 (d, J=8.1 Hz, 1H), 7.31 (ddd, J=8.0, 8.0, 4.7 Hz, 1H), 7.06 (dd, J=11.3, 8.0 Hz, 1H), 4.97 (d, J=6.2 Hz, 2H),

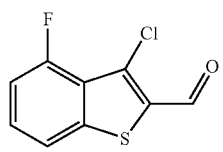

C$_9$H$_4$ClFOS
Exact Mass: 213.97 c) 3-chloro-4-fluoro-benzo[b]thiophene-2-carbaldehyde

A suspension of (3-chloro-4-fluoro-benzo[b]thiophen-2-yl)methanol (1.00 g, 4.63 mmol) and MnO$_2$ (3.10 g, 35.2 mmol) in benzene (50 mL) was stirred at room temperature overnight. The solution was filtered through diatomaceous earth and the was filtrate was concentrated to give the title compound (880 mg, 87%) as an off-white solid: $^1$H NMR (500 MHz, CDCl$_3$) δ 10.32 (s, 1H), 7.63 (dd, J=8.2, 0.4 Hz, 1H), 7.50 (ddd, J=8.1, 8.1, 4.7 Hz, 1H), 7.13 (ddd, J=11.0, 7.9, 0.4 Hz, 1H).

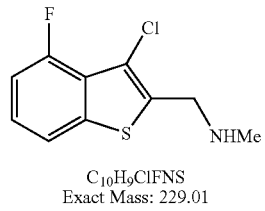 [SMILES: CNCc1sc2cccc(F)c2c1Cl]

C$_{10}$H$_9$ClFNS
Exact Mass: 229.01 d) (3-chloro-4-fluoro-benzo[b]thiophen-2-ylmethyl)methylamine

A solution of 3-chloro-4-fluoro-benzo[b]thiophene-2-carbaldehyde (880 mg, 4.04 mmol) in CH$_3$NH$_2$ (20 mL of a 2.0 M solution in MeOH, 40 mmol) was stirred at room temperature overnight. The mixture was concentrated. The residue was dissolved in EtOH (30 mL), and after cooling in an ice bath, NaBH$_4$ (153 mg, 4.04 mmol) was added. The mixture was slowly warmed to room temperature and then stirred overnight. The mixture was concentrated. The residue was taken up in NaOH (30 mL) and the mixture was extracted with Et$_2$O (3×). The combined organics were washed with satd NaCl, dried (Na$_2$SO$_4$) and concentrated. Purification by column chromatography (silica gel, 95:5 CH$_2$Cl$_2$/MeOH) gave the title compound (443 mg, 48%) as a yellow oil: $^1$H NMR (300 MHz, CDCl$_3$) δ 7.54 (dd, J=8.0, 0.6 Hz, 1H), 7.27 (ddd, J=8.0, 8.0, 4.6 Hz, 1H), 7.03 (ddd, J=11.4, 8.0, 0.6 Hz, 1H), 4.05 (s, 2H), 2.53 (s, 3H), 1.55 (s, 1H).

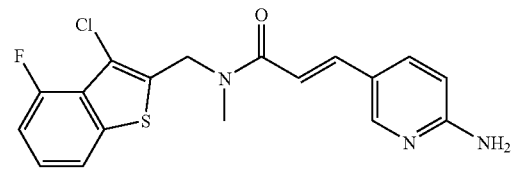

C$_{18}$H$_{15}$ClFN$_3$OS
Exact Mass: 375.06 e) (E)-3-(6-amino-pyridin-3-yl)-N-(3-chloro-4-fluoro-benzo[b]thiophen-2-ylmethyl)-N-methylacrylamide To a solution of 3-(6-amino-pyridin-3-yl)acrylic acid trifluoroacetic acid salt (487 mg, 1.75 mmol) in DMF (10 mL) was added 3-chloro-4-fluoro-benzo[b]thiophen-2-ylmethyl)methylamine (440 mg, 1.92 mmol), EDC (368 mg, 1.92 mmol), HOBt (260 mg, 1.92 mmol), and DIEA (1.0 mL, 6.1 mmol). The mixture was stirred at room temperature overnight. The mixture was diluted with H$_2$O and the solid was collected by filtration. Purification by semi-preparative HPLC (Phenomenex Luna C18(2) 10μ, 250×21 mm, CH$_3$CN/H$_2$O/0.05% TFA) gave a solid. The solid was partitioned between EtOAc and satd NaHCO$_3$. The organic layer was concentrated to give the title compound (257 mg, 39%) as a white solid: MS (ESI) m/e 376 (M+H)$^+$.

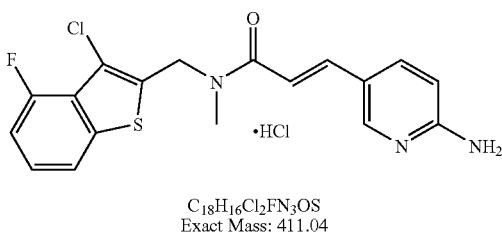 [SMILES: CN(Cc1sc2cccc(F)c2c1Cl)C(=O)/C=C/c1ccc(N)nc1 ; Cl]

C₁₈H₁₆Cl₂FN₃OS
Exact Mass: 411.04 f) (E)-3-(6-amino-pyridin-3-yl)-N-(3-chloro-4-fluoro-benzo[b]thiophen-2-ylmethyl)-N-methylacrylamide hydrochloride A solution of (E)-3-(6-amino-pyridin-3-yl)-N-(3-chloro-4-fluoro-benzo[b]thiophen-2-ylmethyl)-N-methylacrylamide (257 mg, 0.68 mmol) in CH$_2$Cl$_2$ (10 mL) was treated with anhydrous HCl (0.68 mL of a 1.0 M solution in Et$_2$O, 0.68 mmol). The mixture was stirred overnight at room temperature and then diluted with Et$_2$O. The resulting solid was collected by filtration and then dried under vacuum at 50° C. for 2 d to give the title compound (282 mg, 98%) as an off-white solid and as a mixture of amide rotamers: $^1$H NMR (300 MHz, DMSO-d$_6$) δ 8.43-8.33 (m, 4H), 7.87-7.82 (m, 1H), 7.55-7.20 (m, 4H), 7.04-7.00 (m, 1H), 5.15-4.88 (m, 2H), 3.54 (br s, 1H), 3.22-2.97 (m, 3H); MS (ESI) m/e 376 (M+H)$^+$.

Example 14

Preparation of (E)-3-(6-amino-pyridin-3-yl)-N-(3-chloro-7-fluoro-benzo[b]thiophen-2-ylmethyl)-N-methylacryl amide hydrochloride

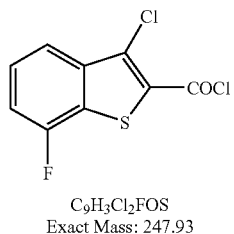 [SMILES: O=C(Cl)c1sc2c(F)cccc2c1Cl]

C₉H₃Cl₂FOS
Exact Mass: 247.93 a) 3-chloro-7-fluoro-benzo[b]thiophene-2-carbonyl chloride

A mixture of 3-(3-fluoro-phenyl)acrylic acid (10.2 g, 61.4 mmol), SOCl$_2$ (22 mL, 301 mmol) and pyridine (0.50 mL, 6.00 mmol) in chlorobenzene (60 mL) was heated to reflux for 3 d. The mixture was cooled to room temperature and concentrated. The residue was triturated with hexanes to give the title compound (7.81 g, 55%) as a yellow solid and as a 6:1 mixture of the 5-fluoro and 7-fluoro isomers. The mixture was used directly in the next step without further purification.

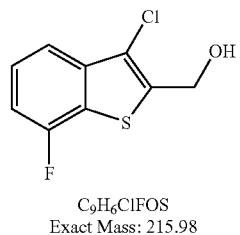 [SMILES: OCc1sc2c(F)cccc2c1Cl]

C₉H₆ClFOS
Exact Mass: 215.98 b) (3-chloro-7-fluoro-benzo[b]thiophen-2-yl)methanol

To an ice-cold suspension of a 6:1 mixture of 3-chloro-5-fluoro-benzo[b]thiophene-2-carbonyl chloride and 3-chloro-7-fluoro-benzo[b]thiophene-2-carbonyl chloride (5.46 g, 23.6 mmol) in THF (120 mL) was added lithium aluminum hydride (11.8 mL of a 1.0 M solution in THF, 11.8 mmol) dropwise. The mixture was stirred for 4 h then quenched with NaOH (0.35 N solution in H$_2$O). The mixture was diluted with Et$_2$O and the solution filtered. The filtrate was dried (Na$_2$SO$_4$) and concentrated. Purification by flash column chromatography (silica gel, hexanes/EtOAc, 9:1 to hexanes/EtOAc 8:2) gave the title compound (600 mg, 4% (2 steps), 7-fluoro isomer) as a light, yellow solid: $^1$H NMR (300 MHz, CDCl$_3$) δ 7.59 (d, J=8.0 Hz, 1H), 7.41 (ddd, J=8.0, 8.0, 4.9 Hz, 1H), 7.10 (dd, J=9.1, 9.1 Hz, 1H), 5.00 (d, J=6.2 Hz, 2H), 2.04 (t, J=6.5 Hz, 1H).

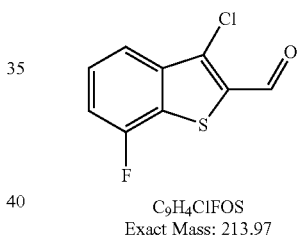

C₉H₄ClFOS
Exact Mass: 213.97 c) 3-chloro-7-fluoro-benzo[b]thiophene-2-carbaldehyde

A suspension of (3-chloro-7-fluoro-benzo[b]thiophen-2-yl)methanol (600 g, 2.78 mmol) and MnO$_2$ (1.69 g, 19.5 mmol) in benzene (25 mL) was stirred at room temperature for 2 d. The solution was filtered through diatomaceous earth and the filtrate concentrated to give the title compound (610 mg, quantitative) as a light, yellow solid: $^1$H NMR (300 MHz, CDCl$_3$) δ 10.35 (s, 1H), 7.83 (d, J=8.1 Hz, 1H), 7.51 (ddd, J=8.0, 8.0, 4.8 Hz, 1H), 7.32-7.26 (m, 1H).

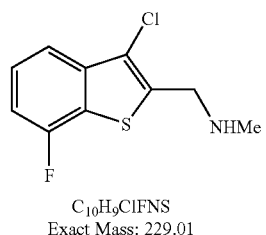 [SMILES: CNCc1sc2c(F)cccc2c1Cl]

C₁₀H₉ClFNS
Exact Mass: 229.01 d) (3-chloro-7-fluoro-benzo[b]thiophen-2-ylmethyl)methylamine

A solution of 3-chloro-7-fluoro-benzo[b]thiophene-2-carbaldehyde (610 mg, 2.78 mmol) in CH$_3$NH$_2$ (20 mL of a 2.0 M solution in MeOH, 40 mmol) was stirred at room temperature overnight. The mixture was concentrated. The residue was dissolved in EtOH (20 mL), and after cooling in an ice bath, NaBH$_4$ (159 mg, 4.20 mmol) was added. The mixture was slowly warmed to room temperature and then stirred overnight. The mixture was concentrated. The residue was taken up in NaOH (20 mL) and the mixture extracted with Et$_2$O (3×). The combined organics were washed with satd NaCl, dried (Na$_2$SO$_4$) and concentrated. Purification by column chromatography (silica gel, 95:5 CH$_2$Cl$_2$/MeOH) gave the title compound (460 g, 70%) as a brown oil: $^1$H NMR (300 MHz, CDCl$_3$) δ 7.56 (d, J=8.0 Hz, 1H), 7.38 (ddd, J=7.9, 7.9, 4.9 Hz, 1H), 7.06 (dd, J=8.8, 8.8 Hz, 1H), 4.09 (s, 2H), 2.53 (s, 3H), 1.55 (s, 1H).

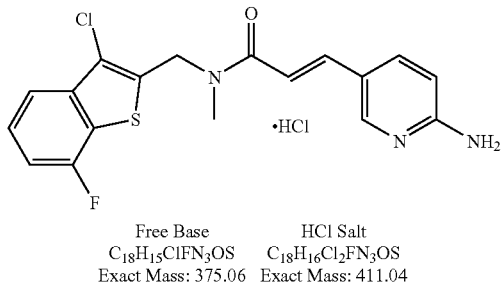 [SMILES: CN(Cc1sc2c(F)cccc2c1Cl)C(=O)/C=C/c1ccc(N)nc1 ; Cl]

Free Base
C$_{18}$H$_{15}$ClFN$_3$OS
Exact Mass: 375.06

HCl Salt
C$_{18}$H$_{16}$Cl$_2$FN$_3$OS
Exact Mass: 411.04 e) (E)-3-(6-amino-pyridin-3-yl)-N-(3-chloro-7-fluoro-benzo[b]thiophen-2-ylmethyl)-N-methylacrylamide To a solution of 3-(6-amino-pyridin-3-yl)acrylic acid trifluoroacetic acid salt (509 mg, 1.83 mmol) in DMF (15 mL) was added 3-chloro-7-fluoro-benzo[b]thiophen-2-ylmethyl)methylamine (460 mg, 2.01 mmol), EDC (385 mg, 2.01 mmol), HOBt (272 mg, 2.01 mmol) and DMA (0.9 mL, 5.5 mmol). The mixture was stirred at room temperature overnight. The mixture was diluted with H$_2$O and the solid collected by filtration. Purification by semi-preparative HPLC (Phenomenex Luna C18(2) 10µ, 250 21.20 mm, CH$_3$CN/H$_2$O/0.05% TFA) gave a solid. The solid was partitioned between EtOAc and satd NaHCO$_3$. The organic layer was concentrated to give to give a pale yellow solid. The solid was dissolved in a minimum amount of hot MeCN. The precipitate was collected by filtration to give the title compound (105 mg, 15%) as a white solid: MS (ESI) m/e 376 (M+H)$^+$.

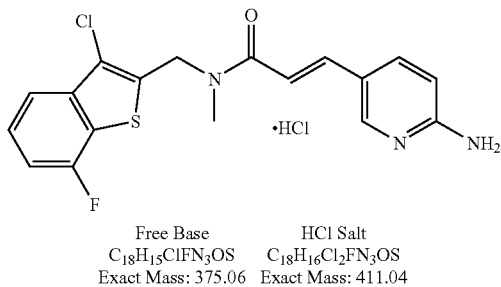 [SMILES: CN(Cc1sc2c(F)cccc2c1Cl)C(=O)/C=C/c1ccc(N)nc1 ; Cl]

Free Base
C$_{18}$H$_{15}$ClFN$_3$OS
Exact Mass: 375.06

HCl Salt
C$_{18}$H$_{16}$Cl$_2$FN$_3$OS
Exact Mass: 411.04 f) (E)-3-(6-amino-pyridin-3-yl)-N-(3-chloro-7-fluoro-benzo[b]thiophen-2-ylmethyl)-N-methylacrylamide hydrochloride A suspension of (E)-3-(6-amino-pyridin-3-yl)-N-(3-chloro-7-fluoro-benzo[b]thiophen-2-ylmethyl)-N-methylacrylamide (105 mg, 0.28 mmol) in CH$_2$Cl$_2$ (10 mL) was treated with anhydrous HCl (0.28 mL of a 1.0 M solution in Et$_2$O, 0.28 mmol) and then the mixture was stirred at room temperature overnight. The mixture was diluted with Et$_2$O. The resulting solid was collected by filtration and dried under vacuum at 50° C. overnight to give the title compound (111 mg, 96%) as an off-white solid and as a mixture of amide rotamers: $^1$H NMR (300 MHz, DMSO-d$_6$) δ 8.43-8.33 (m, 4H), 7.67-7.52 (m, 3H), 7.41-7.35 (m, 1H), 7.25-7.19 (m, 1H), 7.04-7.01 (m, 1H), 5.21-4.92 (m, 2H), 3.63 (br s, 1H), 3.23-2.98 (m, 3H); MS (ESI) m/e 376 (M+H)$^+$.

Example 15

Preparation of (E)-6-{2-[methyl-(3-methyl-benzo[b]thiophen-2-ylmethyl)-carbamoyl]-vinyl}-2-oxo-1,2-dihydro-[1,8]naphthyridine-3-carboxylic acid sodium salt

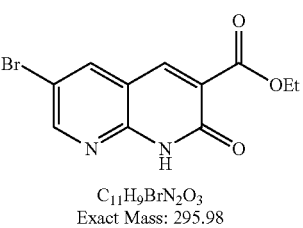 [SMILES: CCOC(=O)c1cc2cc(Br)cnc2[nH]c1=O]

C$_{11}$H$_9$BrN$_2$O$_3$
Exact Mass: 295.98 a) 6-Bromo-2-oxo-1,2-dihydro-[1,8]naphthyridine-3-carboxylic acid ethyl ester A mixture of 2-amino-5-bromo-pyridine-3-carbaldehyde (4.00 g, 14.2 mmol), diethyl malonate (21.6 mL, 142 mmol) and piperidine (7.00 mL, 71.0 mmol) in EtOH (70 mL) was heated to reflux overnight. The mixture was cooled to room temperature and the solid was collected by filtration to give the title compound (2.41 g, 57%) as an off-white solid: $^1$H NMR (300 MHz, CDCl$_3$) δ 12.65 (s, 1H), 8.70 (d, J=2.4 Hz, 1H), 8.56 (d, J=2.4 Hz, 1H), 8.45 (s, 1H), 4.29 (q, J=7.1 Hz, 2H), 1.30 (t, J=7.1 Hz, 3H).

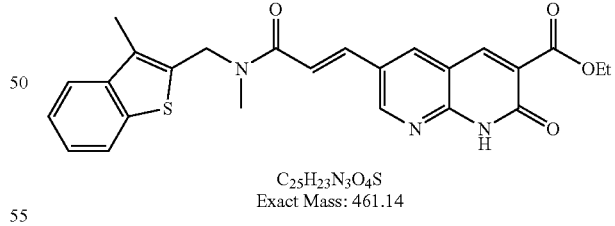

C$_{25}$H$_{23}$N$_3$O$_4$S
Exact Mass: 461.14 b) (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid ethyl ester A suspension of N-methyl-N-(3-methyl-benzo[b]thiophen-2-ylmethyl)acrylamide (500 mg, 2.04 mmol), 6-bromo-2-oxo-1,2-dihydro-[1,8]naphthyridine-3-carboxylic acid ethyl ester (665 mg, 2.24 mmol), (o-tol)$_3$P (135 mg, 0.44 mmol) and DIEA (0.4 mL, 2.45 mmol) in EtCN (10 mL) and DMF (10 mL) was deoxygenated with argon for 30 min.

Pd(OAc)$_2$ (50 mg, 0.22 mmol) was added, the mixture was deoxygenated with argon for 20 min and then heated to reflux overnight. The mixture was cooled to room temperature and concentrated. The residue was partitioned between CH$_2$Cl$_2$ and H$_2$O. The organic layer was washed with satd NaCl, dried (Na$_2$SO$_4$) and concentrated. Purification by column chromatography (silica gel, 89:10:1 CH$_2$Cl$_2$/MeOH/conc NH$_4$OH) gave the title compound (530 mg, 56%) as a yellow solid and as a mixture of amide rotamers: $^1$H NMR (300 MHz, DMSO-d$_6$) δ 12.63 (s, 1H), 8.98 (d, J=2.1 Hz, 1H), 8.67 (s, 1H), 8.44-8.42 (m, 1H), 7.88 (d, J=7.6 Hz, 1H), 7.75-7.52 (m, 2H), 7.43-7.31 (m, 3H), 5.14-4.91 (m, 2H), 4.32-4.25 (m, 2H), 3.18-2.96 (m, 3H), 2.43 (s, 3H), 1.33-1.27 (m, 3H); MS (ESI) m/e 462 (M+H)$^+$.

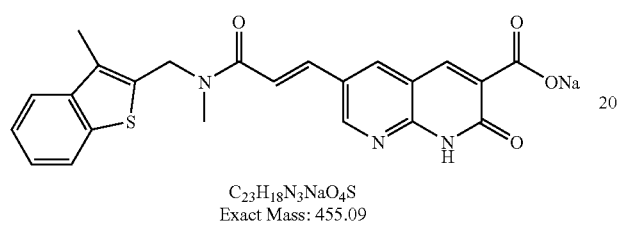

C$_{23}$H$_{18}$N$_3$NaO$_4$S
Exact Mass: 455.09 c) (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid sodium salt To a suspension of (E)-6-{2-[methyl-(3-methyl-benzo[b]thiophen-2-ylmethyl)carbamoyl]vinyl}-2-oxo-1,2-dihydro-[1,8]naphthyridine-3-carboxylic acid ethyl ester (349 mg, 0.76 mmol) in MeOH (10 mL) and CH$_2$Cl$_2$ (5 mL) was added NaOH (1.53 mL of a 0.995 M solution in H$_2$O, 1.53 mmol) dropwise. The mixture was stirred at room temperature overnight. The solid was collected by filtration and then dried under vacuum at 50° C. for 2 d. Trituration with 5:1 MeCN/H$_2$O gave the title compound (85 mg, 25%) as an off-white solid and as a mixture of amide rotamers: $^1$H NMR (300 MHz, DMSO-d$_6$+TFA-d) δ 9.15 (s, 1H), 8.85 (s, 2H), 7.88 (d, J=7.5 Hz, 1H), 7.76-7.58 (m, 2H), 7.46-7.34 (m, 3H), 5.15-4.92 (m, 2H), 3.20-2.98 (m, 3H), 2.44 (s, 3H); MS (ESI) m/e 434 (M−Na+2H)$^+$.

Example 16

Preparation of (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide hydrochloride

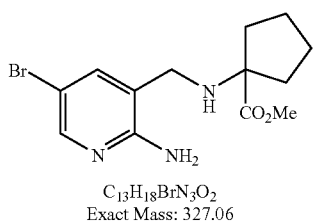 [SMILES: COC(=O)C1(NCc2cc(Br)cnc2N)CCCC1]

C$_{13}$H$_{18}$BrN$_3$O$_2$
Exact Mass: 327.06 a) 1-[(2-amino-5-bromo-pyridin-3-ylmethyl)amino]cyclopentanecarboxylic acid methyl ester To an ice-cold suspension of 5-bromo-3-bromomethyl-pyridin-2-ylamine hydrobromide (8.64 g, 24.9 mmol) and 1-amino-cyclopentanecarboxylic acid methyl ester (3.56 g, 24.9 mmol) in DMF (100 mL) was added Et$_3$N (5.30 mL, 37.4 mmol) slowly. The mixture was stirred for 2 h and then diluted with H$_2$O. The solid was collected by filtration to give the title compound (3.55 g, 43%) as a yellow solid: $^1$H NMR (300 MHz, CDCl$_3$) δ 8.02 (d, J=2.3 Hz, 1H), 7.37 (d, J=2.3 Hz, 1H), 5.49 (s, 2H), 3.76 (s, 3H), 3.52 (s, 2H), 2.12-2.05 (m, 2H), 1.79 (br s, 7H).

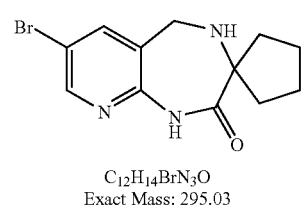 [SMILES: O=C1Nc2ncc(Br)cc2CNC12CCCC2]

C$_{12}$H$_{14}$BrN$_3$O
Exact Mass: 295.03 b) spiro[7-bromo-2-oxo-2,3,4,5-tetrahydro-1H-pyrido[2,3-e][1,4]diazepin-3,1'-cyclopentane]

A solution of 1-[(2-amino-5-bromo-pyridin-3-ylmethyl)amino]cyclopentanecarboxylic acid methyl ester (3.45 g, 10.5 mmol) in DMSO (100 mL) was treated with NaH (60% dispersion in mineral oil, 420 mg, 10.5 mmol) and stirred at room temperature for 2 d. The mixture was diluted with H$_2$O and the solid was collected by filtration. The solid was triturated with CHCl$_3$/MeOH to give the title compound (1.79 g, 58%) as an off-white solid: $^1$H NMR (300 MHz, CDCl$_3$) δ 8.23 (d, J=2.3 Hz, 1H), 8.13 (br s, 1H), 7.51 (d, J=2.0 Hz, 1H), 3.92 (s, 2H), 2.31-2.22 (m, 2H), 1.86-1.73 (m, 7H).

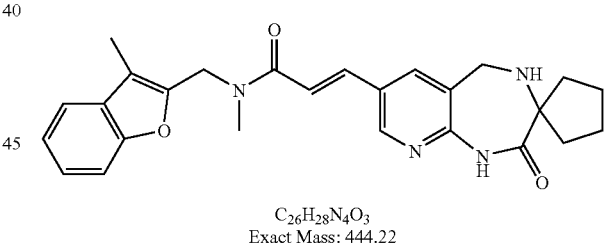

C$_{26}$H$_{28}$N$_4$O$_3$
Exact Mass: 444.22 c) (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide A mixture of spiro[7-bromo-2-oxo-2,3,4,5-tetrahydro-1H-pyrido[2,3-e][1,4]diazepin-3,1'-cyclopentane] (456 mg, 1.54 mmol), N-methyl-N-(3-methyl-benzofuran-2-ylmethyl)acrylamide (320 mg, 1.40 mmol), (o-tol)$_3$P (137 mg, 0.45 mmol) and DMA (0.35 mL, 2.10 mmol) in DMF (10 mL) was deoxygenated with argon for 30 min. Pd(OAc)$_2$ (50 mg, 0.22 mmol) was added, the mixture was deoxygenated with argon again and then heated to 100° C. overnight. The mixture was cooled to room temperature and partitioned between CH$_2$Cl$_2$/H$_2$O. The organic layer was washed with H$_2$O and satd NaCl, dried (Na$_2$SO$_4$) and concentrated. Purification by column chromatography (silica gel, 95:5 CH$_2$Cl$_2$/MeOH) gave a light yellow solid. The solid was suspended in MeOH and the mixture sonicated. The solid was collected by filtration to give the title compound (354 mg, 57%) as an off-white solid and as a mixture of amide rotamers: $^1$H NMR (300 MHz, CDCl$_3$) δ 8.84 (m, 1H), 8.45-8.42 (m, 1H), 7.66 (d, J=15.4 Hz, 1H), 7.55-7.48 (m, 2H), 7.41 (d, J=8.0 Hz, 1H), 7.28-7.21 (m, 2H), 7.15-6.84 (m, 1H), 4.83-4.72 (m, 2H), 3.96 (s, 2H), 3.23-3.09 (m, 3H), 2.33-2.25 (m, 5H), 1.84-1.74 (m, 7H).

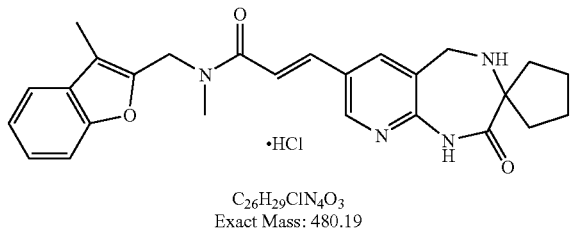 [SMILES: Cc1c(CN(C)C(=O)/C=C/c2cnc3c(c2)CNC2(CCCC2)C(=O)N3)oc2ccccc12 ; Cl]

C$_{26}$H$_{29}$ClN$_4$O$_3$
Exact Mass: 480.19 d) (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide hydrochloride A suspension of (E)-spiro[2-oxo-2,3,4,5-tetrahydro-1H-pyrido[2,3-e][1,4]diazepin-3,1'-cyclopentane]-7-yl-N-(3-methyl-benzofuran-2-ylmethyl)-N-methylacrylamide (354 mg, 0.80 mmol) in CH$_2$Cl$_2$ (15 mL) was treated with anhydrous HCl (0.80 mL of a 1.0 M solution in Et$_2$O, 0.80 mmol) and the mixture was stirred at room temperature overnight. The mixture was diluted with Et$_2$O and then the solid was collected by filtration to give the title compound (305 mg, 80%) as an off-white solid and as a mixture of amide rotamers: $^1$H NMR (300 MHz, DMSO-d$_6$) δ 11.02 (s, 1H), 10.6 (s, 2H), 8.73 (d, J=8.6 Hz, 1H), 8.38 (s, 1H), 7.66-7.22 (m, 6H), 5.02-4.81 (m, 2H), 4.29 (s, 2H), 3.21-2.93 (m, 3H), 2.27 (s, 3H), 2.20-2.16 (m, 2H), 1.90-1.76 (m, 4H), 1.62-1.60 (2H); MS (ESI) m/e 445 (M+H)$^+$.

Example 17

Preparation of (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride

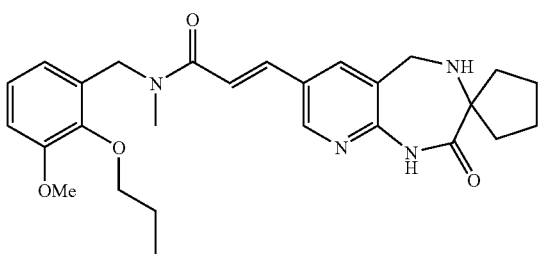

C$_{27}$H$_{34}$N$_4$O$_4$
Exact Mass: 478.26 a) (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide A mixture of spiro[7-bromo-2-oxo-2,3,4,5-tetrahydro-1H-pyrido[2,3-e][1,4]diazepin-3,1'-cyclopentane] (450 mg, 1.52 mmol), N-(3-methoxy-2-propoxybenzyl)-N-methylacrylamide (400 mg, 1.52 mmol), (o-tol)$_3$P (131 mg, 0.43 mmol) and DIEA (0.30 mL, 1.82 mmol) in DMF (10 mL) was deoxygenated with argon for 30 min. Pd(OAc)$_2$ (50 mg, 0.22 mmol) was added, the mixture was deoxygenated with argon and then heated to 100° C. overnight. The mixture was cooled to room temperature and partitioned between CH$_2$Cl$_2$/H$_2$O. The organic layer was washed with H$_2$O and satd NaCl, dried (Na$_2$SO$_4$) and concentrated. Purification by column chromatography (silica gel, CH$_2$Cl$_2$ to 96:4 CH$_2$Cl$_2$/MeOH) gave a light yellow solid. The solid was suspended in MeOH and the mixture sonicated. The solid was collected by filtration to give the title compound (333 mg, 46%) as an off-white solid and as a mixture of amide rotamers: $^1$H NMR (300 MHz, DMSO-d$_6$) δ 8.40-8.28 (m, 2H), 7.69-7.61 (m, 1H), 7.54-7.46 (m, 1H), 7.07-6.71 (m, 4H), 4.81-7.41 (m, 2H), 4.00-3.86 (m, 7H), 3.09 (s, 3H), 2.33-2.26 (m, 2H), 1.84-1.67 (m, 9H), 1.04 (t, J=7.4 Hz, 3H).

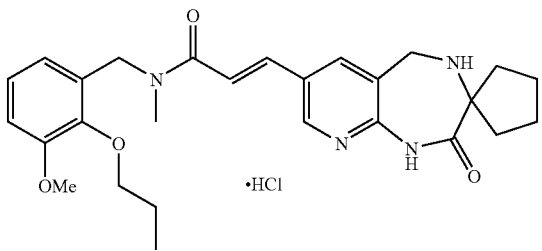

C$_{27}$H$_{35}$ClN$_4$O$_4$
Exact Mass: 514.23 b) (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride A suspension of (E)-spiro[2-oxo-2,3,4,5-tetrahydro-1H-pyrido[2,3-e][1,4]diazepin-3,1'-cyclopentane]-7-yl-N-(3-methoxy-2-propoxybenzyl)-N-methylacrylamide hydrochloride (333 mg, 0.70 mmol) in CH$_2$Cl$_2$ (10 mL) was treated with anhydrous HCl (0.70 mL of a 1.0 M solution in Et$_2$O, 0.70 mmol) and the mixture was stirred at room temperature overnight. The mixture was diluted with Et$_2$O. The resulting solid was collected by filtration and dried under vacuum at 50° C. overnight to give the title compound (293 mg, 81%) as an off-white solid and as a mixture of amide rotamers: $^1$H NMR (300 MHz, DMSO-d$_6$) δ 11.00 (s, 1H), 10.58 (s, 2H), 8.71 (d, J=12.0 Hz, 1H), 8.38-8.31 (m, 1H), 7.08-7.54 (m, 1H), 7.41-7.35 (m, 1H), 7.08-6.95 (m, 2H), 6.69-6.63 (m, 1H), 4.81-4.65 (m, 2H), 4.29-4.26 (m, 2H), 3.92-3.85 (m, 2H), 3.80 (s, 3H), 3.12-2.87 (m, 3H), 2.21-2.10 (m, 2H), 1.90-1.58 (m, 8H), 1.01-0.94 (m, 3H); MS (ESI) m/e 479 (M+H)$^+$.

Example 18

Preparation of (E)-N-(3-ethyl-benzofuran-2-ylmethyl)-N-methyl-3-(2-oxo-2,3,4,5-tetrahydro-1H-pyrido[2,3-e][1,4]diazepin-7-yl)acrylamide hydrochloride

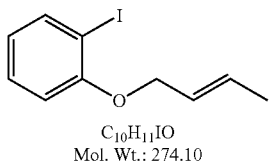

C$_{10}$H$_{11}$IO
Mol. Wt.: 274.10 a) 1-But-2-enyloxy-iodobenzene

An ice-cold solution of 2-iodophenol (10.0 g, 45.4 mmol) in DMF (100 mL) was added dropwise to a solution of NaH (2.16 g, 90.8 mmol) in DMF at 0° C. Crotylbromide (7.97 g, 59.0 mmol) was then added. The mixture was warmed to room temperature and stirred overnight. The reaction was quenched with water (50 mL) and the mixture was extracted with CH$_2$Cl$_2$ (3×). The combined organics were washed with brine and dried over Na$_2$SO$_4$ to give the title compound (12.2 g, 99%) as a yellow oil: $^1$H NMR (500 MHz, DMSO-d$_6$) δ 7.76 (dd, J=7.8, 1.5 Hz, 1H), 7.27-7.22 (m, 1H), 6.80 (dd, J=8.4, 1.2 Hz, 1H), 6.70-6.65 (m, 1H), 5.95-5.80 (m, 1H), 5.75-5.65 (m, 1H), 4.55-4.45 (m, 2H), 1.76-1.70 (m, 3H); ESI MS m/z 275 (M+H)$^+$.

C$_{10}$H$_{10}$O
Exact Mass: 146.07 b) 3-Ethyl-benzofuran

To a solution of 1-but-2-enyloxy-iodobenzene (7.60 g, 27.7 mmol) in DMF (46 mL) was added n-Bu$_4$NCl (8.46 g, 30.4 mmol), Pd(OAc)$_2$ (0.338 g, 1.30 mmol), Na$_2$CO$_3$ (6.01 g, 56.7 mmol) and NaOAc (2.77 g, 27.0 mmol). The mixture was heated to reflux under nitrogen atmosphere overnight. The mixture was diluted with EtOAc and washed with water. The combined organics were washed with brine and dried over Na$_2$SO$_4$. Purification by column chromatography (silica gel, hexanes) gave the title compound (1.74 g, 43%) as a yellow oil: $^1$H NMR (300 MHz, DMSO-d$_6$) δ 7.75 (s, 1H), 7.63-7.61 (m, 1H), 7.55 (t, J=6.6 Hz, 1H), 7.34-7.23 (m, 2H), 2.71-2.63 (m, 2H), 1.28 (t, J=7.5 Hz, 3H); ESI MS m/z 147 (M+H)$^+$.

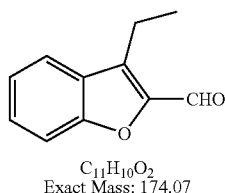

C$_{11}$H$_{10}$O$_2$
Exact Mass: 174.07 c) 3-Ethyl-bezofuran-2-carbadehyde

To a solution of 3-ethyl-benzofuran (1.6 g, 11 mmol) in THF (30 mL) cooled to −40° C. was added n-butyllithium (10.8 mL of a 2.5 M solution in hexane, 27.2 mmol). The mixture was stirred for 15 minutes then DMF (2.78 g, 38.1 mmol) was added. The mixture slowly warmed to room temperature and was stirred overnight under nitrogen atmosphere. The reaction was quenched with saturated NH$_4$Cl and the resulting mixture was extracted with EtOAc (3×). The combined organics were washed with water and brine, dried and concentrated. Purification by column chromatography (silica gel, hexane/EtOAc, 5:1) gave the title compound (1.24 g, 65%) as a yellow oil: $^1$H NMR (500 MHz, DMSO-d$_6$) δ 9.98 (s, 1H), 6.88-6.65 (m, 1H), 6.54 (d, J=0.5 Hz, 2H), 6.41-6.20 (m, 1H), 2.11 (d, J=7.5 Hz, 2H), 0.375 (t, J=7.5 Hz, 3H); ESI MS m/z 175 (M+H)$^+$.

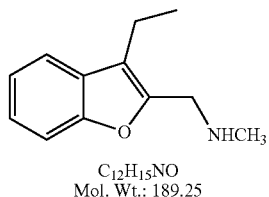

C$_{12}$H$_{15}$NO
Mol. Wt.: 189.25 d) (3-Ethyl-benzofuran-2-ylmethyl)methylamine

3-Ethyl-benzofuran-2-carbaldehyde (1.16 g, 6.65 mmol) was added to a solution of methylamine (26 mL of a 2M solution in MeOH, 52 mmol) and the resulting mixture was stirred overnight. The mixture was concentrated under reduced pressure. The residue was taken up in ethanol (20 mL) and then cooled in an ice-bath. NaBH$_4$ (370 mg, 9.90 mmol) was added in one portion. The mixture was concentrated under reduced pressure and the residue taken up in 1 M NaOH. The mixture was extracted with Et$_2$O (3×). The combined organics were washed with brine, dried and concentrated under reduced pressure to give the title compound (1.12 g, 89%) as a yellow oil: $^1$H NMR (300 MHz, DMSO-d$_6$) δ 7.58 (dd, J=8.4, 6.6 Hz, 1H), 7.46 (d, J=7.2 Hz, 1H), 7.30-7.25 (m, 2H), 3.75 (s, 2H), 2.68 (t, J=7.5 Hz, 2H), 2.26 (s, 3H), 2.05 (br s, 1H), 1.21 (t, J=7.5 Hz, 3H); ESI MS m/z 190 (M+H)$^+$.

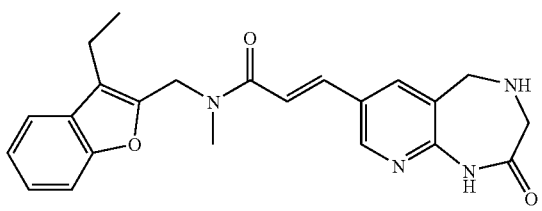

C$_{23}$H$_{24}$N$_4$O$_3$
Mol. Wt.: 404.46 e) (E)-N-(3-ethyl-benzofuran-2-ylmethyl)-N-methyl-3-(2-oxo-2,3,4,5-tetrahydro-1H-pyrido[2,3-e][1,4]diazepin-7-yl)acrylamide A solution of (3-ethyl-benzofuran-2-ylmethyl)methylamine (185 mg, 0.979 mmol) and (i-Pr)₂EtN (0.427 mL, 2.44 mmol) in DMF (25 mL) was treated successively with 3-(2-oxo-2,3,4,5-tetrahydro-1H-pyrido[2,3-e][1,4]diazepin-7-yl)acrylic acid hydrochloride (250 mg, 0.816 mmol), HOBt (115 mg, 0.856 mmol), and EDC (316 mg, 2.44 mmol). After stirring overnight at room temperature, the mixture was diluted with water and then extracted with EtOAc (3×). The combined organics were washed with brine and dried, filtered and concentrated in vacuo. Purification by column chromatography (silica gel, CH₂Cl₂/CH₃OH, 40:2 to 35:2) gave the title compound (125 mg, 37%) as a yellow solid: ESI MS m/z 405 (M+H)⁺.

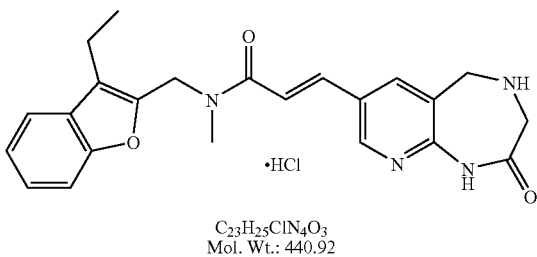 [SMILES: CCc1c(CN(C)C(=O)/C=C/c2cnc3c(c2)CNCC(=O)N3)oc2ccccc12 ; Cl]

C₂₃H₂₅ClN₄O₃
Mol. Wt.: 440.92 f) (E)-N-(3-ethyl-benzofuran-2-ylmethyl)-N-methyl-3-(2-oxo-2,3,4,5-tetrahydro-1H-pyrido[2,3-e][1,4]diazepin-7-yl)acrylamide hydrochloride A suspension of (E)-N-(3-ethyl-benzofuran-2-ylmethyl)-N-methyl-3-(2-oxo-2,3,4,5-tetrahydro-1H-pyrido[2,3-e][1,4]diazepin-7-yl)acrylamide (100 mg, 0.247 mmol) in CH₂Cl₂ (3 mL) and CH₃OH (0.5 mL) was treated with anhydrous HCl (0.123 mL of a 2M solution in Et₂O, 0.247 mmol). After stirring for 1 h, the mixture was diluted with Et₂O (3 mL) and stirred for 10 minutes. The solid was isolated by filtration, washed with Et₂O and dried under vacuum at 50° C. overnight to give the title compound (81.0 mg, 81%) as an off-white solid and as a mixture of amide rotamers: ¹H NMR (500 MHz, DMSO-d₆) δ 10.0 (br s, 2H), 8.82-8.75 (m, 1H), 8.33-8.27 (m, 1H), 7.68-7.55 (m, 3H), 7.50 (t, J=7.5 Hz, 1H), 7.33-7.24 (m, 3H), 5.01-4.81 (m, 2H), 4.26 (s, 2H), 3.84 (s, 2H), 3.20-2.92 (m, 3H), 2.78-2.74 (m, 2H), 1.23-1.19 (m, 3H); ESI MS m/z 405 (M+H)⁺.

Example 19

Preparation of (E)-3-(3,3-Dimethyl-2-oxo-2,3,4,5-tetrahydro 1H-pyrido[2,3-e][1,4]dizepin-7-yl)-N-methyl-N-(3-propyl-benzofuran-2-ylmethyl)acrylamide hydrochloride

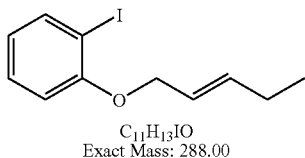

C₁₁H₁₃IO
Exact Mass: 288.00 a) 1-Iodo-2-pent-2-enyloxy-benzene

An ice-cold solution of 2-iodophenol (6.00 g, 272 mmol) in DMF (100 mL) was added dropwise to a solution of NaH (1.30 g, 54.4 mmol) in DMF. 1-Bromo-pent-2-ene (4.87 g, 327 mmol) was then added. The mixture slowly warmed to room temperature overnight. The reaction was quenched with water (50 mL) and the mixture was extracted with CH₂Cl₂ (3×). The combined organics were washed with brine and dried over Na₂SO₄ to give the title compound (8.50 g, 99%) as a yellow oil: ¹H NMR (300 MHz, DMSO-d₆) δ 7.75 (dd, J=7.5, 1.2, Hz, 1H), 7.36-7.30 (m, 1H), 6.98 (d, J=8.1 Hz, 1H), 6.76-6.71 (m, 1H), 6.01-5.89 (m, 1H), 5.67 (t, J=5.7 Hz, 1H), 4.54 (d, J=5.7 Hz, 2H), 2.08 (t, J=7.5 Hz, 2H),

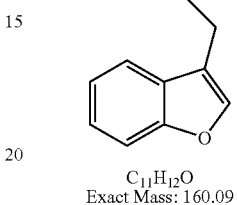

C₁₁H₁₂O
Exact Mass: 160.09 b) 3-Propyl-benzofuran

To a solution of 1-but-2-enyloxy-iodobenzene (4.00 g, 13.8 mmol) in DMF (46 mL) was added n-Bu₄NCl (5.36 g. 19.3 mmol), Pd(OAc)₂ (0.168 g, 0.690 mmol), Na₂CO₃ (2.99 g, 28.2 mmol) and NaOAc (1.13 g, 13.8 mmol). The mixture was heated to reflux under nitrogen atmosphere overnight. The mixture was diluted with EtOAc and washed with water. The aqueous layer was extracted with EtOAc (3×). The combined organics were washed with brine and dried over Na₂SO₄. Purification by column chromatography (silica gel, hexanes) gave the title compound (1.79 g, 81%) as a yellow oil: ¹H NMR (300 MHz, DMSO-d₆) δ 7.75 (s, 1H), 7.63-7.60 (m, 1H), 7.54 (d, J=7.5 Hz, 1H), 7.33-7.22 (m, 2H), 2.64-2.59 (m, 2H), 1.72-1.64 (m, 2H), 0.96 (t, J=7.2 Hz, 3H); ESI MS m/z 161 (M+H)⁺.

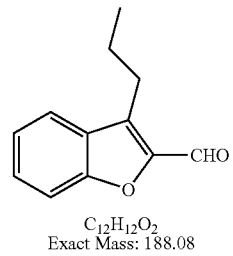

C₁₂H₁₂O₂
Exact Mass: 188.08 c) 3-Propyl-bezofuran-2-carbadehyde

To a solution of 3-propyl-benzofuran (1.79 g, 11.1 mmol) in THF (30 mL) at −30° C. under N₂ was added n-butyllithium (11 mL of a 2.5 M solution in hexane, 27.5 mmol) dropwise. The mixture was stirred for 15 minutes then DMF (2.83 g, 38.8 mmol) was added. The mixture was slowly warmed to room temperature overnight. The reaction was quenched with saturated NH₄Cl and the resulting mixture was extracted with EtOAc (3×). The combined organics were washed with water and brine, and then dried over Na₂SO₄. Purification by column chromatography (silica gel, hexanes/EtOAc, 5:1) gave the title compound (1.45 g, 70%) as a yellow oil: ¹H NMR (300 MHz, DMSO-$d_6$) δ 10.0 (s, 1H), 7.93-7.90 (m, 1H), 7.70 (t, J=8.4 Hz, 1H), 7.62-7.56 (m, 1H), 7.42-7.37 (m, 1H), 3.10 (t, J=7.2 Hz, 2H), 1.77-1.65 (m, 2H), 1.00-0.92 (m, 3H); ESI MS m/z 189 (M+H)$^+$.

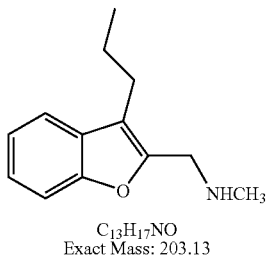

$C_{13}H_{17}NO$
Exact Mass: 203.13 d) Methyl-(3-propyl-benzofuran-2-ylmethyl)amine

To 3-propyl-benzofuran-2-carbaldehyde (1.36 g, 72.2 mmol) was added methylamine (29 mL of a 2 M solution in methanol, 58 mmol). The resulting mixture was stirred overnight at room temperature under nitrogen. The mixture was concentrated under reduced pressure. The residue was taken up in ethanol (20 mL) and the solution was cooled in an ice-bath. NaBH$_4$ (490 mg, 10.8 mmol) was added in one portion. The mixture was concentrated under reduced pressure and the residue taken up in 1 M NaOH. The mixture was extracted with Et$_2$O (3×). The combined organics were washed, dried (Na$_2$SO$_4$), filtered and concentrated under reduced pressure to give the title compound (1.68 g, 99%) as a yellow oil: $^1$H NMR (300 MHz, DMSO-$d_6$) δ 7.60-7.54 (m, 1H), 7.49 (dd, J=7.2, 1.2 Hz, 1H), 7.25-7.20 (m, 2H), 3.76 (s, 2H), 2.65 (t, J=7.2 Hz, 2H), 2.30 (d, J=9.3 Hz, 3H), 1.99 (s, 1H), 1.66-1.58 (m, 2H), 0.94-0.86 (m, 3H); ESI MS m/z 204 (M+H)$^+$.

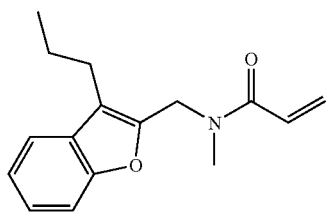

$C_{16}H_{19}NO_2$
Exact Mass: 257.14 e) N-Methyl-N-(3-propyl-benzofuran-2-ylmethyl)acrylamide

A solution of methyl-(3-propyl-benzofuran-2-ylmethyl)amine (1.10 g, 5.41 mmol) in CH$_2$Cl$_2$ (40 mL) was treated with acryloyl chloride (0.45 mL, 5.68 mmol) and triethylamine (1.5 mL, 10.8 mmol). The mixture was stirred at room temperature for 2 h. The solution was washed with water and brine, dried (Na$_2$SO$_4$), filtered and concentrated under reduced pressure to give the title compound (1.46 g, 99%) as a yellow solid: $^1$H NMR (300 MHz, DMSO-$d_6$) δ 7.59 (d, J=5.4 Hz, 1H), 7.49 (d, J=7.5 Hz, 1H), 7.28-7.15 (m, 2H), 6.89-6.70 (m, 1H), 6.20 (t, J=2.4 Hz, 1H), 5.75 (t, J=4.5 Hz, 1H), 4.83-4.71 (m, 2H), 3.33-3.07 (m, 2H), 2.87-2.67 (m, 3H), 1.65-1.58 (m, 2H), 0.95-0.88 (m, 3H); ESI MS m/z 258 (M+H)$^+$.

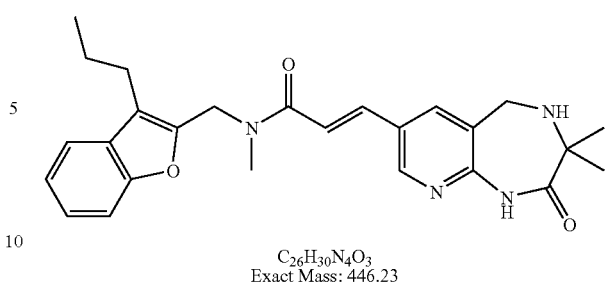

$C_{26}H_{30}N_4O_3$
Exact Mass: 446.23 f) (E)-3-(3,3-Dimethyl-2-oxo-2,3,4,5-tetrahydro 1H-pyrido[2,3-e][1,4]dizepin-7-yl)-N-methyl-N-(3-propyl-benzofuran-2-ylmethyl)acrylamide To 7-bromo-3,3-dimethyl-1,3,4,5-tetrahydro-pyrido[2,3-e][1,4]diazepin-2-one (400 mg, 1.48 mmol) in propionitrile (40 mL) and DMF (10 mL) was added N-methyl-N-(3-propyl-benzofuran-2-ylmethyl)acrylamide (410 mg, 1.63 mmol), (i-Pr)$_2$EtN (0.51 mL, 2.96 mmol), Pd(OAc)$_2$ (332 mg, 0.148 mmol) and P(o-tol)$_3$ (90.1 mg, 0.296 mmol), and the mixture was de-oxygenated with argon for 15 min. The mixture was heated to reflux overnight, allowed to cool and then filtered. The filtrate was concentrated and the residue was dissolved in CH$_2$Cl$_2$ (150 mL). The organic solution was washed with water and brine, dried and the solvent was removed in vacuo. Purification by column chromatography (silica gel, CH$_2$Cl$_2$/MeOH, 20:1) gave the title compound (87.0 mg, 11%) as an off-white solid: MS m/z 447 (M+H)$^+$.

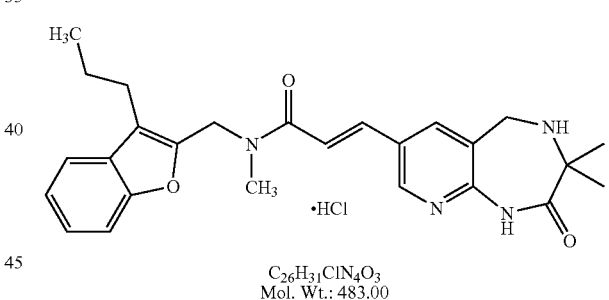

$C_{26}H_{31}ClN_4O_3$
Mol. Wt.: 483.00 g) (E)-3-(3,3-Dimethyl-2-oxo-2,3,4,5-tetrahydro 1H-pyrido[2,3-e][1,4]diazepin-7-yl)-N-methyl-N-(3-propyl-benzofuran-2-ylmethyl)acrylamide hydrochloride A suspension of (E)-3-(3,3-dimethyl-2-oxo-2,3,4,5-tetrahydro 1H-pyrido[2,3-e][1,4]diazepin-7-yl)-N-methyl-N-(3-propyl-benzofuran-2-ylmethyl)acrylamide (84.0 mg, 0.188 mmol) in CH$_2$Cl$_2$ (3 mL) was treated with anhydrous HCl (0.094 mL of a 2 M solution in Et$_2$O, 0.188 mmol). After stirring for 1 h, the mixture was diluted with Et$_2$O (5 mL) and then stirred for 10 min. The solid was isolated by filtration, washed with Et$_2$O, and dried under vacuum at 50° C. overnight to give the title compound (65.0 mg, 72%) as an off-white solid and as a mixture of amide rotamers: $^1$H NMR (300 MHz, DMSO-$d_6$) δ 10.9 (s, 1H), 10.3 (br s, 2H) 8.71-8.65 (m, 1H), 8.37 (s, 1H), 7.60-7.48 (m, 3H), 7.34-7.20 (m, 3H), 5.01-4.81 (m, 2H), 4.41 (s, 2H), 3.20-2.90 (m, 3H), 2.73 (t, J=7.2 Hz, 2H), 1.70-1.61 (m, 8H), 0.93 (t, J=7.5 Hz, 3H); ESI MS m/z 447 (M+H)+.

Example 20

Preparation of (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide hydrochloride

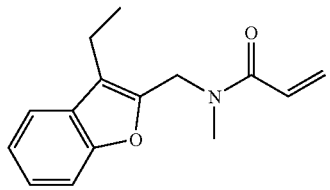

C15H17NO2
Exact Mass: 243.13 a) N-(3-ethyl-benzofuran-2-ylmethyl)-N-methylacrylamide

A solution of N-(3-ethyl-benzofuran-2-ylmethyl)methylamine (860 mg, 4.54 mmol) in CH2Cl2 (32 mL) was treated with acryloyl chloride (0.38 mL, 4.77 mmol) and triethylamine (1.3 mL, 9.08 mmol). The mixture was stirred at room temperature for 2 h. The solution was washed with water and brine, dried (Na2SO4), filtered and concentrated under reduced pressure to give the title compound (1.10 g, 99%) as a yellow solid: 1H NMR (300 MHz, CDCl3) δ 7.55 (dd, J=6.9, 1.8 Hz, 1H), 7.41 (d, J=7.5 Hz, 1H), 7.28-7.20 (m, 2H), 6.59 (t, J=6.6 Hz, 1H), 6.45-6.32 (m, 1H), 5.75-5.70 (m, 1H), 4.78-4.63 (m, 2H), 3.15-3.01 (m, 3H), 2.82-2.70 (m, 2H), 1.35-1.23 (m, 3H); ESI MS m/z 244 (M+H)+.

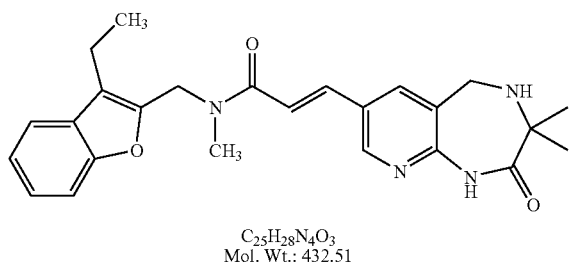 [SMILES: CCc1c(CN(C)C(=O)/C=C/c2cnc3c(c2)CNC(C)(C)C(=O)N3)oc2ccccc12]

C25H28N4O3
Mol. Wt.: 432.51 b) (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide To 7-bromo-3,3-dimethyl-1,3,4,5-tetrahydro-pyrido[2,3-e][1,4]diazepin-2-one (400 mg, 1.48 mmol) in propionitrile (40 mL) and DMF (10 mL) was added N-(3-ethyl-benzofuran-2-ylmethyl)-N-methylacrylamide (410 mg, 1.62 mmol), (i-Pr)2EtN (0.51 mL, 2.96 mmol), Pd(OAc)2 (332 mg, 0.148 mmol) and P(o-tol)3 (90.1 mg, 0.296 mmol), and the mixture was de-oxygenated with argon for 15 min. The mixture was heated to reflux overnight, allowed to cool and then filtered. The filtrate was concentrated and the residue was dissolved in CH2Cl2 (150 mL). The organic solution was washed with water and brine, dried (Na2SO4) and the solvent was removed in vacuo. Purification by column chromatography (silica gel, CH2Cl2/MeOH, 20:1) gave the title compound (130 mg, 20%) as an off-white solid: MS m/z 433 (M+H)+.

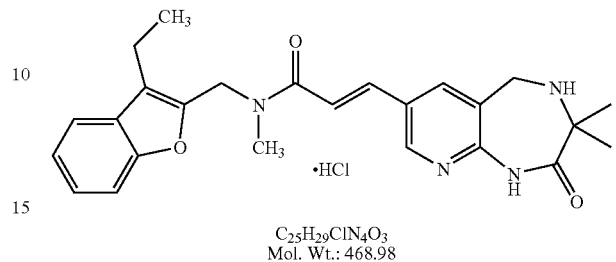

C25H29ClN4O3
Mol. Wt.: 468.98 c) (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide hydrochloride A suspension of (E)-3-(3,3-dimethyl-2-oxo-2,3,4,5-tetrahydro-1H-pyrido[2,3-e][1,4]diazepin-7-yl)-N-(3-ethyl-benzofuran-2-ylmethyl)-N-methylacrylamide (59.0 mg, 0.136 mmol) in CH2Cl2 (4 mL) and CH3OH (0.3 mL) was treated with anhydrous HCl (0.068 mL of a 2 M solution in Et2O, 0.136 mmol). After stirring for 1 h, the mixture was diluted with Et2O (5 mL) and stirred for 10 minutes. The solid was isolated by filtration, washed with Et2O, and dried under vacuum at 50° C. overnight to give the title compound (63.0 mg, 99%) as an off-white solid and as a mixture of amide rotamers: 1H NMR (500 MHz, DMSO-d6) δ 10.9 (s, 1H), 10.5 (br s, 2H) 8.71-8.60 (m, 1H), 8.39 (d, J=8.0 Hz, 1H), 7.65-7.50 (m, 3H), 7.35-7.20 (m, 3H), 4.80-5.01 (m, 2H), 4.40 (s, 2H), 3.20-2.90 (m, 3H), 2.77 (d, J=7.0 Hz, 2H), 1.62 (s, 6H), 1.22 (t, J=7.0 Hz, 3H); ESI MS m/z 433 (M+H)+.

Example 21

Preparation of (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide hydrochloride

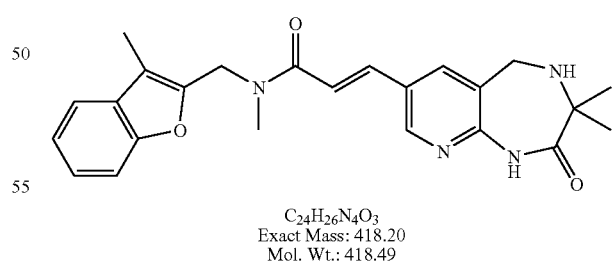

C24H26N4O3
Exact Mass: 418.20
Mol. Wt.: 418.49 a) (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide A suspension of 7-bromo-3,3-dimethyl-1,3,4,5-tetrahydro-pyrido[2,3-e][1,4]diazepin-2-one (0.27 g, 1.0 mmol) and N-methyl-N-(3-methylbenzofuran-2-ylmethyl)acrylamide (0.31 g, 1.4 mmol) in propionitrile (5 mL) and DMF (1.3 mL) was de-oxygenated with Ar for 10 min. The mixture was treated with (i-Pr)$_2$EtN (0.37 mL, 2.1 mmol) and was de-oxygenated with Ar for 10 min. Pd(OAc)$_2$ (22 mg, 0.098 mmol) and P(o-tol)$_3$ (61 mg, 0.20 mmol) were added simultaneously, and the mixture was de-oxygenated a third time for 5 min. The mixture was heated to reflux overnight, then allowed to cool. The resulting precipitate was isolated by filtration, washed with EtOAc, dissolved in CH$_2$Cl$_2$/MeOH (1:1) and the solvent was removed in vacuo. Purification by flash column chromatography (silica gel, CH$_2$Cl$_2$/MeOH, 97:3) gave the title compound (0.25 g, 60%) as a white solid: MS (ESI) m/e 419 (M+H)$^+$.

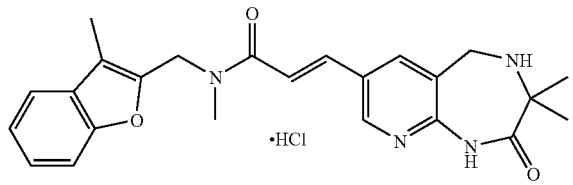

C$_{24}$H$_{27}$ClN$_4$O$_3$
Exact Mass: 454.18
Mol. Wt.: 454.95 b) (E)-3-(3,3-Dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(3-methylbenzofuran-2-ylmethyl)acrylamide (0.20 g, 0.48 mmol) in CH$_2$Cl$_2$ (10 mL) was treated with anhydrous HCl (0.48 mL of a 1.0 M solution in Et$_2$O, 0.48 mmol). After stirring for 45 min, the mixture was diluted with Et$_2$O (50 mL) and stirred for 3 h. The solid was isolated by filtration, washed with Et$_2$O, and dried under vacuum at 50° C. overnight to give the title compound (0.21 g, 97%) as a white powder and as a mixture of amide rotamers: $^1$H NMR (300 MHz, DMSO-d$_6$) δ 10.92 (s, 1H), 10.55 (br s, 2H), 8.68-8.65 (m, 1H), 8.39 (s, 1H), 7.60-7.22 (m, 6H), 5.01-4.81 (m, 2H), 4.40 (s, 2H), 3.20-2.93 (m, 3H), 2.27 (s, 3H), 1.63 (s, 6H); MS (ESI) m/e 419 (M+H)$^+$.

Example 22

Preparation of (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide hydrochloride

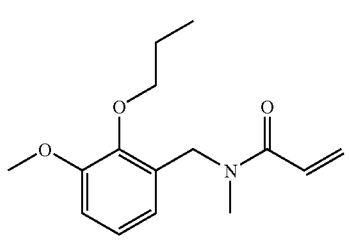

C$_{15}$H$_{21}$NO$_3$
Exact Mass: 263.15
Mol. Wt.: 263.33 a)
N-(3-Methoxy-2-propoxybenzyl)-N-methylacrylamide

A solution of (3-methoxy-2-propoxybenzyl)methylamine (1.00 g, 4.78 mmol) in CH$_2$Cl$_2$ (40 mL) was treated with acryloyl chloride (0.42 mL, 5.2 mmol) followed by Et$_3$N (0.74 mL, 5.3 mmol). After stirring for 1.5 h, the solution was diluted with CH$_2$Cl$_2$ (50 mL) and washed with saturated aqueous NaHCO$_3$ (50 mL). The aqueous layer was extracted with CH$_2$Cl$_2$ (50 mL). The combined organic layers were dried over Na$_2$SO$_4$, filtered and concentrated to give the title compound (1.11 g, 88%) as a tan oil and as a mixture of amide rotamers: $^1$H NMR (300 MHz, CDCl$_3$) δ 7.06-6.94 (m, 2H), 6.85-6.70 (m, 1H), 6.65-6.58 (m, 1H), 6.18-6.13 (m, 1H), 5.73-5.63 (m, 1H), 4.64-4.58 (m, 2H), 3.89-3.84 (m, 2H), 3.79-3.78 (m, 3H), 2.99-2.86 (m, 3H), 1.73-1.66 (m, 2H), 0.97 (t, J=7.4 Hz, 3H).

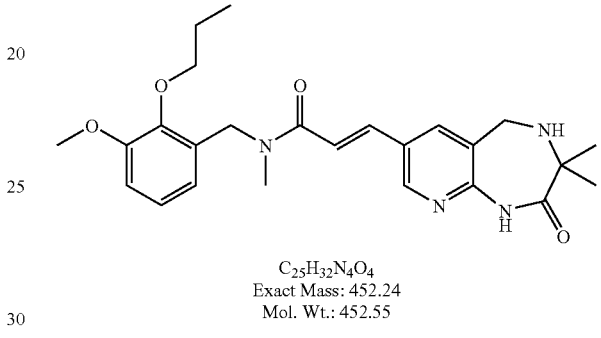

C$_{25}$H$_{32}$N$_4$O$_4$
Exact Mass: 452.24
Mol. Wt.: 452.55 b) (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide A suspension of 7-bromo-3,3-dimethyl-1,3,4,5-tetrahydro-pyrido[2,3-e][1,4]diazepin-2-one (0.30 g, 1.1 mmol) and N-(3-methoxy-2-propoxybenzyl)-N-methylacrylamide (0.35 g, 1.3 mmol) in propionitrile (5 mL) and DMF (1.3 mL) was de-oxygenated with Ar for 5 min. The mixture was treated with (i-Pr)$_2$EtN (0.41 mL, 2.4 mmol) and was de-oxygenated with Ar for 10 min. Pd(OAc)$_2$ (25 mg, 0.11 mmol) and P(o-tol)$_3$ (69 mg, 0.23 mmol) were added simultaneously, and the mixture was de-oxygenated a third time for 5 min. The mixture was heated to reflux overnight, then allowed to cool. The mixture was diluted with Et$_2$O (50 mL) and EtOAc (25 mL), washed with H$_2$O (25 mL), dried over Na$_2$SO$_4$, filtered and concentrated to an orange residue. Purification by flash column chromatography (silica gel, CH$_2$Cl$_2$/MeOH, 98:2 to 97:3) gave the title compound (0.30 g, 60%) as an off-white solid: MS (ESI) m/e 453 (M+H)$^+$.

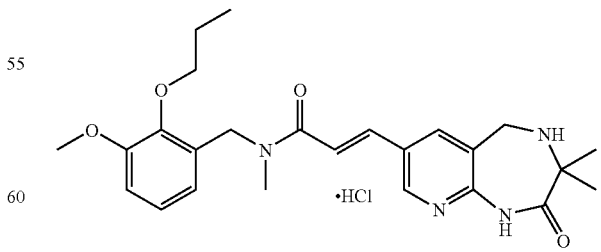

C$_{25}$H$_{33}$ClN$_4$O$_4$
Exact Mass: 488.22
Mol. Wt.: 489.01 c) (E)-3-(3,3-Dimethyl-2-oxo-2,3,4,5-tetrahydro-1H-pyrido[2,3-e][1,4]diazepin-7-yl)-N-(3-methoxy-2-propoxybenzyl)-N-methylacrylamide hydrochloride A suspension of (E)-3-(3,3-dimethyl-2-oxo-2,3,4,5-tetrahydro-1H-pyrido[2,3-e][1,4]diazepin-7-yl)-N-(3-methoxy-2-propoxybenzyl)-N-methylacrylamide (0.19 g, 0.42 mmol) in CH$_2$Cl$_2$ (5 mL) was treated with anhydrous HCl (0.42 mL of a 1.0 M solution in Et$_2$O, 0.42 mmol). After stirring for 1 h, the mixture was diluted with Et$_2$O (50 mL) and allowed to stir for 3 h. The solid was isolated by filtration, washed with Et$_2$O and dried under vacuum at 50° C. for 3 d to give the title compound (0.17 g, 84%) as an off-white powder and as a mixture of amide rotamers: $^1$H NMR (300 MHz, DMSO-d$_6$) δ 10.94-10.92 (m, 1H), 10.47 (br s, 2H), 8.67-8.62 (m, 1H), 8.39-8.32 (m, 1H), 7.60-7.53 (m, 1H), 7.39-7.33 (m, 1H), 7.05-6.95 (m, 2H), 6.69-6.62 (m, 1H), 4.80-4.65 (m, 2H), 4.42-4.38 (m, 2H), 3.92-3.85 (m, 2H), 3.80 (s, 3H), 3.12-2.86 (m, 3H), 1.75-1.67 (m, 2H), 1.63-1.61 (m, 6H), 1.01-0.94 (m, 3H); MS (ESI) m/e 453 (M+H)$^+$.

Example 23

Preparation of (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide hydrochloride

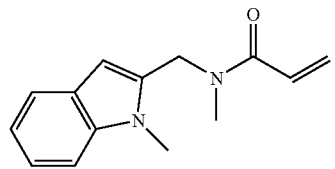

C$_{14}$H$_{16}$N$_2$O
Exact Mass: 228.13
Mol. Wt.: 228.29 a) N-Methyl-N-(1-methyl-1H-indol-2-ylmethyl)acrylamide

A solution of methyl-(1-methyl-1H-indol-2-ylmethyl)amine (2.00 g, 11.5 mmol) in CH$_2$Cl$_2$ (100 mL) was treated with acryloyl chloride (1.03 mL, 12.7 mmol) followed by Et$_3$N (1.8 mL, 13 mmol). After stirring for 2 h, the solution was diluted with CH$_2$Cl$_2$ (100 mL) and washed with saturated aqueous NaHCO$_3$ (200 mL). The aqueous layer was extracted with CH$_2$Cl$_2$ (200 mL). The combined organic layers were dried over Na$_2$SO$_4$, filtered and concentrated to an orange oil. Purification by flash column chromatography (silica gel, CH$_2$Cl$_2$/MeOH, 99.5:0.5 to 99:1) gave the title compound (2.10 g, 80%) as a tan oil: $^1$H NMR (300 MHz, CDCl$_3$) δ 7.59-7.56 (m, 1H), 7.32-7.19 (m, 2H), 7.13-7.08 (m, 1H), 6.66-6.57 (m, 1H), 6.47-6.38 (m, 2H), 5.78-5.74 (m, 1H), 4.88-4.74 (m, 2H), 3.69 (s, 3H), 3.06-2.97 (m, 3H); MS (ESI) m/e 229 (M+H)$^+$.

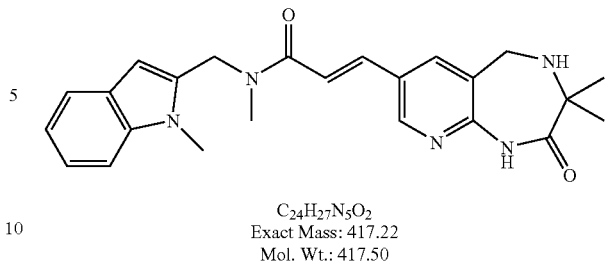

C$_{24}$H$_{27}$N$_5$O$_2$
Exact Mass: 417.22
Mol. Wt.: 417.50 b) (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide A suspension of 7-bromo-3,3-dimethyl-1,3,4,5-tetrahydro-pyrido[2,3-e][1,4]diazepin-2-one (0.30 g, 1.1 mmol) and N-methyl-N-(1-methyl-1H-indol-2-ylmethyl)acrylamide (0.35 g, 1.3 mmol) in propionitrile (5 mL) and DMF (1.3 mL) was de-oxygenated with Ar for 10 min. The mixture was treated with (i-Pr)$_2$EtN (0.41 mL, 2.4 mmol) and was de-oxygenated with Ar for 5 min. Pd(OAc)$_2$ (25 mg, 0.11 mmol) and P(o-tol)$_3$ (70 mg, 0.23 mmol) were added simultaneously, and the mixture was de-oxygenated a third time for 5 min. The mixture was heated to reflux overnight, then allowed to cool. The mixture was diluted with EtOAc (100 mL), washed with H$_2$O (50 mL), dried over Na$_2$SO$_4$, filtered and concentrated to an orange residue. Purification by flash column chromatography (silica gel, CH$_2$Cl$_2$/MeOH, 98:2 to 97:3) gave the title compound (0.24 g, 51%) as a light pink solid: MS (ESI) m/e 418 (M+H)$^+$.

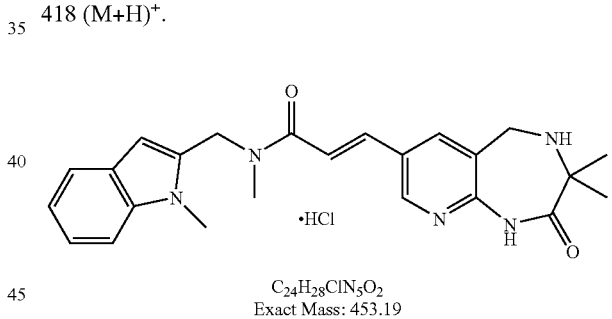

C$_{24}$H$_{28}$ClN$_5$O$_2$
Exact Mass: 453.19
Mol. Wt.: 453.96 c) (E)-3-(3,3-Dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(1-methyl-1H-indol-2-ylmethyl)acrylamide (0.15 g, 0.36 mmol) in CH$_2$Cl$_2$ (5 mL) was treated with anhydrous HCl (0.36 mL of a 1.0 M solution in Et$_2$O, 0.36 mmol). After stirring for 10 min, the mixture was diluted with Et$_2$O (50 mL) and then stirred for 1.5 h. The solid was isolated by filtration, washed with Et$_2$O, and dried under vacuum at 50° C. for 3 d to give the title compound (0.14 g, 83%) as a tan powder and as a mixture of amide rotamers: $^1$H NMR (500 MHz, DMSO-d$_6$) δ 10.90-10.87 (m, 1H), 10.54 (br s, 2H), 8.66-8.63 (m, 1H), 8.39-8.33 (s, 1H), 7.62-7.59 (m, 1H), 7.51-7.32 (m, 3H), 7.14-7.11 (m, 1H), 7.03-6.99 (m, 1H), 6.43-6.19 (m, 1H), 5.07-4.86 (m, 2H), 4.40-4.35 (m, 2H), 3.74-3.69 (m, 3H), 3.13-3.00 (m, 3H), 1.63-1.59 (m, 6H); MS (ESI) m/e 418 (M+H)+.

Example 24

Preparation of (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide hydrochloride

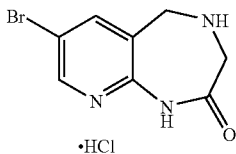

| Salt | Free Base |
|---|---|
| C8H9BrClN3O | C8H8BrN3O |
| Exact Mass: 276.96 | Exact Mass: 240.99 |
| Mol. Wt.: 278.53 | Mol. Wt.: 242.07 | a) 7-Bromo-1,3,4,5-tetrahydropyrido[2,3-e][1,4]diazepin-2-one hydrochloride

A solution of 7-bromo-4-(4-methoxybenzyl)-1,3,4,5-tetrahydropyrido[2,3-e][1,4]diazepin-2-one (3.37 g, 9.30 mmol) in dichloroethane (180 mL) was cooled in an ice bath and treated with ACE-Cl (1.1 mL, 10 mmol). After stirring at 0° C. under $N_2$ for 30 min and then at room temperature for 30 min, the mixture was heated to reflux for 1 h. The mixture was allowed to cool and then concentrated to dryness. Purification by flash column chromatography (silica gel, $CH_2Cl_2$/MeOH, 99:1) gave a white solid. A portion of the solid (1.02 g, 2.93 mmol) was suspended in methanol (50 mL) and heated to reflux for 3 h. The mixture was allowed to cool and the solid was isolated by filtration, washed with MeOH and dried under vacuum at 50° C. overnight to give the title compound (0.66 g, 46%) as a white solid: $^1$H NMR (300 MHz, DMSO-$d_6$) δ 11.05 (s, 1H), 10.30 (br s, 2H), 8.57 (d, J=2.3 Hz, 1H), 8.15 (d, J=2.3 Hz, 1H), 4.24 (s, 2H), 3.79 (s, 2H); MS (ESI) m/e 242 (M+H)+.

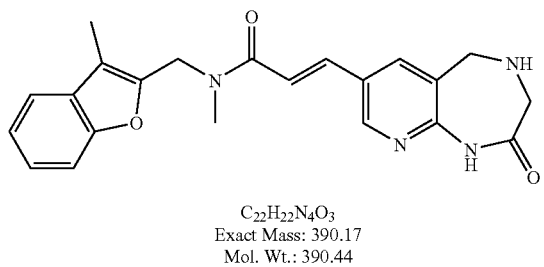 [SMILES: Cc1c(CN(C)C(=O)/C=C/c2cnc3c(c2)CNCC(=O)N3)oc2ccccc12]

C22H22N4O3
Exact Mass: 390.17
Mol. Wt.: 390.44 b) (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide A suspension of 7-bromo-1,3,4,5-tetrahydropyrido[2,3-e][1,4]diazepin-2-one hydrochloride (0.29 g, 1.0 mmol) and N-methyl-N-(3-methylbenzofuran-2-ylmethyl)acrylamide (0.29 g, 1.3 mmol) in propionitrile (5 mL) and DMF (1.3 mL) was de-oxygenated with Ar for 10 min. The mixture was treated with (i-Pr)$_2$EtN (0.56 mL, 3.2 mmol) and was de-oxygenated with Ar for 5 min. Pd(OAc)$_2$ (24 mg, 0.11 mmol) and P(o-tol)$_3$ (64 mg, 0.21 mmol) were added simultaneously, and the mixture was de-oxygenated a third time for 5 min. The mixture was heated to reflux overnight, then allowed to cool. The resulting precipitate was isolated by filtration, dissolved in $CH_2Cl_2$/MeOH and the solvent was removed in vacuo. Purification by flash column chromatography (silica gel, $CH_2Cl_2$/MeOH, 98:2 to 96:4) gave the title compound (0.18 g, 47%) as a white solid: MS (ESI) m/e 391 (M+H)+.

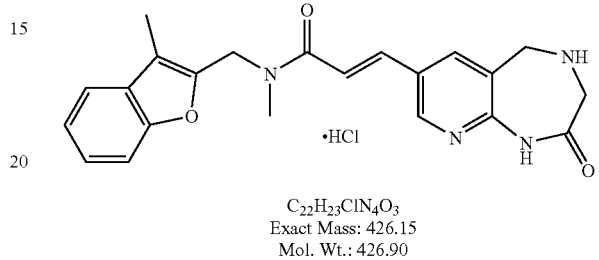

C22H23ClN4O3
Exact Mass: 426.15
Mol. Wt.: 426.90 c) (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide hydrochloride A suspension of (E)-N-Methyl-N-(3-methylbenzofuran-2-ylmethyl)-3-(2-oxo-2,3,4,5-tetrahydro-1H-pyrido[2,3-e][1,4]diazepin-7-yl)acrylamide (0.16 g, 0.40 mmol) in $CH_2Cl_2$ (10 mL) was treated with anhydrous HCl (0.40 mL of a 1.0 M solution in Et$_2$O, 0.40 mmol). After stirring for 45 min, the mixture was diluted with Et$_2$O (50 mL) and then stirred for 1 h. The solid was isolated by filtration, washed with Et$_2$O, and dried under vacuum at 50° C. for 3 d to give the title compound (0.15 g, 90%) as a white powder and as a mixture of amide rotamers: $^1$H NMR (300 MHz, DMSO-$d_6$) δ 11.09 (s, 1H), 10.12 (br s, 2H), 8.79-8.76 (m, 1H), 8.33-8.31 (s, 1H), 7.60-7.24 (m, 6H), 5.01-4.81 (m, 2H), 4.26 (s, 2H), 3.85 (s, 2H), 3.20-2.93 (m, 3H), 2.27 (s, 3H); MS (ESI) m/e 391 (M+H)+.

Example 25

Preparation of (E)-3-(2,2-Dimethyl-3-oxo-3,4-dihydro-2H-pyrido[3,2-b][1,4]oxazin-7-yl)-N-methyl-N-(3-methylbenzofuran-2-ylmethyl)acrylamide

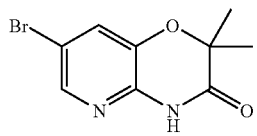

C9H9BrN2O2
Mol. Wt.: 257.08 a) 7-Bromo-2,2-dimethyl-4H-pyrido[3,2-b][1,4]oxazin-3-one

To a mixture of 2-amino-5-bromopyridin-3-ol (0.500 g, 2.64 mmol) and K$_2$CO$_3$ (1.09 g, 7.93 mmol) in acetone (11.0 mL) was added ethyl bromoisobutyrate (0.50 mL, 3.4 mmol). The solution was stirred under N₂ for 18 h and then heated to reflux. After 18 h, the solution was cooled and concentrated. The light-pink, sweet-smelling solid was dissolved in CH$_2$Cl$_2$ (50 mL) and MeOH (5 mL). The solution was diluted with H$_2$O (150 mL) and then washed with CH$_2$Cl$_2$ (3×75 mL). The combined organic layers were washed with brine (2×100 mL), dried (Na$_2$SO$_4$) and concentrated to yield the title compound (0.57 g, 84%) as an off-white solid: ¹H NMR (300 MHz, DMSO-d$_6$) δ 11.39 (s, 1H), 8.03 (d, J=1.2 Hz, 1H), 7.66 (d, 0.9 Hz, 1H), 1.43 (s, 6H).

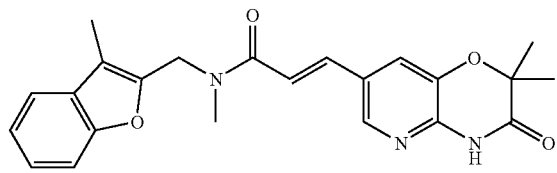

C$_{23}$H$_{23}$N$_3$O$_4$
Mol. Wt.: 405.45 b) (E)-3-(2,2-Dimethyl-3-oxo-3,4-dihydro-2H-pyrido[3,2-b][1,4]oxazin-7-yl)-N-methyl-N-(3-methyl-benzofuran-2-ylmethyl)acrylamide A solution of N-methyl-N-(3-methylbenzofuran-2-ylmethyl)acrylamide (0.231 g, 1.01 mmol) in propionitrile (4 mL) and DMF (0.8 mL) was deoxygenated with Ar for 20 min. The solution was treated with diisopropylethylamine (0.28 mL, 1.64 mmol) and 7-bromo-2,2-dimethyl-4H-pyrido[3,2-b][1,4]oxazin-3-one (0.200 g, 0.775 mmol). The solution was deoxygenated with Ar for 20 min. Pd(OAc)$_2$ (0.017 g, 0.078 mmol) and P(o-tol)$_3$ (0.047 g, 0.15 mmol) were then added and the solution was deoxygenated again with Ar for 10 min. The mixture was heated to reflux for 18 h, then allowed to cool. The mixture was diluted with H$_2$O (100 mL). The resulting solids were collected by filtration and washed with Et$_2$O (50 mL). Residual palladium was removed by silica gel plug (silica gel, 95:5, CH$_2$Cl$_2$/MeOH) the resulting solution concentrated to reveal a light orange solid. The solid was triturated with Et$_2$O and dried to give the title compound (0.14 g, 46%) as a light pink solid and as a mixture of amide rotamers: ¹H NMR (300 MHz, DMSO-d$_6$) δ 11.41 (s, 1H), 8.20-8.19 (m, 1H), 7.97-7.93 (m, 1H), 7.57-7.48 (m, 3H), 7.28-7.23 (m, 3H), 5.00-4.78 (m, 2H), 3.17-2.92 (m, 3H), 2.62 (s, 3H), 1.44 (m, 6H); MS (ESI) m/e 406 (M+H)⁺.

Example 26

Preparation of (E)-3-(2,2-Dimethyl-3,4-dihydro-2H-pyrido[3,2-b][1,4]oxazin-7-yl)-N-methyl-N-(3-methyl-benzofuran-2-ylmethyl)-acrylamide hydrochloride

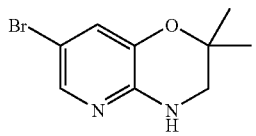

C$_9$H$_{11}$BrN$_2$O
Mol. Wt.: 243.10 a) 7-Bromo-2,2-dimethyl-3,4-dihydro-2H-pyrido[3,2-b][1,4]oxazine

To a solution of 7-bromo-2,2-dimethyl-4H-pyrido[3,2-b][1,4]oxazin-3-one (0.360 g, 1.39 mmol) in THF (8.9 mL) at 0° C. was added BH$_3$ (8.43 mL of a 1.0 M solution in THF, 8.43 mmol). The solution was heated to reflux. After 18 h, the solution was cooled to 0° C. and the reaction quenched with MeOH (15 mL). The mixture was concentrated and the resulting off-white solid was dissolved in MeOH (15 mL) and NaOH (10 mL of a 1 N solution). The mixture was heated at reflux to 4 h. The MeOH was removed under reduced pressure. The resulting precipitate was collected by filtration and washed with H$_2$O (10 mL). The white solid was dried to give the title compound (0.260 g, 76%) as white needles: ¹H NMR (300 MHz, DMSO-d$_6$) δ 7.62 (d, J=2.1 Hz, 1H), 7.10 (d, J=1.5 Hz, 1H), 7.03 (br s, 1H), 3.14 (d, J=2.4 Hz, 2H), 1.25 (s, 6H); MS (ESI) m/e 243 (M+H)⁺.

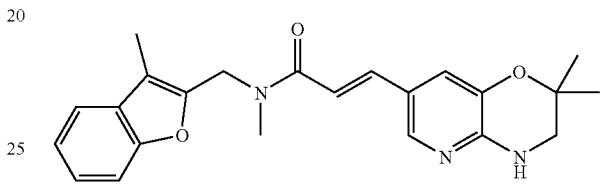

C$_{23}$H$_{25}$N$_3$O$_3$
Mol. Wt.: 391.46 b) (E)-3-(2,2-Dimethyl-3,4-dihydro-2H-pyrido[3,2-b][1,4]oxazin-7-yl)-N-methyl-N-(3-methylbenzofuran-2-ylmethyl)acrylamide A solution of N-methyl-N-(3-methylbenzofuran-2-ylmethyl)acrylamide (0.190 g, 0.637 mmol) in propionitrile (3 mL) and DMF (0.6 mL) was deoxygenated with Ar for 20 min. The solution was treated with diisopropylethylamine (0.23 mL, 1.33 mmol) and 7-bromo-2,2-dimethyl-3,4-dihydro-2H-pyrido[3,2-b][1,4]oxazine (0.154 g, 0.828 mmol). The solution was deoxygenated with Ar for 20 min. Pd(OAc)$_2$ (0.014 g, 0.063 mmol) and P(o-tol)$_3$ (0.038 g, 0.12 mmol) were then added and the solution was deoxygenated again with Ar for 10 min. The mixture was heated to reflux for 2 h, then allowed to cool. The mixture was diluted with H$_2$O (200 mL) and the solution was washed with EtOAc (3×50 mL). The combined organic layers were washed with brine (2×30 mL), dried (Na$_2$SO$_4$) and concentrated to give a dark green oil. Column chromatography (silica gel, CH$_2$Cl$_2$/MeOH, 100 to 98:2) gave the title compound (0.14 g, 59%) as a light yellow solid and as a mixture of amide rotamers: ¹H NMR (500 MHz, DMSO-d$_6$) δ 7.79 (s, 1H), 7.56-7.54 (m, 1H), 7.51-7.47 (m, 2H), 7.41-7.38 (m, 1H), 7.32 (br s, 1H), 7.29-6.93 (m, 3H), 4.95-4.76 (m, 2H), 3.19 (m, 2H), 3.14-2.90 (m, 3H), 2.25 (s, 3H), 1.26 (s, 6H); MS (ESI) m/e 392 (M+H)⁺.

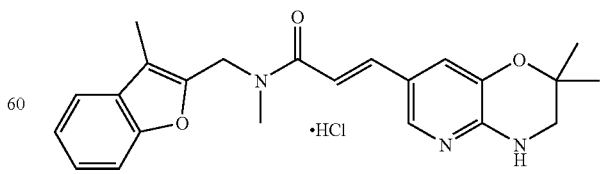

C$_{23}$H$_{26}$ClN$_3$O$_3$
Mol. Wt.: 427.92 c) (E)-3-(2,2-Dimethyl-3,4-dihydro-2H-pyrido[3,2-b][1,4]oxazin-7-yl)-N-methyl-N-(3-methylbenzofuran-2-ylmethyl)acrylamide hydrogen chloride A stirring solution of (E)-3-(2,2-dimethyl-3,4-dihydro-2H-pyrido[3,2-b][1,4]oxazin-7-yl)-N-methyl-N-(3-methylbenzofuran-2-ylmethyl)acrylamide (0.147 g, 0.375 mmol) in CH$_2$Cl$_2$ (4 mL) under N$_2$ was treated with anhydrous HCl (0.18 mL of a 2 M solution in diethyl ether, 0.37 mmol). After stirring for 6 h, the resulting solids were collected by filtration, washed with Et$_2$O (50 mL) and dried to yield the title compound (0.14 g, 88%) as an off-white solid and as a mixture of amide rotamers: $^1$H NMR (300 MHz, DMSO-d$_6$) δ 8.69 (br s, 1H), 8.00-7.94 (m, 2H), 7.57-7.55 (m, 1H), 7.49-7.44 (m, 2H), 7.30-7.14 (m, 3H), 4.99-4.77 (m, 2H), 3.37 (br s, 2H), 3.15-2.90 (m, 3H), 2.25 (s, 3H), 1.32 (s, 6H); MS (ESI) m/e 392 (M+H)$^+$.

Example 27

Preparation of (E)-3-(3,4-Dihydro-2H-pyrido[3,2-b][1,4]oxazin-7-yl)-N-methyl-N-(3-methylbenzofuran-2-ylmethyl)acrylamide hydrochloride

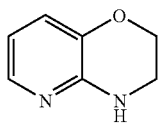

C$_7$H$_8$N$_2$O
Exact Mass: 136.06
Mol. Wt.: 136.15 a) 3,4-Dihydro-2H-pyrido[3,2-b][1,4]oxazine

To an ice-cold solution of 4H-pyrido[3,2-b][1,4]oxazin-3-one (5.00 g, 33.3 mmol) in THF (40 mL) was added lithium aluminum hydride (66.6 mL of a 1.0 M solution in THF, 66.6 mmol). Following the addition, the solution was heated to reflux. After 18 h, the solution was cooled to 0° C. and quenched the reaction with H$_2$O (4 mL) followed by NaOH (4 mL, 15%) and H$_2$O (10 mL). The resulting slurry was filtered over Celite and the filtrate concentrated to give the title compound (3.87 g, 85%) as a blue-gray powder: $^1$H NMR (500 MHz, DMSO-d$_6$) δ 7.53 (dd, J=4.5, 1.0 Hz, 1H), 6.90-6.89 (m, 1H), 6.61 (br s, 1H), 6.44 (dd, J=8.0, 3.0 Hz, 1H), 4.08 (t, J=4.5 Hz, 2H), 3.39-3.36 (m, 2H); MS (ESI) m/e 137 (M+H)$^+$.

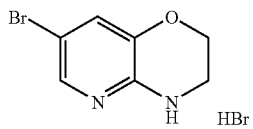

C$_7$H$_8$Br$_2$N$_2$O
Mol. Wt.: 295.96 b) 7-Bromo-2,2-dimethyl-3,4-dihydro-2H-pyrido[3,2-b][1,4]oxazine hydrogen bromide To an ice-cold solution of 3,4-dihydro-2H-pyrido[3,2-b][1,4]oxazine (3.86 g, 28.3 mmol) in acetic acid (71.7 mL) was added Br$_2$ (1.83 mL, 35.6 mmol). The mixture was stirred for 3 h at 0° C. then warmed to ambient temperature. After 2 h, the resulting solids were collected by filtration and washed with EtOAc (400 mL). The solids were dried to give the title compound (6.31 g, 60%) as a dark orange powder: $^1$H NMR (300 MHz, DMSO-d$_6$) δ 12.25 (br s, 1H), 7.77 (t, J=1.8 Hz, 1H), 7.45 (t, J=2.1 Hz, 1H), 4.20 (t, J=4.6 Hz, 2H), 3.48 (t, J=4.6 Hz, 2H); MS (ESI) m/e 215 (M+H)$^+$.

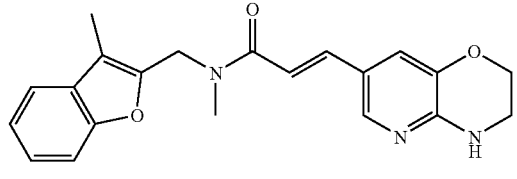

C$_{21}$H$_{21}$N$_3$O$_3$
Exact Mass: 363.16
Mol. Wt.: 363.41 c) (E)-3-(3,4-Dihydro-2H-pyrido[3,2-b][1,4]oxazin-7-yl)-N-methyl-N-(3-methylbenzofuran-2-ylmethyl)acrylamide A solution of N-methyl-N-(3-methylbenzofuran-2-ylmethyl)acrylamide (0.190 g, 0.637 mmol) in propionitrile (3 mL) and DMF (0.6 mL) was deoxygenated with Ar for 20 min. The solution was treated with diisopropylethylamine (0.34 mL, 1.97 mmol) and 7-bromo-2,2-dimethyl-3,4-dihydro-2H-pyrido[3,2-b][1,4]oxazine (0.188 g, 0.828 mmol). The solution was deoxygenated with Ar for 20 min. Pd(OAc)$_2$ (0.014 g, 0.078 mmol) and P(o-tol)$_3$ (0.038 g, 0.15 mmol) were then added and the solution was deoxygenated again with Ar for 20 min. The mixture was heated to reflux for 2 h, then allowed to cool. The mixture was diluted with H$_2$O (200 mL) and the resulting solution was washed with EtOAc (3×50 mL). The combined organic layers were washed with brine (2×30 mL), dried (Na$_2$SO$_4$) and concentrated to a dark green oil. Column chromatography (silica gel, CH$_2$Cl$_2$/MeOH, 100 to 98:2) gave the title compound (0.12 g, 52%) as a light yellow solid and as a mixture of amide rotamers: $^1$H NMR (300 MHz, DMSO-d$_6$) δ 7.83 (br s, 1H), 7.62-7.60 (m, 1H), 7.56-7.51 (m, 2H), 7.48-7.41 (m, 1H), 7.38-7.69 (m, 4H), 5.01-4.95 (m, 2H), 4.03 (s, 2H), 3.48 (s, 2H), 3.06-2.90 (m, 3H), 2.18 (s, 31-1); MS (ESI) m/e 364 (M+H)$^+$.

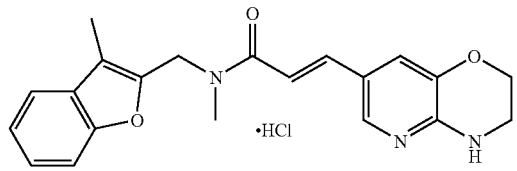

C$_{21}$H$_{22}$ClN$_3$O$_3$
Exact Mass: 399.13
Mol. Wt.: 399.87 d) (E)-3-(3,4-Dihydro-2H-pyrido[3,2-b][1,4]oxazin-7-yl)-N-methyl-N-(3-methylbenzofuran-2-ylmethyl)acrylamide hydrogen chloride A stirring solution of (E)-3-(3,4-dihydro-2H-pyrido[3,2-b][1,4]oxazin-7-yl)-N-methyl-N-(3-methylbenzofuran-2-ylmethyl)acrylamide (0.121 g, 0.332 mmol) in CH$_2$Cl$_2$ (4 mL) under N$_2$ was treated with anhydrous HCl (0.16 mL of a 2 M solution in diethyl ether, 0.33 mmol). After stirring for 72 h, the resulting solids were collected by filtration, washed with Et$_2$O (50 mL) and dried to yield the title compound (0.094 g, 71%) as an off-white solid and as a mixture of amide rotamers: $^1$H NMR (300 MHz, DMSO-d$_6$) δ 8.74 (br s, 1H), 7.97-7.93 (m, 2H), 7.57-7.55 (m, 1H), 7.49-7.77 (m, 2H), 7.30-7.13 (m, 3H), 4.99-4.77 (m, 2H), 4.25 (br s, 2H), 3.57 (m, 2H), 3.16-2.91 (m, 3H), 2.25 (s, 3H); MS (ESI) m/e 364 (M+H)$^+$.

Example 28

Preparation of (E)-N-(2-Ethoxy-3-isopropylbenzyl)-N-methyl-3-(2-oxo-2,3,4,5-tetrahydro-1H-pyrido[2,3-e][1,4]diazepin-7-yl)-acrylamide hydrochloride

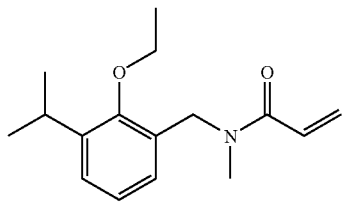

C$_{16}$H$_{23}$NO$_2$
Exact Mass: 261.17 a)
N-(3-Chloro-2-propoxybenzyl)-N-methylacrylamide

To a solution of (2-ethoxy-3-isopropylbenzyl)methylamine (1.00 g, 4.82 mmol) in CH$_2$Cl$_2$ (40 mL) was added acryloyl chloride (0.46 mL, 5.3 mmol) drop-wise. After stirring for five minutes, triethylamine (0.74 mL, 5.3 mmol) was added. The solution was stirred under N$_2$ for 5 hours. The solution was diluted with CH$_2$Cl$_2$ (50 mL) and then washed with H$_2$O (3×50 mL) and brine (2×100 mL), dried over Na$_2$SO$_4$, filtered and concentrated to yield the title compound (1.15 g, 92%) as a clear oil and as a mixture of amide rotamers: $^1$H NMR (300 MHz, DMSO-d$_6$) δ 7.25-7.19 (m, 1H), 7.13-7.03 (m, 1H), 6.89-6.67 (m, 2H), 6.20-6.12 (m, 1H), 5.79-5.53 (m, 1H), 4.68-4.60 (m, 2H), 3.81-3.76 (m, 2H), 3.28-3.23 (m, 1H), 3.01-2.87 (m, 3H), 1.38-1.33 (m, 3H), 1.19-1.16 (m, 6H); MS (ESI) m/e 262 (M+H)$^+$.

b) (E)-N-(2-Ethoxy-3-isopropylbenzyl)-3-[4-(4-methoxybenzyl)-2-oxo-2,3,4,5-tetrahydro-1H-pyrido[2,3-e][1,4]diazepin-7-yl]-N-methylacrylamide A solution of N-(2-ethoxy-3-isopropylbenzyl)-N-methylacrylamide (0.281 g, 1.07 mmol) in propionitrile (4 mL) and DMF (0.8 mL) was deoxygenated with Ar for 20 min. The solution was treated with diisopropylethylamine (0.30 mL, 1.73 mmol) and 7-bromo-4-(4-methoxy-benzyl)-1,3,4,5-tetrahydro-pyrido[2,3-e][1,4]diazepin-2-one (0.300 g, 0.828 mmol). The solution was deoxygenated with Ar for 20 min. Pd(OAc)$_2$ (0.018 g, 0.082 mmol) and P(o-tol)$_3$ (0.050 g, 0.16 mmol) were then added and the solution was deoxygenated again with Ar for 10 min. The mixture was heated to reflux for 1.5 h, then allowed to cool. The mixture was diluted with H$_2$O (100 mL) and then was washed with EtOAc (3×50 mL). The organic layer was washed with brine (2×100 mL), dried (Na$_2$SO$_4$) and concentrated to an orange oil. Purification by column chromatography (silica gel, CH$_2$Cl$_2$ to CH$_2$Cl$_2$/MeOH, 100 to 99.5:0.5) gave the title compound (0.20 g, 44%) as a light yellow solid and as a mixture of amide rotamers: $^1$H NMR (300 MHz, DMSO-d$_6$) δ 10.43-10.41 (m, 1H), 8.55-8.49 (m, 1H), 8.10-8.01 (m, 1H), 7.55-7.50 (m, 1H), 7.35-7.17 (m, 4H), 7.12-7.04 (m, 1H), 6.91-6.85 (m, 3H), 4.80-4.66 (m, 2H), 3.83-3.70 (m, 7H), 3.65-3.62 (m, 2H), 3.41-3.38 (m, 2H), 3.29-3.90 (m, 1H), 2.56-2.51 (m, 3H), 1.39-1.37 (m, 3H), 1.25-1.11 (m, 6H); MS (ESI) m/e 543 (M+H)$^+$.

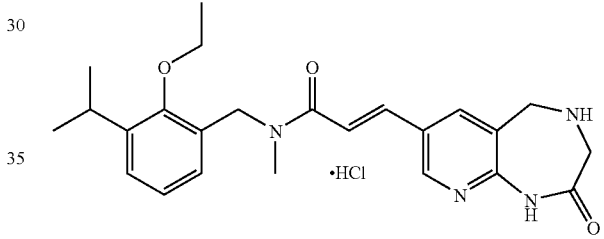

C$_{24}$H$_{31}$ClN$_4$O$_3$
Exact Mass: 458.21 c) (E)-N-(2-Ethoxy-3-isopropylbenzyl)-N-methyl-3-(2-oxo-2,3,4,5-tetrahydro-1H-pyrido[2,3-e][1,4]diazepin-7-yl)acrylamide hydrochloride A suspension of N-(2-ethoxy-3-isopropylbenzyl)-3-[4-(4-methoxybenzyl)-2-oxo-2,3,4,5-tetrahydro-1H-pyrido[2,3-e]

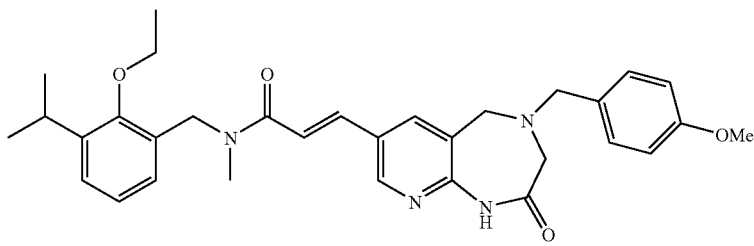

C$_{32}$H$_{38}$N$_4$O$_4$
Exact Mass: 542.29

[1,4]diazepin-7-yl]-N-methylacrylamide (0.200 g, 0.369 mmol) in dichloroethane (8.0 mL) was cooled in an ice bath and treated with 1-chloroethyl chloroformate (0.044 mL, 0.40 mmol). After stirring at 0° C. under $N_2$ for 30 min and then at room temperature for 30 min, the mixture was heated to reflux for 2 h. The mixture was allowed to cool and then concentrated to dryness. Purification by flash column chromatography (silica gel, $CH_2Cl_2$ to $CH_2Cl_2$/MeOH, 100 to 99.5:0.5) gave a white solid (0.128 g, 0.241 mmol). The solid was dissolved in methanol (4 mL) and heated to reflux for 6.5 h. The mixture was allowed to cool and the resulting solid was isolated by filtration, washed with MeOH and $Et_2O$ and dried to give the title compound (1.28 g, 46%) as a white powder and as a mixture of amide rotamers: $^1$H NMR (300 MHz, DMSO-$d_6$) δ 11.08-11.06 (m, 1H), 9.96 (br s, 2H), 8.77-8.71 (m, 1H), 8.32-8.23 (m, 1H), 7.63-7.55 (m, 1H), 7.40-7.32 (m, 1H), 7.26-7.21 (m, 1H), 7.13-7.04 (m, 1H), 6.91-6.84 (m, 1H), 4.83-4.67 (m, 2H), 4.27-4.22 (m, 2H), 3.88-3.78 (m, 4H), 3.29-2.25 (m, 1H), 3.13-2.89 (m, 3H), 1.40-1.35 (m, 3H), 1.19-1.17 (m, 6H); MS (ESI) m/e 423 (M+H)$^+$.

Example 29

Preparation of (E)-N-(2-Isobutoxy-3-methoxybenzyl)-N-methyl-3-(2-oxo-2,3,4,5-tetrahydro-1H-pyrido[2,3-e][1,4]diazepin-7-yl)acrylamide hydrochloride

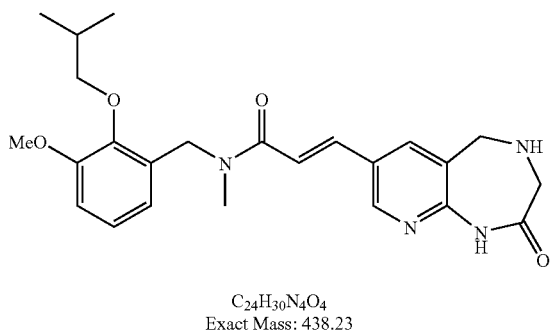 [SMILES: COc1cccc(CN(C)C(=O)/C=C/c2cnc3c(c2)CNCC(=O)N3)c1OCC(C)C]

C$_{24}$H$_{30}$N$_4$O$_4$
Exact Mass: 438.23 a) (E)-N-(2-Isobutoxy-3-methoxybenzyl)-N-methyl-3-(2-oxo-2,3,4,5-tetrahydro-1H-pyrido[2,3-e][1,4] diazepin-7-yl)acrylamide A solution of N-(2-isobutoxy-3-methoxybenzyl)-N-methylacrylamide (0.387 g, 1.40 mmol) in propionitrile (5 mL) and DMF (1 mL) was deoxygenated with Ar for 20 min. Then treated with diisopropylethylamine (0.39 mL, 2.25 mmol) and 7-bromo-1,3,4,5-tetrahydro-pyrido[2,3-e][1,4]diazepin-2-one (0.300 g, 1.07 mmol). The solution was deoxygenated with Ar for 20 min. Then Pd(OAc)$_2$ (0.024 g, 0.10 mmol) and P(o-tol)$_3$ (0.065 g, 0.21 mmol) were added and the solution deoxygenated with Ar for 20 min. The solution was heated to reflux for 18 h, then allowed to cool. The solution was diluted with $H_2O$ (30 mL) and was washed with EtOAc (3×50 mL). The organics were washed with brine (2×100 mL), dried over $Na_2SO_4$, filtered and concentrated to an orange-brown semi-solid. Purification by column chromatography (silica gel, $CH_2Cl_2$ to $CH_2Cl_2$/MeOH, 100 to 95:5) gave the title compound (0.10 g, 23%) as an yellow-orange solid and as a mixture of amide rotamers: $^1$H NMR (300 MHz, DMSO-$d_6$) δ 10.08-10.06 (m, 1H), 8.44-8.39 (m, 1H), 8.02-7.95 (m, 1H), 7.53-7.48 (m, 1H), 7.30-7.25 (m, 1H), 7.04-6.93 (m, 2H), 6.66-6.41 (m, 1H), 4.79-4.64 (m, 2H), 3.91-3.87 (m, 2H), 3.79 (s, 3H), 3.71-3.61 (m, 4H), 3.11-2.87 (m, 4H), 2.03-1.99 (m, 1H), 1.00-0.97 (m, 6H); MS (ESI) m/e 439 (M+H)$^+$.

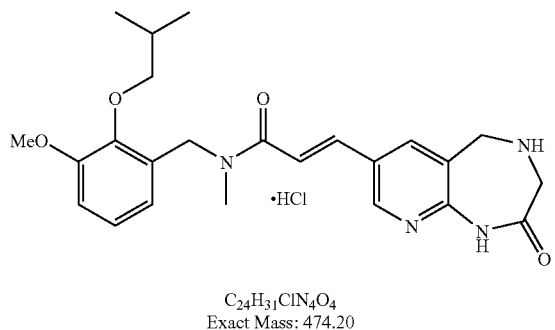 [SMILES: COc1cccc(CN(C)C(=O)/C=C/c2cnc3c(c2)CNCC(=O)N3)c1OCC(C)C ; Cl]

C$_{24}$H$_{31}$ClN$_4$O$_4$
Exact Mass: 474.20 b) (E)-N-(2-Isobutoxy-3-methoxybenzyl)-N-methyl-3-(2-oxo-2,3,4,5-tetrahydro-1H-pyrido[2,3-e][1,4] diazepin-7-yl)acrylamide hydrochloride A stirring solution of (E)-N-(2-isobutoxy-3-methoxybenzyl)-N-methyl-3-(2-oxo-2,3,4,5-tetrahydro-1H-pyrido[2,3-e][1,4]diazepin-7-yl)acrylamide (0.108 g, 0.246 mmol) in $CH_2Cl_2$ (3 mL) under $N_2$ was treated with HCl (0.12 mL of a 2.0 M solution in diethyl ether, 24 mmol). After stirring for 18 h, the resulting solid was collected by filtration and washed with $Et_2O$ (100 mL) and dried. The solid was dissolved in $CH_2Cl_2$ (2 mL) and layered with hexanes (5 mL). The resulting solids were collected by filtration, washed with $Et_2O$ (50 mL) and dried to yield the target compound (0.052 g, 45%) as a tan solid and as a mixture of amide rotamers: $^1$H NMR (300 MHz, DMSO-$d_6$) δ 11.09-11.07 (m, 1H), 10.03 (br s, 2H), 8.77-8.71 (m, 1H), 8.31-8.24 (m, 1H), 7.62-7.54 (m, 1H), 7.38-7.31 (m, 1H), 7.05-6.59 (m, 2H), 6.68-6.59 (m, 1H), 4.81-4.65 (m, 2H), 4.27-4.23 (m, 2H), 3.85-3.82 (m, 2H), 3.79 (s, 3H), 3.72-3.68 (m, 2H), 3.12-2.88 (m, 3H), 2.06-1.97 (m, 1H), 1.00-0.98 (m, 6H); MS (ESI) m/e 439 (M+H)$^+$.

Example 30

Preparation of (E)-3-[6-Amino-5-(1-hydroxy-1-methyl-ethyl)-pyridin-3-yl]-N-methyl-N-(3-methyl-benzofuran-2-ylmethyl)-acrylamide

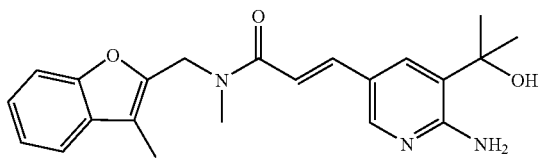 [SMILES: Cc1c(CN(C)C(=O)/C=C/c2cnc(N)c(C(C)(C)O)c2)oc2ccccc12]

a) 2-(2-Amino-5-bromo-pyridin-3-yl)-propan-2-ol

A solution of 2-Amino-5-bromo-nicotinic acid methyl ester (2.89 g, 13.5 mmol) in anhydrous THF (50 mL) was cooled to 0° C., then treated with a slow dropwise addition of 3.0 M methyl magnesium chloride in THF (20.85 mL, 62.5 mmol) over 30 min. The resulting solution was warmed to room temperature and stirred for 20 h. The reaction was then cooled to 0° C. and quenched with saturated NH₄Cl solution (10 mL). The solution was then diluted with water (100 mL) and extracted with ethyl acetate (2×100 mL). The combined organic fractions were washed with H₂O (100 mL), brine (100 mL), dried over MgSO₄ then concentrated to give a yellow residue. This residue was subjected to flash chromatography on silica gel using 50% ethyl acetate:hexanes to give the title compound as a yellow crystalline solid. Yield: 2.74 g (95%); ¹H NMR (300 MHz, DMSO-d₆) δ 7.89 (s, 1H), 7.40 (s, 1H), 6.27 (br s, 2H), 5.49 (s, 1H), 1.46 (s, 6H); ESI MS m/z 231 (100%); 233 (100%) [C₈H₁₁N₂OBr+H]⁺ b) (E)-3-[6-Amino-5-(1-hydroxy-1-methyl-ethyl)-pyridin-3-yl]-acrylic acid tert-butyl ester A suspension of 2-(2-Amino-5-bromo-pyridin-3-yl)-propan-2-ol (200 mg, 0.86 mmol), tert-butyl acrylate (628 μL, 4.3 mmol) and (i-Pr)₂EtN (452 μL, 2.6 mmol) in DMF (10 mL) was de-oxygenated with Ar for 30 min. The mixture was treated with Pd(OAc)₂ (19.4 mg, 0.09 mmol) and P(o-tol)₃ (51.7 mg, 0.18 mmol) then heated to 110° C. for 20 h. The hot mixture was filtered through a pad of celite. The filtrate was diluted with H₂O (100 mL) then extracted with ethyl acetate (2×100 mL). The combined organic fractions were dried over MgSO₄, and subjected to flash chromatography on silica gel using 50% ethyl acetate:hexanes. The appropriate fractions were collected and concentrated to yield a yellow crystalline solid. Yield: 153 mg (64%); ¹H NMR (300 MHz, DMSO-d₆) δ 8.09 (d, J=2.1 Hz, 1H), 7.65 (d, J=2.4 Hz, 1H), 7.45 (d, J=15.8 Hz, 1H), 6.69 (s, 2H), 6.32 (d, J=15.8 Hz, 1H), 5.53 (s, 1H), 1.52 (s, 6H), 1.48 (s, 9H); ESI MS m/z 279 [C₁₅H₂₂N₂O₃+H]⁺ c) (E)-3-[6-Amino-5-(1-hydroxy-1-methyl-ethyl)-pyridin-3-yl]-acrylic acid hydrochloride A suspension of (E)-3-[6-Amino-5-(1-hydroxy-1-methyl-ethyl)-pyridin-3-yl]-acrylic acid tert-butyl ester (0.13 g, 0.47 mmol) in CH₂Cl₂ (6 mL) was treated with TFA (6 mL). After stirring at room temperature for 2 h, the solution was concentrated in vacuo. The resulting oil was treated with anhydrous HCl in dioxane (3 mL, 4.0 M) and sonicated until the oil was converted to a fine off-white solid. After stirring for 20 min, the suspension was concentrated. The solid was washed with Et₂O, isolated by filtration and dried under vacuum. Yield: 0.11 g (92%); ¹H NMR (300 MHz, DMSO-d₆) δ 8.29 (d, J=1.5 Hz, 1H), 8.23 (br, s, 2H), 8.13 (d, J=1.8 Hz, 1H), 7.52 (d, J=16.1 Hz, 1H), 6.65 (d, J=16.1 Hz, 1H), 4.29 (s, 1H), 1.56 (s, 6H); ESI MS m/z 223 [C₁₁H₁₀N₂O₄+H]⁺ d) (E)-3-[6-Amino-5-(1-hydroxy-1-methyl-ethyl)-pyridin-3-yl]-N-methyl-N-(3-methyl-benzofuran-2-ylmethyl)-acrylamide EDC (98 mg, 0.51 mmol) was added to a suspension of 3-[6-Amino-5-(1-hydroxy-1-methyl-ethyl)-pyridin-3-yl]-acrylic acid hydrochloride (110 mg, 0.43 mmol), HOBt (63 mg, 0.47 mmol), methyl-(3-methyl-benzofuran-2-ylmethyl)-amine (110 mg, 0.47 mmol) and (i-Pr)₂EtN (0.36 mL, 2.1 mmol) in DMF (7 mL). The mixture was allowed to stir overnight at 40° C. The mixture was cooled to 0° C. and diluted with H₂O (60 mL) with rapid stirring. Only a small amount of precipitate was formed, therefore the product was extracted using EtOAc (2×50 mL), the combined organic layers washed with brine (60 mL), dried over MgSO₄ and dried under high vacuum. The solid was then subjected to flash chromatography on silica gel using 10% methanol:dichloromethane. Yield: 77.6 mg (48%); ¹H NMR (300 MHz, DMSO-d₆) δ 8.13 (s, 1H), 7.70 (s, 1H), 7.58 (d, J=7.9 Hz, 1H), 7.50 (d, J=7.6 Hz, 1H), 7.44 (s, 1H), 7.23-7.32 (m, 2H), 6.98 (d, J=17.7 Hz, 1H), 6.59 (s, 2H), 5.51 (s, 1H), 5.00 and 4.80 (2×s, 2H), 3.20 and 2.99 (2×s, 3H), 2.28 (s, 3H), 1.54 (s, 6H); ESI MS m/z 380.2 [C₂₂H₂₅N₃O₃+H]⁺

Example 31

Preparation of (E)-3-[6-Amino-5-(1-hydroxy-1-methyl-ethyl)-pyridin-3-yl]-N-methyl-N-(1-methyl-1H-indol-2-ylmethyl)-acrylamide

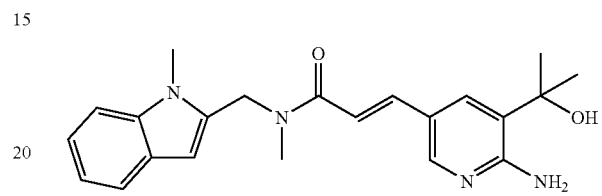

EDC (0.13 g, 0.70 mmol) was added to a suspension of (E)-3-[6-Amino-5-(1-hydroxy-1-methyl-ethyl)-pyridin-3-yl]-acrylic acid hydrochloride (0.15 g, 0.58 mmol), HOBt (0.09 g, 0.64 mmol), Methyl-(1-methyl-1H-indol-2-ylmethyl)-amine (0.11 g, 0.64 mmol) and (i-Pr)₂EtN (0.49 mL, 2.9 mmol) in DMF (8 mL). The mixture was allowed to stir overnight at 35° C. The mixture was cooled to 0° C. and diluted with H₂O (60 mL) with rapid stirring. The resulting precipitate was filtered, washed with H₂O (20 mL) then dried under high vacuum. The solid was then triturated with Et₂O, and the resultant white solid was collected, to yield 36 mg of product. An extraction on the original filtrate was done using EtOAc (2×75 mL) and the combined organic layers were washed with brine (100 mL), dried over MgSO₄, and concentrated in vacuo. The resulting off-white solid was subjected to flash chromatography on silica gel using 10% methanol:dichloromethane. Yield: 138 mg (79.5%); ¹H NMR (300 MHz, DMSO-d₆) δ 8.14 (s, 1H), 7.68 (s, 1H), 7.52-7.40 (m, 3H), 7.15-6.98 (m, 3H), 6.58 (s, 2H), 6.41 and 6.25 (2×s, 1H), 5.49 (s, 1H), 5.04 and 4.85 (2×s, 2H), 3.69 (s, 3H), 3.10 and 2.98 (2×s, 3H), 1.53 (s, 6H); ESI MS m/z 379 [C₂₂H₂₆N₄O₂+H]⁺

Example 32

Preparation of (E)-3-[6-Amino-5-(1-hydroxy-1-methyl-ethyl)-pyridin-3-yl]-N-methyl-N-(2-methyl-benzofuran-3-ylmethyl)-acrylamide

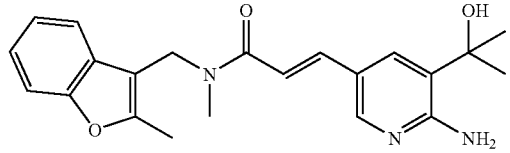 [SMILES: Cc1oc2ccccc2c1CN(C)C(=O)/C=C/c1cnc(N)c(C(C)(C)O)c1]

EDC (0.13 g, 0.70 mmol) was added to a suspension of (E)-3-[6-Amino-5-(1-hydroxy-1-methyl-ethyl)-pyridin-3-yl]-acrylic acid hydrochloride (0.15 g, 0.58 mmol), HOBt (0.09 g, 0.64 mmol), methyl-(2-methyl-benzofuran-3-ylmethyl)-amine (0.11 g, 0.64 mmol) and (i-Pr)₂EtN (0.60 mL, 2.48 mmol) in DMF (6 mL). The mixture was allowed to stir overnight at room temperature. The mixture was cooled to 0°

C. and diluted with H₂O (15 mL) with rapid stirring. The resulting precipitate was filtered, washed with H₂O (20 mL) then dried under high vacuum. The solid was then triturated with Et₂O, and the resultant beige solid was collected, to yield 160 mg (73%) of product. ¹H NMR (300 MHz, DMSO-$d_6$) δ 8.14 (s, 1H), 7.67-7.47 (m, 4H), 7.26-6.99 (m, 3H), 6.58 (s, 2H), 5.49 (s, 1H), 4.80 and 4.74 (2×s, 2H), 3.04 and 2.85 (2×s, 3H), 2.52 (s, 3H), 1.53 (s, 6H); ESI MS m/z 380 $[C_{22}H_{25}N_3O_3+H]^+$

Example 33

Preparation of (E)-3-(6-amino-pyridin-3-yl)-N-(3-cyano-1H-indol-2-ylmethyl)-N-methyl-acrylamide

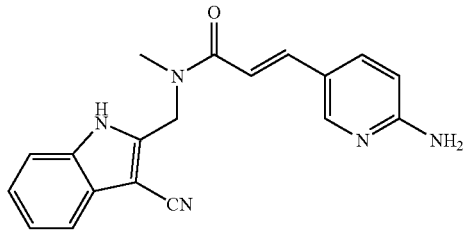 [SMILES: CN(Cc1[nH]c2ccccc2c1C#N)C(=O)/C=C/c1ccc(N)nc1]

a) 1-diethoxymethyl-1H-indole-3-carbonitrile

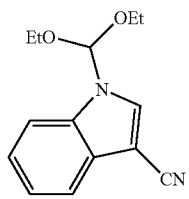 [SMILES: CCOC(OCC)n1cc(C#N)c2ccccc21]

1H-Indole-3-carbonitrile (5.07 g, 35.7 mmol) was heated with triethylorthoformate (60 mL) in a pressure vessel at 160° C. for 3 d. Upon cooling, the solvent was evaporated and the residue was submitted to chromatography (20% ether in hexanes) to afford the title compound (7.46 g, 86%). NMR (300 MHz, CDCl₃, δ): 7.92 (s, 1H), 7.76 (m, 1H), 7.62 (m, 1H), 7.32 (m, 2H), 6.23 (s, 1H), 3.63 (m, 4H), 1.23 (t, J=7.2 Hz, 6H).

b) 1-diethoxymethyl-2-formyl-1H-indole-3-carbonitrile

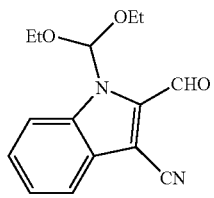 [SMILES: CCOC(OCC)n1c(C=O)c(C#N)c2ccccc21]

tert-Butyl lithium (18.1 mL, 31 mmol, 1.7M in pentane) was added to a THF (100 mL) solution of 1-diethoxymethyl-1H-indole-3-carbonitrile (6.83 g, 28 mmol) at −78° C. The mixture was warmed to 10° C., stirred for 30 min at this temperature, cooled to −78° C. and heated with DMF (20 mL). The mixture was warmed to 10° C., stirred for 30 min at this temperature, cooled to −78° C. and quenched with a saturated aqueous solution of NaHCO₃. The resulting mixture was treated with ether (200 mL); the organic layer was washed with water and brine, dried and evaporated to dryness. NMR (300 MHz, CDCl₃, δ): 10.24 (s, 1H), 8.10 (d, J=7.7 Hz, 1H), 7.91 (d, J=7.7 Hz, 1H), 7.53 (t, J=7.7 Hz, 1H), 7.43 (t, J=7.5 Hz, 1H), 7.34 (s, 1H), 3.80 (m, 2H), 3.52 (m, 2H), 1.26 (t, J=6.4 Hz, 1H).

c) 2-formyl-1H-indole-3-carbonitrile

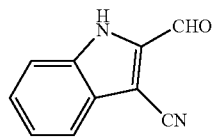 [SMILES: N#Cc1c(C=O)[nH]c2ccccc12]

Hydrochloric acid (4 mL, 20%) was added to a THF (100 mL) solution of 1-diethoxymethyl-2-formyl-1H-indole-3-carbonitrile (5.33 g, 19.57 mmol) at 0° C. The mixture was stirred at 20° C. for 41 h then treated with 5% aqueous K₂CO₃ (25 mL). The reaction mixture was concentrated to 50 mL and treated with methylene chloride (200 mL). The organic layer was washed with water, dried and evaporated to afford the title compound (2.81 g, 84%). ¹H NMR (300 MHz, DMSO-$d_6$, δ): 13.20 (s, br, 1H), 10.02 (s, 1H), 7.82 (d, J=8.0 Hz, 1H), 7.63 (d, J=7.7 Hz, 1H), 7.51 (t, J=7.1 Hz, 1H), 7.37 (t, J=7.5 Hz, 1H).

d) 2-methylaminomethyl-1H-indole-3-carbonitrile

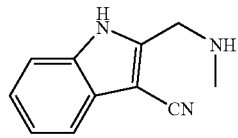

Methylamine (6.2 mL, 49.4 mmol, 33% in EtOH) was added to a MeOH (50 mL) solution of 2-formyl-1H-indole-3-carbonitrile (2.80 g, 16.5 mmol) at 0° C. Upon stirring for 5 h at 0° C., NaBH₄ (740 mg, 19.8 mmol) was added to the solution and the stirring was continued for 16 h. The mixture was diluted with water, extracted with methylene chloride; the organic layer was dried and evaporated. The crude residue was subjected to chromatography (1-5% MeOH in methylene chloride). The desired fractions were collected and concentrated; the residue was recrystallized from a methylene chloride/hexane mixture to afford the title compound (2.30 g, 75%). ¹H NMR (300 MHz, DMSO-$d_6$, δ): 7.54 (m, 1H), 7.48 (m, 1H), 7.21 (m, 2H), 3.93 (s, 2H), 2.31 (s, 3H). MS (ESI): m/e 186 (M+H)⁺.

e) 3-(6-amino-pyridin-3-yl)-N-(3-cyano-1H-indol-2-ylmethyl)-N-methyl-acrylamide

EDC (250 mg, 1.3 mmol) was added to a solution of (E)-3-(6-Amino-pyridin-3-yl)-acrylic acid (172 mg, 1.05 mmol), 2-methylaminomethyl-1H-indole-3-carbonitrile (186 mg, 1.0 mmol), HOBt.H₂O (135 mg, 1.0 mmol) and DIPEA (510

μL, 3.0 mmol) in dry DMF (4 mL). After 3 d of stirring, the mixture was diluted with water (50 mL) at 10° C. The resulting precipitate was filtered, washed with water and dried to afford the title compound (277 mg, 84%). $^1$H NMR (300 MHz, DMSO-$d_6$, δ): 12.1 (m, 1H), 8.16 (s, 1H), 7.84 (s, 1H), 7.5 (m, 3H), 7.2 (m, 2H), 6.97 (m, 1H), 6.44 (s, 2H), 5.08 and 4.88 (rotamers, 2s, 2H), 3.22 and 2.96 (rotamers, 2s, 3H). MS (ESI): m/e 332 (M+H)$^+$.

Example 34

Preparation of (E)-N-(3-cyano-1H-indol-2-ylmethyl)-N-methyl-3-(7-oxo-5,6,7,8-tetrahydro-[1,8]naphthyridin-3-yl)-acrylamide

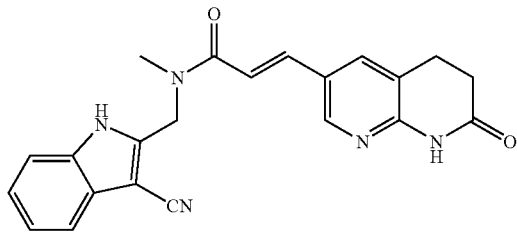

EDC (250 mg, 1.3 mmol) was added to a solution of 3-(7-Oxo-5,6,7,8-tetrahydro-[1,8]naphthyridin-3-yl)-acrylic acid hydrochloride (267 mg, 1.05 mmol), 2-methylaminomethyl-1H-indole-3-carbonitrile (186 mg, 1.0 mmol), HOBt.H$_2$O (135 mg, 1.0 mmol) and DIPEA (510 μL, 3.0 mmol) in dry DMF (4 mL). After 3 days of stirring, the mixture was diluted with water (50 mL) at 10° C. The precipitate was filtered, washed with water and dried. The solid was stirred in MeOH (10 mL), filtered and dried to afford 239 mg (62%) title compound. NMR (300 MHz, DMSO-$d_6$, δ): 12.28 and 12.09 (rotamers, 2 s, 1H), 10.66 (s, 1H), 8.37 (s, 1H), 8.11 and 8.05 (rotamers, 2s, 1H), 7.52 (m, 3H), 7.22 (m, 3H), 5.13 and 4.90 (rotamers, 2s, 2H), 3.27 and 2.97 (rotamers, 2s, 3H), 2.92 (m, 2H), 2.55 (m, 2H). MS (ESI): m/e 386 (M+H)$^+$.

Example 35

Preparation of (E)-N-Methyl-N-(3-methyl-benzofuran-2-ylmethyl)-3-(3-oxo-2,3,4,5-tetrahydro-1H-pyrido[2,3-e][1,4]diazepin-7-yl)-acrylamide hydrochloride

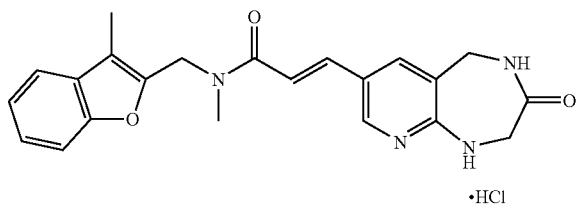 [SMILES: Cc1c(CN(C)C(=O)/C=C/c2cnc3c(c2)CNC(=O)CN3)oc2ccccc12 ; Cl]

a) (3-Cyanopyridin-2-ylamino)-acetic acid ethyl ester

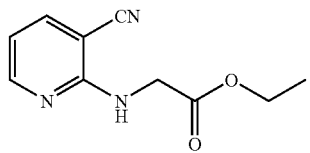

2-Chloro-3-cyanopyridine (10.0 g, 72 mmol) was dissolved into anhydrous DMSO (200 ml). Glycine ethyl ester hydrochloride (11 g, 79 mmol) and sodium carbonate (4.5 g, 42 mmol) were added and the mixture was stirred for 10 min under argon. Potassium fluoride (4.2 g, 72 mmol) was added and the mixture was heated to 120° C. for 48 h. The mixture was cooled to room temperature and added to water (400 mL). The crude product was extracted with CH$_2$Cl$_2$ (4×100 mL), dried over MgSO$_4$ and concentrated to an orange solid which was purified by silica gel (CH$_2$Cl$_2$) to give an orange solid (7.5 g, 51%). $^1$H NMR (300 MHz, CDCl$_3$) δ 8.27 (dd, J=5.0, 2.0 Hz, 1H), 7.69 (dd, J=7.6, 2.0 Hz, 1H), 6.66 (dd, J=7.6, 5.0 Hz, 1H), 5.70 (bs, 1H), 4.21-4.28 (m, 4H), 1.29 (t, J=7.2 Hz, 3H); ESI MS m/z 206 [C$_{10}$H$_{11}$N$_3$O$_2$+H]$^+$.

b) (3-Formylpyridin-2-ylamino)acetic acid ethyl ester)

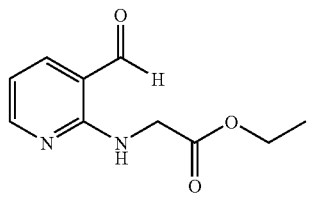

(3-Cyanopyridin-2-ylamino)acetic acid ethyl ester (2.6 g, 12.6 mmol) was dissolved into a 1:1:2 mixture of H$_2$O/CH$_3$COOH/pyridine (75 mL) under argon. Sodium hypophosphite (5.0 g) and Raney nickel (2.0 g) were added and the mixture was stirred at room temperature for 3 h. The slurry was filtered through a bed of celite and the filter cake was washed with water. Concentrated NH$_4$OH was added to the filtrate until pH 10 was reached. The solution was extracted with ethyl acetate (4×50 mL). The organic phase was washed with brine (50 mL), dried over MgSO$_4$ and concentrated. The product was purified by silica gel chromatography (CH$_2$Cl$_2$/EtOAc 9:1) to give the title compound as a clear yellow oil (2.16 g, 83%). $^1$H NMR (300 MHz, CDCl$_3$) δ 9.86 (s, 1H), 8.69 (bs, 1H), 8.31 (dd, J=4.8, 1.9 Hz, 1H), 7.79 (dd, J=7.6, 2.0 Hz, 1H), 6.72 (dd, J=7.6, 4.8 Hz, 1H), 4.32 (d, J=5.5 Hz, 2H), 4.24 (q, J=7.0 Hz, 2H), 1.29 (t, J=7.2 Hz, 3H).

c) 1,2,4,5-Tetrahydro-pyrido[2,3-e][1,4]diazepin-3-one

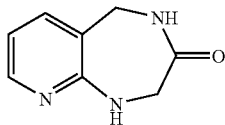

Raney nickel (3 g) was added to anhydrous methanol (50 mL) under argon and washed with anhydrous methanol (4×50 mL) (3-Cyanopyridin-2-ylamino)-acetic acid ethyl ester (3.35 g, 16.3 mmol) was dissolved in methanol (50 mL) and added to the Raney nickel slurry. The reaction vessel was purged with argon for 10 min. Sodium methoxide solution (16.3 mmol, 3.75 mL) was added and the argon purge was repeated (5 min). The reaction flask was charged with $H_2$ and stirred at room temperature for 48 h. Dilute HCl (16.3 mL of a 1 M solution) was added and the flask was purged with argon for 30 min. The slurry was filtered through celite and the filter cake was washed with 1:1 methanol/water. The filtrate was concentrated and extracted with ethyl acetate (4×100 mL), dried over $MgSO_4$ and concentrated to afford the title compound as a beige solid (850 mg, 30%). $^1$H NMR (300 MHz, DMSO-$d_6$) δ 8.07 (t, J=5.2 Hz, 1H), 7.82 (dd, J=4.9, 1.5 Hz, 1H), 7.21 (dd, J=7.1, 1.6 Hz, 1H), 6.69 (t, J=5.0 Hz, 1H), 6.43 (dd, J=7.2, 5.0 Hz, 1H), 4.24 (d, J=5.9 Hz, 2H), 3.91 (d, J=5.1 Hz, 2H).

d) 7-Bromo-1,2,4,5-tetrahydro-pyrido[2,3-e][1,4]diazepin-3-one

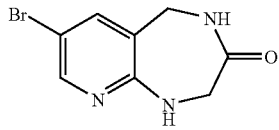

1,2,4,5-Tetrahydro-pyrido[2,3-e][1,4]diazepin-3-one (164 mg, 1.0 mmol) was dissolved into acetic acid (1 mL). Bromine (160 mg, 1.0 mmol) was added dropwise at room temperature and the solution was stirred overnight. Hexane (5 mL) was added and the orange precipitate was filtered and dried in vacuo. The title compound was isolated as an orange solid (190 mg, 78%). $^1$H NMR (300 MHz, DMSO-$d_6$) δ 8.26 (t, J=5.7 Hz, 1H), 8.06 (d, J=2.1 Hz, 1H), 7.81 (d, J=2.1 Hz, 1H), 4.35 (d, J=5.7 Hz, 2H), 4.08 (s, 2H).

e) 3-(3-Oxo-2,3,4,5-tetrahydro-1H-pyrido[2,3-e][1,4]diazepin-7-yl)-acrylic acid tert-butyl ester

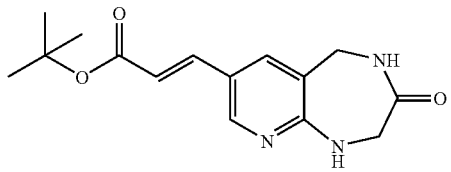 [SMILES: CC(C)(C)OC(=O)/C=C/c1cnc2c(c1)CNC(=O)CN2]

7-Bromo-1,2,4,5-tetrahydro-pyrido[2,3-e][1,4]diazepin-3-one (145 mg, 0.6 mmol) and tert-butyl acrylate (307 mg, 2.4 mmol) were dissolved in DMF (3 mL) and the reaction vessel was purged with argon for 5 min. Tri-o-tolylphosphine (37 mg, 0.12 mmol) and palladium acetate (14 mg, 0.06 mmol) were added and the solution was degassed with argon. Diisopropylethylamine (0.23 mL, 1.32 mmol) was added and the solution was degassed with argon, sealed and heated to 90° C. for 16 h. The reaction was cooled to room temperature and filtered through a bed of celite. The filter cake was washed with ethyl acetate (50 mL) and the filtrate was washed with $H_2O$ (5 mL) and brine (5 mL), dried over $MgSO_4$ and concentrated to a brown oil. The oil was subjected to silica gel chromatography (5% MeOH/$CH_2Cl_2$ to 10% MeOH/$CH_2Cl_2$) to yield the title compound as a yellow solid (96 mg, 52%). $^1$H NMR (300 MHz, DMSO-$d_6$) δ 8.18 (t, J=5.7 Hz, 1H), 8.07 (d, J=2.1 Hz, 1H), 7.37 (d, J=15.8 Hz, 1H), 7.35 (t, J=5.3 Hz, 1H), 6.24 (d, J=15.8 Hz, 1H), 4.28 (d, J=5.7 Hz, 2H), 3.98 (d, J=5.1 Hz, 2H), 1.45 (s, 9H); ESI MS m/z 290 $[C_{15}H_{19}N_3O_3+H]^+$.

f) 3-(3-Oxo-2,3,4,5-tetrahydro-1H-pyrido[2,3-e][1,4]diazepin-7-yl)-acrylic acid

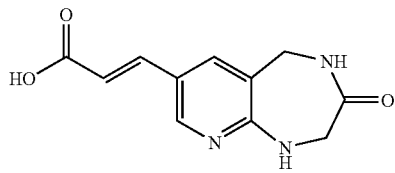 [SMILES: O=C(O)/C=C/c1cnc2c(c1)CNC(=O)CN2]

3-(3-Oxo-2,3,4,5-tetrahydro-1H-pyrido[2,3-e][1,4]diazepin-7-yl)-acrylic acid tert-butyl ester (96 mg, 0.31 mmol) was dissolved into 1:1 $CH_2Cl_2$/TFA (2 mL) and stirred at room temperature for 30 min. The solvents were removed in vacuo to afford the title compound as a brown solid (44 mg, 61%) and as a mixture of amide rotomers. $^1$H NMR (300 MHz, DMSO-$d_6$). δ 8.18 (t, J=5.7 Hz, 1H), 8.07 (d, J=2.1 Hz, 1H), 7.37 (d, J=15.8 Hz, 1H), 7.35 (t, J=5.3 Hz, 1H), 6.24 (d, J=15.8 Hz, 1H), 4.28 (d, J=5.7 Hz, 2H), 3:98 (d, J=5.1 Hz, 2H), 1.45 (s, 9H).

g) (E)-N-Methyl-N-(3-methyl-benzofuran-2-ylmethyl)-3-(3-oxo-2,3,4,5-tetrahydro-1H-pyrido[2,3-e][1,4]diazepin-7-yl)-acrylamide hydrochloride EDC (0.05 g, 0.27 mmol) was added to a suspension of 3-(3-Oxo-2,3,4,5-tetrahydro-1H-pyrido[2,3-e][1,4]diazepin-7-yl)-acrylic acid (51 mg, 0.22 mmol), HOBt (0.03 g, 0.24 mmol), methyl-(3-methyl-benzofuran-2-ylmethyl)-amine (53 mg, 0.3 mmol), and (i-Pr)$_2$EtN (0.22 mL, 1.32 mmol) in DMF (5 mL). The mixture was allowed to stir overnight at 40° C. The mixture was cooled to 0° C. and diluted with $H_2O$ (15 mL) with rapid stirring. The resulting precipitate was filtered, washed with $H_2O$ (5 mL) then dried under high vacuum. The solid was then subjected to flash chromatography on silica gel using 5% methanol:dichloromethane. To yield the product as free base fractions containing product are combined and concentrated to dryness.

To obtain the hydrochloride salt, fractions containing product were combined and treated with 1.25 mL of 2.0 M HCl in $Et_2O$. The resulting suspension was concentrated, triturated with $Et_2O$ (12 mL) then filtered to give the title compound as a beige solid (59 mg, 63%). $^1$H NMR (300 MHz, DMSO-$d_6$) δ 8.42 (bs, 1H), 8.23 (bs, 2H), 7.57-7.43 (m, 4H), 7.30-7.08

(m, 3H), 4.97-4.78 (m, 2H), 4.41-4.39 (m, 2H), 4.19 (s, 2H), 2.88-2.72 (m, 3H), 2.25 (s, 3H); ESI MS m/z 391 [$C_{22}H_{22}N_4O_3$+H]$^+$.

Example 36

Preparation of (E)-N-(1,2-Dimethyl-1H-indol-3-ylmethyl)-N-methyl-3-(3-oxo-2,3,4,5-tetrahydro-1H-pyrido[2,3-e][1,4]diazepin-7-yl)-acrylamide

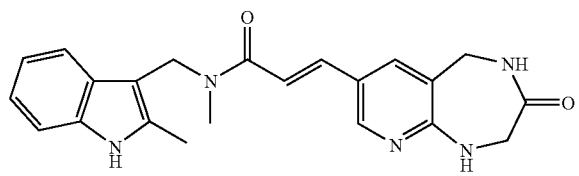 [SMILES: Cc1[nH]c2ccccc2c1CN(C)C(=O)/C=C/c1cnc2c(c1)CNC(=O)CN2]

According to the method of example 35g, 3-(3-Oxo-2,3,4,5-tetrahydro-1H-pyrido[2,3-e][1,4]diazepin-7-yl)-acrylic acid (100 mg, 0.43 mmol) and methyl-(2-methyl-1H-indol-3-ylmethyl)-amine (91 mg, 0.52 mmol) were coupled to yield the title compound as a brown solid (55 mg, 33%) and as a mixture of amide rotamers. NMR (300 MHz, DMSO-d$_6$) δ 11.03-10.87 (m, 1H), 8.18-8.10 (m, 2H), 7.80-7.72 (m, 1H), 7.53-7.40 (m, 2H), 7.33-7.24 (m, 2H), 7.02-6.86 (m, 2H), 4.84-4.71 (m, 2H), 4.28-4.08 (m, 2H), 3.98-3.82 (s, 2H), 2.92-2.72 (m, 3H), 2.40-2.37 (s, 3H); ESI MS m/z 390 [$C_{22}H_{23}N_5O_2$+H]$^+$.

Example 37

Preparation of (E)-N-Methyl-N-(2-methyl-benzofuran-3-ylmethyl)-3-(4-methyl-3-oxo-2,3,4,5-tetrahydro-1H-pyrido[2,3-e][1,4]diazepin-7-yl)-acrylamide hydrochloride

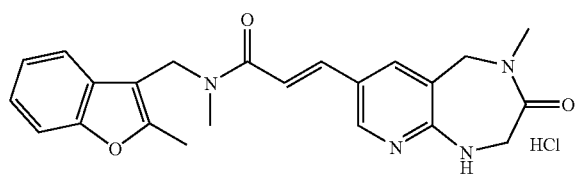 [SMILES: Cc1oc2ccccc2c1CN(C)C(=O)/C=C/c1cnc2c(c1)CN(C)C(=O)CN2 ; Cl]

a) 7-Bromo-4-methyl-1,2,4,5-tetrahydro-pyrido[2,3-e][1,4]diazepin-3-one

(3-Cyanopyridin-2-ylamino)-acetic acid ethyl ester (2.16 g, 10.4 mmol) was dissolved in anhydrous methanol (25 mL) under argon. Methylamine (33% solution in ethanol, 3.9 mL, 31.2 mmol) was added and the solution was stirred 3 h. The solvent was removed in vacuo and the residue was dissolved into anhydrous methanol (25 mL). Sodium borohydride (400 mg, 10.5 mmol) was added and the mixture was stirred overnight at room temperature. The solvent was removed in vacuo and the residue was treated with saturated NaHCO$_3$ solution (25 mL); the aqueous mixture was extracted with ethyl acetate (3×25 mL). The organic phase was washed with brine (10 mL), dried over MgSO$_4$ and concentrated to a green solid (1.2 g, 65%). The solid was dissolved in acetic acid (12 mL) and bromine (1.03 g, 6.8 mmol) was added dropwise. The reaction was stirred at room temperature for 72 h and treated with diethyl ether (50 mL). The resulting orange precipitate was collected by filtration and purified by silica gel chromatography (5% MeOH/CH$_2$Cl$_2$) to afford the title compound as a yellow solid (310 mg, 18%). $^1$H NMR (300 MHz, CD$_3$OD) δ 7.91 (d, J=2.3 Hz, 1H), 7.52 (d, J=2.3 Hz, 1H), 4.62 (s, 2H), 4.21 (s, 2H), 3.07 (s, 3H).

b) 3-(4-Methyl-3-oxo-2,3,4,5-tetrahydro-1H-pyrido[2,3-e][1,4]diazepin-7-yl)-acrylic acid tert-butyl ester

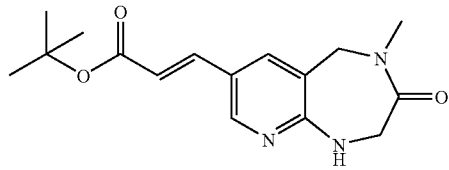 [SMILES: CN1Cc2cc(/C=C/C(=O)OC(C)(C)C)cnc2NCC1=O]

According to the procedure of Example 35e 7-bromo-4-methyl-1,2,4,5-tetrahydro-pyrido[2,3-e][1,4]diazepin-3-one (310 mg, 1.22 mmol) was converted via Heck coupling to the title compound which was isolated as a brown oil (220 mg, 60%). $^1$H NMR (300 MHz, DMSO-d$_6$) δ 8.08 (d, J=1.8 Hz, 1H), 7.77 (d, J=2.1 Hz, 1H), 7.44 (t, J=4.8 Hz, 1H), 7.37 (d, J=16.1 Hz, 1H), 6.24 (d, J=15.7 Hz, 1H), 4.54 (s, 2H), 4.09 (d, J=5.5 Hz, 2H), 2.72 (s, 3H), 1.45 (s, 9H).

c) 3-(4-Methyl-3-oxo-2,3,4,5-tetrahydro-1H-pyrido[2,3-e][1,4]azepin-7-yl)-acrylic acid

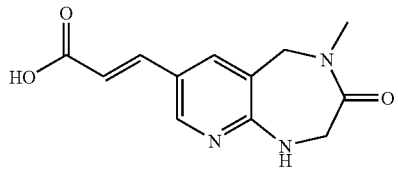 [SMILES: CN1Cc2cc(/C=C/C(=O)O)cnc2NCC1=O]

According to the procedure of Example 35f, 3-(4-methyl-3-oxo-2,3,4,5-tetrahydro-1H-pyrido[2,3-e][1,4]diazepin-7-yl)-acrylic acid tert-butyl ester (220 mg, 0.72 mmol) was converted to the title compound which was isolated as a brown solid (quantitative).

d) (E)-N-Methyl-N-(2-methyl-benzofuran-3-ylmethyl)-3-(4-methyl-3-oxo-2,3,4,5-tetrahydro-1H-pyrido[2,3-e][1,4]diazepin-7-yl)-acrylamide hydrochloride According to the method of example 35g, 3-(4-Methyl-3-oxo-2,3,4,5-tetrahydro-1H-pyrido[2,3-e][1,4]diazepin-7-yl)-acrylic acid (69 mg, 0.28 mmol) and methyl-(2-methyl-benzofuran-3-ylmethyl)amine (60 mg, 0.34 mmol) were coupled to yield the title compound as a solid (52 mg, 42%) and as a mixture of amide rotomers. NMR (300 MHz, DMSO-d$_6$) δ 8.75 (bs, 1H), 8.33-8.26 (m, 2H), 7.54-7.44 (m, 3H), 7.22-7.10 (m, 3H), 4.90-4.66 (m, 4H), 4.11 (s, 2H), 3.02-2.72 (m, 9H); ESI MS m/z 405 [C$_{23}$H$_{24}$N$_4$O$_3$+H]$^+$.

Example 38

Preparation of (E)-N-Methyl-N-(3-methyl-benzofuran-2-ylmethyl)-3-(4-methyl-3-oxo-2,3,4,5-tetrahydro-1H-pyrido[2,3-e][1,4]diazepin-7-yl)-acrylamide hydrochloride

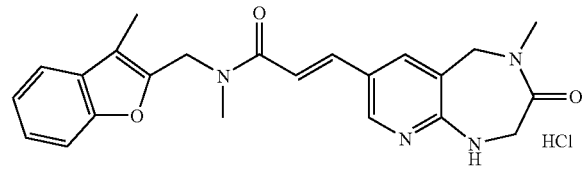 [SMILES: Cc1c(CN(C)C(=O)/C=C/c2cnc3c(c2)CN(C)C(=O)CN3)oc2ccccc12 ; Cl]

According to the method of Example 35g 3-(4-methyl-3-oxo-2,3,4,5-tetrahydro-1H-pyrido[2,3-e][1,4]diazepin-7-yl)-acrylic acid (190 mg, 0.4 mmol) and methyl-(3-methyl-benzofuran-2-ylmethyl)-amine (88 mg, 0.5 mmol) were coupled to yield the title compound as a solid (100 mg, 56%) and as a mixture of amide rotomers. $^1$H NMR (300 MHz, DMSO-d$_6$) δ 8.61 (bs, 1H), 8.30-8.24 (m, 2H), 7.59-7.44 (m, 3H), 7.30-7.08 (m, 3H), 4.97-4.67 (m, 4H), 4.31 (s, 2H), 3.17-2.89 (m, 6H), 2.25 (s, 3H); ESI MS m/z 405 [C$_{23}$H$_{24}$N$_4$O$_3$+H]$^+$.

Example 39

Preparation of (E)-N-(3-Methoxy-2-propoxy-benzyl)-N-methyl-3-(4-methyl-3-oxo-2,3,4,5-tetrahydro-1H-pyrido[2,3-e][1,4]diazepin-7-yl)-acrylamide

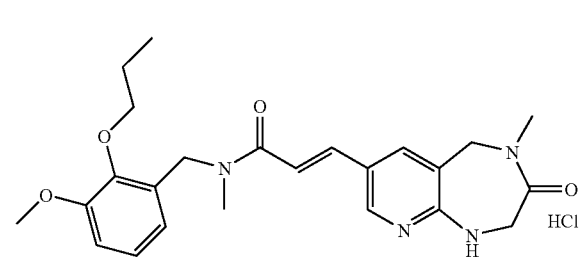 [SMILES: CCCOc1c(CN(C)C(=O)/C=C/c2cnc3c(c2)CN(C)C(=O)CN3)cccc1OC ; Cl]

According to the method of example 35g, 3-(4-methyl-3-oxo-2,3,4,5-tetrahydro-1H-pyrido[2,3-e][1,4]diazepin-7-yl)-acrylic acid (100 mg, 0.21 mmol) and (3-methoxy-2-propoxy-benzyl)methylamine (63 mg, 0.3 mmol) were coupled to yield the title compound as a solid (43 mg, 48%) and as a mixture of amide rotomers. $^1$H NMR (300 MHz, DMSO-d$_6$) δ 8.55 (bs, 1H), 8.30-8.20 (m, 2H), 7.49-7.42 (m, 1H), 7.19-7.15 (m, 1H), 7.08-6.90 (m, 2H), 6.63 (t, J=7.2 Hz, 1H), 4.76-4.63 (m, 4H), 4.30 (s, 2H), 3.90-3.84 (m, 2H), 3.78 (s, 3H), 3.09-2.83 (m, 6H), 1.62-1.72 (m, 2H), 0.99-0.95 (m, 3H); ESI MS m/z 439 [C$_{24}$H$_{30}$N$_4$O$_4$+H]$^+$.

Example 40

Preparation of (E)-N-Methyl-N-(2-methyl-1H-indol-3-ylmethyl)-3-(4-methyl-3-oxo-2,3,4,5-tetrahydro-1H-pyrido[2,3-e][1,4]diazepin-7-yl)-acrylamide

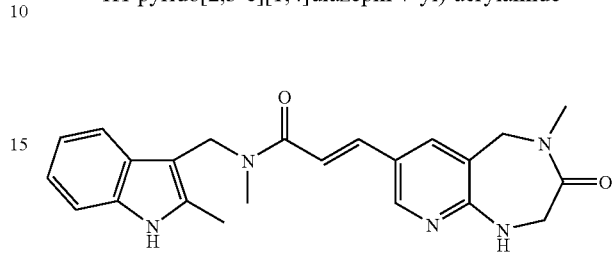

According to the method of example 35g, 3-(4-methyl-3-oxo-2,3,4,5-tetrahydro-1H-pyrido[2,3-e][1,4]diazepin-7-yl)-acrylic acid (69 mg, 0.28 mmol) and methyl-(2-methyl-1H-indol-3-ylmethyl)amine (60 mg, 0.34 mmol) were coupled to yield the title compound as a white powder and as a mixture of amide rotomers (40 mg, 35%). $^1$H NMR (300 MHz, DMSO-d$_6$) δ 10.86 (s, 1H), 8.12 (bs, 1H), 7.77 (bs, 1H), 7.49-7.41 (m, 2H), 7.34-7.30 (m, 1H), 7.25-7.22 (m, 1H), 7.00-6.85 (m, 3H), 4.84-4.71 (m, 2H), 4.53 (s, 2H), 4.09-4.07 (m, 2H), 2.93-2.91 (m, 6H), 2.40 (bs, 3H); ESI MS m/z 404.

Example 41

Preparation of (E)-N-(3-Methoxy-2-propoxy-benzyl)-N-methyl-3-(2-oxo-2,3,4,5-tetrahydro-1H-pyrido[2,3-e][1,4]diazepin-7-yl)-acrylamide hydrochloride

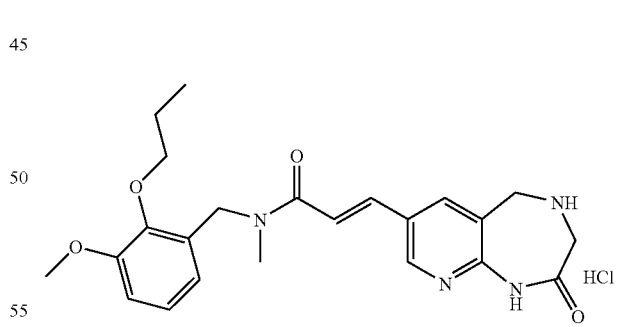

According to the method of Example 35g, 3-(2-oxo-2,3,4,5-tetrahydro-1H-pyrido[2,3-e][1,4]diazepin-7-yl)-acrylic acid (152 mg, 0.5 mmol) and (3-methoxy-2-propoxy-benzyl)methylamine (125 mg, 0.6 mmol) were coupled. The resulting free base was converted to the hydrochloride salt according the method of Example 35g to yield the title compound as a solid (56 mg, 24%). $^1$H NMR (300 MHz, DMSO-d$_6$) δ 11.06-11.04 (m, 1H), 10.29 (bs, 1H), 8.75-8.69 (m, 1H), 8.32-8.24 (m, 1H), 7.60-7.53 (m, 1H), 7.37-7.32 (m, 1H), 7.04-6.93 (m, 2H), 6.69-6.60 (m, 1H), 4.79-4.64 (m, 2H), 4.27-4.22 (m, 2H), 3.91-3.81 (m, 4H), 3.78 (s, 3H), 2.88-2.72 (m, 3H), 1.73-1.66 (m, 2H), 1.00-0.93 (m, 3H); ESI MS m/z 425 [C$_{23}$H$_{28}$N$_4$O$_4$+H]$^+$.

Example 42

Preparation of (E)-N-Methyl-N-(2-methyl-1H-indol-3-ylmethyl)-3-(4-methyl-2-oxo-2,3,4,5-tetrahydro-1H-pyrido[2,3-e][1,4]diazepin-7-yl)-acrylamide

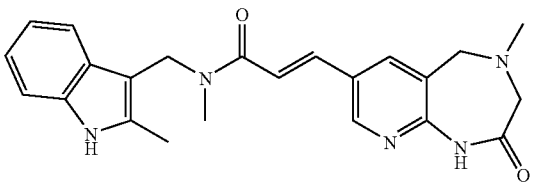 [SMILES: Cc1[nH]c2ccccc2c1CN(C)C(=O)/C=C/c1cnc2c(c1)CN(C)CC(=O)N2]

According to the method of example 35g, methyl-(2-methyl-1H-indol-3-ylmethyl)amine (115 mg, 0.66 mmol) and 3-(4-Methyl-2-oxo-2,3,4,5-tetrahydro-1H-pyrido[2,3-e][1,4]diazepin-7-yl)-acrylic acid (192 mg, 0.6 mmol) were coupled to give crude product. Purification by column chromatography (silica gel, CH$_2$Cl$_2$/MeOH/NH$_3$, 9:4.55:0.05) gave title compound (24 mg, 9%) as a white solid and as a mixture of amide rotomers. $^1$H NMR (300 MHz, DMSO-d$_6$) δ 8.48 (s, 1H), 7.95-8.01 (m, 2H), 7.56-7.60 (m, 2H), 7.47-7.50 (m, 1H), 7.16-7.26 (m, 2H), 6.92-7.05 (m, 2H), 3.90 (s, 2H), 3.56 (s, 2H), 3.02 (s, 2H), 2.93 (s, 3H), 2.83 (s, 3H), 2.46 (s, 3H); MS (ESI) m/e 404 (C$_{23}$H$_{25}$N$_5$O$_2$+H)$^+$.

Example 43

Preparation of (E)-3-(6-Amino-pyridin-3-yl)-N-(3-chloro-benzofuran-2-ylmethyl)-N-methyl-acrylamide hydrochloride

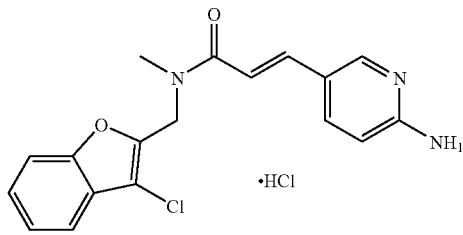 [SMILES: CN(Cc1oc2ccccc2c1Cl)C(=O)/C=C/c1ccc(N)nc1 ; Cl]

a) 2-Carboxymethoxybenzoic acid

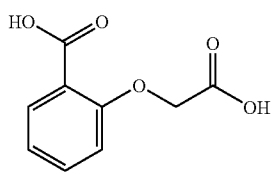

To a solution of salicylic acid (20 g, 145 mmol) in water (200 mL) is added carefully sodium hydroxide (60 g, 1.45 mol) followed by chloroacetic acid (27 g, 290 mmol). The mixture is refluxed for 5 d, cooled to room temperature and the precipitate is filtered and dried. Trituration with hexanes yielded the title compound (6.84 g, 24%) as a pink solid. $^1$H NMR (400 MHz, DMSO-d$_6$) δ 7.65-7.66 (dd, 1H, J=8.0, 2.0 Hz), 7.45-7.47 (dd, 1H, J=8.0, 2.0 Hz), 6.97-7.05 (m, 2H), 4.77 (s, 2H).

b) 3-Chlorobenzofuran-2-carboxaldehyde

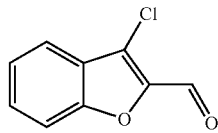 [SMILES: O=Cc1oc2ccccc2c1Cl]

To a cooled solution of phosphorus oxychloride (19 mL, 209 mmol) in DMF (40 mL) is slowly added 2-carboxymethoxybenzoic acid (6.84 g, 35 mmol) in portions. The mixture is warmed to room temperature for 30 min and then heated to 90° C. overnight. The mixture is cooled to room temperature and poured carefully into ice water, extracted with ethyl acetate (3×50 mL), dried with sodium sulfate and concentrated in vacuo. Purification by column chromatography (silica, hexanes/ethyl acetate, 4:1) gave title compound (1.62 g, 26%) as an orange solid. $^1$H NMR (400 MHz, DMSO-d$_6$) δ 9.98 (s, 1H), 7.82-7.88 (m, 2H), 7.69-7.73 (m, 1H), 5.51-7.56 (m, 1H).

c) (3-Chloro-benzofuran-2-ylmethyl)methylamine

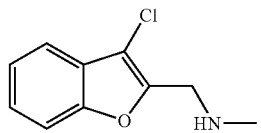

To a solution of 3-chlorobenzofuran-2-carboxaldehyde (1.62 g, 8.9 mmol) in methanol (50 mL) is added N-methylamine (33% solution in ethanol, 1.11 g, 35.9 mmol) and stirred overnight at room temperature. The mixture is concentrated in vacuo, re-solvated in methanol (50 mL) and cooled in an ice bath. Sodium borohydride (407 mg, 10.8 mmol) is added in portions and the mixture stirred at room temperature for 4 h. The mixture is concentrated in vacuo, re-solvated in 1.3M sodium hydroxide solution, stirred for 20 min, extracted with ethyl acetate, dried with sodium sulfate and concentrated. Purification by column chromatography (silica, CH$_2$Cl$_2$/MeOH, 9/1) gave title compound (1.43 g, 82%) as a colorless oil. $^1$H NMR (300 MHz, DMSO-d$_6$) δ 7.55-7.63 (m, 2H), 7.33-7.42 (m, 2H), 3.93 (s, 2H), 2.27 (s, 3H).

d) (E)-3-(6-Amino-pyridin-3-yl)-N-(3-chloro-benzofuran-2-ylmethyl)-N-methyl-acrylamide hydrochloride EDC (0.21 g, 1.08 mmol) was added to a suspension of 3-(6-amino-pyridin-3-yl)-acrylic acid (148 mg, 0.9 mmol), HOBt (134 mg, 1 mmol), (3-chloro-benzofuran-2-ylmethyl) methylamine (194 mg, 0.99 mmol), and (i-Pr)$_2$EtN (0.75 mL, 4.46 mmol) in DMF (16 mL). The mixture was stirred overnight at room temperature then cooled to 0° C. and diluted with H₂O (32 mL) with rapid stirring. The resulting precipitate was collected by filtration, washed with H₂O (32 mL) and dried under high vacuum. The residue was re-solvated in methylene chloride (5 mL) and a solution of 2M HCl in ether (2 mL) was added to precipitate the hydrogen chloride salt. The precipitate was collected by filtration and dried to give the title compound (295 mg, 89%) as a white solid and as a mixture of amide rotomers. ¹H NMR (300 MHz, DMSO-d₆) δ 8.40-8.42 (m, 3H), 7.57-7.65 (m, 2H), 7.38-7.46 (m, 3H), 6.98-7.03 (m, 1H), 4.86-5.05 (rotamers, 2s, 2H), 3.20 (s, 3H); MS (ESI) m/e 342 (C₁₈H₁₆ClN₃O₂+H)⁺.

Example 44

Preparation of (E)-N-(3-Chloro-benzofuran-2-ylmethyl)-N-methyl-3-(7-oxo-5,6,7,8-tetrahydro-[1,8]naphthyridin-3-yl)-acrylamide

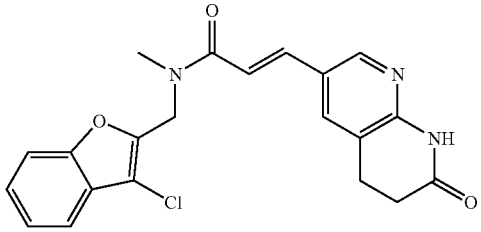 [SMILES: CN(Cc1oc2ccccc2c1Cl)C(=O)/C=C/c1cnc2c(c1)CCC(=O)N2]

According to the method of example 43d, 3-(7-Oxo-5,6,7,8-tetrahydro-[1,8]naphthyridin-3-yl)-acrylic acid (203 mg, 0.8 mmol) and (3-chloro-benzofuran-2-ylmethyl)methylamine (172 mg, 0.88 mmol) were coupled to yield the title compound (176, 56%) as a white solid and as a mixture of amide rotomers. NMR (300 MHz, DMSO-d₆) δ 10.63 (s, 1H), 8.40 (s, 1H), 8.09 (s, 1H), 7.21-7.64 (m, 6H), 4.84-5.08 (rotamers, 2s, 2H), 3.22 (s, 3H), 2.91-2.96 (m, 2H), 2.52-2.59 (m, 2H); MS (ESI) m/e 396 (C₂₁H₁₈ClN₃O₃+H)⁺.

Example 45

Preparation of (E)-N-(3-Chloro-benzofuran-2-ylmethyl)-N-methyl-3-(2-oxo-2,3,4,5-tetrahydro-1H-pyrido[2,3-e][1,4]diazepin-7-yl)-acrylamide hydrochloride

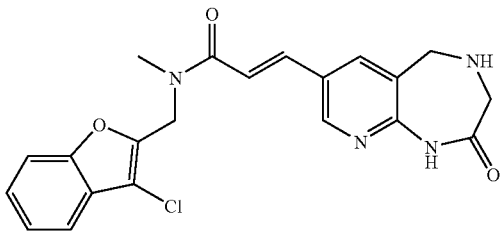 [SMILES: CN(Cc1oc2ccccc2c1Cl)C(=O)/C=C/c1cnc2c(c1)CNCC(=O)N2]

According to the method of example 43d, 3-(2-oxo-2,3,4,5-tetrahydro-1H-pyrido[2,3-e][1,4]diazepin-7-yl)-acrylic acid hydrochloride (152 mg, 0.5 mmol) and (3-chloro-benzofuran-2-ylmethyl)methylamine (108 mg, 0.55 mmol) were coupled to yield crude product which was triturated with methanol and ether several times and dried. The residue was re-solvated in methylene chloride (5 mL) and a solution of 2M HCl in ether (2 mL) was added to precipitate the hydrogen chloride salt. The precipitate was collected by filtration and dried to give the title compound (42 mg, 19%) as a white solid and as a mixture of amide rotomers. ¹H NMR (400 MHz, DMSO-d₆) δ 10.06 (s, 1H), 8.45 (s, 1H), 8.01 (s, 1H), 7.38-7.68 (m, 6H), 4.88-5.08 (rotamers, 2s, 2H), 3.90 (s, 2H), 3.63 (s, 2H), 3.31 (s, 3H); MS (ESI) m/e 411 (C₂₁H₁₉ClN₄O₃+H)⁺.

Example 46

Preparation of (E)-N-(1H-Indol-5-ylmethyl)-N-methyl-3-(7-oxo-5,6,7,8-tetrahydro-[1,8]naphthyridin-3-yl)-acrylamide

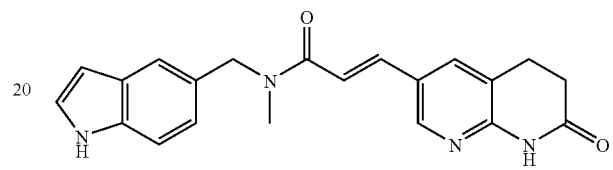

According to the procedure of Example 35g (1H-indol-5-yl-methyl)-methyl-amine (257 mg, 1.62 mmol) and (E)-3-(7-oxo-5,6,7,8-tetrahydro-[1,8]naphthyridin-3-yl)acrylic acid hydrochloride (312 mg, 1.23 mmol), were coupled to give crude product. Purification by column chromatography (silica gel, 5% MeOH/CH₂Cl₂) gave the title compound (172 mg, 39%) as a white solid and a mixture of amide rotomers: ¹H NMR (300 MHz, DMSO-d₆) δ 11.06-11.05 (m, 1H), 10.63-10.61 (m, 1H), 8.36-8.34 (m, 1H), 8.06 (s, 1H), 7.56-7.19 (m, 5H), 7.02-6.96 (m, 1H), 6.38 (s, 1H), 4.84-4.65 (m, 2H), 3.06-2.85 (m, 5H), 2.55-2.52 (m, 2H); ESI MS m/e 361 [C₂₁H₂₀N₄O₂+H]⁺.

Example 47

Preparation of (E)-N-Methyl-N-(1-methyl-1H-indol-5-ylmethyl)-3-(7-oxo-5,6,7,8-tetrahydro-[1,8]naphthyridin-3-yl)-acrylamide a) Methyl-(1-methyl-1H-indol-5-ylmethyl)-amine

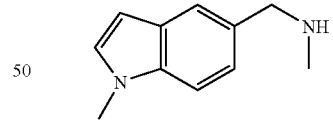

1-Methyl-1H-indole-5-carbaldehyde (338 mg, 2.13 mmol) was dissolved in anhydrous methanol (10 ml). Methylamine (0.80 ml of 33% solution in ethanol, 6.43 mmol) was added and the reaction was stirred for 3 h. The solution was concentrated to a brown oil and then dissolved in anhydrous methanol (10 ml). Sodium borohydride (83.0 mg, 2.19 mmol) was added and the mixture was stirred overnight at room temperature. Water (4 ml) was added and the solution was concentrated. Sodium hydroxide (8 ml, 1N) was added and the aqueous layer was extracted with ethyl acetate (3×20 ml). Combined organic layers were dried over MgSO₄, filtered and concentrated to afford methyl-(1-methyl-1H-indol-5-yl-methyl)-amine (167 mg, 45%) as an orange oil: ¹H NMR (400 MHz, DMSO-d₆) δ 7.44 (s, 1H), 7.34 (d, J=8.0 Hz, 1H), 7.261

(d, J=3.2 Hz, 1H), 7.11 (d, J=12.0 Hz, 1H), 6.345 (d, J=4.0 Hz, 1H), 3.75 (s, 3H), 3.70 (s, 2H), 2.25 (s, 3H).

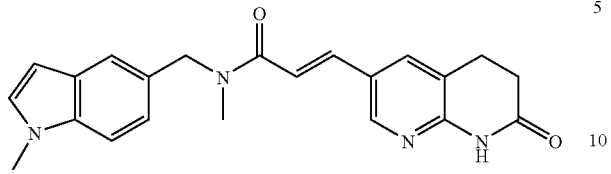

b) Preparation of N-Methyl-N-(1-methyl-1H-indol-5-ylmethyl)-3-(7-oxo-5,6,7,8-tetrahydro-[1,8]naphthyridin-3-yl)-acrylamide According to the procedure of Example 35g, (methyl-(1-methyl-1H-indol-5-ylmethyl)-amine (155 mg, 0.89 mmol) and (E)-3-(7-oxo-5,6,7,8-tetrahydro-[1,8]naphthyridin-3-yl) acrylic acid hydrochloride (229 mg, 0.90 mmol), were coupled to give crude product. Purification by column chromatography (silica gel, 5% MeOH/CH$_2$Cl$_2$) gave the title compound (217 mg, 65%) as a red solid and a mixture of amide rotamers: $^1$H NMR (400 MHz, DMSO-d$_6$) δ 10.63-10.62 (m, 1H), 8.36-8.33 (m, 1H), 8.06 (s, 1H), 7.56-7.51 (m, 1H), 7.43-7.19 (m, 4H), 7.08-7.01 (m, 1H), 6.38 (s, 1H), 4.85-4.67 (m, 2H), 3.76 (s, 3H), 3.06-2.85 (m, 5H), 2.54-2.52 (m, 2H); ESI MS m/z 375 [C$_{22}$H$_{22}$N$_4$O$_2$+H]$^+$.

Example 48

Preparation of (E)-N-(3-tert-Butyl-2-propoxy-benzyl)-N-methyl-3-(7-oxo-5,6,7,8-tetrahydro-[1,8]naphthyridin-3-yl)-acrylamide a) 3-tert-Butyl-2-propoxy-benzaldehyde

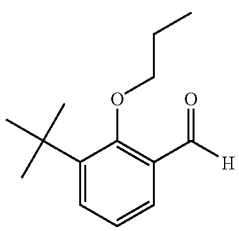 [SMILES: CCCOc1c(C=O)cccc1C(C)(C)C]

To a solution of 3-tert-butyl-2-hydroxy-benzaldehyde (2.04 g, 11.5 mmol) and K$_2$CO$_3$ (7.91 g, 57.3 mmol) in anhydrous DMF (23 ml) was added 1-iodopropane (2.34 ml, 24.0 mmol). The reaction mixture was left to stir for 48 h at room temperature. The reaction mixture was diluted with water (100 ml) and extracted with ethyl acetate (3×50 ml). Combined organic layers were washed with water (50 ml) and brine (50 ml), dried over MgSO$_4$, filtered and the solvent was removed in vacuo to give a yellow oil. Purification by column chromatography (silica gel, gradient elution of hexanes to 20% EtOAc/hexanes) gave 3-tert-butyl-2-propoxy-benzaldehyde (2.55 g, 99%) as a yellow oil: $^1$H NMR (400 MHz, DMSO-d$_6$) δ 10.21 (s, 1H), 7.62 (s, 1H), 7.61 (s, 1H), 7.19 (t J=8.0, 1H), 3.89 (t, J=8.0 Hz, 2H), 1.91-1.82 (m, 2H), 1.37 (s, 9H), 1.03 (t, J=8.0 Hz, 3H).

b) (3-tert-Butyl-2-propoxy-benzyl)methyl-amine

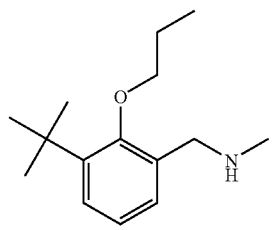 [SMILES: CCCOc1c(CNC)cccc1C(C)(C)C]

3-tert-Butyl-2-propoxy-benzaldehyde (1.15 g, 5.21 mmol) was dissolved in anhydrous methanol (25 ml). Methylamine (2.00 ml of 33% solution in ethanol, 16.1 mmol) was added and the reaction was stirred for 3 h. The solution was concentrated to a yellow oil and then dissolved in anhydrous methanol (25 ml). Sodium borohydride (198 mg, 5.23 mmol) was added and the mixture was stirred overnight at room temperature. Water (10 ml) was added and the solution was concentrated. Sodium hydroxide (30 ml, 1N) was added and the aqueous layer was extracted with ethyl acetate (3×50 ml). Combined organic layers were dried over MgSO$_4$, filtered and concentrated to afford (3-tert-butyl-2-propoxy-benzyl)-methyl-amine (1.18 g, 96%) as a clear oil: $^1$H NMR (400 MHz, DMSO-d$_6$) δ 7.28 (d, J=8.0 Hz, 1H), 7.15 (d, J=8.0 Hz, 1H), 6.97 (y J=8.0, y1H), 3.79 (t, J=4.0 Hz, 2H), 3.61 (s, 2H), 2.28 (s, 3H), 1.80-1.75 (m, 2H), 1.33 (s, 9H), 1.03 (t, J=8.0 Hz, 3H).

c) N-(3-tert-Butyl-2-propoxy-benzyl)-N-methyl-3-(7-oxo-5,6,7,8-tetrahydro-[1,8]naphthyridin-3-yl)-acrylamide

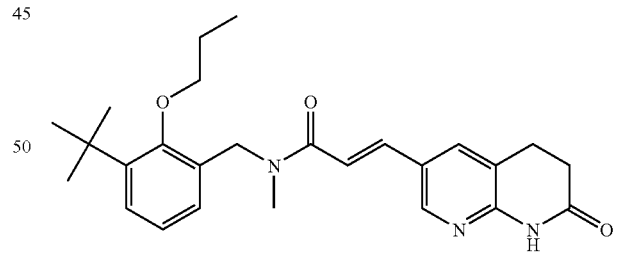

According to the procedure of Example 35g, 3-tert-butyl-2-propoxy-benzyl)-methyl-amine (368 mg, 1.56 mmol) and (E)-3-(7-oxo-5,6,7,8-tetrahydro-[1,8]naphthyridin-3-yl) acrylic acid hydrochloride (402 mg, 1.58 mmol), were coupled to give crude product. Purification by column chromatography (silica gel, gradient elution of 50% EtOAc/Hexane to EtOAc) gave the title compound as an off-white solid (519 mg, 76%) as a mixture of amide rotamers: $^1$H NMR (300 MHz, DMSO-d$_6$) δ 10.65-10.64 (m, 1H), 8.38-8.31 (m, 1H), 8.10-7.93 (m, 1H), 7.55-7.48 (m, 1H), 7.29-7.22 (m, 2H), 7.07-6.90 (m, 2H), 4.80-4.69 (m, 2H), 3.81-3.73 (m, 2H), 3.06-2.85 (m, 5H), 2.57-2.54 (m, 2H), 1.90-1.79 (m, 2H), 1.37 (s, 9H), 1.09-1.02 (m, 3H); ESI MS m/e 436 $[C_{26}H_{33}N_3O_3+H]^+$.

Example 49

Preparation of (E)-N-Methyl-N-(1-methyl-1H-indol-6-ylmethyl)-3-(7-oxo-5,6,7,8-tetrahydro-[1,8]naphthyridin-3-yl)-acrylamide a) 1-Methyl-1H-indole-6-carbaldehyde

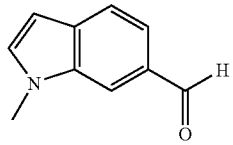

Dess-Martin periodane (2.56 g, 6.04 mmol) was dissolved into anhydrous $CH_2Cl_2$ (25 ml). (1H-Indol-6-yl)-methanol (883 mg, 6.04 mmol) in anhydrous $CH_2Cl_2$ (20 ml) was added and the mixture was stirred for 1 h. Aqueous sodium hydroxide (12 ml of 1N solution) was added and the reaction was stirred for 30 min. The organic layer was separated and washed with water (10 ml), brine (10 ml), dried over $MgSO_4$, filtered and concentrated to a thick brown oil. Purification by column chromatography (silica gel, gradient elution of 2% $MeOH/CH_2Cl_2$ to 5% $MeOH/CH_2Cl_2$) gave 1H-indole-6-carbaldehyde (212 mg, 24%) as a brown solid: $^1$H NMR (300 MHz, DMSO-$d_6$) δ 11.67 (bs, 1H), 9.99 (s, 1H), 7.97 (s, 1H), 7.70-7.65 (m, 2H), 7.54-7.50 (m, 1H), 6.59-5.54 (m, 1H).

b) 1-Methyl-1H-indole-6-carbaldehyde

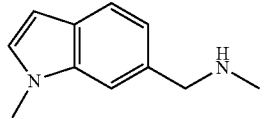

1-Methyl-1H-indole-6-carbaldehyde (146 mg, 0.91 mmol) was dissolved in anhydrous methanol (4 ml). Methylamine (0.35 ml of 33% solution in ethanol, 2.81 mmol) was added and the reaction was stirred for 3 h. The solution was concentrated to a yellow oil and then dissolved in anhydrous methanol (4 ml). Sodium borohydride (34.9 mg, 0.92 mmol) was added and the mixture was stirred overnight at room temperature. Water (10 ml) was added and the solution was concentrated. Sodium hydroxide (10 ml, 1N) was added and the aqueous layer was extracted with ethyl acetate (3×20 ml). Combined organic layers were dried over $MgSO_4$, filtered and concentrated to afford methyl-(1-methyl-1H-indol-6-ylmethyl)-amine (139 mg, 87%) as a yellow oil: $^1$H NMR (400 MHz, DMSO-$d_6$) δ 7.44 (d, J=8.0 Hz, 1H), 7.34 (s, 1H), 7.240 (d, J=3.6, 1H), 6.98 (d, J=8.0 Hz, 1H), 6.345 (d, J=4.0 Hz, 1H)), 3.75 (s, 3H), 3.73 (s, 2H), 2.27 (s, 3H).

c) Preparation of N-Methyl-N-(1-methyl-1H-indol-6-ylmethyl)-3-(7-oxo-5,6,7,8-tetrahydro-[1,8]naphthyridin-3-yl)-acrylamide

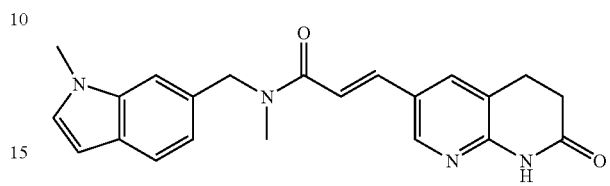

According to the procedure of Example 35g methyl-(1-methyl-1H-indol-6-ylmethyl)-amine (129 mg, 0.74 mmol) and (E)-3-(7-oxo-5,6,7,8-tetrahydro-[1,8]naphthyridin-3-yl) acrylic acid hydrochloride (190 mg, 0.75 mmol), were coupled to give crude product. Purification by column chromatography (silica gel, 5% $MeOH/CH_2Cl_2$) gave the title compound (180 mg, 65%) as a pink solid and a mixture of amide rotomers: $^1$H NMR (400 MHz, DMSO-$d_6$) δ 10.64-10.62 (m, 1H), 8.36-8.33 (m, 1H), 8.07-8.06 (m, 1H), 7.55-7.47 (m, 2H), 7.39-7.21 (m, 3H), 6.95-6.88 (m, 1H), 6.38-6.37 (m, 1H), 4.89-4.71 (m, 2H), 3.76-3.74 (m, 3H), 3.08-2.85 (m, 5H), 2.54-2.52 (m, 2H); ESI MS m/z 375 $[C_{22}H_{22}N_4O_2+H]^+$.

Example 50

Preparation of (E)-N-(3,4-Dihydro-2H-benzo[b][1,4] dioxepin-6-ylmethyl)-N-methyl-3-(7-oxo-5,6,7,8-tetrahydro-[1,8]naphthyridin-3-yl)-acrylamide a) (3,4-Dihydro-2H-benzo[b][1,4]dioxepin-6-ylmethyl)-methyl-amine

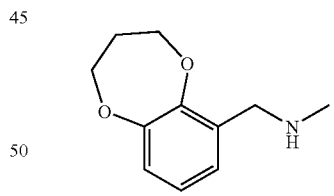

3,4-Dihydro-2H-benzo[b][1,4]dioxepine-6-carbaldehyde (269 mg, 1.51 mmol) was dissolved in anhydrous methanol (7 ml). Methylamine (0.60 ml of 33% solution in ethanol, 4.82 mmol) was added and the reaction was stirred for 3 hours. The solution was concentrated to a yellow oil and then dissolved in anhydrous methanol (7 ml). Sodium borohydride (58.3 mg, 1.54 mmol) was added and the mixture was stirred overnight at room temperature. Water (10 ml) was added and the solution was concentrated. Sodium hydroxide (20 ml, 1N) was added and the aqueous layer was extracted with ethyl acetate (3×40 ml). Combined organic layers were dried over $MgSO_4$, filtered and concentrated to afford (3,4-dihydro-2H-benzo[b] [1,4]dioxepin-6-ylmethyl)-methyl-amine (251 mg, 86%) as a brown oil: $^1$H NMR (400 MHz, DMSO-$d_6$) δ 6.96 (dd, J=8.0, 4.0 Hz, 1H), 6.88-6.82 (m, 2H), 4.10-4.05 (m, 4H), 3.60 (s, 2H), 2.25 (s, 3H), 2.10-2.06 (m, 2H).

b) N-(3,4-Dihydro-2H-benzo[b][1,4]dioxepin-6-ylmethyl)-N-methyl-3-(7-oxo-5,6,7,8-tetrahydro-[1,8]naphthyridin-3-yl)-acrylamide

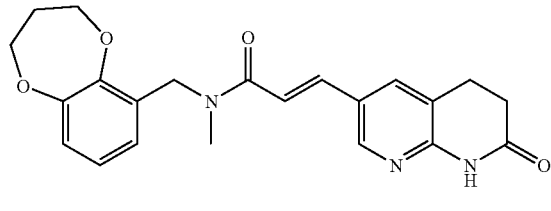 [SMILES: CN(Cc1cccc2c1OCCCO2)C(=O)/C=C/c1cnc2c(c1)CCC(=O)N2]

According to the procedure of Example 35g (3,4-dihydro-2H-benzo[b][1,4]dioxepin-6-ylmethyl)-methyl-amine (239 mg, 1.24 mmol) and (E)-3-(7-oxo-5,6,7,8-tetrahydro-[1,8]naphthyridin-3-yl)acrylic acid hydrochloride (318 mg, 1.25 mmol), were coupled to give crude product. Purification by column chromatography (silica gel, 5% MeOH/CH$_2$Cl$_2$) gave the title compound (385 mg, 79%) as a yellow solid and a mixture of amide rotamers: $^1$H NMR (400 MHz, DMSO-d$_6$) δ 10.66-10.63 (m, 1H), 8.36-8.32 (m, 1H), 8.07-8.03 (m, 1H), 7.51-7.46 (m, 1H), 7.30-721 (m, 1H), 6.93-6.88 (m, 2H), 6.78-6.76 (m, 1H), 4.76-4.59 (m, 2H), 4.13-4.06 (m, 4H), 3.11-2.84 (m, 5H), 2.54-2.52 (m, 2H), 2.11-2.07 (m, 2H); ESI MS m/e 394 [C$_{22}$H$_{23}$N$_3$O$_4$+H]$^+$.

Example 51

Preparation of (E)-N-(2,2-Dimethyl-2,3-dihydro-benzofuran-7-ylmethyl)-N-methyl-3-(7-oxo-5,6,7,8-tetrahydro-[1,8]naphthyridin-3-yl)-acrylamide a) (2,2-Dimethyl-2,3-dihydro-benzofuran-7-ylmethyl)-methyl-amine

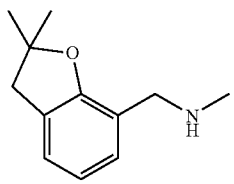

2,2-Dimethyl-2,3-dihydro-benzofuran-7-carbaldehyde (281 mg, 1.59 mmol) was dissolved in anhydrous methanol (7 ml). Methylamine (0.63 ml of 33% solution in ethanol, 4.82 mmol) was added and the reaction was stirred for 3 h. The solution was concentrated to a yellow oil and then dissolved in anhydrous methanol (7 ml). Sodium borohydride (61.5 mg, 1.63 mmol) was added and the mixture was stirred overnight at room temperature. Water (5 ml) was added and the solution was concentrated. Sodium hydroxide (20 ml, 1N) was added and the aqueous layer was extracted with ethyl acetate (3×40 ml). Combined organic layers were dried over MgSO$_4$, filtered and concentrated to afford (2,2-Dimethyl-2,3-dihydro-benzofuran-7-ylmethyl)-methyl-amine (303 mg, 99%) as a yellow oil: $^1$H NMR (300 MHz, DMSO-d$_6$) δ 7.06-7.02 (m, 2H), 6.76-6.71 (m, 1H), 3.52 (s, 2H), 2.97 (s, 2H), 2.24 (s, 3H), 1.39 (s, 6H).

b) N-(2,2-Dimethyl-2,3-dihydro-benzofuran-7-ylmethyl)-N-methyl-3-(7-oxo-5,6,7,8-tetrahydro-[1,8]naphthyridin-3-yl)-acrylamide

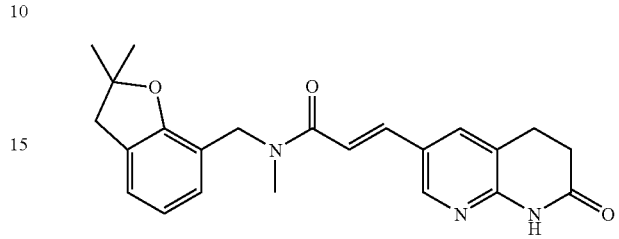

According to the procedure of Example 35g, (2,2-dimethyl-2,3-dihydro-benzofuran-7-ylmethyl)-methyl-amine (284 mg, 1.48 mmol) and (E)-3-(7-oxo-5,6,7,8-tetrahydro-[1,8]naphthyridin-3-yl)acrylic acid hydrochloride (382 mg, 1.50 mmol), were coupled to give crude product. Purification by column chromatography (silica gel, 5% MeOH/CH$_2$Cl$_2$) gave the title compound (422 mg, 73%) as an orange solid and a mixture of amide rotamers. $^1$H NMR (300 MHz, DMSO-d$_6$) δ 10.65-10.64 (m, 1H), 8.35-8.34 (m, 1H), 8.06-8.01 (m, 1H), 7.51-7.44 (m, 1H), 7.37-7.07 (m, 2H), 6.92-6.89 (m, 1H), 6.81-6.73 (m, 1H), 4.65-4.49 (m, 2H), 3.11-2.87 (m, 7H), 2.55-2.53 (m, 2H), 1.42-1.39 (m, 6H); ESI MS m/e 392 [C$_{23}$H$_{25}$N$_3$O$_3$+H]$^+$.

Example 52

Preparation of (E)-N-(1H-Indol-4-ylmethyl)-N-methyl-3-(7-oxo-5,6,7,8-tetrahydro-[1,8]naphthyridin-3-yl)-acrylamide a) (1H-Indol-4-yl)-methanol

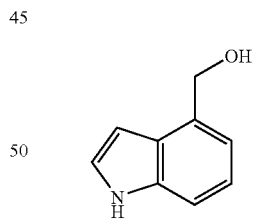

1H-Indole-6-carboxylic acid (1.00 g, 6.23 mmol) was dissolved into anhydrous THF (20 ml) under argon. The solution was cooled in an ice bath and lithium aluminum hydride (13.1 ml of 1M solution in THF, 13.1 mmol) was added dropwise. The reaction mixture was allowed to warm to room temperature and stir overnight. The reaction mixture was cooled to 0° C. and ethyl acetate (10 ml) was carefully added, followed by methanol (5 ml) and water (5 ml). The mixture was stirred for 30 min and filtered through celite. The solution was concentrated and dissolved in ethyl acetate (200 ml) and washed with brine (2×100 ml), dried over MgSO$_4$, filtered and concentrated to yield (1H-indol-4-yl)-methanol (471 mg, 52%) as an orange oil: $^1$H NMR (400 MHz, DMSO-d$_6$) δ 11.04 (bs, 1H), 7.30-7.26 (m, 2H), 7.05-6.98 (m, 2H), 6.48-6.47 (m, 1H), 5.04 (t, J=4.0 Hz, 1H), 4.74 (d, J=8.0 Hz, 2H).

b) 1H-Indole-4-carbaldehyde

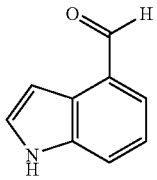 [SMILES: O=Cc1cccc2[nH]ccc12]

Dess-Martin periodane (1.04 g, 2.46 mmol) was dissolved into anhydrous CH$_2$Cl$_2$ (10 ml). (1H-Indol-4-yl)-methanol (449 mg, 3.07 mmol) in anhydrous CH$_2$Cl$_2$ (10 ml) was added and the mixture was stirred for 1 h. Sodium hydroxide (50 ml of 1N solution) and ether (50 ml) were added and the reaction was stirred for 30 min. The organic layer was separated and washed with water (10 ml), brine (10 ml), dried over MgSO$_4$, filtered and concentrated to a thick brown oil. Purification by column chromatography (silica gel, gradient elution of 2% MeOH/CH$_2$Cl$_2$ to 5% MeOH/CH$_2$Cl$_2$) gave 1H-indole-4-carbaldehyde (235 mg, 53%) as a yellow solid: $^1$H NMR (300 MHz, DMSO-d$_6$) δ 11.59 (bs, 1H), 10.18 (s, 1H), 7.78-7.75 (m, 1H), 7.66-7.60 (m, 2H), 7.33-7.28 (m, 1H), 7.08 (d, J=3.0 Hz, 1H).

c) (1H-Indol-4-ylmethyl)-methyl-amine

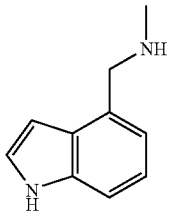

1H-Indole-4-carbaldehyde (219 mg, 1.51 mmol) was dissolved in anhydrous methanol (7 ml). Methylamine (0.60 ml of 33% solution in ethanol, 4.82 mmol) was added and the reaction was stirred for 3 h. The solution was concentrated to an orange solid and then dissolved in anhydrous methanol (7 ml). Sodium borohydride (58.0 mg, 1.53 mmol) was added and the mixture was stirred overnight at room temperature. Water (10 ml) was added and the solution was concentrated. Sodium hydroxide (10 ml, 1N) was added and the aqueous layer was extracted with ethyl acetate (3×20 ml). Combined organic layers were dried over MgSO$_4$, filtered and concentrated to afford (1H-indol-4-ylmethyl)-methyl-amine (229 mg, 94%) as a brown solid: $^1$H NMR (400 MHz, DMSO-d$_6$) δ 11.03 (bs, 1H), 7.29-7.24 (m, 2H), 7.03-6.93 (m, 2H), 6.51-6.50 (m, 1H), 3.88 (s, 2H), 2.30 (s, 3H).

d) N-(1H-Indol-4-ylmethyl)-N-methyl-3-(7-oxo-5,6,7,8-tetrahydro-[1,8]naphthyridin-3-yl)-acrylamide

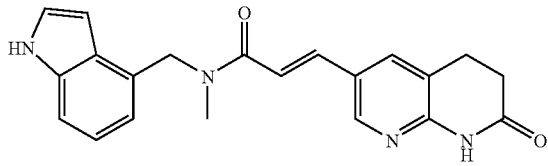 [SMILES: CN(Cc1cccc2[nH]ccc12)C(=O)/C=C/c1cnc2c(c1)CCC(=O)N2]

According to the procedure of Example 35g, (1H-indol-4-ylmethyl)-methyl-amine (223 mg, 1.39 mmol) and (E)-3-(7-oxo-5,6,7,8-tetrahydro-[1,8]naphthyridin-3-yl)acrylic acid hydrochloride (359 mg, 1.41 mmol), were coupled to give crude product. Purification by column chromatography gave the title compound (369 mg, 73%) as a pink solid and a mixture of amide rotomers: $^1$H NMR (400 MHz, DMSO-d$_6$) δ 11.20-11.14 (m, 1H), 10.65-10.62 (m, 1H), 8.38-8.32 (m, 1H), 8.08-7.99 (m, 1H), 7.59-7.53 (m, 1H), 7.37-7.21 (m, 3H), 7.09-7.03 (m, 1H), 6.89-6.76 (m, 1H), 6.51 (s, 1H), 5.06-4.88 (m, 2H), 3.04-2.83 (m, 5H), 2.56-2.52 (m, 2H); ESI MS m/z 361 [C$_{21}$H$_{20}$N$_4$O$_2$+H]$^+$.

Example 53

Preparation of (E)-3-(2,2-Dimethyl-3-oxo-3,4-dihydro-2H-pyrido[3,2-b][1,4]oxazin-7-yl)-N-methyl-N-(1-methyl-1H-indol-2-ylmethyl)-acrylamide

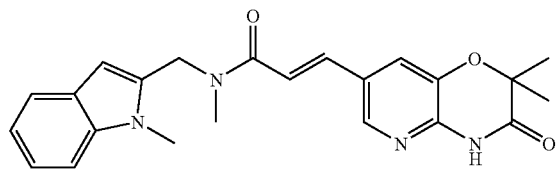 [SMILES: CN(Cc1cc2ccccc2n1C)C(=O)/C=C/c1cnc2c(c1)OC(C)(C)C(=O)N2]

According to the procedure of Example 43d, methyl-(1-methyl-1H-indol-2-ylmethyl)-amine (124 mg, 0.71 mmol) and 3-(2,2-dimethyl-3-oxo-3,4-dihydro-2H-pyrido[3,2-b][1,4]oxazin-7-yl)-acrylic acid (160 mg, 0.64 mmol), were coupled to yield the title compound (167 mg, 64%) as a white solid and as a mixture of amide rotomers. $^1$H NMR (400 MHz, DMSO-d$_6$) δ 11.03-11.04 (m, 1H), 8.15-8.20 (m, 1H), 7.89-7.94 (m, 1H), 7.41-7.56 (m, 3H), 7.39-7.41 (m, 1H), 7.00-7.12 (m, 1H), 6.14-6.99 (m, 1H), 4.87-5.05 (m, 2H), 3.68-3.72 (m, 3H), 2.99-3.10 (m, 3H), 1.39-1.44 (m, 6H); MS (ESI) m/e 405 (C$_{23}$H$_{24}$N$_4$O$_3$+H)$^+$.

Example 54

Preparation of (E)-3-(2,2-Dimethyl-3-oxo-3,4-dihydro-2H-pyrido[3,2-b][1,4]oxazin-7-yl)-N-methyl-N-(2-methyl-benzofuran-3-ylmethyl)-acrylamide

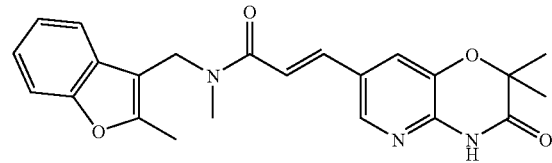 [SMILES: Cc1oc2ccccc2c1CN(C)C(=O)/C=C/c1cnc2c(c1)OC(C)(C)C(=O)N2]

According to the procedure of Example 43d, methyl-(2-methyl-benzofuran-3-ylmethyl)-amine (124 mg, 0.71 mmol) and 3-(2,2-dimethyl-3-oxo-3,4-dihydro-2H-pyrido[3,2-b][1,4]oxazin-7-yl)-acrylic acid (160 mg, 0.64 mmol) were coupled to yield the title compound (211 mg, 81%) as a white solid and as a mixture of amide rotomers. $^1$H NMR (400 MHz, DMSO-d$_6$) δ 11.39 (1s, 1H), 8.20 (1s, 1H), 7.92 (1s, 1H), 7.54-7.58 (m, 2H), 7.46-7.48 (m, 1H), 7.17-7.25 (m,

Example 55

Preparation of (E)-3-(2,2-Dimethyl-3-oxo-3,4-dihydro-2H-pyrido[3,2-b][1,4]oxazin-7-yl)-N-(3-methoxy-2-propoxy-benzyl)-N-methyl-acrylamide)

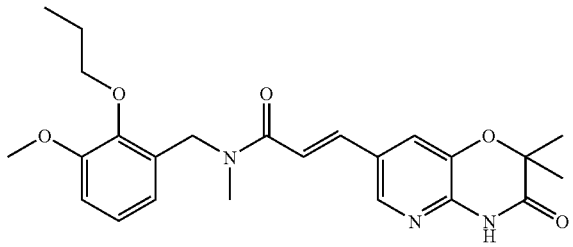 [SMILES: CCCOc1c(CN(C)C(=O)/C=C/c2cnc3c(c2)OC(C)(C)C(=O)N3)cccc1OC]

To a solution of (3-methoxy-2-propoxy-benzyl)-methylamine (115 mg, 0.55 mmol) in DMF (5 mL) were added in sequential order 3-(2,2-dimethyl-3-oxo-3,4-dihydro-2H-pyrido[3,2-b][1,4]oxazin-7-yl)-acrylic acid (181 mg, 0.5 mmol), 1-hydroxybenzotriazole (74 mg, 0.55 mmol), diisopropylethylamine (261 uL, 1.5 mmol), and N-(3-dimethylaminopropyl)-N'-ethylcarbodiimide (110 mg, 0.55 mmol). The reaction was placed in a microwave at 130° C. for 5 min. The solution was cooled in an ice bath and water was added with rapid stirring. The precipitate was filtered, dried and triturated with diethyl ether to yield the title compound (164 mg, 75%) as a white solid and as a mixture of amide rotamers: $^1$H NMR (400 MHz, DMSO-$d_6$) δ 11.37-11.39 (m, 1H), 8.14-8.18 (m, 1H), 7.87-7.93 (m, 1H), 7.47-7.53 (m, 1H), 7.27-7.34 (m, 1H), 6.92-7.09 (m, 3H), 6.60-6.66 (m, 1H), 4.62-4.79 (m, 2H), 3.84-3.90 (m, 2H), 3.78 (s, 3H), 2.88-3.09 (m, 3H), 1.70-1.74 (m, 2H), 1.40-1.49 (m, 6H), 0.93-0.99 (m, 3H); MS (ESI) m/e 440 ($C_{24}H_{29}N_3O_5$+H)$^+$.

Example 56

Preparation of (E)-3-(3,4-Dihydro-2H-pyrido[3,2-b][1,4]oxazin-7-yl)-N-methyl-N-(2-methyl-benzofuran-3-ylmethyl)-acrylamide hydrochloride

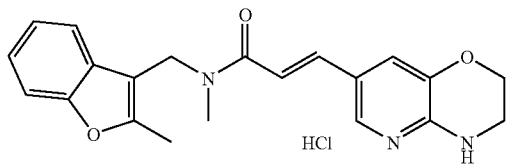 [SMILES: Cc1oc2ccccc2c1CN(C)C(=O)/C=C/c1cnc2c(c1)OCCN2 ; Cl]

To a solution of methyl-(2-methyl-benzofuran-3-ylmethyl)-amine (159 mg, 0.91 mmol) in DMF (5 mL) were added in sequential order 3-(3,4-dihydro-2H-pyrido[3,2-b][1,4]oxazin-7-yl)-acrylic acid hydrochloride (171 mg, 0.83 mmol), 1-hydroxybenzotriazole (127 mg, 0.91 mmol), diisopropylethylamine (289 uL, 1.06 mmol), and N-(3-dimethylaminopropyl)-N'-ethylcarbodiimide (182 mg, 0.91 mmol). The mixture was stirred at room temperature overnight, cooled in an ice bath and treated with water under rapid stirring. The resulting precipitate was collected by filtration, dried and triturated with diethyl ether to yield a pale yellow solid. The solid was re-solvated in methylene chloride (5 mL) and a solution of 2M HCl in ether (2 mL) was added to precipitate an orange solid. The precipitated solid was collected by filtration, dried and triturated with diethyl ether to yield the title compound (118 mg, 39%) as a mixture of amide rotamers. $^1$H NMR (400 MHz, DMSO-$d_6$) δ 8.76 (1s, 1H), 7.93-7.97 (m, 1H), 7.47-7.59 (m, 3H), 7.12-7.27 (m, 3H), 4.73-4.94 (m, 2H), 4.27 (m, 2H), 3.59 (m, 5H), 3.04 (s, 3H), 2.52 (s, 3H); MS (ESI) m/e 364 ($C_{21}H_{21}N_3O_3$+H)$^+$.

Example 57

Preparation of (E)-N-Methyl-N-(2-methyl-benzofuran-3-ylmethyl)-3-(3-oxo-3,4-dihydro-2H-pyrido[3,2-b][1,4]oxazin-7-yl)-acrylamide

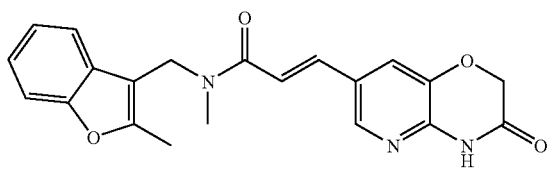 [SMILES: Cc1oc2ccccc2c1CN(C)C(=O)/C=C/c1cnc2c(c1)OCC(=O)N2]

To a solution of methyl-(2-methyl-benzofuran-3-ylmethyl)-amine (152 mg, 0.87 mmol) in DMF (5 mL) were added in sequential order 3-(3-Oxo-3,4-dihydro-2H-pyrido[3,2-b][1,4]oxazin-7-yl)-acrylic acid (175 mg, 0.79 mmol), 1-hydroxybenzotriazole (121 mg, 0.87 mmol), diisopropylethylamine (412 uL, 2.37 mmol), and N-(3-dimethylaminopropyl)-N'-ethylcarbodiimide (174 mg, 0.87 mmol). The mixture was stirred at room temperature overnight, cooled in an ice bath and treated with water under rapid stirring. The precipitated product was filtered and dried, triturated with diethyl ether to yield the title compound (125 mg, 42%) as a light brown solid and as a mixture of amide rotamers. $^1$H NMR (400 MHz, DMSO-$d_6$) δ 11.46 (s, 1H), 8.21 (s, 1H), 7.89 (s, 1H), 7.50-7.59 (m, 3H), 7.19-7.26 (m, 3H), 4.74 (s, 2H), 4.70 (s, 2H), 3.06 (s, 3H), 2.52 (s, 3H); MS (ESI) m/e 378 ($C_{21}H_{19}N_3O_4$+H)$^+$.

Example 58

Preparation of (E)-N-Methyl-N-(3-methyl-benzofuran-2-ylmethyl)-3-(3-oxo-3,4-dihydro-2H-pyrido[3,2-b][1,4]oxazin-7-yl)-acrylamide

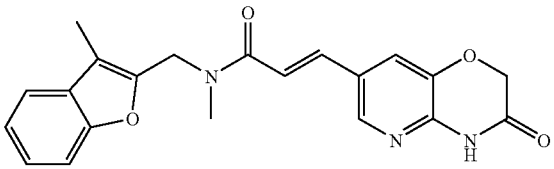 [SMILES: Cc1c(CN(C)C(=O)/C=C/c2cnc3c(c2)OCC(=O)N3)oc2ccccc12]

To a solution of methyl-(3-methyl-benzofuran-2-ylmethyl)-amine (152 mg, 0.87 mmol) in DMF (5 mL) were added in sequential order 3-(3-Oxo-3,4-dihydro-2H-pyrido[3,2-b][1,4]oxazin-7-yl)-acrylic acid (175 mg, 0.79 mmol), 1-hydroxybenzotriazole (121 mg, 0.87 mmol), diisopropylethylamine (412 uL, 2.37 mmol), and N-(3-dimethylaminopropyl)-N'-ethylcarbodiimide (174 mg, 0.87 mmol). The mixture was stirred at room temperature overnight, cooled in an ice bath and treated with water under rapid stirring. The precipitated product was filtered and dried, triturated with diethyl ether to yield the title compound (150 mg, 50%) as a light brown solid and as a mixtures of amide rotamers. $^1$H NMR (400 MHz, DMSO-d$_6$) δ 11.46 (s, 1H), 8.19 (s, 1H), 7.89 (s, 1H), 7.5-7.59 (m, 3H), 7.24-7.32 (m, 3H), 4.8-5.02 (m, 2H), 4.70 (s, 2H), 2.95-3.19 (m, 3H), 2.28 (s, $^3$H); MS (ESI) m/e 378 (C$_{21}$H$_{19}$N$_3$O$_4$+H)$^+$.

Example 59

Preparation of (E)-N-(3-Chloro-benzofuran-2-ylmethyl)-3-(2,2-dimethyl-3-oxo-3,4-dihydro-2H-pyrido[3,2-b][1,4]oxazin-7-yl)-N-methyl-acrylamide

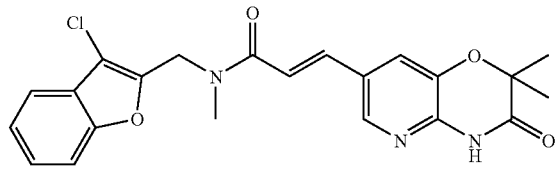 [SMILES: CN(Cc1oc2ccccc2c1Cl)C(=O)/C=C/c1cnc2c(c1)OC(C)(C)C(=O)N2]

To a solution of (3-chloro-benzofuran-2-ylmethyl)-methyl-amine (151 mg, 0.77 mmol) in DMF (5 mL) were added in sequential order 3-(2,2-dimethyl-3-oxo-3,4-dihydro-2H-pyrido[3,2-b][1,4]oxazin-7-yl)-acrylic acid (174 mg, 0.7 mmol), 1-hydroxybenzotriazole (107 mg, 0.77 mmol), diisopropylethylamine (366 uL, 2.1 mmol), and N-(3-dimethylaminopropyl)-N'-ethylcarbodiimide (154 mg, 0.77 mmol). The mixture was stirred at room temperature overnight, cooled in an ice bath and treated with water under rapid stirring. The precipitated product was filtered and dried, triturated with diethyl ether to yield the title compound (218 mg, 73%) as a light yellow solid. $^1$H NMR (400 MHz, DMSO-d6) δ 11.43 (s, 1H), 8.21 (s, 1H), 7.96 (s, 1H), 7.53-7.67 (m, 3H), 7.40-7.44 (m, 3H), 4.89-5.11 (m, 2H), 2.97-3.23 (m, 3H), 1.46 (s, 6H); MS (ESI) m/e 426 (C$_{22}$H$_{20}$ClN$_3$O$_4$+H)$^+$.

Example 60

Preparation of (E)-N-methyl-(1H-indol-2-ylmethyl)-3-(7-oxo-5,6,7,8-tetrahydro-[1,8]napthyridin-3-yl) acrylamide a) Preparation of 3-methyl-2-(methylaminomethyl)indole

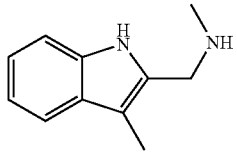

Methylamine (0.34 mL, 8.4 mmol, 33% in ethanol) was added to a solution of 3-methylindole-2-carboxaldehyde (447 mg, 2.8 mmol) in methanol (10 mL) and stirred for 5 hours. Sodium borohydride (104 mg, 2.8 mmol) was slowly added at 0° C. The resultant mixture was warmed to room temperature and stirred overnight. Water (2 mL) was added slowly at 0° C. and the mixture was evaporated to a paste. The paste was partitioned between water (2 mL) and dichloromethane (15 mL). The layers were separated and the aqueous layer was extracted with dichloromethane (2×15 mL). The combined organic phases were dried and evaporated to afford title compound (348 mg, 71%). NMR (400 MHz, DMSO-d$_6$): 10.63 (s, 1H), 7.38 (d, J=7.7 Hz, 1H), 7.25 (d, J=8.0 Hz, 1H), 6.99 (t, J=8.0 Hz, 1H), 6.92 (t, J=6.6 Hz, 1H), 3.73 (s, 2H), 2.25 (s, 3H), 2.19 (s, 3H).

b) Preparation of N-methyl-(1H-indol-2-ylmethyl)-3-(7-oxo-5,6,7,8-tetrahydro-[1,8]napthyridin-3-yl) acrylamide

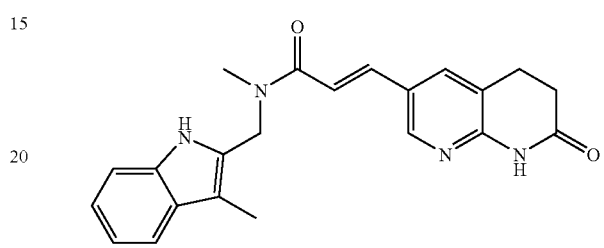

EDC (498 mg, 2.6 mmol) was added to a solution of 3-methyl-2-(methylaminomethyl)indole (348 mg, 2.0 mmol), 3-(7-oxo-5,6,7,8-tetrahydro-[1,8]naphthyridin-3-yl)-acrylic acid hydrochloride (533 mg, 2.1 mmol), HOBT.H$_2$O (270 mg, 2.0 mmol) and DIPEA (1.04 mL, 6 mmol) in DMF (5 mL). After stirring overnight, the mixture was slowly diluted with water (50 mL). The resulting precipitate was collected by filtration washed with water and dried. The precipitate was suspended in MeOH (10 mL), stirred for 60 hours, filtered and dried to afford title compound (203 mg, 27%). $^1$H NMR (300 MHz, DMSO-d$_6$, 8): 10.77 and 10.58 (rotamers, 2s, br, 1H), 10.64 (s, br, 1H), 8.37 (d, J=1.9 Hz, 1H), 8.08 (s, 1H), 7.58-6.92 (m, 6H), 4.91 and 4.75 (rotamers, 2s, 2H), 3.09 and 2.91 (rotamers, 2s, 3H), 2.90 (m, 2H), 2.53, (m, 2H), 2.25 (s, 3H). MS (ESI): m/e 375 (M+H)$^+$.

Example 61

Preparation of (E)-3-(2,2-dimethyl-3,4-dihydro-2H-pyrido[3,2-b][1,4]oxazin-7-yl)-N-methyl-N-((3-methylbenzofuran-2-yl)methyl)acrylamide hydrochloride

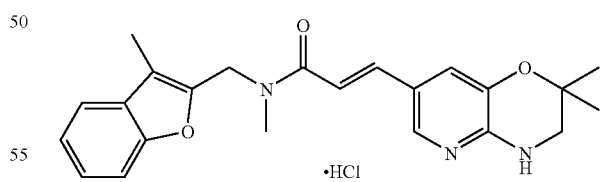

To a solution of methyl-(3-methyl-benzofuran-2-ylmethyl)-amine (88 mg, 0.5 mmol) in DMF (5 mL) were added in sequential order 3-(2,2-dimethyl-3,4-dihydro-2H-pyrido[3,2-b][1,4]oxazin-7-yl)acrylic acid hydrochloride (107 mg, 0.46 mmol), 1-hydroxybenzotriazole (68 mg, 0.5 mmol), diisopropylethylamine (240 uL, 1.38 mmol), and N-(3-dimethylaminopropyl)-N'-ethylcarbodiimide (100 mg, 0.5 mmol). The mixture was stirred at room temperature overnight, cooled in an ice bath and water added with rapid stirring. The product was extracted with ethyl acetate (3×10 mL), dried with sodium sulfate, filtered and concentrated. The free base was re-solvated in methylene chloride (5 mL) and a solution of 4M HCl in dioxane (1 mL) was added to precipitate the hydrogen chloride salt as a pale yellow solid (84 mg, 43%): $^1$H NMR (400 MHz, DMSO-d6) δ 8.94 (1s, 1H), 8.01-8.06 (m, 2H), 7.47-7.58 (m, 3H), 7.16-7.25 (m, 3H), 4.73-4.94 (rotamers, 2s, 2H), 3.42 (s, 2H), 3.04 (s, 3H), 2.42 (s, 3H), 1.34 (s, 6H); MS (ESI) m/e 392 $(C_{23}H_{25}N_3O_3+H)^+$.

Example 62

Preparation of (E)-3-(6-aminopyridin-3-yl)-N-((5-fluoro-3-methylbenzo[b]thiophen-2-yl)methyl)-N-methylacrylamide hydrochloride

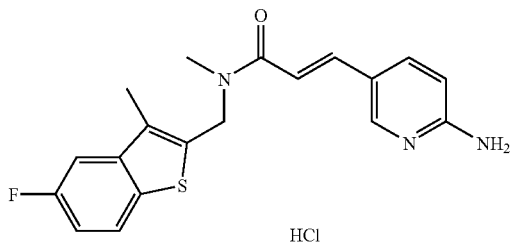 [SMILES: Cc1c(CN(C)C(=O)/C=C/c2ccc(N)nc2)sc2ccc(F)cc12 ; Cl]

To a solution of (5-fluoro-1-methyl-1H-indol-2-yl)-N-methylmethanamine (168 mg, 0.8 mmol) in DMF (5 mL) were added in sequential order (E)-3-(6-aminopyridin-3-yl)acrylic acid (120 mg, 0.73 mmol), 1-hydroxybenzotriazole (111 mg, 0.8 mmol), diisopropylethylamine (391 uL, 2.19 mmol), and N-(3-dimethylaminopropyl)-N'-ethylcarbodiimide (160 mg, 0.8 mmol). The mixture was stirred at room temperature overnight, cooled in an ice bath and water added with rapid stirring. The product was extracted with ethyl acetate (3×10 mL), dried, filtered and concentrated. The crude free base was re-solvated in methylene chloride (10 mL) to which was added HCl (1 mL, 4M in dioxane), with the product precipitating out with the addition of ether. The title compound is triturated with ether (2×10 mL) to yield the product as a pale brown solid (76 mg, 25%): $^1$H NMR (300 MHz, DMSO-d6) δ 8.2-8.49 (m, 3H), 7.86-7.99 (m, 1H), 7.46-7.64 (m, 2H), 7.16-7.29 (m, 2H), 6.99 (d, J=12.0 Hz, 1H), 4.83-5.13 (rotamers, 2s, 2H), 2.95-3.16 (rotamers, 2s, 3H), 2.41 (s, 3H); MS (ESI) m/e 356 $(C_{19}H_{18}FN_3OS+H)^+$.

Example 63

Preparation of (E)-N-((3-chlorobenzofuran-2-yl)methyl)-N-methyl-3-(3-oxo-3,4-dihydro-2H-pyrido[3,2-b][1,4]oxazin-7-yl)acrylamide

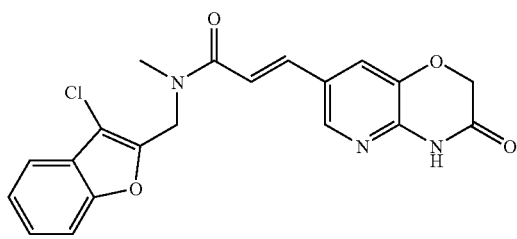 [SMILES: CN(Cc1oc2ccccc2c1Cl)C(=O)/C=C/c1cnc2c(c1)OCC(=O)N2]

To a solution of (3-chlorobenzofuran-2-yl)-N-methylmethanamine (100 mg, 0.51 mmol) in DMF (5 mL) were added in sequential order (E)-3-(3-oxo-3,4-dihydro-2H-pyrido[3,2-b][1,4]oxazin-7-yl)acrylic acid (107 mg, 0.46 mmol), 1-hydroxybenzotriazole (71 mg, 0.51 mmol), diisopropylethylamine (243 uL, 1.39 mmol), and N-(3-dimethylaminopropyl)-N'-ethylcarbodiimide (102 mg, 0.51 mmol). The mixture was stirred at room temperature overnight, cooled in an ice bath and water was added with rapid stirring. The product precipitated and was filtered, triturated with ether and dried to yield title compound as a white solid (55 mg, 30%): $^1$H NMR (400 MHz, CDCl$_3$) δ 9.21 (s, 1H), 8.12-8.19 (m, 1H), 7.28-7.6 (m, 7H), 4.81-4.95 (rotamers, 2s, 2H), 4.714 (s, 2H); 3.21 (s, 3H); MS (ESI) m/e 398 $(C_{20}H_{16}ClN_3O_4+H)^+$.

Example 64

Preparation of (E)-N-(3-methoxy-2-propoxybenzyl)-N-methyl-3-(3-oxo-3,4-dihydro-2H-pyrido[3,2-b][1,4]oxazin-7-yl)acrylamide

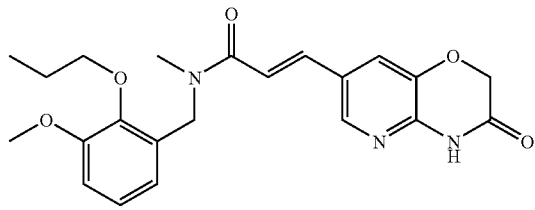 [SMILES: CCCOc1c(CN(C)C(=O)/C=C/c2cnc3c(c2)OCC(=O)N3)cccc1OC]

To a solution of (3-methoxy-2-propoxyphenyl)-N-methylmethanamine (75 mg, 0.36 mmol) in DMF (5 mL) were added in sequential order (E)-3-(3-oxo-3,4-dihydro-2H-pyrido[3,2-b][1,4]oxazin-7-yl)acrylic acid (75 mg, 0.26 mmol), 1-hydroxybenzotriazole (50 mg, 0.36 mmol), diisopropylethylamine (150 uL, 0.67 mmol), and N-(3-dimethylaminopropyl)-N'-ethylcarbodiimide (72 mg, 0.36 mmol). The mixture was placed in a microwave at a temperature of 140° C. for 8 minutes. The product precipitated with the addition of water and was filtered, triturated with ether and dried to yield title compound as a white solid (38 mg, 36%): $^1$H NMR (400 MHz, CDCl$_3$) δ 8.03-8.12 (rotamers, 2s, 1H), 7.63-7.69 (dd, J=15.2 Hz, J=11.2 Hz, 1H), 7.44-7.35 (rotamers, 2s, 1H), 7.02-7.04 (m, 1H), 6.80-6.91 (m, 2H), 6.72 (d, J=7.2 Hz, 1H), 4.67-4.81 (rotamers, 4s, 4H), 3.91-4.01 (m, 2H), 3.90 (2s, rotomers, 3H), 3.10 (s, 3H), 1.76-1.89 (m, 2H), 1.05 (t, J=7.2 Hz, 3H); MS (ESI) m/e 412 $(C_{22}H_{25}N_3O_5+H)^+$.

Example 65

Preparation of (E)-N-((3-isopropylbenzofuran-2-yl)methyl)-N-methyl-3-(3-oxo-3,4-dihydro-2H-pyrido[3,2-b][1,4]oxazin-7-yl)acrylamide a) 1-iodo-2-(3-methylbut-2-enyloxy)benzene

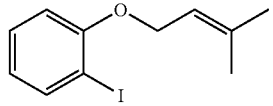

To a solution of 2-iodophenol (3.69 g, 16.8 mmol) in THF (50 mL) is added NaH (804 mg, 33.5 mmol) portion wise and stirred for 30 min at room temperature. 3,3-Dimethylallylbromide (3.9 mL, 33.5 mmol) was added and the reaction was stirred over night at room temperature. The reaction is quenched with water (20 mL) and extracted with diethyl ether (3×25 mL), the organic layers are dried over magnesium sulfate, filtered and concentrated. The compound was purified on silica gel using 100% hexanes as the eluent to yield 4.78 g (98%) of the title compound as a pale yellow oil: $^1$H NMR (300 MHz, CDCl$_3$) δ 7.77 (d, J=6.0 Hz, 1H), 7.35 (t, J=9.0 Hz, 1H), 7.02 (d, J=9.0 Hz, 1H), 6.74 (t, J=9.0 Hz, 1H), 5.45 (m, 1H), 4.60 (d, J=6.0 Hz, 2H), 1.75 (2s, 6H)

b) 3-isopropylbenzofuran

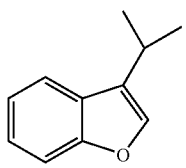

A solution of 1-iodo-2-(3-methylbut-2-enyloxy)benzene (5 g, 17.3 mmol) in propionitrile (10 mL) and diisopropylethylamine (9 mL, 52 mmol) is degassed with argon for 15 min. To this solution is added palladium acetate (423 mg, 1.73 mmol) and the reaction is heated to 100° C. overnight. The reaction is then cooled to room temperature and passed through a pad of celite, washing the filter cake with ethyl acetate (50 mL). The ethyl acetate and amine base are then removed under vacuum. The crude reaction mixture is then chromatographed using 100% hexanes to yield title compound as a colorless oil in 52% yield (1.3 g): $^1$H NMR (300 MHz, CDCl$_3$) δ 7.7 (s, 1H), 7.68 (d, J=9.0 Hz, 1H), 7.55 (d, J=9.0 Hz, 1H), 7.32-7.24 (m, 2H), 3.11-3.07 (m, 1H), 1.32 (2s, 6H).

c) 3-isopropylbenzofuran-2-carbaldehyde

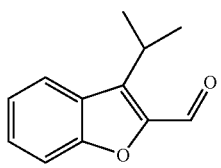

To a cooled (0° C.) solution of 3-isopropylbenzofuran (250 mg, 1.56 mmol) in THF (1 mL) is added nBuLi (2 mL, 2 mmol) drop wise and the reaction is stirred for 30 minutes. DMF (1 mL) was added to the reaction and stirred at room temperature overnight. The solution is placed in an ice bath and carefully quenched with 5% aqueous 110 solution (2 mL), and extracted with ethyl acetate (3×5 mL), dried over sodium sulfate and concentrated. The product was purified on silica with 100% hexanes to yield title compound in as a colorless oil (250 mg, 85%): $^1$H NMR (400 MHz, CDCl$_3$) δ 10.10 (s, 1H), 7.78 (d, 1H, J=9.0 Hz), 7.55 (d, 1H, J=9.0 Hz), 7.32-7.24 (m, 2H), 3.11-3.07 (m, 1H), 1.33-1.31 (2s, 6H).

d) (3-isopropylbenzofuran-2-yl)-N-methylmethanamine

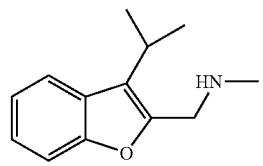

To a solution of 3-isopropylbenzofuran-2-carbaldehyde (250 mg, 1.33 mmol) in anhydrous methanol (8 mL) is added a solution of n-methylamine in ethanol (0.281 mL, 5.32 mmol) and the reaction is stirred at room temperature overnight under an atmosphere of argon. The solution is then concentrated, and re-solvated in methanol (8 mL) and cooled in an ice bath. Sodium borohydride (0.152 g, 4 mmol) was added portion wise and the reaction was stirred at room temperature under argon for 6 h. The solution is concentrated, and re-solvated in 1.3N NaOH (5 mL) and ether (5 mL) and stirred for 1 h. The ether layer was collected. The aqueous layer was washed with ether (2×10 mL), and the combined organic layers were dried over magnesium sulfate, filtered and concentrated in vacuo. Purification by chromatography (silica gel, 9:1 DCM:MeOH) yielded the title compound as a yellow oil (228 mg, 85%): $^1$H NMR (400 MHz, DMSO-d$_6$) δ 7.70 (d, J=4.0 Hz, 1H), 7.46 (d, J=8.0 Hz, 1H), 7.25-7.16 (m, 2H), 3.75 (s, 2H), 3.15-3.22 (m, 1H), 2.25 (s, 3H), 1.36-1.34 (2s, 6H).

Preparation of (E)-N-((3-isopropylbenzofuran-2-yl)methyl)-N-methyl-3-(3-oxo-3,4-dihydro-2H-pyrido[3,2-b][1,4]oxazin-7-yl)acrylamide To a solution of (3-isopropylbenzofuran-2-yl)-N-methylmethanamine (115 mg, 0.57 mmol) in DMF (5 mL) were added in sequential order 3-(2,2-dimethyl-3,4-dihydro-2H-pyrido[3,2-b][1,4]oxazin-7-yl)acrylic acid hydrochloride (118 mg, 0.51 mmol), 1-hydroxybenzotriazole (77 mg, 0.57 mmol), diisopropylethylamine (289 uL, 1.54 mmol), and N-(3-dimethylaminopropyl)-N'-ethylcarbodiimide (109 mg, 0.57 mmol). The mixture was stirred at room temperature overnight, cooled in an ice bath and water was added with rapid stirring. The product was extracted with ethyl acetate (3×10 mL), dried over sodium sulfate, filtered and concentrated to give a light brown solid (14 mg, 7%): $^1$H NMR (400 MHz, CD$_3$OD) δ 11.42 (s, 1H), 8.17-8.16 (m, 1H), 7.89-7.86 (m, 1H), 7.74-7.72 (m, 2H), 7.24-7.30 (m, 2H), 7.22-7.17 (m, 2H), 4.97 (s, 2H), 4.78 (s, 2H), 3.15 (s, 3H), 3.10-3.14 (m, 1H), 1.34 (s, 6H); MS (ESI) m/e 406 $(C_{23}H_{23}N_3O_4+H)^+$.

Example 66

Preparation of (E)-N-((3-ethylbenzofuran-2-yl)methyl)-N-methyl-3-(3-oxo-3,4-dihydro-2H-pyrido[3,2-b][1,4]oxazin-7-yl)acrylamide

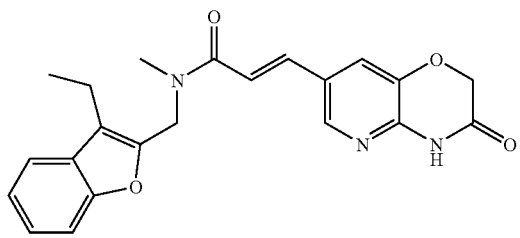 [SMILES: CCc1c(CN(C)C(=O)/C=C/c2cnc3c(c2)OCC(=O)N3)oc2ccccc12]

To a solution of (3-ethylbenzofuran-2-yl)-N-methylmethanamine (115 mg, 0.6 mmol) in DMF (5 mL) were added in sequential order (E)-3-(3-oxo-3,4-dihydro-2H-pyrido[3,2-b][1,4]oxazin-7-yl)acrylic acid (140 mg, 0.54 mmol), 1-hydroxybenzotriazole (84 mg, 0.6 mmol), diisopropylethylamine (282 uL, 1.62 mmol), and N-(3-dimethylaminopropyl)-N'-ethylcarbodiimide (120 mg, 0.6 mmol). The mixture was stirred at room temperature overnight, cooled in an ice bath and water added with rapid stirring. The product precipitated and was filtered, triturated with ether and dried to yield the title compound as a white solid (113 mg, 52%): $^1$H NMR (400 MHz, DMSO-$d_6$) δ 11.41 (s, 1H), 8.19 (s, 1H), 7.88 (d, J=6.4 Hz, 1H), 7.66 (d, J=7.6 Hz, 1H), 7.51-7.49 (m, 2H), 7.29-7.25 (m, 3H), 4.99-4.79 (rotamers, 2s, 2H), 4.68 (s, 2H), 3.39 (s, 3H), 2.79-2.73 (m, 2H), 1.23-1.20 (m, 3H); MS (ESI) m/e 392 $(C_{22}H_{21}N_3O_4+H)^+$.

Example 67

Preparation of (E)-N-((5-fluoro-3-methylbenzo[b]thiophen-2-yl)methyl)-N-methyl-3-(3-oxo-3,4-dihydro-2H-pyrido[3,2-b][1,4]oxazin-7-yl)acrylamide

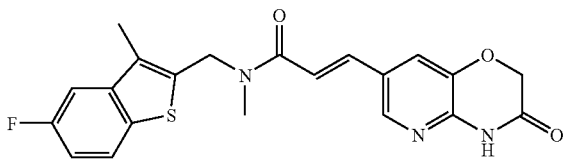 [SMILES: Cc1c(CN(C)C(=O)/C=C/c2cnc3c(c2)OCC(=O)N3)sc2ccc(F)cc12]

To a solution of (5-fluoro-3-methylbenzo[b]thiophen-2-yl)-N-methyl methanamine (200 mg, 0.96 mmol) in DMF (5 mL) were added in sequential order (E)-3-(3-oxo-3,4-dihydro-2H-pyrido[3,2-b][1,4]oxazin-7-yl)acrylic acid (185 mg, 0.87 mmol), 1-hydroxybenzotriazole (133 mg, 0.96 mmol), diisopropylethylamine (454 uL, 2.61 mmol), and N-(3-dimethylaminopropyl)-N'-ethylcarbodiimide (192 mg, 0.96 mmol). The mixture was stirred at room temperature overnight, cooled in an ice bath and water added with rapid stirring. The product was extracted with ethyl acetate (3×10 mL), dried with sodium sulfate, filtered and concentrated. The crude product was purified using preparative HPLC to give the title compound (45 mg, 13%): $^1$H NMR (400 MHz, DMSO-$d_6$) δ 11.42 (bs, 1H), 8.19 (s, 1H), 7.89-7.87 (m, 2H), 7.55-7.51 (m, 2H), 7.22-7.18 (m, 2H), 5.12-4.87 (2s, 2H, rotamers), 4.68 (s, 2H), 3.54 (s, 3H), 2.39 (s, 3H). MS (ESI) m/e 412 $(C_{21}H_{18}FN_3O_3S+H)^+$.

Example 68

Preparation of (E)-N-((5-fluoro-3-methylbenzo[b]thiophen-2-yl)methyl)-N-methyl-3-(7-oxo-5,6,7,8-tetrahydro-1,8-naphthyridin-3-yl)acrylamide

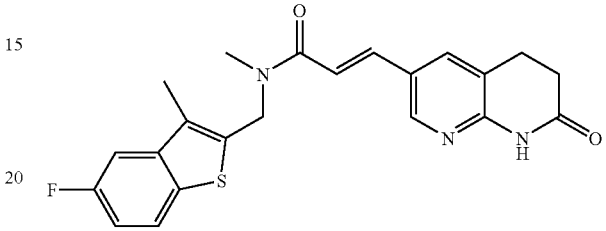

To a solution of (5-fluoro-3-methylbenzo[b]thiophen-2-yl)-N-methylmethanamine (168 mg, 0.8 mmol) in DMF (5 mL) were added in sequential order (E)-3-(7-oxo-5,6,7,8-tetrahydro-1,8-naphthyridin-3-yl)acrylic acid (159 mg, 0.73 mmol), 1-hydroxybenzotriazole (111 mg, 0.8 mmol), diisopropylethylamine (381 uL, 2.19 mmol), and N-(3-dimethylaminopropyl)-N'-ethylcarbodiimide (160 mg, 0.8 mmol). The mixture was stirred at room temperature overnight, cooled in an ice bath and water added with rapid stirring. The product precipitated and was filtered, triturated with ether and dried to yield the title compound as a pale brown solid (224 mg, 75%): $^1$H NMR (300 MHz, DMSO-$d_6$) δ 10.65 (s, 1H), 8.37 (s, 1H), 8.08 (s, 1H), 7.76-8.00 (m, 1H), 7.39-7.63 (m, 2H), 7.02-7.33 (m, 2H), 4.87-5.11 (rotamers, 2s, 2H), 3.16 (s, 3H), 2.56-2.89 (m, 2H), 2.49-2.51 (m, 2H), 2.39 (s, $^3$H); MS (ESI) m/e 410 $(C_{22}H_{20}FN_3O_2S+H)^+$.

Example 69

Preparation of (E)-N-((5-fluoro-1-methyl-1H-indol-2-yl)methyl)-N-methyl-3-(7-oxo-5,6,7,8-tetrahydro-1,8-naphthyridin-3-yl)acrylamide

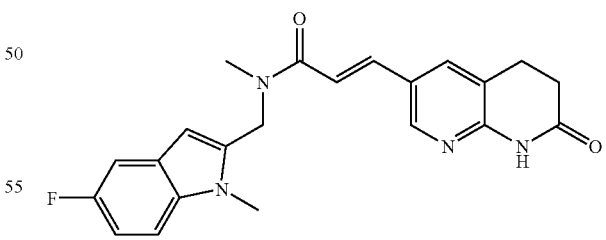

To a solution of (5-fluoro-1-methyl-1H-indol-2-yl)-N-methylmethanamine (70 mg, 0.36 mmol) in DMF (5 mL) were added in sequential order (E)-3-(7-oxo-5,6,7,8-tetrahydro-1,8-naphthyridin-3-yl)acrylic acid (72 mg, 0.33 mmol), 1-hydroxybenzotriazole (49 mg, 0.36 mmol), diisopropylethylamine (191 uL, 1.1 mmol), and N-(3-dimethylaminopropyl)-N'-ethylcarbodiimide (72 mg, 0.36 mmol). The mixture was stirred at room temperature overnight, cooled in an ice bath and water added with rapid stirring. The product precipitated and was filtered, triturated with ether and dried to yield title compound as a pale brown solid (97 mg, 76%): $^1$H NMR (300 MHz, DMSO-$d_6$) δ 10.68 (s, 1H), 8.40 (s, 1H), 8.08-8.18 (m, 1H), 7.91-8.08 (m, 1H), 7.52-7.68 (m, 1H), 7.37-7.52 (m, 1H), 7.13-7.36 (m, 2H), 6.42 (s, 1H), 4.86-5.06 (rotamers, 2s, 2H), 3.71 (s, 3H), 3.14 (m, 2H), 2.81-2.97 (m, 2H), 2.75 (s, 3H); MS (ESI) m/e 393 ($C_{22}H_{21}FN_4O_2$+H)$^+$.

Example 70

Preparation of (E)-N-((3-ethylbenzofuran-2-yl)methyl)-N-methyl-3-(7-oxo-5,6,7,8-tetrahydro-1,8-naphthyridin-3-yl)acrylamide

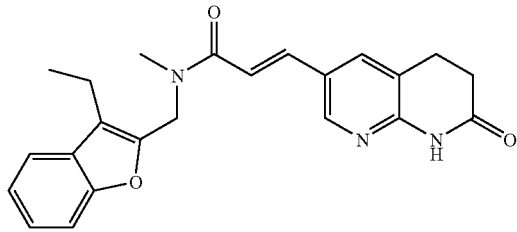 [SMILES: CCc1c(CN(C)C(=O)/C=C/c2cnc3c(c2)CCC(=O)N3)oc2ccccc12]

To a solution of (3-ethylbenzofuran-2-yl)-N-methylmethanamine (89 mg, 0.49 mmol) in DMF (5 mL) were added in sequential order (E)-3-(7-oxo-5,6,7,8-tetrahydro-1,8-naphthyridin-3-yl)acrylic acid (111 mg, 0.44 mmol), 1-hydroxybenzotriazole (68 mg, 0.49 mmol), diisopropylethylamine (232 uL, 1.34 mmol), and N-(3-dimethylaminopropyl)-N'-ethylcarbodiimide (98 mg, 0.49 mmol). The mixture was stirred at room temperature overnight, cooled in an ice bath and water added with rapid stirring. The product precipitated and was filtered, triturated with ether and dried to yield title compound as a pale brown solid (134 mg, 70%): $^1$H NMR (300 MHz, DMSO-$d_6$) δ 10.67 (s, 1H), 8.37 (s, 1H), 8.09 (s, 1H), 7.96 (s, 1H), 7.18-7.64 (m, 5H), 4.81-5.01 (rotamers, 2s, 2H), 3.27-3.61 (m, 2H), 2.90 (d, J=9.0 Hz, 2H), 2.73-2.78 (m, 2H), 2.51-2.59 (m, 3H), 1.23 (t, J=9.0 Hz, 3H); MS (ESI) m/e 390 ($C_{23}H_{23}N_3O_3$+H)$^+$.

Example 71

Preparation of (E)-N-((3-isopropylbenzofuran-2-yl)methyl)-N-methyl-3-(7-oxo-5,6,7,8-tetrahydro-1,8-naphthyridin-3-yl)acrylamide

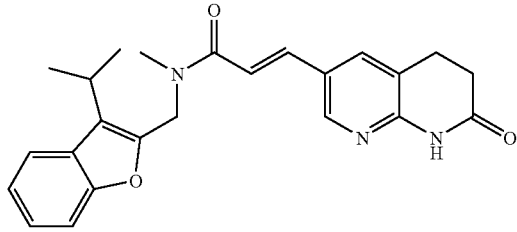 [SMILES: CC(C)c1c(CN(C)C(=O)/C=C/c2cnc3c(c2)CCC(=O)N3)oc2ccccc12]

To a solution of (3-isopropylbenzofuran-2-yl)-N-methylmethanamine (115 mg, 0.57 mmol) in DMF (5 mL) were added in sequential order (E)-3-(7-oxo-5,6,7,8-tetrahydro-1,8-naphthyridin-3-yl)acrylic acid (111 mg, 0.51 mmol), 1-hydroxybenzotriazole (77 mg, 0.57 mmol), diisopropylethylamine (289 uL, 1.54 mmol), and N-(3-dimethylaminopropyl)-N'-ethylcarbodiimide (109 mg, 0.57 mmol). The mixture was stirred at room temperature overnight, cooled in an ice bath and water added with rapid stirring. The product precipitated and was filtered, triturated with ether and dried to yield the title compound as a white solid (38 mg, 17%): $^1$H NMR (400 MHz, DMSO-$d_6$) δ 10.62 (s, 1H), 8.38 (s, 1H), 8.07 (s, 1H), 7.75-7.73 (d, J=7.6 Hz, 1H), 7.53-7.49 (m, 2H), 7.26-7.18 (m, 3H), 4.99-4.80 (rotamers, 2s, 2H), 3.40-3.35 (m, 1H), 3.32 (s, 3H), 2.91-2.89 (m, 2H), 2.55-2.53 (m, 2H), 1.37-1.36 (d, J=6.8 Hz, 6H); MS (ESI) m/e 404 ($C_{24}H_{25}N_3O_3$+H)$^+$.

Example 72

Preparation of (E)-N-(benzofuran-5-ylmethyl)-N-methyl-3-(7-oxo-5,6,7,8-tetrahydro-1,8-naphthyridin-3-yl)acrylamide a) benzofuran-5-yl-N-methylmethanamine

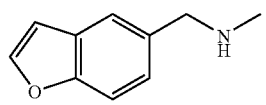

Benzofuran-5-carbaldehyde (315 mg, 2.16 mmol) was dissolved in anhydrous methanol (10 mL). Methylamine (0.86 mL of 33% solution in ethanol, 6.91 mmol) was added and the reaction was stirred for 3 h. The solution was concentrated to a brown oil and then dissolved in anhydrous methanol (10 mL). Sodium borohydride (83.2 mg, 2.20 mmol) was added and the mixture was stirred overnight at room temperature. Water (5 mL) was added and the solution was concentrated. Sodium hydroxide (10 mL, 1N) was added and the aqueous layer was extracted with ethyl acetate (3×20 mL). Combined organic layers were dried over MgSO$_4$, filtered and concentrated to afford benzofuran-5-yl-N-methylmethanamine (316 mg, 91%) as a light brown oil: $^1$H NMR (400 MHz, DMSO-$d_6$) δ 7.93 (s, 1H), 7.56 (s, 1H), 7.50 (d, J=8.4 Hz, 1H), 7.25 (d, J=8.4 Hz, 1H), 6.90 (s, 1H), 3.70 (s, 2H), 3.17 (s, 3H).

(E)-N-(benzofuran-5-ylmethyl)-N-methyl-3-(7-oxo-5,6,7,8-tetrahydro-1,8-naphthyridin-3-yl)acrylamide

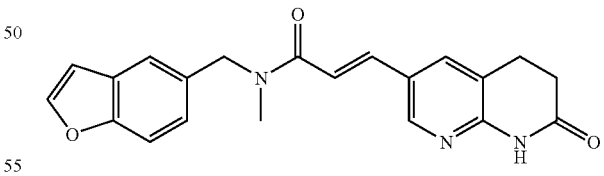

To a solution of benzofuran-5-yl-N-methylmethanamine (297 mg, 1.84 mmol), 3-(7-oxo-5,6,7,8-tetrahydro-[1,8]naphthyridin-3-yl)-acrylic acid hydrochloride (474 mg, 1.86 mmol), HOBt (252 mg, 1.86 mmol) and DIPEA (1.32 mL, 7.58 mmol) in anhydrous DMF (30 mL) was added EDC hydrochloride (357 mg, 1.86 mmol). The mixture was stirred overnight at 40° C. Water (70 mL) was added and the solution was stirred for 1 h. The reaction mixture was extracted with ethyl acetate (3×100 mL). Combined organic layers were washed with water (50 mL) and brine (50 mL) and concentrated to give a red solid which was purified by column chromatography (silica gel, 5% MeOH/CH$_2$Cl$_2$) to afford (E)-N-(benzofuran-5-ylmethyl)-N-methyl-3-(7-oxo-5,6,7,8-tetrahydro-1,8-naphthyridin-3-yl)acrylamide (381 mg, 57%) as a red solid and a mixture of amide rotamers: $^1$H NMR (400 MHz, DMSO-d$_6$) 10.64-10.62 (m, 1H), 8.36-8.33 (m, 1H), 8.07 (s, 1H), 7.97 (s, 1H), 7.59-7.49 (m, 3H), 7.38-7.17 (m, 2H), 6.94 (m, 1H), 4.89-4.69 (m, 2H), 3.10-2.85 (m, 5H), 2.54-2.52 (m, 2H); ESI MS m/z 362 [C$_{21}$H$_{19}$N$_3$O$_3$+H]$^+$.

Example 73

Preparation of (E)-N-(benzo[b]thiophen-5-ylmethyl)-N-methyl-3-(7-oxo-5,6,7,8-tetrahydro-1,8-naphthyridin-3-yl)acrylamide a) benzo[b]thiophene-5-carbaldehyde

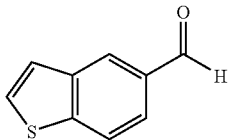 [SMILES: O=Cc1ccc2sccc2c1]

Benzo[b]thiophen-5-ylmethanol (311 mg, 1.89 mmol) was dissolved in anhydrous benzene (20 mL). MnO$_2$ (1317 mg, 15.2 mmol) was added and the reaction was stirred for 12 h. The solution was filtered through celite and the filter cake was washed with ethyl acetate (50 mL). The filtrate was concentrated under vacuum to give the product (284 mg, 92%) as an off-white solid: $^1$H NMR (400 MHz, DMSO-d$_6$) δ 10.09 (s, 1H), 8.46-8.45 (m, 1H), 8.21 (d, J=8.4 Hz, 1H), 7.94 (d, J=5.6 Hz, 1H), 7.81 (dd, J=8.4, 1.2 Hz, 1H), 7.66 (d, J=5.6 Hz, 1H).

b) benzo[b]thiophen-5-yl-N-methylmethanamine

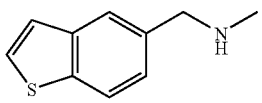

Benzo[b]thiophene-5-carbaldehyde (276 mg, 1.70 mmol) was dissolved in anhydrous methanol (8.0 mL). Methylamine (0.68 mL of 33% solution in ethanol, 5.46 mmol) was added and the reaction was stirred for 3 h. The solution was concentrated to a white solid and then dissolved in anhydrous methanol (10 mL). Sodium borohydride (66.0 mg, 1.75 mmol) was added and the mixture was stirred overnight at room temperature. Water (8.0 mL) was added and the solution was concentrated. Sodium hydroxide (10 mL, 1N) was added and the aqueous layer was extracted with ethyl acetate (3×20 mL). Combined organic layers were dried over MgSO$_4$, filtered and concentrated to afford benzo[b]thiophen-5-yl-N-methylmethanamine (269 mg, 89%) as a yellow oil: $^1$H NMR (300 MHz, DMSO-d$_6$) δ 7.90 (d, J=8.7 Hz, 1H), 7.79 (s, 1H), 7.71 (d, J=5.7 Hz, 1H), 7.40 (d, J=5.4 Hz, 1H), 7.32 (d, J=8.1 Hz, 1H), 3.73 (s, 2H), 2.26 (s, 3H).

(E)-N-(benzo[b]thiophen-5-ylmethyl)-N-methyl-3-(7-oxo-5,6,7,8-tetrahydro-1,8-naphthyridin-3-yl)acrylamide

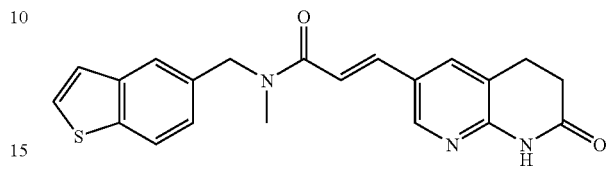

To a solution of benzo[b]thiophen-5-yl-N-methylmethanamine (260 mg, 1.47 mmol), 3-(7-oxo-5,6,7,8-tetrahydro-[1,8]naphthyridin-3-yl)-acrylic acid hydrochloride (377 mg, 1.48 mmol), HOBt (200 mg, 1.48 mmol) and DIPEA (1.05 mL, 6.03 mmol) in anhydrous DMF (24 mL) was added EDC hydrochloride (284 mg, 1.48 mmol). The mixture was stirred overnight at 40° C. Water (50 mL) was added and the solution was stirred for 1 h. The reaction mixture was extracted with ethyl acetate (3×80 mL). Combined organic layers were washed with water (50 mL) and brine (50 mL) and concentrated to give an orange solid which was purified by column chromatography (silica gel, 5% MeOH/CH$_2$Cl$_2$) to afford (E)-N-(benzo[b]thiophen-5-ylmethyl)-N-methyl-3-(7-oxo-5,6,7,8-tetrahydro-1,8-naphthyridin-3-yl)acrylamide (430 mg, 78%) as a pink solid and a mixture of amide rotamers: $^1$H NMR (400 MHz, DMSO-d$_6$) δ 10.67-10.64 (m, 1H), 8.37-8.33 (m, 1H), 8.08-8.05 (m, 1H), 8.00-7.95 (m, 1H), 7.75-7.71 (m, 2H), 7.56-7.52 (m, 1H), 7.45-7.43 (m, 1H), 7.37-7.22 (m, 2H), 4.93-4.73 (m, 2H), 3.12-2.86 (m, 5H), 2.54-2.51 (m, 2H); ESI MS m/z 378 [C$_{21}$H$_{19}$N$_3$O$_2$S+H]$^+$.

Example 74

Preparation of (E)-N-methyl-N-((1-methyl-1H-indol-4-yl)methyl)-3-(7-oxo-5,6,7,8-tetrahydro-1,8-naphthyridin-3-yl)acrylamide a) 1-Methyl-1H-indole-4-carbaldehyde

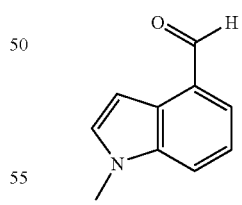

To a solution of 1H-indole-4-carbaldehyde (413 mg, 2.85 mmol) in anhydrous DMF (6.5 mL) was added sodium hydride (171 mg of 60% dispersion in oil, 4.27 mmol). The mixture was stirred for 40 min at room temperature. Methyl iodide (0.36 mL, 5.78 mmol) was then added and the reaction mixture was stirred for 12 h at room temperature. Water was added (25 mL) and the mixture was extracted with ethyl acetate (3×25 mL). Combined organic layers were washed with water (20 mL) and brine (20 mL), dried over Na$_2$SO$_4$, filtered and concentrated to a yellow oil. Purification by column chromatography (silica gel, $CH_2Cl_2$) gave 1-methyl-1H-indole-4-carbaldehyde (452 mg g, 99%) as a yellow oil: $^1$H NMR (400 MHz, DMSO-$d_6$) δ 10.20 (s, 1H), 7.84 (d, J=8.0 Hz, 1H), 7.68 (d, J=7.2 Hz, 1H), 7.58 (d, J=2.8 Hz, 1H), 7.38-7.34 (m, 1H), 7.08 (d, J=3.2 Hz, 1H), 3.87 (s, 3H).

b) N-methyl(1-methyl-1H-indol-4-yl)methanamine

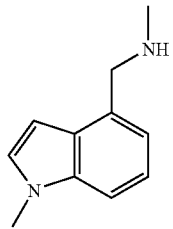

1-Methyl-1H-indole-4-carbaldehyde (427 mg, 2.68 mmol) was dissolved in anhydrous methanol (12 mL). Methylamine (1.07 mL of 33% solution in ethanol, 8.59 mmol) was added and the reaction was stirred for 3 h. The solution was concentrated to a yellow oil and then dissolved in anhydrous methanol (12 mL). Sodium borohydride (104 mg, 2.74 mmol) was added and the mixture was stirred overnight at room temperature. Water (10 mL) was added and the solution was concentrated. Sodium hydroxide (20 mL, 1N) was added and the aqueous layer was extracted with ethyl acetate (3×30 mL). Combined organic layers were dried over $Na_2SO_4$, filtered and concentrated to afford N-methyl(1-methyl-1H-indol-4-yl)methanamine (432 mg, 92%) as a yellow oil: $^1$H NMR (400 MHz, DMSO-$d_6$) δ 7.29-7.26 (m, 2H), 7.10-7.06 (m, 1H), 7.00-6.98 (m, 1H), 6.51 (d, J=3.2 Hz, 1H), 3.87 (s, 2H), 3.76 (s, 3H), 2.29 (s, 3H).

(E)-N-methyl-N-((1-methyl-1H-indol-4-yl)methyl)-3-(7-oxo-5,6,7,8-tetrahydro-1,8-naphthyridin-3-yl)acrylamide

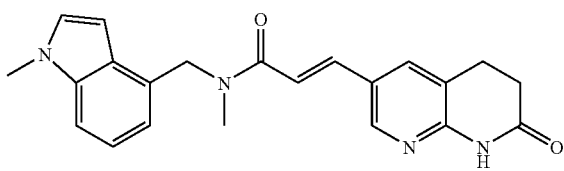 [SMILES: CN(Cc1cccc2c1ccn2C)C(=O)/C=C/c1cnc2c(c1)CCC(=O)N2]

To a solution of N-methyl(1-methyl-1H-indol-4-yl)methanamine (418 mg, 2.40 mmol), 3-(7-oxo-5,6,7,8-tetrahydro-[1,8]naphthyridin-3-yl)-acrylic acid hydrochloride (617 mg, 2.42 mmol), HOBt (327 mg, 2.42 mmol) and DIPEA (1.71 mL, 9.82 mmol) in anhydrous DMF (40 mL) was added EDC hydrochloride (460 mg, 2.40 mmol). The mixture was stirred overnight at 40° C. Water (60 mL) was added and the solution was stirred for 1 h. The reaction mixture was extracted with $CH_2Cl_2$ (3×100 mL). Combined organic layers were washed with water (50 mL) and brine (50 mL) and concentrated to give a red solid which was purified by column chromatography (silica gel, 5% MeOH/$CH_2Cl_2$) to afford (E)-N-methyl-N-((1-methyl-1H-indol-4-yl)methyl)-3-(7-oxo-5,6,7,8-tetrahydro-1,8-naphthyridin-3-yl)acrylamide (320 mg, 36%) as a pink solid and a mixture of amide rotamers: $^1$H NMR (400 MHz, DMSO-$d_6$) δ 10.64-10.61 (m, 1H), 8.36-8.32 (m, 1H), 8.07-7.98 (m, 1H), 7.56-7.51 (m, 1H), 7.37-7.23 (m, 3H), 7.19-7.09 (m, 1H), 6.92-6.79 (m, 1H), 6.49-6.48 (m, 1H), 5.05-4.87 (m, 2H), 3.78-3.77 (m, 3H), 3.01-2.82 (m, 5H), 2.54-2.52 (m, 2H); ESI MS m/z 375 $[C_{22}H_{22}N_4O_2+H]^+$.

Example 75

Preparation of (E)-N-((1-ethyl-1H-indol-4-yl)methyl)-N-methyl-3-(7-oxo-5,6,7,8-tetrahydro-1,8-naphthyridin-3-yl)acrylamide a) 1-ethyl-1H-indole-4-carbaldehyde

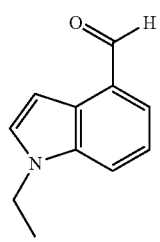

To a solution of 1H-indole-4-carbaldehyde (2.00 g, 13.8 mmol) in anhydrous DMF (6.5 mL) was added sodium hydride (827 mg of 60% dispersion in oil, 20.7 mmol). The mixture was stirred for 30 min at room temperature. Ethyl iodide (2.22 mL, 27.5 mmol) was then added and the reaction mixture was stirred for 12 h at room temperature. Water was added (100 mL) and the mixture was extracted with ethyl acetate (3×100 mL). Combined organic layers were washed with brine (100 mL), dried over $Na_2SO_4$, filtered and concentrated to an orange oil. Purification by column chromatography (silica gel, gradient elution of $CH_2Cl_2$ to 5% MeOH/$CH_2Cl_2$) gave the title compound (1-ethyl-1H-indole-4-carbaldehyde) (2.43 g, 99%) as a yellow oil: $^1$H NMR (300 MHz, DMSO-$d_6$) δ 10.19 (s, 1H), 7.88 (d, J=8.1 Hz, 1H), 7.68-7.64 (m, 2H), 7.37-7.32 (m, 1H), 7.08 (d, J=3.0, 1H), 4.28 (q, J=7.2 Hz, 2H), 1.36 (t, J=7.2 Hz, 3H).

b) ((1-ethyl-1H-indol-4-yl)-N-methylmethanamine)

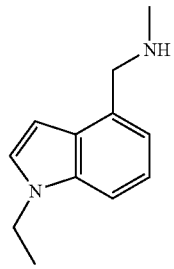

1-Ethyl-1H-indole-4-carbaldehyde (2.40 mg, 13.8 mmol) was dissolved in anhydrous methanol (62 mL). Methylamine (6.00 mL of 33% solution in ethanol, 48.2 mmol) was added and the reaction was stirred for 3 h. The solution was concentrated to a greenish brown oil and then dissolved in anhydrous methanol (62 mL). Sodium borohydride (539 mg, 14.3 mmol) was added and the mixture was stirred overnight at room temperature. Water (90 mL) was added and the solution was concentrated. Sodium hydroxide (15 mL, 1N) was added and the aqueous layer was extracted with ethyl acetate (3×50 mL). Combined organic layers were dried over $Na_2SO_4$, filtered and concentrated to afford the title compound ((1-ethyl-1H-indol-4-yl)-N-methylmethanamine) (2.36 g, 91%) as a yellow oil: ¹H NMR (300 MHz, DMSO-$d_6$) δ 7.33-7.30 (m, 2H), 7.10-6.97 (m, 2H), 6.52 (d, J=3.0 Hz, 1H), 4.17 (q, J=7.2 Hz, 2H), 3.88 (s, 2H), 2.30 (s, 3H), 1.33 (t, J=7.2 Hz, 3H).

c) (N-((1-ethyl-1H-indol-4-yl)methyl)-N-methylacrylamide)

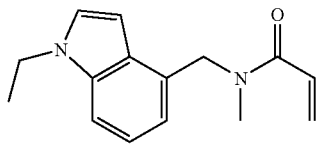 [SMILES: C=CC(=O)N(C)Cc1cccc2c1ccn2CC]

N-((1-ethyl-1H-indol-4-yl)methyl)-N-methylacrylamide was prepared according to the method of Preparation 47 except substituting ((1-ethyl-1H-indol-4-yl)-N-methylmethanamine) for methyl-(3-methyl-benzo[b]thiophen-2-ylmethyl)amine. The title compound (918 mg, 64%) was obtained as a yellow oil and a mixture of amide rotomers: ¹H NMR (400 MHz, DMSO-$d_6$) δ 7.41-7.35 (m, 2H), 7.13-7.07 (m, 1H), 6.88-6.72 (m, 2H), 6.48-6.45 (m, 1H), 6.22-6.16 (m, 1H), 5.73-5.62 (m, 1H), 4.89-4.81 (m, 2H), 4.23-4.15 (m, 2H), 2.91-2.90 (m, 3H), 1.34 (t, J=7.2 Hz, 3H).

(E)-N-((1-ethyl-1H-indol-4-yl)methyl)-N-methyl-3-(7-oxo-5,6,7,8-tetrahydro-1,8-naphthyridin-3-yl)acrylamide

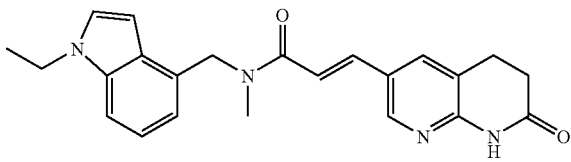 [SMILES: CCn1ccc2c(CN(C)C(=O)/C=C/c3cnc4c(c3)CCC(=O)N4)cccc21]

The title compound was prepared according to the procedure of Example 2, except substituting (N-((1-ethyl-1H-indol-4-yl)methyl)-N-methylacrylamide) for N-methyl-N-(3-methyl-benzo[b]thiophen-2-ylmethyl)acrylamide and 6-bromo-3,4-dihydro-1,8-naphthyridin-2(1H)-one for 7-bromo-3,3-dimethyl-1,3,4,5-tetrahydro-pyrido[2,3-e][1,4]diazepin-2-one. The title compound (329 mg, 46%) was obtained as an off-white solid and a mixture of amide rotomers: ¹H NMR (400 MHz, DMSO-$d_6$) δ 10.62-10.58 (m, 1H), 8.38-7.98 (m, 2H), 7.57-7.53 (m, 1H), 7.42-7.08 (m, 4H), 6.92-6.78 (m, 1H), 6.51 (s, 1H), 5.05-4.88 (m, 2H), 4.22-4.19 (m, 2H), 3.04-2.85 (m, 5H), 2.55-2.50 (m, 2H), 1.35 (t, J=7.2 Hz, 3H); ESI MS m/z 389 [$C_{23}H_{24}N_4O_2$+H]⁺.

Example 76

Preparation of (E)-N-((1H-benzo[d]imidazol-5-yl)methyl)-N-methyl-3-(7-oxo-5,6,7,8-tetrahydro-1,8-naphthyridin-3-yl)acrylamide a) ((1H-benzo[d]imidazol-5-yl)methanol)

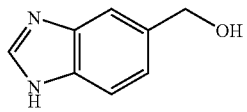 [SMILES: OCc1ccc2[nH]cnc2c1]

1H-benzo[d]imidazole-5-carboxylic acid (5.39 g, 33.3 mmol) was dissolved into anhydrous THF (100 ml) under argon. The solution was cooled in an ice bath and lithium aluminum hydride (70.0 ml of 1M solution in THF, 70.0 mmol) was added dropwise. The reaction mixture was allowed to warm to room temperature and stir overnight. The reaction mixture was cooled to 0° C. and ethyl acetate (90 ml) was carefully added, followed by methanol (15 ml) and water (15 ml). The mixture was stirred for 1 h and filtered through celite. The Solution was concentrated and dissolved in THF (200 ml) and washed with brine (2×100 ml), dried over $Na_2SO_4$, filtered and concentrated to yield the title compound ((1H-benzo[d]imidazol-5-yl)methanol) (1.26 g, 26%) as a yellow solid: ¹H NMR (400 MHz, DMSO-$d_6$) δ 8.15 (s, 1H), 7.54-7.47 (m, 2H), 7.13 (s, 1H), 5.14 (s, 1H), 4.58 (s, 2H).

b) (1H-benzo[d]imidazole-5-carbaldehyde)

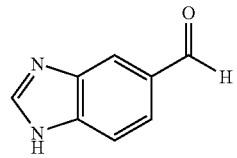 [SMILES: O=Cc1ccc2[nH]cnc2c1]

To a stirring solution of (1H-benzo[d]imidazol-5-yl)methanol (501 mg, 3.38 mmol) in benzene (35 mL) was added $MnO_2$ (2.35, 27.0 mmol). After stirring at room temperature for 12 h the reaction was then filtered through celite and the filter cake was washed with THF (200 mL). The Filtrate was concentrated to give the title compound (1H-benzo[d]imidazole-5-carbaldehyde) (201 mg, 41%) as a white solid: ¹H NMR (400 MHz, DMSO-$d_6$) δ 12.90 (bs, 1H), 10.04 (s, 1H), 8.43 (s, 1H), 8.19 (s, 1H), 7.75 (s, 2H).

c) ((1H-benzo[d]imidazol-5-yl)-N-methylmethanamine)

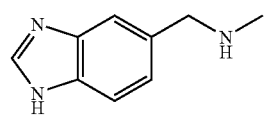

Prepared according to the procedure of Preparation 1, except substituting (1H-benzo[d]imidazole-5-carbaldehyde) for the 1-propyl-naphthalene-2-carbaldehyde. The title compound (176 mg, 60%) was obtained as an off-white oil: ¹H NMR (400 MHz, DMSO-$d_6$) δ 8.13 (s, 1H), 7.49 (bs, 2H), 7.14 (d, J=7.2 Hz, 1H), 3.72 (s, 2H), 2.27 (s, 3H).

(E)-N-((1H-benzo[d]imidazol-5-yl)methyl)-N-methyl-3-(7-oxo-5,6,7,8-tetrahydro-1,8-naphthyridin-3-yl)acrylamide

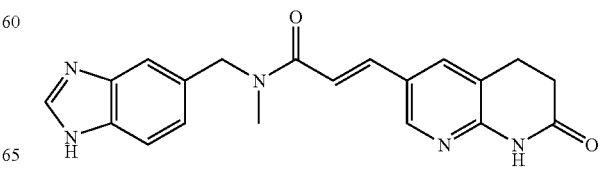

According to the procedure of Example 1 (a), except substituting ((1H-benzo[d]imidazol-5-yl)-N-methylmethanamine) for the methyl-(1-propyl-naphthalen-2-ylmethylamine), and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride. Purification by preparative HPLC (water/acetonitrile/0.05% TFA mixture) gave the title compound ((E)-N-((1H-benzo[d]imidazol-5-yl)methyl)-N-methyl-3-(7-oxo-5,6,7,8-tetrahydro-1,8-naphthyridin-3-yl)acrylamide) (143 mg, 37%) as a white solid and a mixture of amide rotamers: $^1$H NMR (400 MHz, DMSO-d$_6$) δ 10.60 (m, 1H), 8.36 (m, 1H), 8.21 (s, 1H), 8.07 (s, 1H), 7.59-7.21 (m, 4H), 7.12-7.08 (m, 1H), 4.91-4.72 (m, 2H), 3.10-2.86 (m, 5H), 2.55-2.49 (m, 2H); ESI MS m/z 362 [C$_{20}$H$_{19}$N$_5$O$_2$+H]$^+$.

Example 77

Preparation of (E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride a) ethyl 2-(((2-amino-5-bromopyridin-3-yl)methyl)(phenyl)amino)acetate

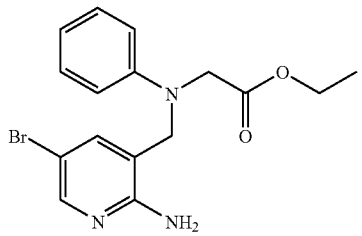 [SMILES: CCOC(=O)CN(Cc1cc(Br)cnc1N)c1ccccc1]

To a solution of phenyl glycine ethyl ester (4.94 g, 27.6 mmol) and K$_2$CO$_3$ (11.42 g, 82.7 mmol) in anhydrous DMF (300 mL) under argon was added 5-bromo-3-(bromomethyl)pyridin-2-amine hydrobromide (9.52 g, 27.6 mmol). The mixture was stirred for 12 h at 40° C. Water (500 mL) was added and the mixture was extracted with ethyl acetate (3×500 mL). Combined organic layers were washed with water (2×400 mL) and brine (400 mL), dried over MgSO$_4$, filtered and concentrated to a brown oil. Purification by column chromatography (silica gel, gradient elution of 30% ethyl acetate/hexanes to 80% ethyl acetate/hexanes) gave ethyl 2-(((2-amino-5-bromopyridin-3-yl)methyl)(phenyl)amino)acetate (3.41 g, 34%) as a yellow solid: $^1$H NMR (300 MHz, DMSO-d$_6$) δ 7.89-7.88 (m, 1H), 7.36-7.35 (m, 1H), 7.17-7.11 (m, 2H), 6.68-6.64 (m, 1H), 6.47-6.44 (m, 2H), 6.09 (s, 2H), 4.30-4.29 (m, 4H), 4.12 (q, J=6.9 Hz, 2H), 1.19 (t, J=6.9 Hz, 3H).

b) 7-bromo-4-phenyl-4,5-dihydro-1H-pyrido[2,3-e][1,4]diazepin-2(3H)-one

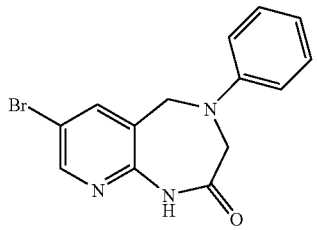 [SMILES: O=C1CN(c2ccccc2)Cc2cc(Br)cnc2N1]

Ethyl 2-(((2-amino-5-bromopyridin-3-yl)methyl)(phenyl)amino)acetate (3.29 g, 9.0 mmol) was dissolved in anhydrous DMSO (105 mL) under Argon. NaH (361 mg of 60% dispersion in oil, 9.00 mmol) was added and the reaction was stirred for 12 h at room temperature. Water (200 mL) was added and the mixture was extracted with CH$_2$Cl$_2$ (4×100 mL). Combined organic layers were washed with water (200 mL) and brine (100 mL), dried over Na$_2$SO$_4$, filtered and concentrated to afford 7-bromo-4-phenyl-4,5-dihydro-1H-pyrido[2,3-e][1,4]diazepin-2(3H)-one (2.95 g, 99%) as an orange solid: $^1$H NMR (300 MHz, DMSO-d$_6$) δ 10.08 (s, 1H), 8.21 (d, J=2.4 Hz, 1H), 8.10 (d, J=2.4 Hz, 1H), 7.17-7.12 (m, 2H), 6.82-6.80 (m, 2H), 6.71-6.66 (m, 1H), 4.79 (s, 2H), 4.47 (s, 2H).

((E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride)

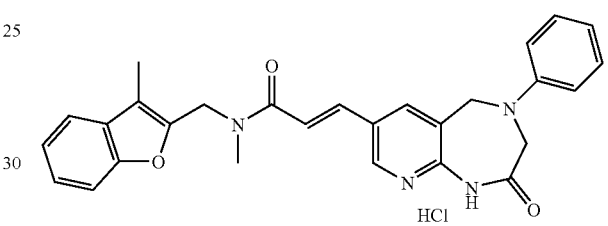

A solution of 7-bromo-4-phenyl-4,5-dihydro-1H-pyrido[2,3-e][1,4]diazepin-2(3H)-one (415 mg, 1.31 mmol), N-methyl-N-((3-methylbenzofuran-2-yl)methyl)acrylamide (473 mg, 2.06 mmol) and DIPEA (0.45 mL, 2.58 mmol) in anhydrous DMF (3.0 mL) and propionitrile (9.0 mL) was prepared in a pressure flask. Argon was bubbled into the mixture with stirring for 30 min. Next P(o-tol)$_3$ (79.4 mg, 0.261 mmol) and Pd(OAc)$_2$ (29.3 mg, 0.131 mmol) were added to the mixture and argon was bubbled into the reaction for an additional 5 min. The reaction was then sealed and was left to stir for 12 h at 110° C. The reaction was then allowed to cool to room temperature and was filtered through celite. The filter cake was washed with EtOAc (100 mL) and the filtrate was washed with water (50 mL) and brine (50 mL), dried over Na$_2$SO$_4$ and concentrated to give a brown oil. Purification by preparative HPLC (water/acetonitrile/0.05% TFA mixture) gave the desired product as a yellow solid which was dissolved in CH$_2$Cl$_2$ (6.0 mL). To the mixture was added HCl (142 µl of 1M solution in ether, 0.142 mmol) and the mixture was stirred for 5 minutes and then concentrated under high vacuum to give the title compound ((E)-N-methyl-N-((3-methylbenzofuran-2-yl)methyl)-3-(2-oxo-4-phenyl-2,3,4,5-tetrahydro-1H-pyrido[2,3-e][1,4]diazepin-7-yl)acrylamide hydrochloride) (41.2 mg, 6.0%) as a yellow solid and a mixture of amide rotamers: $^1$H NMR (300 MHz, DMSO-d$_6$) δ 10.10 (s, 1H), 8.44-8.40 (m, 1H), 8.27 (s, 1H), 7.55-7.47 (m, 3H), 7.30-7.21 (m, 3H), 7.7.16-7.10 (m, 2H), 6.82-6.79 (m, 2H), 6.69-6.63 (m, 1H), 5.00-4.80 (m, 4H), 4.49 (s, 2H), 3.19-2.93 (m, 3H), 2.26 (s, 3H); ESI MS m/z 467 [C$_{28}$H$_{26}$N$_4$O$_3$+H]$^+$.

Example 78

Preparation of (E)-3-((6-aminopyridin-3-yl)-N-methyl-N-((3-methyl-1H-indol-2-yl)methyl)acrylamide

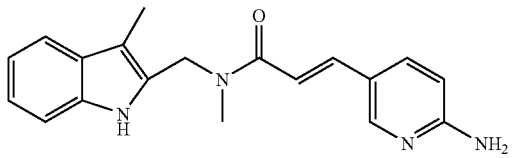 [SMILES: Cc1c(CN(C)C(=O)/C=C/c2ccc(N)nc2)[nH]c2ccccc12]

EDC (438 mg, 1.1 mmol) was added to a solution of N-methyl-(3-methyl-1H-indol-2-yl)methanamine (170 mg, 0.9 mmol), (E)-3-(6-aminopyrid-3-yl)acrylic acid hydrochloride (176 mg, 1.0 mmol), HOBT.H$_2$O (130 mg, 0.9 mmol) and DIPEA (0.58 mL, 2.7 mmol) in dry DMF (5 mL). After stirring overnight, water was added. The precipitate that formed was washed with ethyl acetate and dried to afford the title compound (65 mg, 23%). $^1$H NMR (300 MHz, DMSO-d$_6$) δ 10.75-0.54 (rotamers, s, 1H), 8.15 (d, J=7.2 Hz, 1H), 7.94 (s, 1H), 7.84 (d, J=7.7 Hz, 1H), 7.40 (d, J=7.0 Hz, 1H), 7.31 (d, J=7.9 Hz, 1H), 7.02-6.97 (m, 2H), 6.47-6.41 (m, 2H), 5.01-4.85 (rotamers, s, 2H), 4.72 (s, 3H), 2.23 (s, 3H); MS (ESI): m/e 321.3 (C$_{19}$H$_{20}$N$_4$O+H)$^+$.

Example 79

Preparation of (E)-N-methyl-N-((3-methyl-1H-indol-2-yl)methyl)-3-(3-oxo-3,4-dihydro-2H-pyrido[3,2-b][1,4]oxazin-7-yl)acrylamide

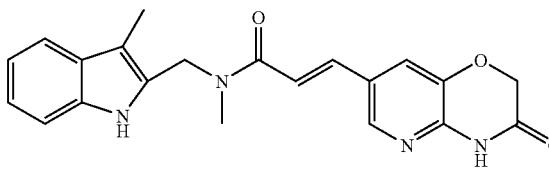

EDC (149 mg, 1.3 mmol) was added to a solution of N-methyl(3-methyl-1H-indol-2-yl)methanamine (110 mg, 1.0 mmol), (E)-3-(3-oxo-3,4-dihydro-2H-pyrido[3,2-b][1,4]oxazin-7-yl)acrylic acid hydrochloride (220 mg, 1.1 mmol), HOBT.H$_2$O (81 mg, 1.0 mmol) and DIPEA (0.43 mL, 3.0 mmol) in dry DMF (5 mL). After stirring overnight, water was added. The precipitate that formed was washed with ethyl acetate and dried to afford the title compound (12 mg, 4%). $^1$H NMR (300 MHz, DMSO-d$_6$) δ 8.25 (s, 1H), 7.97 (s, 1H), 7.77 (d, J=7.1 Hz, 1H), 7.60 (s, 1H), 7.45 (d, J=7.4 Hz, 1H), 7.34 (m, 2H), 7.18 (s, 1H), 7.11 (m, 1H), 4.90-4.79 (rotamers, s, 2H), 4.72 (s, 2H), 4.60 (s, 3H), 2.31 (s, 3H); MS (EST): m/e 377.2 (C$_{21}$H$_{20}$N$_4$O$_3$+H)$^+$.

Example 80

Preparation of (E)-N-((3,7-dimethyl-1H-indol-2-yl)methyl)-N-methyl-3-(3-oxo-3,4-dihydro-2H-pyrido[3,2-b][1,4]oxazin-7-yl)acrylamide a) ethyl 3,7-dimethyl-1H-indole-2-carboxylate

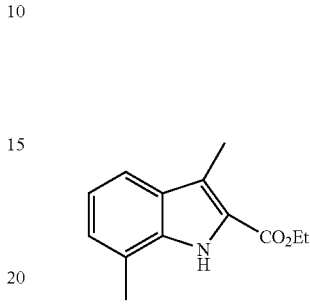

A suspension of 1-o-tolylhydrazine (3.8 g, 30.9 mmol) in ethanol was warmed to 50° C. A solution of α-ketobutyric acid (3.16 g, 30.9 mmol) in ethanol was added and the mixture stirred at rt overnight. Hydrogen chloride was bubbled through the solution for 30 min and the mixture heated at reflux for 2 h then evaporated in vacuo. The crude reaction was chromatographed over silica gel eluting with ethyl acetate/hexane (5%) to afford the title compound (1.84 g, 27%). $^1$H NMR (400 MHz, CDCl$_3$) δ 8.55 (s, 1H), 7.50 (d, J=7.8 Hz, 1H), 7.09 (d, J=6.9 Hz, 1H), 7.03 (t, J=7.6 Hz, 1H), 4.41 (q, J=7.1 Hz, 2H), 2.59 (s, 3H), 2.48 (s, 3H), 1.44 (t, J=7.2 Hz, 3H).

b) (3,7-Dimethyl-1H-indol-2-yl)methanol

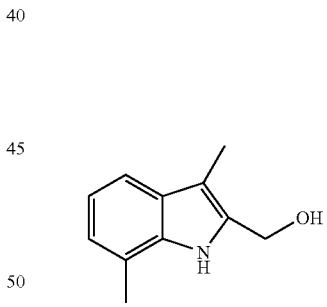

A solution of ethyl 3,7-dimethyl-1H-indole-2-carboxylate (1.84 g, 8.4 mmol) in THF (20 mL) was added to an ice-cooled solution of 1.0 M LAH in THF (17.8 mL 17.8 mmol) and stirred overnight. The reaction was quenched with ethyl acetate (5 mL) and 15% aqueous sodium hydroxide (5 mL), filtered through celite and evaporated in vacuo. The crude reaction was chromatographed over silica gel eluting with methanol/dichloromethane (1%) to afford the title compound (440 mg, 30%). $^1$H NMR (400 MHz, CDCl$_3$) δ 8.39 (s, 1H), 7.39 (d, J=7.7 Hz, 1H), 7.06 (t, J=7.2 Hz, 1H), 6.99 (d, J=7.1 Hz, 1H), 4.82 (s, 2H), 4.11 (q, J=7.1 Hz, 2H), 2.45 (s, 3H), 2.28 (s, 3H), 1.26 (t, J=7.1 Hz, 3H).

c) 3,7-Dimethyl-1H-indole-2-carbaldehyde

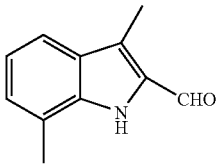

A mixture of (3,7-dimethyl-1H-indol-2-yl)methanol (440 mg, 2.5 mmol) and manganese dioxide (1.09 g, 12.5 mmol) in dichloromethane (15 mL) was stirred overnight at rt. The mixture was filtered and evaporated. The crude was chromatographed over silica gel eluting with ethyl acetate/hexane (5% and 7.5%) to afford the title compound (200 mg, 46%). $^1$H NMR (400 MHz, CDCl$_3$) δ 10.00 (s, 1H), 8.75 (s, 1H), 7.51 (d, J=7.2 Hz, 1H), 7.15 (d, J=7.4 Hz, 1H), 7.05 (t, J=7.3 Hz, 1H), 2.61 (s, 3H), 2.45 (s, 3H).

d) (3,7-Dimethyl-1H-indol-2-yl)-N-methanamine

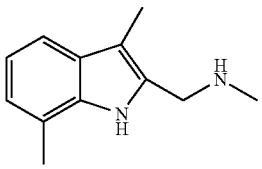

Methylamine (0.43 mL, 3.4 mmol) was added to a solution of 3,7-dimethyl-1H-indole-2-carbaldehyde (200 mg, 1.1 mmol) in methanol (5 mL) and stirred for 5 h. The mixture was cooled to 0° C. and sodium borohydride (40.7 mg, 1.1 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (120 mg, 57%). $^1$H NMR (400 MHz, CDCl$_3$) δ 8.40 (s, 1H), 7.36 (d, J=7.7 Hz, 1H), 7.00 (t, J=7.6 Hz, 1H), 6.94 (d, J=7.0 Hz, 1H), 3.89 (s, 2H), 2.48 (s, 3H), 2.45 (s, 3H), 2.27 (s, 3H).

(E)-N-((3,7-dimethyl-1H-indol-2-yl)methyl)-N-methyl-3-(3-oxo-3,4-dihydro-2H-pyrido[3,2-b][1,4]oxazin-7-yl)acrylamide

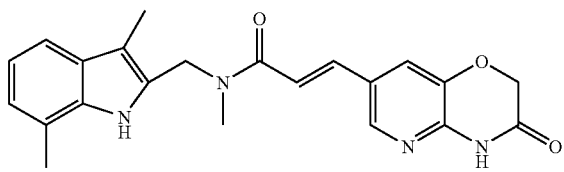 [SMILES: Cc1c(CN(C)C(=O)/C=C/c2cnc3c(c2)OCC(=O)N3)[nH]c2c(C)cccc12]

EDC (157 mg, 0.8 mmol) was added to a solution of (3,7-dimethyl-1H-indol-2-yl)-N-methanamine (120 mg, 0.6 mmol), (E)-3-(3-oxo-3,4,dihydro-2H-pyrido[3,2-b][1,4]oxazin-7-yl)acrylic acid hydrochloride (177 mg, 0.7 mmol), HOBT.H$_2$O (85 mg, 0.6 mmol) and DIPEA (0.45 mL, 2.5 mmol) in dry DMF (5 mL). After stirring overnight, water was added. The precipitate that formed was washed with ethyl acetate and dried (14 mg, 6%). $^1$H NMR (400 MHz, DMSO-d$_6$) δ 11.41 (s, 1H), 10.60-10.52 (rotamers, s, 1H), 8.19 (s, 1H), 7.87 (s, 1H), 7.50 (d, J=7.6 Hz, 1H), 7.25 (d, J=6.8 Hz, 1H), 6.88 (m, 2H), 4.90-4.77 (rotamers, s, 2H), 4.68 (s, 3H), 3.05 (s, 2H), 2.84 (s, 1H), 2.44 (s, 3H), 2.21 (s, 3H); MS (ESI): m/e 391.1 (C$_{22}$H$_{22}$N$_4$O$_3$+H)$^+$.

Example 81

(E)-N-methyl-N-((3-methyl-7-(trifluoromethyl)-1H-indol-2-yl)methyl-3-(7-oxo-5,6,7,8-tetrahydro-1,8-naphthyridin-3-yl)acrylamide

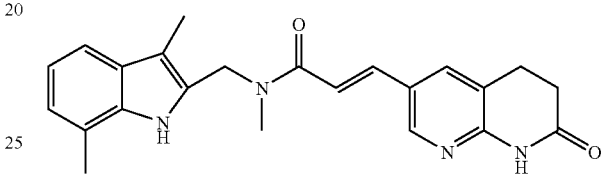

EDC (250 mg, 1.3 mmol) was added to a solution of (3,7-dimethyl-1H-indol-2-yl)-N-methanamine (174 mg, 1.0 mmol), (E)-3-(2-methylene-1,2,3,4-tetrahydroquinolin-6-yl)acrylic acid hydrochloride (369 mg, 1.1 mmol), HOBT.H$_2$O (136 mg, 1.0 mmol) and DIPEA (0.72 mL, 4.0 mmol) in dry DMF (5 mL). After stirring overnight, water was added. The precipitate that formed was washed with ethyl acetate and dried to afford the title compound (3 mg, 0.7%). $^1$H NMR (400 MHz, DMSO-d$_6$) δ 9.56 (s, 1H), 8.76 (s, 1H), 8.30 (s, 1H), 7.77 (s, 1H), 7.65 (d, J=7.8 Hz, 1H), 7.38 (d, J=7.2 Hz, 1H), 7.0 (m, 2H), 6.84 (d, J=7.2 Hz, 1H), 4.72 (s, 2H), 3.15 (s, 3H), 3.01 (t, J=6.8 Hz, 2H), 2.71 (t, J=6.9 Hz, 2H), 2.44 (s, 3H), 2.38 (s, 3H); MS (ESI): m/e 389.2 (C$_{23}$H$_{24}$N$_4$O$_2$+H)$^+$.

Example 82

Preparation of (E)-N-((3-ethyl-1H-indol-2-yl)methyl)-N-methyl-3-(7-oxo-5,6,7,8-tetrahydro-1,8-naphthyridin-3-yl)acrylamide a) N-methyl-1H-indole-2-carboxamide

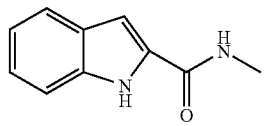

EDC (7.7 g, 40.3 mmol) was added to a solution of indole-2-carboxylic acid (5 g, 13.1 mmol), methylamine, 33% in ethanol (5.6 mL, 15.5 mmol), HOBT (4.1 g, 13.1 mmol) and DIPEA (2.1 mL, 12.4 mmol) in THF, anhydrous (45 mL) and stirred overnight. The crude mixture was evaporated in vacuo and chromatographed over silica eluting with methanol/dichloromethane (0-2%) to afford the title compound (3.51 g, 66%). $^1$H NMR (300 MHz, DMSO-d$_6$) δ 11.53 (s, 1H), 8.43

(s, 1H), 7.57 (d, J=7.9 Hz, 1H), 7.39 (d, J=8.2 Hz, 1H), 7.15 (t, J=8.2 Hz, 1H), 7.03 (s, 1H), 6.98 (t, J=7.9 Hz, 1H), 2.79 (d, J=4.7 Hz, 3H)

b) 3-formyl-N-methyl-1H-indole-2-carboxamide

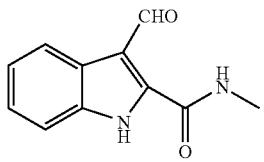

Oxalyl chloride (2.6 mL, 30 mmol) was added drop-wise to an ice-cooled solution of dimethylformamide (34 mL) and dichloromethane (90 mL), then N-methyl-1H-indole-2-carboxamide (3.51 g, 20 mmol) was added and the mixture stirred at rt for 1 h. Water was added and the resulting precipitate filtered, washed with water and diethyl ether. The product was dried to afford the title compound (2.03 g, 50%). $^1$H NMR (300 MHz, DMSO-$d_6$) δ 12.58 (s, 1H), 10.2 (s, 1H), 9.51 (s, 1H), 8.26 (d, J=7.5 Hz, 1H), 7.66 (d, J=8.6 Hz, 1H), 7.47-7.10 (m, 2H), 2.73 (d, J=4.6 Hz, 3H).

c) N-methyl-3-vinyl-1H-indole-2-carboxamide

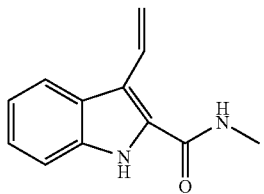

n-Butyllithium (2.5M in hexanes) (48.6 mL, 121.7 mmol) was added dropwise to an ice-cooled solution of methyl triphenylphosphoniumbromide (43.5 g, 121.7 mmol) in THF (500 mL). The mixture was stirred at 0° C. for 1 h then at rt for 2 h. 3-Formyl-N-methyl-1H-indole-2-carboxamide (1.96 g, 9.7 mmol) in THF (100 mL) was added and the mixture stirred at rt for 2 h. The solvent was evaporated and the residue dissolved in ethyl acetate and washed twice with water. The organic phase was dried over magnesium bromide and evaporated in vacuo. The crude mixture was chromatographed over silica gel eluting with 40% ethyl acetate in hexanes to afford the title compound (730 mg (38%). $^1$H NMR (300 MHz, DMSO-$d_6$) δ 11.48 (s, 1H), 8.04 (s, 1H), 7.92 (d, J=8.0 Hz, 1H), 7.42 (d, J=7.9 Hz, 1H), 7.33 (d, J=18 Hz, 1H), 7.22 (t, J=7.6 Hz, 1H), 7.09 (t, J=7.2 Hz, 1H), 5.77 (d, J=18.4 Hz, 1H), 5.27 (d, J=11.6 Hz, 1H), 2.81 (s, 3H).

d) 3-ethyl-N-methyl-1H-indole-2-carboxamide

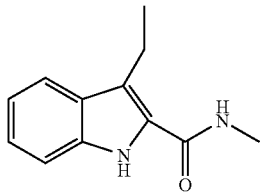

A mixture of N-methyl-3-vinyl-1H-indole-2-carboxamide (1.1 g, 5.4 mmol) and 10% Pd/C (55 mg) in ethyl acetate (150 mL) was stirred for 3 h under an atmosphere of hydrogen. The mixture was filtered through celite and evaporated to afford the title compound (970 mg 90%). $^1$H NMR (400 MHz, DMSO-$d_6$) δ 11.05 (s, 1H), 7.80 (s, 1H), 7.59 (d, J=7.6 Hz, 1H), 7.36 (d, J=8.4 Hz, 1H), 7.17 (t, J=6.8 Hz, 1H), 7.04 (t, J=6.0 Hz, 1H), 3.01 (q, J=7.4 Hz, 2H), 2.81 (d, J=4.6 Hz, 3H), 1.17 (t, J=7.4 Hz, 3H).

e) N-methyl(3-vinyl-1H-indol-2-yl)methanamine

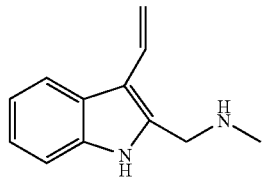

A solution of N-methyl-3-vinyl-1H-indole-2-carboxamide (740 mg, 3.7 mmol) in dioxane was added slowly to an ice-cooled solution of lithium aluminium hydride (2.1 g, 55.5 mmol) in dioxane (100 mL). The mixture was stirred at reflux overnight. Excess lithium aluminium hydride was quenched with 15% NaOH (10 mL) and the mixture separated. The aqueous phase was washed twice with ethyl acetate and the combined organic phases dried to afford the title compound (430 mg 61%). $^1$H NMR (400 MHz, DMSO-$d_6$) δ 11.09 (s, 1H), 7.75 (d, J=8 Hz, 1H), 7.49 (d, J=6.4 Hz, 1H), 7.09-7.05 (m, 2H), 7.04-6.90 (m, 1H), 5.54 (d, J=16 Hz, 1H), 5.06 (d, J=10.0 Hz, 1H), 3.84 (s, 2H), 2.27 (s, 3H).

f) (3-ethyl-1H-indol-2-yl)-N-methylmethanamine

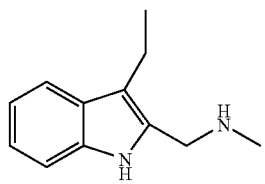

A solution of 3-ethyl-N-methyl-1H-indole-2-carboxamide (970 mg, 4.80 mmol) in dioxane was added slowly to an ice-cooled solution of lithium aluminium hydride (273 mg, 72 mmol) in dioxane (10 mL). The mixture was stirred at reflux overnight. Excess lithium aluminium hydride was quenched with 15% NaOH (2 mL) and the mixture separated. The aqueous phase was washed twice with ethyl acetate and the combined organic phases dried to afford the title compound (550 mg, 61%). $^1$H NMR (400 MHz, DMSO-$d_6$) δ 10.59 (s, 1H), 7.42 (d, J=8 Hz, 1H), 7.25 (d, J=7.6 Hz, 1H), 7.00 (t, J=7.2 Hz, 1H), 6.89 (t, J=7.2 Hz, 1H), 3.75 (s, 2H), 2.66 (q, J=7.5 Hz, 2H), 2.27 (s, 3H), 1.14 (t, J=7.6 Hz, 3H).

Preparation of (E)-N-((3-ethyl-1H-indol-2-yl)methyl)-N-methyl-3-(7-oxo-5,6,7,8-tetrahydro-1,8-naphthyridin-3-yl)acrylamide

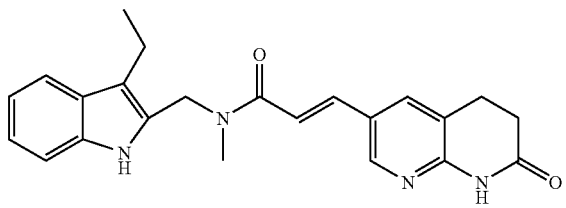 [SMILES: CCc1c(CN(C)C(=O)/C=C/c2cnc3c(c2)CCC(=O)N3)[nH]c2ccccc12]

EDC (83 mg, 0.4 mmol) was added to a solution of (3-ethyl-1H-indol-2-yl)-N-methylmethanamine (62.7 mg, 0.3 mmol), (E)-3-(7-oxo-5,6,7,8-tetrahydro-1,8-naphthyridin-3-yl)acrylic acid hydrochloride (240 mg, 0.8 mmol), HOBT.H$_2$O (101 mg, 0.7 mmol) and DIPEA (0.58 mL, 2.7 mmol) in dry DMF (5 mL). After stirring overnight, water was added. The precipitate that formed was washed with ethyl acetate and dried to afford the title compound (77.8 mg, 67%). $^1$H NMR (400 MHz, DMSO-d$_6$) δ 10.61-10.59 (rotamers, s, 2H), 8.36 (s, 1H), 8.07 (s, 1H), 7.51-7.46 (m, 3H), 7.30 (d, J=7.8 Hz, 1H), 7.03 (t, J=7.6 Hz, 1H), 6.95 (t, J=7.2 Hz, 1H), 4.94 (s, 2H), 4.90-4.75 (rotamers, s, 3H), 3.29 (m, 2H), 3.08-2.91 (m, 4H), 1.13 (t, J=7.6 Hz, 3H); MS (ESI): m/e 389.2 (C$_{23}$H$_{24}$N$_4$O$_2$+H)$^+$.

Example 83

Preparation of (E)-N-((3-ethyl-1H-indol-2-yl)methyl)-N-methyl-3-(3-oxo-3,4-dihydro-2H-pyrido[3,2-b][1,4]oxazin-7-yl)acrylamide

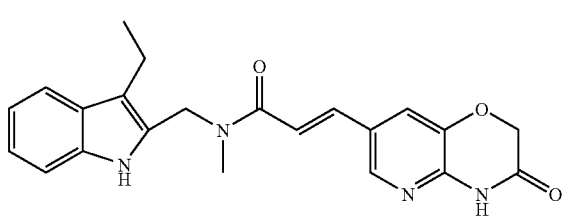 [SMILES: CCc1c(CN(C)C(=O)/C=C/c2cnc3c(c2)OCC(=O)N3)[nH]c2ccccc12]

EDC (116 mg, 0.6 mmol) was added to a solution of (3-ethyl-1H-indol-2-yl)-N-methylmethanamine (87 mg, 0.46 mmol), (E)-3-(3-oxo-3,4-dihydro-2H-pyrido[3,2-b][1,4]oxazin-7-yl)acrylic acid hydrochloride (123.65 mg, 1.05 mmol), HOBT.H$_2$O (62 mg, 0.46 mmol) and DIPEA (0.33 mL, 1.8 mmol) in dry DMF (5 mL). After stirring overnight, water was added. The precipitate that formed was washed with ethyl acetate and dried to afford the title compound (76.2 mg, 42%). $^1$H NMR (400 MHz, DMSO-d$_6$) δ 11.41 (s, 1H), 8.18 (s, 1H), 7.88 (s, 1H), 7.46 (t, J=7.9 Hz, 2H), 7.25 (d, J=7.9 Hz, 1H), 7.03 (t, J=7.6 Hz, 1H), 6.95 (t, J=7.1 Hz, 2H), 4.92 (s, 2H), 4.90-4.74 (rotamers, s, 2H), 4.68 (s, 3H), 3.08 (m, 2H), 1.13 (t, J=7.4 Hz, 3H); MS (ESI): m/e 391.1 (C$_{22}$H$_{22}$N$_4$O$_3$+H)$^+$.

Example 84

Preparation of (E)-N-methyl-3-(3-oxo-3,4-dihydro-2H-pyrido[3,2-b][1,4]oxazin-7-yl)-N-((3-vinyl-1H-indol-2-yl)methyl)acrylamide

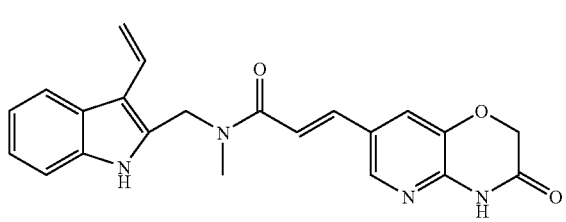 [SMILES: C=Cc1c(CN(C)C(=O)/C=C/c2cnc3c(c2)OCC(=O)N3)[nH]c2ccccc12]

EDC (73 mg, 0.3 mmol) was added to a solution of N-methyl(3-vinyl-1H-indol-2-yl)methanamine (54.7 mg, 0.29 mmol), (E)-3-(3-oxo-3,4-dihydro-2H-pyrido[3,2-b][1,4]oxazin-7-yl)acrylic acid hydrochloride (79 mg, 0.3 mmol), HOBT.H$_2$O (39 mg, 0.29 mmol) and DIPEA (0.21 mL, 1.1 mmol) in dry DMF (5 mL). After stirring overnight, water was added. The precipitate that formed was washed with ethyl acetate and dried to afford the title compound (26 mg, 23%). $^1$H NMR (400 MHz, DMSO-d$_6$) δ 11.41 (s, 1H), 11.20-11.05 (rotamers, s, 1H), 8.18 (s, 1H), 7.87 (s, 1H), 7.80 (d, J=7.8 Hz, 1H), 7.51 (d, J=15.6 Hz, 1H), 7.38 (d, J=7.7 Hz, 1H), 7.22 (d, J=15.6 Hz, 1H), 7.10 (t, J=7.1 Hz, 1H), 7.07-6.98 (m, 2H), 5.62 (d, J=17.9 Hz, 1H), 5.12 (d, J=11.0 Hz, 1H), 5.03 (s, 2H), 4.68 (s, 3H), 3.09 (s, 2H); MS (ESI): m/e 389.1 (C$_{22}$H$_{20}$N$_4$O$_3$+H)$^+$.

Example 85

Preparation of (E)-N-((1,3-dimethyl-1H-indol-2-yl)methyl)-N-methyl-3-(3-oxo-3,4-dihydro-2H-pyrido[3,2-b][1,4]oxazin-7-yl)acrylamide

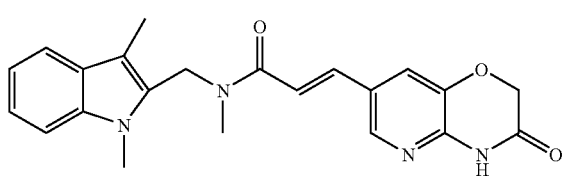 [SMILES: Cc1c(CN(C)C(=O)/C=C/c2cnc3c(c2)OCC(=O)N3)n(C)c2ccccc12]

a) 1,3-dimethyl-1H indole

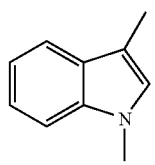

Sodium hydride (600 mg, 16.6 mmol) was added to a solution of 3-methylindole (2 g, 15.2 mmol) in DMF (10 mL).

The mixture was stirred for 30 min and iodomethane was added in one portion. The mixture was cooled in an icebath and left to warm to rt overnight. The mixture was evaporated and the residue dissolved in ethyl acetate. The solution was washed with water and brine, dried over magnesium sulfate and evaporated. The crude reaction was chromatographed over silica gel eluting with hexane and ethyl acetate/hexane (20 and 50%) to afford the title compound (1.3 g, 59%). $^1$H NMR (400 MHz, CDCl$_3$) δ 7.46 (d, J=8 Hz, 1H), 7.34 (d, J=8 Hz, 1H), 7.12 (t, J=7.8 Hz, 1H), 7.06 (s, 1H), 7.00 (t, J=7.6 Hz, 1H), 3.70 (s, 3H), 2.23 (s, 3H)

b) 1,3-dimethyl-1H indole-2-carbaldehyde

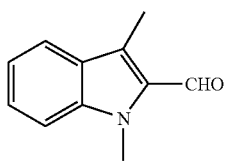

Phosphorous oxychloride (0.0.93 mL, 9.7 mmol) was added dropwise with stirring to DMF (5 mL) at 10° C. over 20 min. 1,3-dimethyl-1H indole (1.3 g mg, 8.9 mmol) in DMF (5 mL) was added slowly with stirring and the mixture was heated for 3 h at 98-100° C. Excess concentrated aqueous solution of sodium acetate was added. The mixture was stirred for 30 min at 28° C. and extracted with ethyl acetate, dried and evaporated. The crude mixture was chromatographed over silica gel eluting with hexane/ether to afford the title compound (1.5 g, 97%). $^1$H NMR (400 MHz, DMSO-d$_6$) δ 10.15 (s, 1H), 7.74 (d, J=7.6 Hz, 1H), 7.53 (d, J=7.8 Hz, 1H), 7.42 (t, J=8.0 Hz, 1H), 7.15 (t, J=7.6 Hz, 1H), 3.99 (s, 3H), 2.60 (s, 3H)

c)
(1,3-dimethyl-1H-indol-2-yl)-N-methylmethanamine

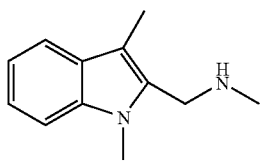

Methylamine (0.53 mL, 13.1 mmol) was added to a solution of 1,3-dimethyl-1H indole-2-carbaldehyde (760 mg, 4.3 mmol) in methanol (15 mL) and stirred for 5 h. The mixture was cooled to 0° C. and sodium borohydride (159 mg, 4.3 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (690 mg, 85%). $^1$H NMR (400 MHz, DMSO-d$_6$) δ 7.44 (d, J=7.8 Hz, 1H), 7.34 (d, J=8.1 Hz, 1H), 7.10 (t, J=7.6 Hz, 1H), 6.98 (t, J=8.0 Hz, 1H), 3.77 (s, 2H), 3.71 (s, 3H), 2.27 (s, 3H), 2.23 (s, 3H).

EDC (132.5 mg, 0.6 mmol) was added to a solution of (1,3-dimethyl-1H-indol-2-yl)-N-methylmethanamine (100 mg, 0.5 mmol), (E)-3-(3-oxo-3,4,dihydro-2H-pyrido[3,2-b][1,4]oxazin-7-yl)acrylic acid hydrochloride (143 mg, 0.55 mmol), HOBT.H$_2$O (72 mg, 0.5 mmol)) and DIPEA (0.38 mL, 2.1 mmol) in dry DMF (5 mL). After stirring overnight, water was added. The precipitate that formed was washed with ethyl acetate and dried to afford the title compound (144 mg, 74%). $^1$H NMR (400 MHz, DMSO-d$_6$) δ 11.51 (s, 1H), 8.24 (s, 1H), 7.94 (d, J=7.6 Hz, 1H), 7.60-7.48 (m, 2H), 7.38 (m, 1H), 7.20-7.28 (m, 1H), 7.14 (t, J=7.8 Hz, 1H), 7.07 (d, J=7.5 Hz, 1H), 5.11 (s, 2H), 5.01-4.98 (rotamers, s, 2H), 4.77 (s, 3H), 3.80 (s, 3H), 2.31 (s, 3H); MS (ESI): m/e 391.2 (C$_{22}$H$_{22}$N$_4$O$_3$+H)$^+$.

Example 86

(E)-N-((1,3-dimethyl-1H-indol-2-yl)methyl)-N-methyl-3-(2-oxo-4-phenyl-2,3,4,5-tetrahydro-1H-pyrido[2,3-e][1,4]diazepin-7-yl)acrylamide

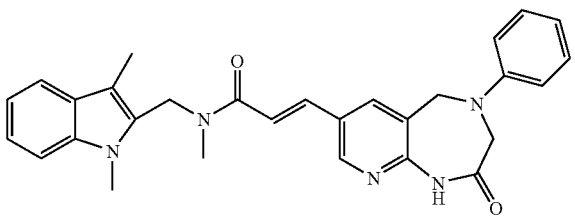 [SMILES: Cc1c(CN(C)C(=O)/C=C/c2cnc3c(c2)CN(c2ccccc2)CC(=O)N3)n(C)c2ccccc12]

A solution of N-((1,3-dimethyl-1H-indol-2-yl)methyl)-N-methylacrylamide (92 mg, 0.3 mmol) and DIPEA (0.16 mL, 0.9 mmol) in DMF (5 mL) was purged with argon for 10 min. Pd(OAc)$_2$ (6 mg, 0.03 mmol) and P(o-Tol)$_3$ (18 mg, 0.06 mmol) were added and the mixture was purged with argon and heated to 100° C. The crude mixture was filtered and water was added. The precipitate that formed was washed with ethyl acetate and dried to afford the title compound (144 mg, 74%). $^1$H NMR (400 MHz, DMSO-d$_6$) δ 10.06-9.95 (rotamers, s, 1H), 8.32 (d, J=8.0 Hz, 2H), 7.57 (s, 1H), 7.50 (t, J=7.6 Hz, 2H), 7.38 (m, 3H), 7.12 (t, J=7.6 Hz, 2H), 7.03 (t, J=7.6 Hz, 1H), 6.84-6.35 (m, 2H), 4.90-4.80 (rotamers, s, 2H), 4.80 (s, 2H), 4.50 (s, 3H), 3.63 (s, 3H), 2.98 (s, 2H), 2.32 (s, 3H); MS (ESI): m/e 480.2 (C$_{29}$H$_{29}$N$_5$O$_2$+H)$^+$.

Example 87

Preparation of (E)-N-methyl-N-((3-methyl-7-(trifluoromethyl)-1H-indol-2-yl)methyl)-3-(3-oxo-3,4-dihydro-2H-pyrido[3,2-b][1,4]oxazin-7-yl)acrylamide

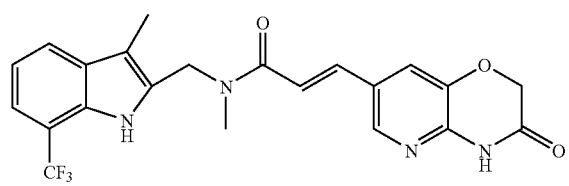 [SMILES: Cc1c(CN(C)C(=O)/C=C/c2cnc3c(c2)OCC(=O)N3)[nH]c2c(C(F)(F)F)cccc12]

a) Ethyl 3-methyl-7-(trifluoromethyl)-1H-indole-2-carboxylate

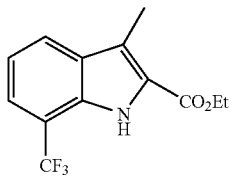 [SMILES: CCOC(=O)c1[nH]c2c(C(F)(F)F)cccc2c1C]

A solution of sodium nitrite (2.3 g, 34 mmol) was added dropwise to a mixture of trifluoromethyl aniline (3.85 mL, 31 mmol), HCl (7.5 mL) and water (15 mL) at −5° C. After the addition, the mixture was stirred at 0° C. for 15 min and brought to pH 3-4 by addition of sodium acetate. In a separate flask, a solution of ethyl α-ethylacetoacetate (5 mL, 31 mmol) in ethanol (25 mL) at 0° C. was treated with a solution of potassium hydroxide (1.74 g, 31 mmol) in water (10 mL) followed by addition of ice. The diazonium salt was immediately added to this alkaline solution. The mixture was adjusted to pH 5-6 by adding sodium acetate and stirred at 0° C. for 3 h. The solution was kept overnight at 4° C. and extracted with ethyl acetate, washed with brine, dried over magnesium sulfate and most of the solvent removed. The crude mixture was added dropwise to a solution of ethanolic HCl (25 mL) at 78° C. and stirred for 2 h at 78° C. The mixture was evaporated and chromatographed over silica gel eluting with ethyl acetate/hexane (3%) to afford the title compound (2.26 g, 26%). $^1$H NMR (400 MHz, CDCl$_3$) δ 8.92 (s, 1H), 7.79 (d, J=8 Hz, 1H), 7.55 (d, J=7.2 Hz, 1H), 7.15 (t, J=7.6 Hz, 1H), 4.41 (q, J=6.9 Hz, 2H), 2.60 (s, 3H), 1.42 (t, J=6.9 Hz, 3H)

b) (3-Methyl-7-(trifluoromethyl)-1H-indol-2-yl)methanol

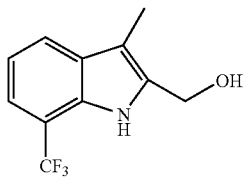 [SMILES: Cc1c(CO)[nH]c2c(C(F)(F)F)cccc12]

A solution of ethyl 3-methyl-7-(trifluoromethyl)-1H-indole-2-carboxylate (2.2 g, 8.1 mmol) in THF (50 mL) was added to an ice cooled solution of 1M LAH in THF (16.2 mL, 16.2 mmol) and stirred overnight. The reaction was quenched with ethyl acetate and sodium hydroxide, filtered through celite and evaporated to afford the title compound (1.03 g, 57%). $^1$H NMR (400 MHz, CDCl$_3$) δ 8.74 (s, 1H), 7.66 (d, J=7.9 Hz, 1H), 7.40 (d, J=7.3 Hz, 1H), 7.12 (t, J=4.7 Hz, 1H), 4.81 (s, 2H), 2.26 (s, 3H)

c) 3-Methyl-7-(trifluoromethyl)-1H-indole-2-carbaldehyde

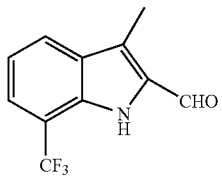 [SMILES: Cc1c(C=O)[nH]c2c(C(F)(F)F)cccc12]

A mixture of (3-methyl-7-(trifluoromethyl)-1H-indol-2-yl)methanol (1.03 g, 4.4 mmol) and manganese (IV) oxide (1.95 g, 22.4 mmol) in dichloromethane (15 mL) was stirred overnight. The mixture was filtered through celite and evaporated to afford the title compound (510 mg, 51%). $^1$H NMR (400 MHz, CDCl$_3$) δ 10.08 (s, 1H), 8.95 (s, 1H), 7.87 (d, J=7.9 Hz, 1H), 7.62 (d, J=7.1 Hz, 1H), 7.20 (t, J=7.7 Hz, 1H), 2.65 (s, 3H)

d) N-methyl(3-methyl-7-trifluoromethyl)-1H-indol-2-yl)methanamine

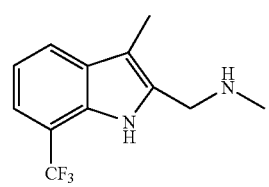 [SMILES: CNCc1[nH]c2c(C(F)(F)F)cccc2c1C]

Methylamine (0.28 mL, 6.7 mmol) was added to a solution of 3-methyl-7-(trifluoromethyl)-1H-indole-2-carbaldehyde (510 mg, 2.2 mmol) in methanol (5 mL) and stirred for 5 h. The mixture was cooled to 0° C. and sodium borohydride (83 mg, 2.2 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (310 mg, 58%). $^1$H NMR (400 MHz, CDCl$_3$) δ 8.93 (s, 1H), 7.66 (d, J=7.8 Hz, 1H), 7.38 (d, J=7.4 Hz, 1H), 7.11 (t, J=7.5 Hz, 1H), 3.90 (s, 2H), 2.48 (s, 3H), 2.28 (s, 3H).

EDC (160 mg, 0.78 mmol) was added to a solution of N-methyl(3-methyl-7-trifluoromethyl)-1H-indol-2-yl)methanamine (155 mg, 0.6 mmol), (E)-3-(3-oxo-3,4,dihydro-2H-pyrido[3,2-b][1,4]oxazin-7-yl)acrylic acid hydrochloride (180 mg, 0.7 mmol), HOBT.H$_2$O (86 mg, 0.6 mmol) and DIPEA (0.46 mL, 2.5 mmol) in dry DMF (5 mL). After stirring overnight, water was added. The precipitate that formed was washed with ethyl acetate and dried to afford the title compound (72 mg, 27%). $^1$H NMR (400 MHz, DMSO-d$_6$) δ 11.41 (s, 1H), 11.10-10.89 (rotamers, s, 1H), 8.20 (s, 1H), 7.80 (d, J=8.0 Hz, 1H), 7.76 (d, J=7.5 Hz, 1H), 7.54 (s, 1H), 7.41 (d, J=7.5 Hz, 1H), 7.31-7.20 (m, 2H), 5.05-4.81 (rotamers, s, 2H), 4.68 (s, 2H), 3.08 (s, 3H), 2.21 (s, 3H); MS (ESI): m/e 445.1 (C$_{22}$H$_{19}$F$_3$N$_4$O$_3$+H)$^+$.

Example 88

(E)-N-methyl-N-((3-methyl-7-(trifluoromethyl)-1H-indol-2-yl)methyl)-3-(7-oxo-5,6,7,8-tetrahydro-1,8-naphthyridin-3-yl)acrylamide

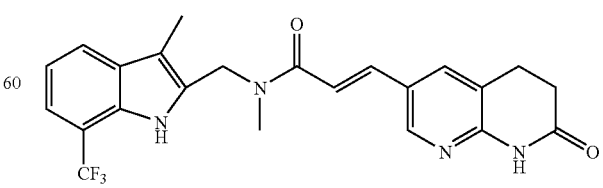

EDC (159 mg, 0.78 mmol) was added to a solution of N-methyl(3-methyl-7-trifluoromethyl)-1H-indol-2-yl)

methanamine (155 mg, 0.6 mmol), (E)-3-(2-methylene-1,2,3,4-tetrahydroquinolin-6-yl)acrylic acid hydrochloride (172 mg, 0.67 mmol), HOBT.H$_2$O (86 mg, 0.6 mmol) and DIPEA (0.46 mL, 2.5 mmol) in dry DMF (5 mL). After stirring overnight, water was added. The precipitate that formed was washed with ethyl acetate and dried to afford the title compound (157 mg, 60%). $^1$H NMR (400 MHz, DMSO-d$_6$) δ 11.05-10.90 (rotamers, s, 1H), 10.61 (s, 1H), 8.37 (s, 1H), 8.07 (s, 1H), 7.76 (d, J=7.7 Hz, 1H), 7.56-7.40 (m, 2H), 7.17-7.13 (m, 2H), 5.05-4.82 (rotamers, s, 2H), 3.10 (s, 2H), 2.84 (s, 3H), 2.32 (s, 3H); MS (ESI): m/e 443.1 (C$_{23}$H$_{21}$F$_3$N$_4$O$_2$+H)$^+$.

Example 89

Preparation of (D-N-((7-ethyl-3-methyl-1H-indol-2-yl)methyl)-N-methyl-3-(3-oxo-3,4-dihydro-2H-pyrido[3,2-b][1,4]oxazin-7-yl)acrylamide a) Ethyl 7-ethyl-3-methyl-1H-indole-2-carboxylate

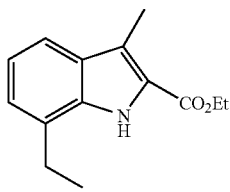 [SMILES: CCOC(=O)c1[nH]c2c(CC)cccc2c1C]

A solution of sodium nitrite (6.24 g, 90.64 mmol) was added dropwise to a mixture of 2-ethyl aniline (10.2 mL, 82.4 mmol), conc.HCl (20 mL) and water (30 mL) at −5° C. After the addition, the mixture was stirred at 0° C. for 15 min and brought to pH 3-4 by addition of sodium acetate. In a separate flask, a solution of ethyl α-ethylacetoacetate (14.6 mL, 90.64 mmol) in ethanol (50 mL) at 0° C. was treated with a solution of potassium hydroxide (5.08 g, 90.64 mmol) in water (20 mL) followed by addition of ice. The diazonium salt was immediately added to this alkaline solution. The mixture was adjusted to pH 5-6 by adding sodium acetate and stirred at 0° C. for 3 h. The solution was kept overnight at 4° C. and extracted with ethyl acetate, washed with brine, dried over magnesium sulfate and most of the solvent removed. The crude mixture was added dropwise to a solution of ethanolic HCl (50 mL) at 78° C. and stirred for 2 h at 78° C. The mixture was evaporated and chromatographed over silica gel eluting with ethyl acetate/hexane (3%) to afford the title compound (2.2 g, 11%). $^1$H NMR (400 MHz, CDCl$_3$) δ 8.52 (s, 1H), 7.48 (d, J=8 Hz, 1H), 7.12 (d, J=6.8 Hz, 1H), 7.06 (t, J=7.2 Hz, 1H), 4.38 (q, J=7.3 Hz, 2H), 2.82 (q, J=7.6 Hz, 2H), 2.58 (s, 3H), 1.40 (t, J=7.2 Hz, 3H), 1.33 (t, J=7.6 Hz, 3H)

b) (7-Ethyl-3-methyl-1H-indol-2-yl)methanol

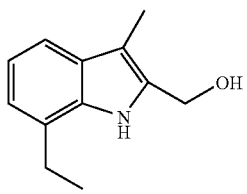

A solution of ethyl 7-ethyl-3-methyl-1H-indole-2-carboxylate (2.2 g, 9.5 mmol) in THF (50 mL) was added to an ice cooled solution of 1M LAH in THF (19 mL, 19.0 mmol) and stirred overnight. The reaction was quenched with ethyl acetate and sodium hydroxide, filtered through celite and evaporated to afford the title compound (1.6 g, 100%). $^1$H NMR (400 MHz, CDCl$_3$) δ 8.45 (s, 1H), 7.39 (d, J=6.5 Hz, 1H), 7.04 (m, 2H), 4.80 (s, 2H), 2.83 (q, J=4.8 Hz, 2H), 2.28 (s, 3H), 1.34 (t, J=4.4 Hz, 3H)

c) 7-Ethyl-3-methyl-1H-indole-2-carbaldehyde

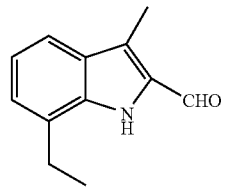

A mixture of (7-ethyl-3-methyl-1H-indol-2-yl)methanol (1.6 g, 9.1 mmol) and manganese (IV) oxide (3.97 g, 45.7 mmol) in dichloromethane (15 mL) was stirred overnight. The mixture was filtered through celite and evaporated to afford the title compound (1.1 mg, 65%). $^1$H NMR (400 MHz, CDCl$_3$) δ 10.02 (s, 1H), 8.90 (s, 1H), 7.53 (d, J=8.0 Hz, 1H), 7.19 (d, J=7.6 Hz, 1H), 7.10 (t, J=7.7 Hz, 1H), 2.83 (q, J=7.5 Hz, 2H), 2.62 (s, 3H), 1.31 (t, J=7.5 Hz, 3H)

d) (7-Ethyl-3-methyl-1H-indol-2-yl)-N-methanamine

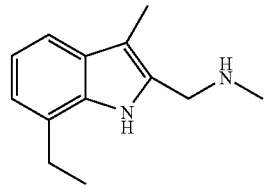

Methylamine (0.7 mL, 17.6 mmol) was added to a solution of 7-ethyl-3-methyl-1H-indole-2-carbaldehyde (1.1 mg, 5.8 mmol) in methanol (5 mL) and stirred for 5 h. The mixture was cooled to 0° C. and sodium borohydride (218 mg, 5.8 mmol) added slowly. The mixture was warmed to rt and stirred overnight. Water (3 mL) was added slowly at 0° C. and evaporated to a paste. Water was added and the mixture extracted with dichloromethane. The organic phase was washed with water, dried and evaporated to afford the title compound (826 mg, 75%). $^1$H NMR (400 MHz, CDCl$_3$) δ 8.22 (s, 1H), 7.34 (d, J=7.7 Hz, 1H), 7.01 (t, J=7.6 Hz, 1H), 6.96 (d, J=6.8 Hz, 1H), 3.87 (s, 2H), 2.79 (q, J=7.5 Hz, 2H), 2.45 (s, 3H), 2.24 (s, 3H), 1.31 (t, J=7.6 Hz, 3H)

(E)-N-((7-ethyl-3-methyl-1H-indol-2-yl)methyl)-N-methyl-3-(3-oxo-3,4-dihydro-2H-pyrido[3,2-b][1,4]oxazin-7-yl)acrylamide

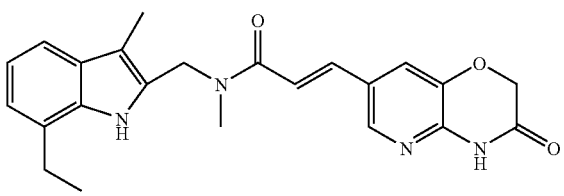 [SMILES: CCc1cccc2c(C)c(CN(C)C(=O)/C=C/c3cnc4c(c3)OCC(=O)N4)[nH]c12]

EDC (147 mg, 0.7 mmol) was added to a solution of (7-ethyl-3-methyl-1H-indol-2-yl)-N-methanamine (108.7 mg, 0.5 mmol), (E)-3-(3-oxo-3,4,dihydro-2H-pyrido[3,2-b][1,4]oxazin-7-yl)acrylic acid hydrochloride (151 mg, 0.6 mmol), HOBT.H$_2$O (73 mg, 0.5 mmol) and DIPEA (0.39 mL, 2.1 mmol) in dry DMF (5 mL). After stirring overnight, water was added. The precipitate that formed was washed with ethyl acetate and dried to afford the title compound (25 mg, 0.001%). $^1$H NMR (400 MHz, DMSO-d$_6$) δ 9.34 (s, 1H), 8.92 (s, 1H), 8.15 (s, 1H), 7.65 (d, J=7.6 Hz, 1H), 7.41 (s, 1H), 7.38 (d, J=7.2 Hz, 1H), 7.05 (m, 2H), 6.80 (d, J=7.5 Hz, 1H), 4.70 (s, 2H), 3.15 (s, 3H), 2.88 (q, J=7.0 Hz, 2H), 2.40 (s, 3H), 1.30 (t, J=7.2 Hz, 3H); MS (ESI): m/e 405.2 (C$_{23}$H$_{24}$N$_4$O$_3$+H)$^+$.

Example 90

(E)-N-((7-ethyl-3-methyl-1H-indol-2-yl)methyl)-N-methyl-3-(7-oxo-5,6,7,8-tetrahydro-1,8-naphthyridin-3-yl)acrylamide

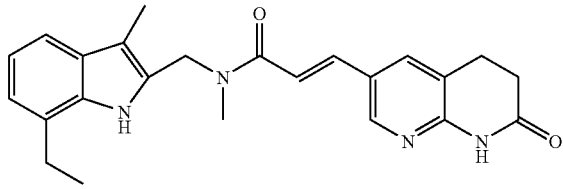 [SMILES: CCc1cccc2c(C)c(CN(C)C(=O)/C=C/c3cnc4c(c3)CCC(=O)N4)[nH]c12]

EDC (138 mg, 0.7 mmol) was added to a solution of (7-ethyl-3-methyl-1H-indol-2-yl)-N-methanamine (112.2 mg, 0.5 mmol), (E)-3-(2-methylene-1,2,3,4-tetrahydroquinolin-6-yl)acrylic acid hydrochloride (155 mg, 0.6 mmol) HOBT.H$_2$O (75 mg, 0.5 mmol) and DIPEA (0.4 mL, 2.2 mmol) in dry DMF (5 mL). After stirring overnight, water was added. The precipitate that formed was washed with ethyl acetate and dried to afford the title compound (90 mg, 44.7%). $^1$H NMR (400 MHz, DMSO-d$_6$) δ 11.50 (s, 1H), 10.44 (s, 1H), 8.39 (s, 1H), 8.29 (s, 1H), 8.09 (m, 1H), 7.85 (d, J=7.6 Hz, 1H), 7.5 (d, J=7.0 Hz, 1H), 7.34 (d, J=7.8 Hz, 1H), 6.88 (m, 2H), 5.05-4.85 (rotamers, s, 2H), 3.22 (m, 2H), 3.15 (s, 3H), 2.88 (q, J=7.0 Hz, 2H), 2.70 (m, 2H), 2.40 (s, 3H), 1.30 (t, J=7.2 Hz, 3H); MS (ESI): m/e 419 (C$_{24}$H$_{26}$N$_4$O$_2$+H)$^+$.

Example 91 a) Ethyl 5-bromo-3,6-dimethyl-1H-indole-2-carboxylate

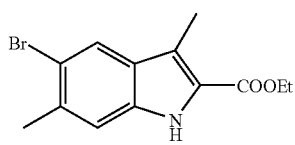 [SMILES: CCOC(=O)c1[nH]c2cc(C)c(Br)cc2c1C]

A solution of NaNO$_2$ (1.52 g, 22 mmol) in water (4 mL) was added to a vigorously stirred mixture of 4-bromo-3-methylaniline (3.72 g, 20 mmol) at −5° C. After 30 min stirring, the solution was adjusted to pH 5 with NaOAc (1.40 g). A cold solution of ethyl 2-ethyl-3-oxobutanoate (4.0 g, 22 mmol) and KOH (1.36 g, 22 mmol) in EtOH (16 mL) were added followed by crushed ice (~30 g). NaOAc was added if necessary to adjust the pH to 5. The mixture was stirred for 5 h at 0° C. then kept at this temperature overnight. The solution was extracted with EtOAc, washed with brine, dried and evaporated to 8 mL. This solution was added to a solution of HCl (25 mL, 7M in EtOH). It was further refluxed for 3 h. Upon cooling in an ice bath, water (200 mL) was added slowly. The precipitate was filtered, washed with water and dried to afford 5.36 g (91%) as a 1:1 mixture of the title compound and its ethyl 5-bromo-3,4-dimethyl-1H-indole-2-carboxylate isomer. $^1$H NMR (300 MHz, CDCl$_3$), δ, mix 8.66 and 8.54 (2s, br, 1H), 7.83 and 7.23 (2s, 2×0.5H), 7.42 and 7.05 (2d, J=8.7 Hz, 2×0.5H), 4.41 (q, J=7.2 Hz, 2H), 2.81, 2.79, 2.53 and 2.49 (4s, 4×1.5H), 1.42 (t, J=7.2 Hz, 3H).

b) 5-Bromo-3,6-dimethyl-1H-indole-2-carboxylic acid

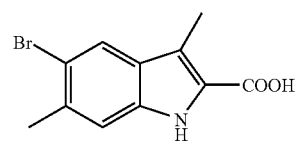

A 1:1 isomeric mixture of ethyl 5-bromo-3,6-dimethyl-1H-indole-2-carboxylate and 5-bromo-3,4-dimethyl-1H-indole-2-carboxylate (5.36 g, 18.1 mmol) was dissolved in EtOH (20 mL) and KOH (3.6 g, 54 mmol). The mixture was refluxed for 3 h and gave 4.67 g (99%) of a 1:1 isomeric mixture of the corresponding acids. The mixture was acidified and the precipitate that formed was filtered and dried at 120° C. to afford the title compound (4.39 g, 90.6%). $^1$H NMR (300 MHz, DMSO-d$_6$) δ, mix 12.96 (s, 1H), 11.50 and 11.40 (2s, 2×0.5H), 7.85 and 7.33 (2s, 2×0.5H), 7.34 and 7.16 (2d, J=8.7 Hz, 2×0.5H), 2.76, 2.73, 2.49 and 2.47 (4s, 4×1.5H).

c) 5-Bromo-3,6-dimethyl-1H-indole

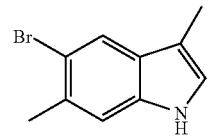

A 1:1 mixture of 5-bromo-3,6-dimethyl-1H-indole-2-carboxylic acid and 5-bromo-3,4-dimethyl-1H-indole-2-carboxylic acid (4.39 g, 16.4 mmol) in quinoline (10 mL) with copper powder (250 mg) was stirred at 240° C. for 3 h to give the corresponding mixture of the decarboxylated products. Upon cooling, ether (200 mL) was added and the mixture acidified with 5N HCl. The layers were separated, the organics were washed with brine, dried and evaporated. Chromatography (silica, 15% CH$_2$Cl$_2$ in hexane) and crystallization from a CH$_2$Cl$_2$/hexane mixture afforded the title compound (1.35 g 37%). $^1$H NMR (300 MHz, CDCl$_3$). δ 7.74 (s, 1H), 7.21 (is, 1H), 6.90 (s, 1H), 2.48 (s, 3H), 2.27 (s, 3H).

d) 3,6-Dimethyl-1H-indole-5-carbaldehyde

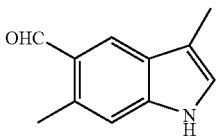

tert-Butyl lithium (16.7 mL, 28.3 mmol, 1.7 M in pentanes) was added to a dry ether (20 mL) solution of 5-bromo-3,6-dimethyl-1H-indole (1.27 g, 5.67 mmol) at −78° C. under Argon. The mixture was stirred at 0° C. for 30 min then cooled to −78° C. DMF (18 mL) was added and the mixture was stirred at 0° C. for 1 h. The reaction was quenched with cold, saturated NH$_4$Cl solution at −78° C. The mixture was diluted with ether and hexane, washed with brine, dried and evaporated. Crystallization from a CH$_2$Cl$_2$/hexane mixture afforded the title compound (810 mg 82%). $^1$H NMR (300 MHz, CDCl$_3$) δ 10.29 (s, 1H), 8.06 (s, 1H), 8.00 (s, br, 1H), 7.15 (1s, 1H), 6.97 (s, 1H), 2.76 (s, 3H), 2.36 (s, 3H).

e)
3,6-dimethyl-1H-indol-5-yl)-N-methylmethanamine

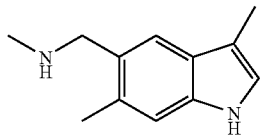

Methylamine (2.4 mL, 19 mmol, 33% in EtOH) was added to a MeOH (10 mL) solution of 3,6-dimethyl-1H-indole-5-carbaldehyde (810 mg, 4.7 mmol). The mixture was stirred for 5 h at 21° C. The mixture was cooled to 0° C. and NaBH$_4$ (180 mg, 4.7 mmol) was added slowly. The mixture was stirred at 21° C. for 16 h, water (1 mL) was added then it was evaporated to a paste. This was diluted with CH$_2$Cl$_2$, washed with water, dried over K$_2$CO$_3$ and evaporated to afford the title compound (848 mg 96%). (300 MHz, CDCl$_3$) δ 7.77 (s, br, 1H), 7.47 (s, br, 1H), 7.26 (1s, 1H), 6.87 (s, 1H), 3.83 (s, 2H), 2.54 (s, 3H), 2.45 (s, 3H), 2.31 (s, 3H).

Preparation of (E)-N-((3,6-dimethyl-1H-indol-5-yl)methyl)-N-methyl-3-(7-oxo-5,6,7,8-tetrahydro-1,8-naphthyridin-3-yl)acrylamide

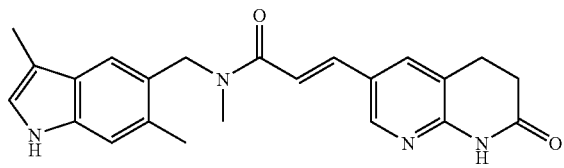 [SMILES: Cc1cc2[nH]cc(C)c2cc1CN(C)C(=O)/C=C/c1cnc2c(c1)CCC(=O)N2]

EDC (132 mg, 0.69 mmol) was added to a solution of 3,6-dimethyl-1H-indol-5-yl)-N-methylmethanamine (100 mg, 0.5 mmol), (E)-3-(2-methylene-1,2,3,4-tetrahydroquinolin-6-yl)acrylic acid hydrochloride (148 mg, 0.6 mmol) HOBT.H$_2$O (71.8 mg, 0.5 mmol) and DIPEA (0.38 mL, 2.2 mmol) in dry DMF (5 mL). After heating overnight, water was added. The precipitate that formed was washed with ethyl acetate and dried to afford the title compound (33 mg, 17%). $^1$H NMR (300 MHz, DMSO-d$_6$) δ, 10.70-10.60 (m, 2H), 8.32-8.22 (rotamers, s, 1H), 8.00-7.95 (rotamers, s, 2H), 7.54 (d, J=7.6 Hz, 1H), 7.32 (m, 1H), 7.09 (m, 1H), 6.98 (s, 1H), 4.89-4.72 (rotamers, s, 2H), 3.32 (m, 2H), 3.02 (m, 2H), 2.84 (s, 3H), 2.46 (s, 3H), 2.31 (s, 3H); m/e 389.2 (C$_{23}$H$_{24}$N$_4$O$_2$+H)$^+$.

Example 92

Preparation of (E)-N-((3,6-dimethyl-1H-indol-5-yl)methyl)-N-methyl-3-(3-oxo-3,4-dihydro-2H-pyrido[3,2-b][1,4]oxazin-yl)acrylamide

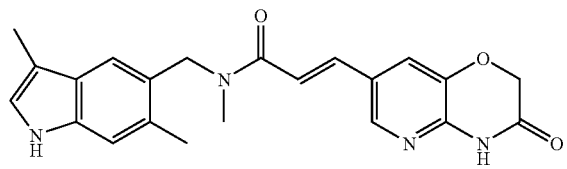 [SMILES: Cc1cc2[nH]cc(C)c2cc1CN(C)C(=O)/C=C/c1cnc2c(c1)OCC(=O)N2]

EDC (198 mg, 1.0 mmol) was added to a solution of (7-ethyl-3-methyl-1H-indol-2-yl)-N-methanamine (150 mg, 0.8 mmol), (E)-3-(3-oxo-3,4,dihydro-2H-pyrido[3,2-b][1,4]oxazin-7-yl)acrylic acid hydrochloride (224 mg, 0.87 mmol) HOBT.H$_2$O (107 mg, 0.8 mmol) and DIPEA (0.57 mL, 3.1 mmol) in dry DMF (5 mL). After heating overnight, water was added. The precipitate that formed was washed with ethyl acetate and dried (184 mg, 59%). $^1$H NMR (300 MHz, DMSO-d$_6$) δ, 11.42 (s, 1H), 10.45 (s, 1H), 8.24-8.05 (rotamers, s, 1H), 7.98-7.80 (rotamers, s, 2H), 7.54 (d, J=7.4 Hz, 1H), 7.24 (m, 1H), 7.14 (m, 1H), 6.98 (s, 1H), 4.90-4.78 (rotamers, s, 2H), 3.05 (s, 2H), 2.84 (s, 3H), 2.45 (s, 3H), 2.31 (s, 3H); m/e 391.1 (C$_{22}$H$_{22}$N$_4$O$_3$+H)$^+$.

Example 93

Preparation of (E)-N-methyl-N-((3-methylbenzofuran-2-yl)methyl)-3-(7-oxo-7,8-dihydro-1,8-naphthyridin-3-yl)acrylamide a) (E)-tert-butyl 3-(2-amino-5-bromopyridin-3-yl)acrylate

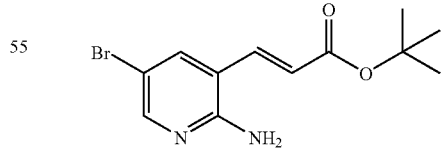

A reaction vessel was charged with 5-bromo-3-iodopyridin-2-amine (1 g, 3.35 mmol), tert-butyl acrylate (0.97 mL, 6.69 mmol), and (i-Pr)$_2$EtN (1.75 mL, 10.01 mmol) followed by propionitrile (20 mL) and then DMF (5 mL). The solution was de-oxygenated with argon for 15 minutes. The mixture was treated with Pd(OAc)$_2$ (75 mg, 0.34 mmol) and P(o-tol)$_3$ (204 mg, 0.67 mmol) then heated to 90° C. for 16 h (overnight) then filtered through a pad of silica gel. The filtrate was concentrated and dried under reduced pressure to give a dark brown residue which was subjected to flash chromatography on silica gel using 20% ethyl acetate:hexanes to 40% ethyl acetate:hexanes. The appropriate fractions were collected and concentrated to give a yellow solid. Yield: 700 mg (70%); $^1$H NMR (300 MHz, DMSO-$d_6$) δ 8.06 (d, 1H, J=2.3 Hz), 8.03 (d, 1H, J=2.3 Hz), 7.61 (d, 1H, J=15.0 Hz), 6.58 (s, 2H), 6.50 (d, 1H, J=15.0 Hz), 1.50 (s, 9H); ESI MS m/z 299 (100%); 301 (100%) $[C_{12}H_{15}N_2O_2Br+H]^+$ b) 6-bromo-1,8-naphthyridin-2(1H)-one

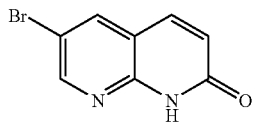

A solution of (E)-tert-butyl 3-(2-amino-5-bromopyridin-3-yl)acrylate (2.5 g, 8.35 mmol) in anhydrous methanol (50 mL) was treated with sodium methoxide (8.5 mL of a 4.9 M solution, 41.75 mmol). The solution was heated at reflux for 2 h then cooled to room temperature. The mixture was cooled in an ice-H$_2$O bath and treated with H$_2$O (100 mL) under rapid stirring to give a precipitate. The solid was filtered and washed with H$_2$O (20 mL). The filtrate was neutralized with 1 M HCl(aq) to form a precipitate. The solid was filtered and washed with H$_2$O (20 mL). The solids were combined and dried under reduced pressure to give an off-white solid (1.75 g, 93%). NMR (300 MHz, DMSO-$d_6$) δ 8.43 (d, 1H, J=2.5 Hz), 8.06 (d, 1H, J=2.5 Hz), 7.60 (d, 1H, J=9.1 Hz), 6.44 (d, 1H, J=9.1 Hz); ESI MS m/z 225 (100%); 227 (100%) $[C_8H_5N_2OBr+H]^+$ c) (E)-tert-butyl 3-(7-oxo-7,8-dihydro-1,8-naphthyridin-3-yl)acrylate

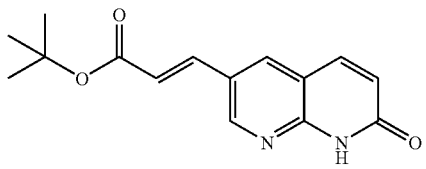 [SMILES: CC(C)(C)OC(=O)/C=C/c1cnc2[nH]c(=O)ccc2c1]

A reaction vessel was charged with 6-bromo-1,8-naphthyridin-2(1H)-one (1.5 g, 6.69 mmol), tert-butyl acrylate (4.86 mL, 33.45 mmol), and (i-Pr)$_2$EtN (3.5 mL, 20.07 mmol) followed by DMF (40 mL). The solution was de-oxygenated with argon for 20 min. The mixture was treated with Pd(OAc)$_2$ (150 mg, 0.67 mmol) and P(o-tol)$_3$ (407 mg, 1.34 mmol) then heated to 100° C. for 15 h (overnight). A TLC analysis indicated that only the starting arylhalide is present. At this time the mixture was a yellow suspension. To this mixture was added 20 DMSO (20 mL) and an additional 75 mg of Pd(OAc)$_2$. The mixture was heated at 100° C. for 24 h. After cooling, the dark mixture was filtered through celite and the filter cake was rinsed with EtOAc (100 mL). The filtrate was extracted with EtOAc (2×100 mL). The combined organic fractions were washed with brine (2×100 mL), H$_2$O (100 mL), dried over MgSO$_4$ and filtered through a pad of silica gel. The filtrate was concentrated to about 50 mL then treated with about 150 mL hexanes to form a precipitate. The precipitate was filtered to give the product as a light brown solid. Yield: 700 mg (39%); $^1$H-NMR (300 MHz, DMSO-$d_6$) δ 12.36 (s, 1H), 8.83 (d, 1H, J=2.3 Hz), 8.53 (d, 1H, J=2.3 Hz), 7.89 (d, 1H, J=9.0 Hz), 7.64 (d, 1H, J=18.0 Hz), 6.65 (d, 1H, J=18.0 Hz), 6.62 (m, 1H), 1.51 (s, 9H); ESI MS m/z 273 $[C_{15}H_{16}N_2O_3+H]^+$ d) (E)-3-(7-oxo-7,8-dihydro-1,8-naphthyridin-3-yl)acrylic acid Hydrochloride

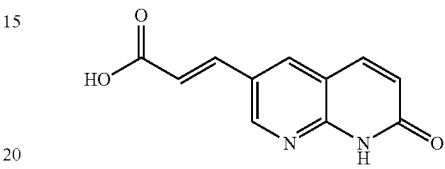

A suspension of (E)-tert-butyl 3-(7-oxo-7,8-dihydro-1,8-naphthyridin-3-yl)acrylate (500 mg, 1.84 mmol) in CH$_2$Cl$_2$ (7 mL) was treated with trifluoroacetic acid (7 mL). The mixture became homogeneous and it was stirred at room temperature for 1 h. The solution was concentrated to dryness and treated with 4M HCl in dioxane (5 mL). The suspension was sonicated for 20 min, diluted with Et$_2$O (50 mL) and sonicated for an additional 20 min. The solid was filtered and dried under reduced pressure overnight. Yield: 450 mg (96.8%) $^1$H-NMR (300 MHz, DMSO-$d_6$) δ 12.4 (br s, 1H), 8.82 (s, 1H), 8.52 (s, 1H), 7.91 (d, 1H, J=9.0 Hz), 7.67 (d, 1H, J=15.0 Hz), 6.67 (d, 1H, J=15.0 Hz), 6.61 (m, 1H); ESI MS m/z 217 $[C_{11}H_8N_2O_3+]^+$ (E)-N-methyl-N-((3-methylbenzofuran-2-yl)methyl)-3-(7-oxo-7,8-dihydro-1,8-naphthyridin-3-yl)acrylamide

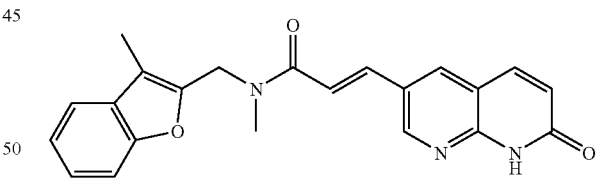

EDC (0.18 g, 0.95 mmol) was added to a suspension of (E)-3-(7-oxo-7,8-dihydro-1,8-naphthyridin-3-yl)acrylic acid hydrochloride (0.20 g, 0.79 mmol), HOBt (0.12 g, 0.87 mmol), Methyl-(3-methyl-benzofuran-2-ylmethyl)-amine (0.15 g, 0.87 mmol) and (i-Pr)$_2$EtN (0.8 mL, 4.74 mmol) in DMF (10 mL). The mixture was heated at 40° C. overnight then diluted with H$_2$O (30 mL) with rapid stirring. The resulting precipitate was filtered, washed with H$_2$O (20 mL) and dried under high vacuum for 4 hours. The solid was suspended in 50% Et$_2$O:hexanes (20 mL), sonicated then filtered and dried under vacuum overnight. Yield: 0.13 g (44.1%) as a mixture of amide rotamers; $^1$H NMR (300 MHz, DMSO-$d_6$) δ 12.33 (s, 1H), 8.90 and 8.87 (2×s, 1H), 8.53 (s, 1H), 7.91 (d, 1H, J=9 Hz), 7.65-7.25 (m, 6H), 6.63 (d, 1H, J=9.0 Hz), 5.04 and 4.83 (2×s, 2H), 3.23 and 2.96 (2×s, 3H), 2.29 (s, 3H); ESI MS m/z 374 [C$_{22}$H$_{19}$N$_3$O$_3$+H]$^+$

Example 94

Preparation of (E)-3-(6,6-dimethyl-7-oxo-5,6,7,8-tetrahydro-1,8-naphthyridin-3-yl)-N-methyl-N-((3-methylbenzofuran-2-yl)methyl)acrylamide 6-bromo-3,3-dimethyl-3,4-dihydro-1,8-naphthyridin-2(1H)-one

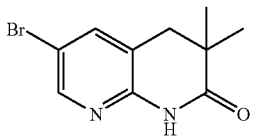

A mixture of activated Zn (1.0 g, 15 mmol) and ethyl 2-bromo-2-methylpropanoate (1.24 mL, 6.4 mmol) in THF (8 mL) were added together at 0° C. and stirred for 6 h while warming to room temperature. To this mixture a dropwise solution of 5-bromo-3-(bromomethyl)pyridin-2-amine in THF (5 mL) was added via canula and the reaction mixture was stirred for a further 19 h at rt. The mixture was diluted with ethyl acetate (25 mL) and washed with saturated aqueous NH$_4$Cl (50 mL) and brine (50 mL), dried over magnesium sulphate, and concentrated in vacuo. The crude yellow solid product was triturated with diethyl ether and filtered to obtain the white solid product. Yield 158 mg (49%); $^1$H NMR (300 MHz, DMSO-d$_6$) δ 10.61 (s, 1H), 8.23 (s, 1H), 7.87 (s, 1H), 2.81 (s, 2H), 1.04 (s, 6H); ESI MS m/z 255, 257 [C$_{10}$H$_{11}$N$_2$OBr+H]$^+$.

(E)-tert-butyl-3-(6,6-dimethyl-7-oxo-5,6,7,8-tetrahydro-1,8-naphthyridin-3-yl)acrylate

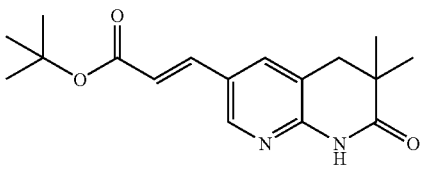 [SMILES: CC(C)(C)OC(=O)/C=C/c1cnc2c(c1)CC(C)(C)C(=O)N2]

A suspension of 6-bromo-3,3-dimethyl-3,4-dihydro-1,8-naphthyridin-2(1H)-one (434 mg, 1.7 mmol), tert-butyl acrylate (1.23 mL, 8.5 mmol) and (i-Pr)$_2$EtN (0.9 mL, 5.1 mmol) in DMF (25 mL) was de-oxygenated with Ar for 30 min. The mixture was treated with Pd(OAc)$_2$ (38 mg, 0.17 mmol) and P(o-tol)$_3$ (103 mg, 0.34 mmol) then heated to 110° C. for 22 h. The hot mixture was filtered through a pad of celite and washed with ethyl acetate (50 mL). The filtrate was diluted with H$_2$O (100 mL) and extracted with ethyl acetate (2×50 mL). The combined organic layers were washed with water, then brine, dried over magnesium sulphate, and concentrated in vacuo. The resulting brown solid was then triturated with a diethyl ether followed by filtration to yield the white solid product. Yield 178 mg (35%); $^1$H NMR (300 MHz, DMSO-d$_6$) δ 10.68 (s, 1H), 8.39 (s, 1H), 8.04 (s, 1H), 7.52 (d, J=16.1 Hz, 1H), 6.52 (d, J=15.8 Hz, 1H), 2.80 (s, 2H), 1.49 (s, 9H), 1.09 (s, 6H); ESI MS m/z 303 [C$_{17}$H$_{22}$N$_2$O$_3$+H]$^+$ (E)-3-(6,6-dimethyl-7-oxo-5,6,7,8-tetrahydro-1,8-naphthyridin-3-yl)acrylic acid

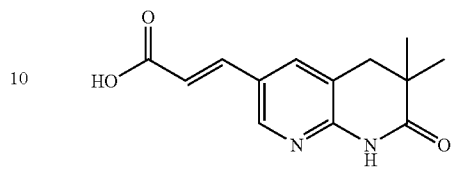

A solution of (E)-tert-butyl 3-(6,6-dimethyl-7-oxo-5,6,7,8-tetrahydro-1,8-naphthyridin-3-yl)acrylate (165 mg, 0.55 mmol) in CH$_2$Cl$_2$ (10 mL) was treated with TFA (10 mL). After stirring at room temperature for 2 h, the solution was concentrated in vacuo. The resulting crude product was treated with anhydrous HCl in dioxane (4 mL, 4.0 M) and sonicated for 15 min. The off-white solid product was then isolated by filtration and dried under vacuum. Yield: 152 mg (quant); $^1$H NMR (300 MHz, DMSO-d$_6$) δ 10.71 (s, 1H), 8.38 (s, 1H), 8.04 (s, 1H), 7.56 (d, J=16.1 Hz, 1H), 6.54 (d, J=16.1 Hz, 1H), 2.81 (s, 2H), 1.09 (s, 6H); ESI MS m/z 247 [C$_{13}$H$_{14}$N$_3$O$_4$+H]$^+$ (E)-3-(6,6-dimethyl-7-oxo-5,6,7,8-tetrahydro-1,8-naphthyridin-3-yl)-N-methyl-N-((3-methylbenzofuran-2-yl)methyl)acrylamide

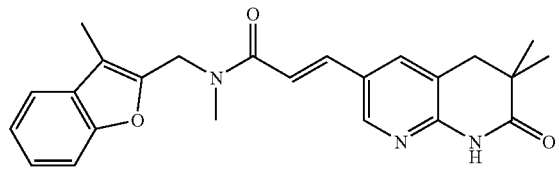 [SMILES: Cc1c(CN(C)C(=O)/C=C/c2cnc3c(c2)CC(C)(C)C(=O)N3)oc2ccccc12]

EDC (102 mg, 0.53 mmol) was added to a suspension of (E)-3-(6,6-dimethyl-7-oxo-5,6,7,8-tetrahydro-1,8-naphthyridin-3-yl)acrylic acid hydrochloride (125 mg, 0.44 mmol), HOBt (66 mg, 0.49 mmol), N-methyl(3-methylbenzofuran-2-yl)methanamine (92 mg, 0.49 mmol) and (i-Pr)$_2$EtN (0.37 mL, 2.2 mmol) in DMF (5 mL). The mixture was allowed to stir for 23 h at 40° C. The mixture was cooled to room temperature and diluted with water (20 mL) at 0° C. to yield a brown precipitate, which was collected by suction filtration. The solid was then triturated with diethyl ether to obtain an off-white solid product. Yield: 137 mg (81%); $^1$H NMR (300 MHz, DMSO-d$_6$) δ 10.64 (s, 1H), 8.40 (s, 1H), 8.09 (s, 1H), 7.59-7.19 (m, 6H), 4.91 (s, 2H), 3.09 (s, 3H), 2.81 (s, 2H), 2.28 (s, 3H), 1.09 (s, 6H); ESI MS m/z 404 [C$_{24}$H$_{25}$N$_3$O$_3$+H]$^+$.

Example 95 a) (S)-ethyl 2-(3-cyanopyridin-2-ylamino)propanoate

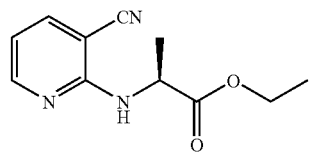 [SMILES: CCOC(=O)[C@H](C)Nc1ncccc1C#N]

A solution of 2-chloro-3-cyanopyridine (2 g, 14.4 mmol), L-alanine ethyl ester hydrochloride (3.3 g, 21.6 mmol), sodium carbonate (5.9 g, 43 mmol) in pyridine (1.75 mL) and DMF (20 mL) was heated to 125° C. for 36 h. The reaction was quenched with water and extracted with ethyl acetate (3×15 mL). The product was purified using column chromatography (10% MeOH in CH$_2$Cl$_2$) to yield a pale yellow solid (720 mg, 23%): $^1$H NMR (400 MHz, CDCl$_3$) δ 8.26 (d, J=4.8 Hz, 1H), 7.69-7.67 (m, 1H), 6.67-6.64 (m, 1H), 4.77-4.74 (m, 1H), 4.23-4.19 (m, 2H), 1.54 (d, J=7.2 Hz, 3H), 1.30-1.26 (m, 3H).

b) (S)-2-methyl-1,2,4,5-tetrahydropyrido[2,3-e][1,4]diazepin-3-one

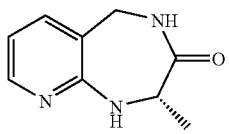

To a solution of (S)-ethyl 2-(3-cyanopyridin-2-ylamino)propanoate (720 mg, 3.28 mmol) in methanol (10 mL) and sodium methoxide (3.28 mmol) is added a pinch of Raney nickel and the reaction was stirred under hydrogen for 6 h. Once the reaction was complete, 1 eq of HCl was added and the solution filtered through celite, and washed with methanol. The solution was concentrated and re-solvated in ethyl acetate (10 mL) and washed with water (20 mL), the organic layers were combined, dried over sodium sulfate and concentrated. The residue was purified by preparative HPLC to yield a white solid (136 mg, 23%): $^1$H NMR (400 MHz, CD$_3$OD) δ 7.87 (s, 1H), 7.32 (s, 1H), 6.60-6.57 (m, 1H), 4.99 (d, J=16.4 Hz, 1H), 4.12-4.10 (m, 1H), 3.87 (d, J=16.4 Hz, 1H), 1.38 (d, J=6.8 Hz, 3H).

c) (S)-7-bromo-2-methyl-1,2,4,5-tetrahydropyrido[2,3-e][1,4]diazepin-3-one

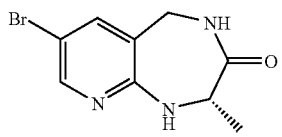

Bromine (43 ul, 0.84 mmol) was added drop wise to a solution of (S)-2-methyl-1,2,4,5-tetrahydropyrido[2,3-e][1,4]diazepin-3-one (136 mg, 0.77 mmol) in acetic acid (10 mL). The reaction was stirred at room temperature for 3 h. The reaction was quenched with sat. NaHCO$_3$ (10 mL) and extracted with ethyl acetate (3×15 mL), dried over sodium sulfate and concentrated to give the title compound (140 mg, 71%): $^1$H NMR (400 MHz, CDCl$_3$) δ 7.93 (s, 1H), 7.31 (s, 1H), 7.20 (b, 1H), 5.95 (bs, 1H), 4.97-4.91 (m, 1H), 4.72-4.70 (m, 1H), 3.85-3.79 (m, 1H), 1.47 (d, J=6.4 Hz, 3H).

(S,E)-N-methyl-3-(2-methyl-3-oxo-2,3,4,5-tetrahydro-1H-pyrido[2,3-e][1,4]diazepin-7-yl)-N-((3-methylbenzofuran-2-yl)methyl)acrylamide trifluoroacetic acid salt

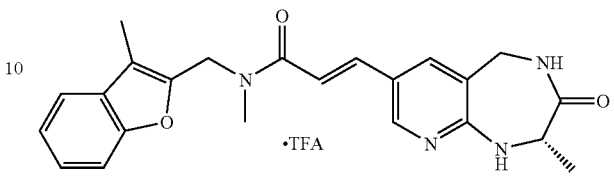

To a solution of (S)-tert-butyl 7-bromo-3-methyl-2,3-dihydro-1H-pyrido[2,3-e][1,4]diazepine-4(5H)-carboxylate (70 mg, 0.27 mmol), tri(o-tolyl)phosphine (17 mg, 0.056 mmol), diisopropylethylamine (105 uL, 0.56 mmol), N-methyl-N-((3-methyl-3a,7a-dihydrobenzofuran-2-yl)methyl)acrylamide (125 mg, 0.55 mmol) in DMF (5 mL) was added palladium acetate (7 mg, 0.027 mmol) and the reaction heated to 90° C. overnight. The reaction was cooled to room temperature and passed through a pad of celite. The filter cake was washed with ethyl acetate (10 mL). The reaction was washed with water (10 mL) and extracted with ethyl acetate (2×15 mL), dried over sodium sulfate and concentrated. The residue was then re-dissolved in methylene chloride (5 mL) and cooled to 0° C. Trifluoroacetic acid (1 mL) was added and reaction stirred at room temperature for 1 h. The solution was concentrated and purified using preparative HPLC to yield a yellow solid (88 mg, 57%) as the TFA salt: $^1$H NMR (400 MHz, DMSO-d$_6$) δ 8.29-8.01 (m, 2H), 7.57 (s, 1H), 7.55-7.42 (m, 3H), 7.30-7.22 (m, 2H), 4.96-4.90 (m, 31-1), 4.78 (s, 1H), 3.98 (m, 1H), 3.16 (s, 2H), 2.90 (s, 1H), 2.26 (s, 3H), 1.26 (d, J=6.4 Hz, 3H). MS (ESI) m/e 405 (C$_{23}$H$_{24}$N$_4$O$_3$+H)$^+$.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

Heath, et al. *Nature* 406: 145 2000; Bergler, et al, 1994, *J. Biol. Chem.* 269, 5493-5496; Heath, et al, 1996, *J. Biol. Chem.* 271, 1833-1836; Grassberger, et al, 1984 *J. Med Chem* 27 947-953; Turnowsky, et al, 1989, *J. Bacteriol.,* 171, 6555-6565; McMurry, et al, 1998 *Nature* 394, 531-532; Levy, et al, 1999 *Nature* 398, 383-384; Ward, et al, 1999 *Biochem.* 38, 12514-12525; Heck, *Org. Reactions* 1982, 27, 345; *J. Het. Chem.* 1978, 15, 249-251; Morb. Mortal Wkly Rep. 1998; 46:71-80; Standards, N.C.f.C.L., Methods for Dilution Antimicrobial Susceptibility Tests for Bacteria that Grow Aerobically; Approved Standard—Fifth Edition. 2000; Baxter, D. F., et al., A novel membrane potential-sensitive fluorescent dye improves cell-based assays for ion channels. J Biomol Screen, 2002 7(1): p. 79-85; Ahmed, S. A., R. M. Gogal, Jr., and J. E. Walsh, A new rapid and simple non-radioactive assay to monitor and determine the proliferation of lymphocytes: an alternative to [3H]thymidine incorporation assay. J Immunol Methods, 1994 170(2): p. 211-24; http://bbrp.lln-l.gov/bbrp/html/microbe.html; http://artedi.ebc.uu.se/

Projects/Francisella/; U.S. patent application Ser. Nos. 08/790,043; 10/009,219; 10/089,019; 09/968,129; 09/968,123; 09/968,236; 09/959,172; 09/979,560; 09/980,369; 10/089,755; 10/089,739; 10/089,740; PCT Application Nos. PCT/US03/38706; WO 0027628; WO 0210332; U.S. Provisional Application Nos. 60/431,406; 60/465,583; U.S. Pat. Nos. 6,531,126; 6,527,759; 6,518,270; 6,518,239; 6,517,827; 6,461,829; 6,448,054; 6,423,341; 6,495,551; 6,486,149; 6,441,162; 6,436,980; 6,399,629; 6,518,263; 6,503,881; 6,503,881; 6,486,148; 6,465,429; 6,388,070; 6,531,649; 6,531,465; 6,528,089; 6,521,408; 6,518,487; 6,531,508; 6,514,962; 6,503,953; 6,492,351; 6,486,148; 6,461,607; 6,448,054; 6,495,161; 6,495,158; 6,492,351; 6,486,165; 6,531,465; 6,514,535; 6,489,318; 6,497,886; 6,503,953; 6,503,539; 6,500,459; 6,492,351; 6,500,463; 6,461,829; 6,448,238; 6,432,444; 6,333,045; 6,291,462; 6,221,859; 6,514,986; 6,340,689; 6,309,663; 6,303,572; 6,277,836; 6,367,985; 6,468,964; 6,461,607; 6,448,449; 6,436,980; 6,423,741; 6,406,880; 6,395,746; 6,346,391; 6,294,192; 6,267,985; 6,235,908; 6,515,113; 6,509,327; 6,503,955; 5,525,066; 6,531,291; 6,517,827; 6,514,953; 6,514,541; 6,428,579; 6,451,339; 6,461,607; 6,461,829; 6,503,906; 6,518,239; 6,133,260; 6,174,878; 6,184,380; 6,187,341; 6,194,429; 6,194,441; 6,198,000; 6,221,859; 6,221,864; 6,239,113; 6,239,141; and 6,248,363.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:
1. A compound of formula I:

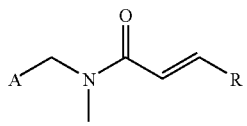

wherein, independently for each occurrence,
A is a monocyclic ring of 4-7 atoms containing 0-2 heteroatoms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from N, S or O and the rings are optionally substituted with one or more groups selected from $C_{1-4}$ alkyl, OR", CN, $OCF_3$, F, Cl, Br, I; wherein R" is H, alkyl, aralkyl, or heteroaralkyl;

R is

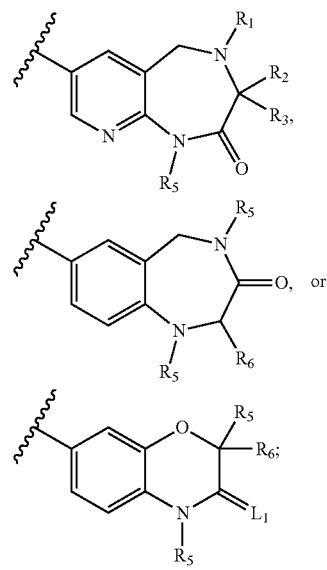

wherein, independently for each occurrence,
$R_1$ is H, alkyl, or aryl;
$R_2$ and $R_3$ taken together form a spirocyclic ring, wherein the spirocyclic ring is a 3-10 membered cycloalkyl ring, or a 3-10 membered saturated or unsaturated heterocyclic ring containing 1-4 heteroatoms selected from the group consisting of nitrogen, oxygen, and sulfur;
$R_5$ is H, alkyl, or aryl;
$R_6$ is H, alkyl, or aryl; and
$L_1$ is O or $H_2$;
or a pharmaceutically acceptable salt thereof.

2. The compound of claim 1, wherein A is selected from the following:

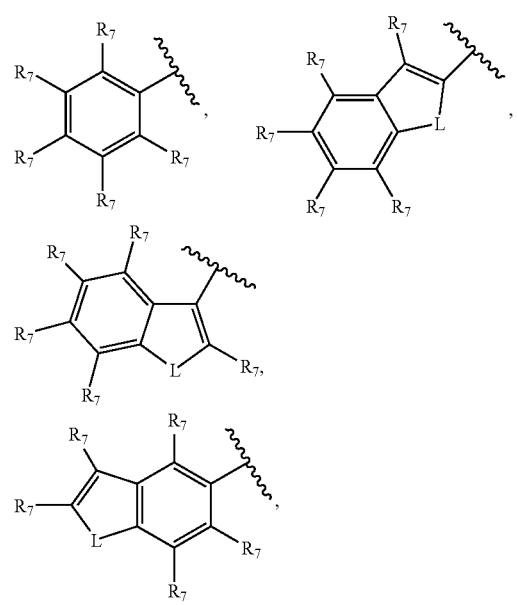

-continued
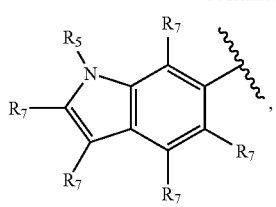
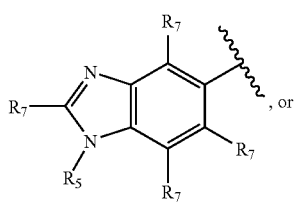
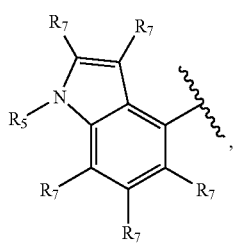
wherein, independently for each occurrence,
R$_7$ is H, C$_{1-4}$ alkyl, C$_{1-4}$ haloalkyl, C$_{1-4}$ alkenyl, OR", CN, OCF$_3$, F, Cl, Br, I; wherein R" is H, alkyl, aralkyl, or heteroaralkyl; and
L is O, S, or NR$_5$.
3. The compound of claim 1, wherein A is selected from the following:
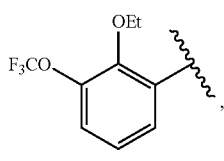, 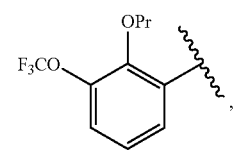,
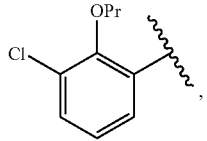, 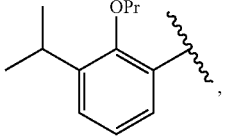,
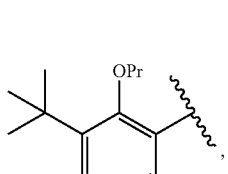, 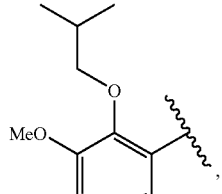,
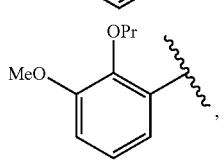, 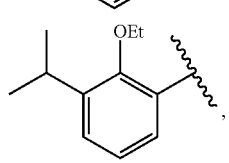,
-continued
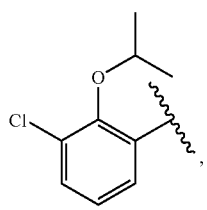, 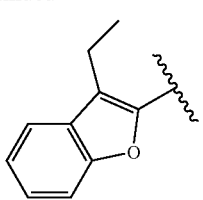,
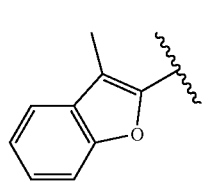, 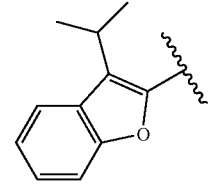,
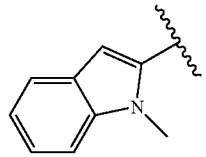, 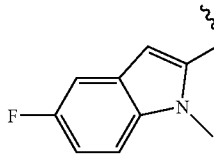,
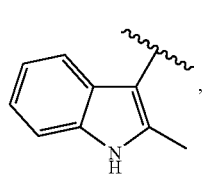, 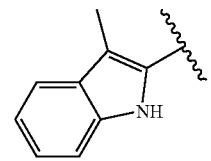,
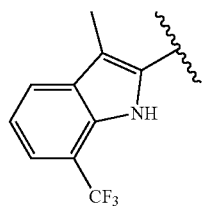, 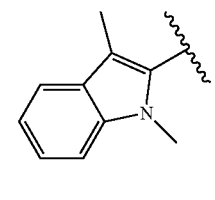,
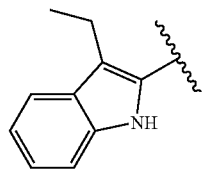, 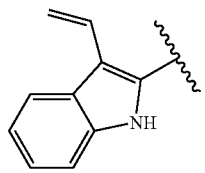,
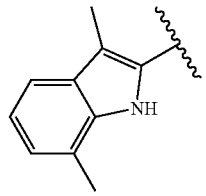, 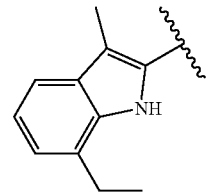,
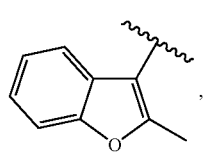, 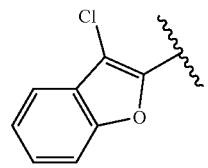,
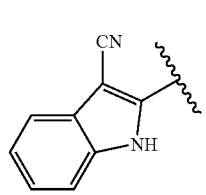, 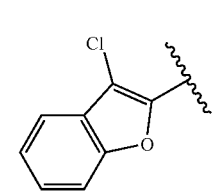, -continued
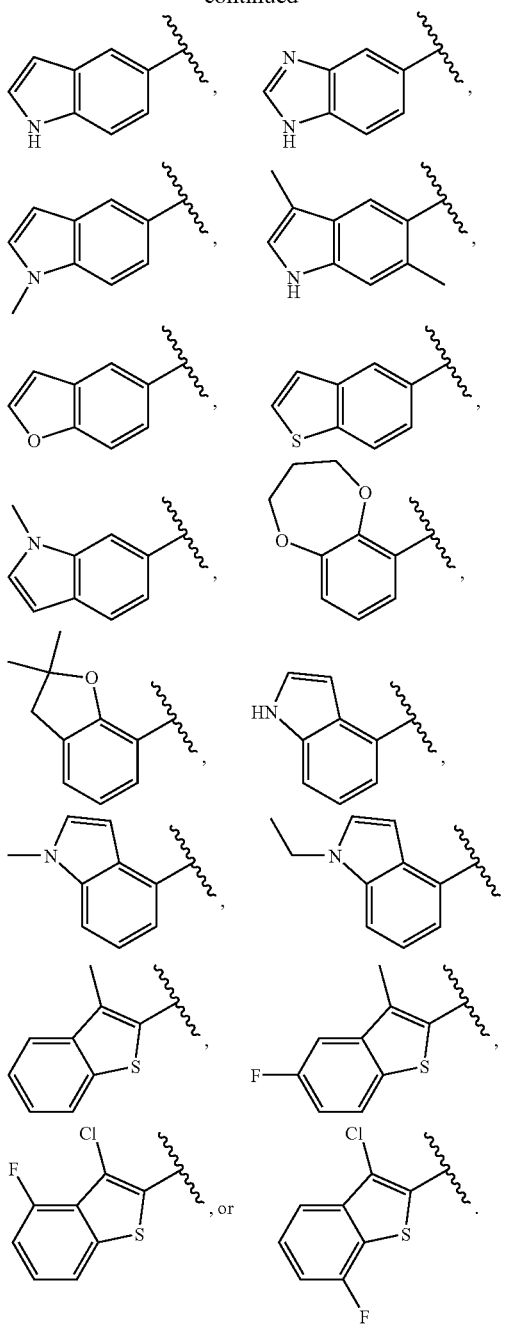
4. The compound of claim 2, wherein the compound has formula Ia:
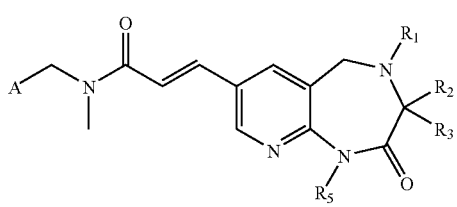
wherein:
A is selected from the following:
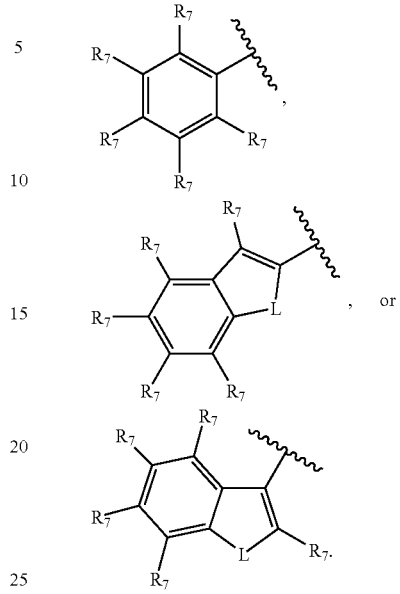
5. The compound of claim 2, wherein the compound has formula Ie:
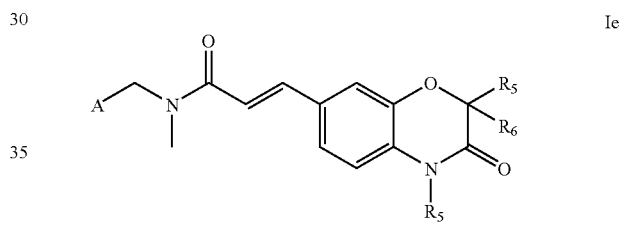
wherein:
A is selected from the following:
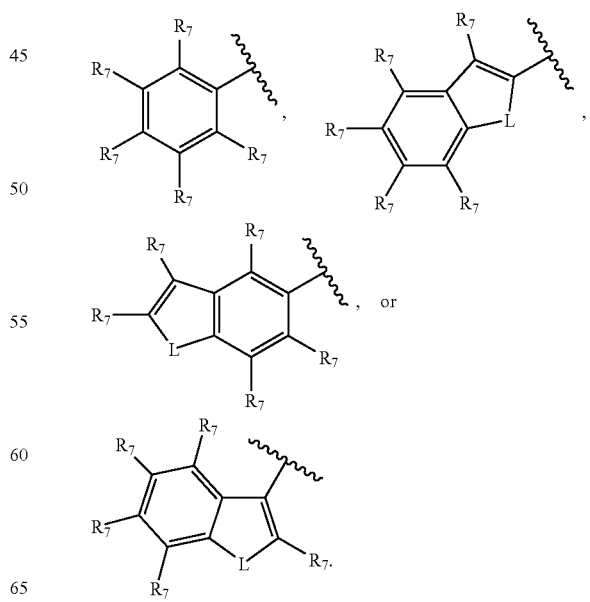

6. The compound of claim 2, wherein the compound has formula If:

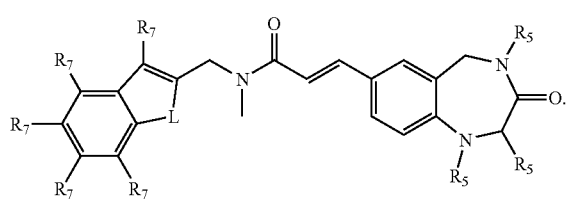

7. The compound of claim 1, wherein the compound is selected from the following:

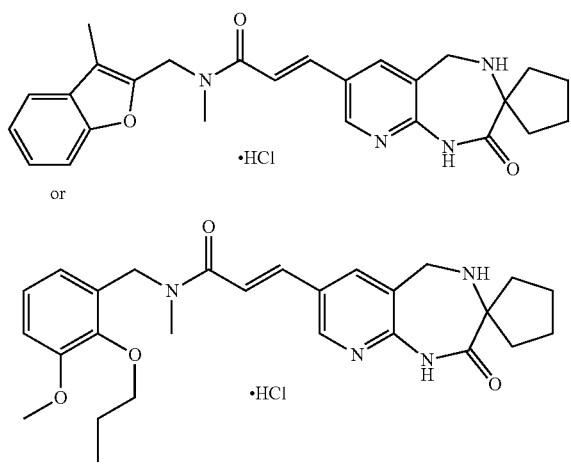

8. A pharmaceutical composition comprising a compound of claim 1 and a pharmaceutically acceptable carrier or excipient.

9. The composition of claim 8, wherein the composition is formulated for intraveneous administration.

10. The composition of claim 8, wherein the composition is formulated for injectable administration.

11. The composition of claim 8, wherein the composition is formulated for topical application.

12. The composition of claim 8, wherein the composition is formulated as a suppository.

13. The composition of claim 8, wherein the composition is formulated for systemic administration.

14. The composition of claim 8, wherein the composition is formulated for oral administration.

15. A method of treating a subject with a bacterial infection comprising administering to the subject the pharmaceutical composition of claim 8.

16. The method of claim 15, wherein the subject is a mammal.

17. The method of claim 16, wherein the mammal is a human.

18. A method of disinfecting an inanimate surface comprising administering to the inanimate surface a compound of claim 1.

19. A kit comprising the pharmaceutical composition of claim 14 and instructions for use thereof.

20. The compound of claim 1, wherein the spirocyclic ring is a 5-membered cycloalkyl ring.

21. The compound of claim 1, wherein the spirocyclic ring is a 6-membered cycloalkyl ring.

22. The compound of claim 1, wherein the spirocyclic ring is a 7-membered cycloalkyl ring.

* * * * *

UNITED STATES PATENT AND TRADEMARK OFFICE
CERTIFICATE OF CORRECTION

PATENT NO. : 8,450,307 B2
APPLICATION NO. : 11/628569
DATED : May 28, 2013
INVENTOR(S) : Bruce J. Sargent et al.

Page 1 of 1

It is certified that error appears in the above-identified patent and that said Letters Patent is hereby corrected as shown below:

In the claims

At column 210, claim number 19, line number 29, please delete "claim 14" and insert --claim 8-- in its place.

Signed and Sealed this
Thirtieth Day of July, 2013

Teresa Stanek Rea
*Acting Director of the United States Patent and Trademark Office*